United States Patent
Haketa et al.

(10) Patent No.: US 10,790,449 B2
(45) Date of Patent: Sep. 29, 2020

(54) COMPOUND, MATERIAL FOR ORGANIC ELECTROLUMINESCENCE ELEMENT, ORGANIC ELECTROLUMINESCENCE ELEMENT, AND ELECTRONIC DEVICE

(71) Applicant: IDEMITSU KOSAN CO., LTD., Chiyoda-ku (JP)

(72) Inventors: Tasuku Haketa, Chiba (JP); Masahiro Kawamura, Chiba (JP); Yumiko Mizuki, Basel (CH); Yoichi Ikeda, Itabashi-ku (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 454 days.

(21) Appl. No.: 15/502,689

(22) PCT Filed: Jun. 14, 2016

(86) PCT No.: PCT/JP2016/067694
§ 371 (c)(1),
(2) Date: Feb. 8, 2017

(87) PCT Pub. No.: WO2016/204150
PCT Pub. Date: Dec. 22, 2016

(65) Prior Publication Data
US 2017/0222152 A1 Aug. 3, 2017

(30) Foreign Application Priority Data
Jun. 16, 2015 (JP) ................. 2015-120993

(51) Int. Cl.
| | | |
|---|---|---|
| H01L 51/00 | (2006.01) | |
| C09K 11/06 | (2006.01) | |
| C07D 209/86 | (2006.01) | |
| C09K 11/02 | (2006.01) | |
| H01L 51/50 | (2006.01) | |

(52) U.S. Cl.
CPC ........ *H01L 51/0054* (2013.01); *C07D 209/86* (2013.01); *C09K 11/025* (2013.01); *C09K 11/06* (2013.01); *H01L 51/0072* (2013.01); *H01L 51/0085* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5012* (2013.01); *H01L 51/5016* (2013.01); *H01L 51/5056* (2013.01); *H01L 51/5072* (2013.01)

(58) Field of Classification Search
CPC .... C07D 209/86; C09K 11/025; C09K 11/06; C09K 2211/1007; C09K 2211/1011; C09K 2211/1029; C09K 2211/1044; C09K 2211/1059; C09K 2211/1088; C09K 2211/1092; C09K 2211/185; H01L 51/0054; H01L 51/0072; H01L 51/0085; H01L 51/5012; H01L 51/5016; H01L 51/5056; H01L 51/5072
See application file for complete search history.

(56) References Cited

U.S. PATENT DOCUMENTS

| | | | | |
|---|---|---|---|---|
| 6,821,643 B1 * | 11/2004 | Hu | ......................... | C09K 11/06 252/301.23 |
| 2004/0076853 A1 * | 4/2004 | Jarikov | .................. | C09K 11/06 428/690 |

(Continued)

FOREIGN PATENT DOCUMENTS

| | | |
|---|---|---|
| CN | 103187531 A | 7/2013 |
| CN | 105315229 A | 2/2016 |

(Continued)

OTHER PUBLICATIONS

Machine translation for JP 2005-240008 A (publication date: Sep. 2005). (Year: 2005).*

(Continued)

Primary Examiner — Dawn L Garrett
(74) Attorney, Agent, or Firm — Oblon, McClelland, Maier & Neustadt, L.L.P.

(57) ABSTRACT

Provided are an organic EL device having a high emission efficiency, a material for organic EL devices, which is capable of realizing the same, and the like. More specifically, provided are a compound represented by the following formula (1), a material for organic electroluminescence devices, which contains the compound, an organic electroluminescence device using the compound, and an electronic equipment provided with the organic electroluminescence device:

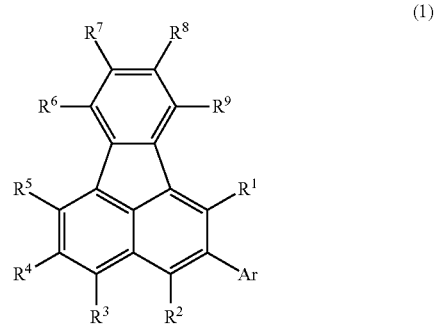

(1)

wherein Ar represents a substituted or unsubstituted aryl group having 6 to 50 ring carbon atoms, a substituted or unsubstituted heteroaryl group having 5 to 50 ring atoms, or a group formed by a combination of these groups, and W to $R^9$ each independently represent a hydrogen atom or a substituent, provided that any pair of $R^2$ and $R^3$, $R^3$ and $R^4$, $R^4$ and $R^5$, $R^6$ and $R^7$, $R^7$ and $R^8$, and $R^8$ and $R^9$ are optionally bonded to each other to form a benzene ring.

29 Claims, 1 Drawing Sheet

(56) References Cited

U.S. PATENT DOCUMENTS

| | | |
|---|---|---|
| 2008/0207864 A1 | 8/2008 | Nakagawa et al. |
| 2009/0015144 A1 | 1/2009 | Takashima et al. |
| 2009/0278118 A1 | 11/2009 | Ohrui et al. |
| 2011/0227052 A1 | 9/2011 | Kamatani et al. |
| 2011/0251446 A1 | 10/2011 | Kamatani et al. |
| 2012/0223295 A1 | 9/2012 | Inoue et al. |
| 2013/0292662 A1 | 11/2013 | Hashimoto et al. |
| 2014/0048784 A1 | 2/2014 | Inoue et al. |
| 2014/0100367 A1 | 4/2014 | Yoon et al. |
| 2014/0312331 A1 | 10/2014 | Inoue et al. |
| 2015/0236264 A1* | 8/2015 | Kim .................. H01L 51/0054 257/40 |
| 2015/0243891 A1 | 8/2015 | Kato et al. |
| 2015/0249219 A1 | 9/2015 | Inoue et al. |
| 2017/0186967 A1* | 6/2017 | Hayashi ............... C07D 401/10 |
| 2017/0213982 A1* | 7/2017 | Hayama ............... H01L 51/0067 |

FOREIGN PATENT DOCUMENTS

| | | | |
|---|---|---|---|
| EP | 2 891 648 A1 | | 7/2015 |
| JP | 10-189248 A | | 7/1998 |
| JP | 11-149987 A | | 6/1999 |
| JP | 2005-68367 A | | 3/2005 |
| JP | 2005-240008 A | * | 9/2005 |
| JP | 2008-156315 A | | 7/2008 |
| JP | 2008-227089 A | | 9/2008 |
| JP | 2009-256348 A | | 11/2009 |
| JP | 2010-111635 A | | 5/2010 |
| JP | 2010-121035 A | | 6/2010 |
| JP | 2010-143879 A | | 7/2010 |
| JP | 2011-231086 A | | 11/2011 |
| JP | 2012-144459 A | | 8/2012 |
| JP | 2014-522401 A | | 9/2014 |
| JP | 2014-531419 A | | 11/2014 |
| JP | 2015-71567 A | | 4/2015 |
| JP | 2015-096486 A | * | 5/2015 |
| KR | 10-2012-0044523 A | | 5/2012 |
| KR | 10-2016-0049083 A | | 5/2016 |
| WO | 2005/090365 A1 | | 9/2005 |
| WO | 2008/059713 A1 | | 5/2008 |
| WO | 2012/108388 A1 | | 8/2012 |
| WO | 2012/141273 A1 | | 10/2012 |
| WO | WO 2013/032278 A1 | * | 3/2013 |
| WO | WO 2015/008866 | | 1/2015 |
| WO | 2015/162912 A1 | | 10/2015 |
| WO | 2015/182547 A1 | | 12/2015 |
| WO | 2016/017514 A1 | | 2/2016 |
| WO | 2016/122150 A2 | | 8/2016 |

OTHER PUBLICATIONS

Machine translation for JP 2015-096486 A (publication date May 2015). (Year: 2015).*
Machine translation for CN 103187531 A (publication date Jul. 2013). (Year: 2013).*
Extended European Search Report dated Jan. 31, 2019 in Patent Application No. 16811624.2.
Supplementary partial European Search Report dated Nov. 7, 2018 in European Patent Application No. 16811624.2.
International Search Report dated Aug. 16, 2016 in PCT/JP2016/067694 filed Jun. 14, 2016.
Kenji Funaki et al., "Palladium-catalyzed Direct C—H Bond Arylation of Simple Arenes with Aryltrimethylsilanes", Chemical Letters, vol. 40, No. 9, 2011, pp. 1050-1052.
Jiajia Zhang et al., "Synthesis of an Extremely Crowded Naphthalene via a Stable Norbornadienone", Journal of the American Chemical Society, vol. 123, No. 44, 2011, pp. 10919-10926.
Naoto Hayashi et al., "An unusual cobalt-mediated cleavage of a hindered alkyne", Tetrahedron Letters, vol. 41, No. 22, 2000, pp. 4261-4264.
Kung K. Wang et al., "Thermolysis of Benzoenyne-Allenes to Form Biradicals and Subsequent Intramolecular Trapping with a Tetraarylallene to Generate Two Triarylmethyl Radical Centers", Journal of Organic Chemistry, vol. 64, No. 5, 1999, pp. 1650-1656.
H. Vogler et al., "The Electronic Structures and Spectra of Benzocyclobutenes and of Biphenylene Derivatives", Journal of the American Chemical Society, vol. 99, No. 14, 1977, pp. 4599-4604.
European Search Report dated Nov. 24, 2016 in European Application 15819013.2.
Office Action dated Jan. 14, 2020, in Japanese patent application No. 2016-571754, (w/English translation) (13 pages).
Office Action dated Jul. 1, 2020, in CN Patent Application No. 201680002212.0, w/ English translation—24 pages.

* cited by examiner

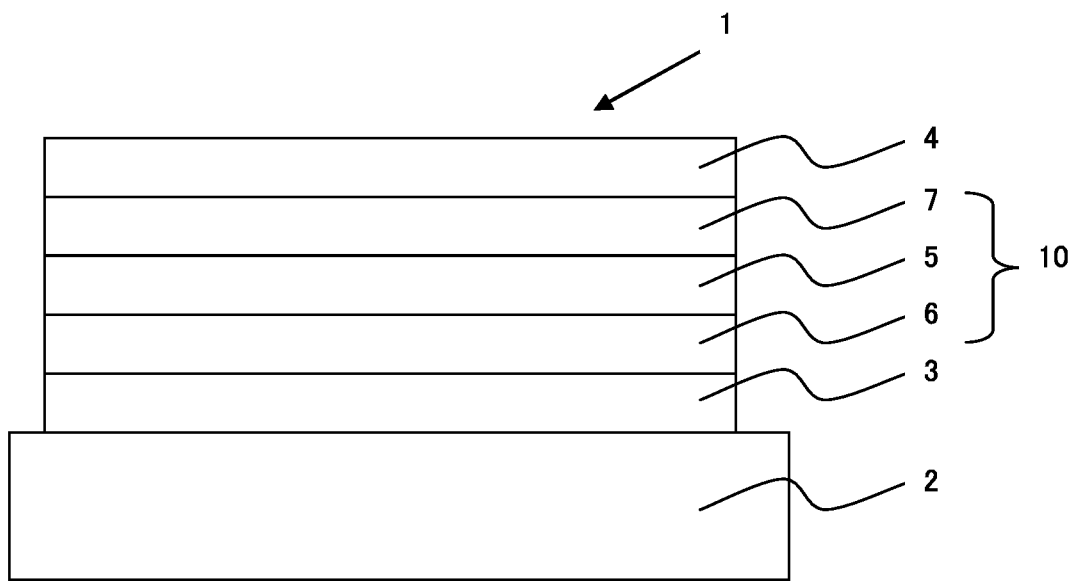

COMPOUND, MATERIAL FOR ORGANIC ELECTROLUMINESCENCE ELEMENT, ORGANIC ELECTROLUMINESCENCE ELEMENT, AND ELECTRONIC DEVICE

TECHNICAL FIELD

The present invention relates to a compound, a material for an organic electroluminescence device, including the compound, an organic electroluminescence device using the compound, and an electronic equipment provided with the organic electroluminescence device.

BACKGROUND ART

An electroluminescence device (hereinafter this may be abbreviated as an organic EL device) using an organic substance is expected to be hopeful for use for solid light emission-type, inexpensive large-area full-color display device, and many developments for the device are under way. In general, an organic EL device is composed of a light emitting layer and pair of opposite electrodes that sandwich the light emitting layer. When voltage is applied across the electrodes, electrons are injected from the cathode side and holes are injected from the anode side. Further, the electrons recombine with the holes in the light emitting layer to form an excited state, and light is emitted when the excited state returns to the ground state.

In addition, an organic EL device can provide a wide variety of light emitting colors, using various light emitting materials in the light emitting layer, and therefore intensive studies for practical use of the device in displays and others are conducted. In particular, studies on light emitting materials for the three primary colors, red, green and blue, are most extensively conducted, and the materials are studied intensively for the improvement of the properties.

As materials for such organic EL devices, a compound having an unsubstituted carbazolyl group via an unsubstituted benzene ring in a fluoranthene skeleton and the like are disclosed in PTL 1; use of a compound, in which the 7-positioned and/or the 10-positioned carbon atoms constituting a fluoranthene skeleton are substituted with nitrogen atoms, in an organic EL device is disclosed in PTL 2; an acenaphthopyridine derivative having a pyridyl group or a quinolyl group in a fluoranthene skeleton is disclosed in PTL 3; and an azaindenoglycerin derivative having a fluoranthene skeleton is disclosed in PTL 4.

CITATION LIST

Patent Literature

PTL 1: KR 2012-044523 A
PTL 2: JP 2005-68367 A
PTL 3: JP 2009-256348 A
PTL 4: JP 2010-111635 A

SUMMARY OF INVENTION

Technical Problem

However, there is a demand for further development of materials useful for organic EL devices for the purpose of further improving the device performance in the field of organic EL devices.

Therefore, it is an object of the present invention to provide an organic EL device having a high emission efficiency, and a material for organic EL devices, which is capable of realizing the organic EL device.

Solution to Problem

The present inventors have assiduously studied to attain the above-described object and, as a result, they have found that an organic EL device having a high emission efficiency is obtained by incorporation of a specific substituent at the 2-position of the fluoranthene skeleton.

That is, according to one embodiment of the present invention, the following [1] to [4] are provided.

[1] A compound represented by the following general formula (1);

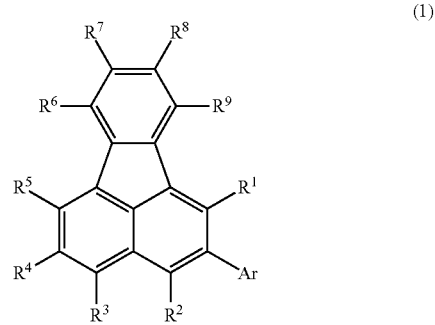

in the general formula (1), Ar represents a substituted or unsubstituted aryl group having 6 to 50 ring carbon atoms, a substituted or unsubstituted heteroaryl group having 5 to 50 ring atoms, or a group formed by a combination of these groups; and $R^1$ to $R^9$ each independently represent a hydrogen atom or a substituent, provided that $R^2$ and $R^3$, $R^3$ and $R^4$, $R^4$ and $R^5$, $R^6$ and $R^7$, $R^7$ and $R^8$, and $R^8$ and $R^9$ are optionally bonded to each other to form a benzene ring.

[2] A material for organic electroluminescence devices, containing the compound described in [1].

[3] An organic electroluminescence device including a cathode, an anode, and an organic thin film layer formed of one layer or plural layers, which is sandwiched between the anode and the cathode, in which the organic thin film layer contains a light emitting layer, and at least one layer of the organic thin film layer contains the compound described in [1].

[4] An electronic equipment provided with the organic electroluminescence device described in [3].

Advantageous Effects of Invention

By using the compound of the present invention as a material for organic EL devices, an organic EL device having a high emission efficiency is obtained.

BRIEF DESCRIPTION OF DRAWINGS

FIGURE is a view showing the schematic configuration of an organic EL device in one embodiment of the present invention.

DESCRIPTION OF EMBODIMENTS

In this description, the "XX to YY carbon atoms" in an expression "a substituted or unsubstituted ZZ group having XX to YY carbon atoms" refer to the number of the carbon atoms of the unsubstituted ZZ group, and when the ZZ group has a substituent, the carbon atoms of the substituent are not included.

Also in this description, the "XX to YY atoms" in an expression "a substituted or unsubstituted ZZ group having XX to YY atoms" refer to the number of the atoms of the unsubstituted ZZ group, and when the ZZ group has a substituent, the atoms of the substituent are not included.

In this description, the number of ring carbon atoms represents the number of the carbon atoms included in the atoms which are members constituting the ring itself of a compound having a structure in which atoms are bonded to a ring (for example, a monocyclic compound, a fused ring compound, a cross-linked compound, a carbocyclic compound, and a heterocyclic compound). In the case where the ring is substituted with a substituent, the carbon in the substituent is not included in the ring carbon atoms. The same applies to "the number of ring carbon atoms" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. In the case where a benzene ring or a naphthalene ring has, for example, an alkyl group substituted therein as a substituent, the carbon atoms of the alkyl group are not counted as the ring carbon atoms. Further, in the case where, for example, a fluorene ring as a substituent (inclusive of a spirofluorene ring) is bonded to a fluorene ring, the carbon atoms of the fluorene ring as a substituent are not counted as the ring carbon atoms.

Moreover, in this description, the number of ring atoms represents the number of the atoms which are members constituting the ring itself of a compound (for example, a monocyclic compound, a fused ring compound, a cross-linked compound, a carbocyclic compound, and a heterocyclic compound) having a structure (for example, a monocyclic ring, a fused ring, and a ring assembly) in which atoms are bonded to a ring. The atom not constituting the ring (for example, hydrogen atoms for saturating the valence of the atom which forms the ring) and the atom in a substituent, in the case where the ring is substituted with a substituent, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atoms bonded to each of carbon atoms of a pyridine ring and a quinazoline ring, or atoms constituting a substituent are not counted as the ring atoms. In addition, in the case where, for example, a fluorene ring as a substituent (inclusive of a spirofluorene ring) is bonded to a fluorene ring, the atoms of the fluorene ring as a substituent are not counted as the ring atoms.

Moreover, in this description, the definition of the "hydrogen atom" includes isotopes different in the neutron numbers, that is, light hydrogen (protium), heavy hydrogen (deuterium), and tritium.

In this description, the "heteroaryl group" and the "heteroarylene group" are each a group having at least one hetero atom as a ring atom. The hetero atom is preferably at least one selected from a nitrogen atom, an oxygen atom, a sulfur atom, a silicon atom, and a selenium atom.

In this description, the "substituted or unsubstituted carbazolyl group" represents any of the following carbazolyl group:

[Chem. 2]

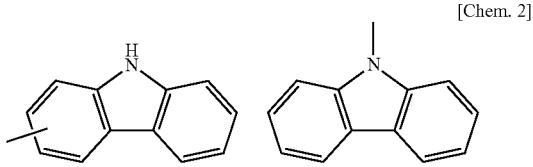

and a substituted carbazolyl group in which the carbazolyl group further has an arbitrary substituent.

In addition, arbitrary substituents in the substituted carbazolyl group may be bonded to form a fused ring, the substituted carbazolyl group may contain a hetero atom such as a nitrogen atom, an oxygen atom, a sulfur atom, a silicon atom, and a selenium atom, and the bonding position may be any one of 1- to 9-positions. Specific examples of such a substituted carbazolyl group include groups shown below.

[Chem. 3]

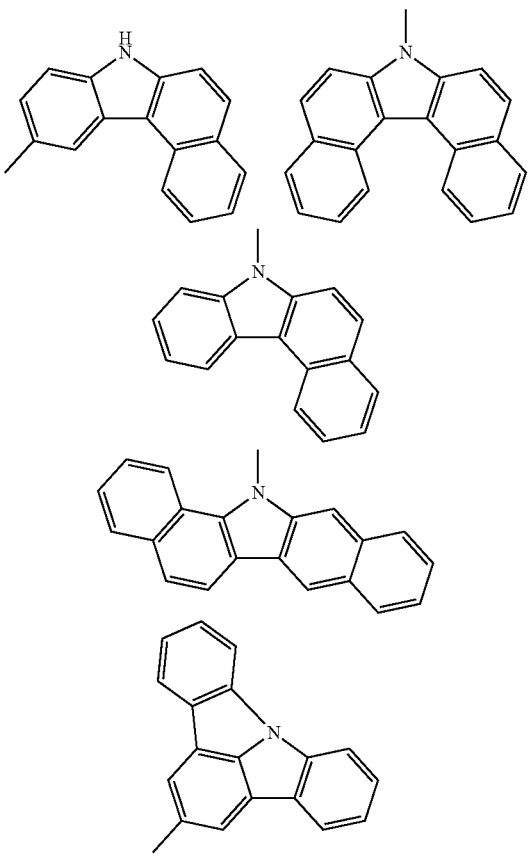

In this description, the "substituted or unsubstituted dibenzofuranyl group" and the "substituted or unsubstituted dibenzothiophenyl group" each represent the following dibenzofuranyl group and dibenzothiophenyl group:

[Chem. 4]

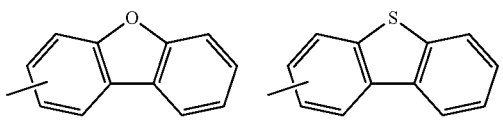

and a substituted dibenzofuranyl group and a substituted dibenzothiophenyl group, in which the substituted dibenzofuranyl group and the substituted dibenzothiophenyl group further have arbitrary substituents.

In addition, arbitrary substituents in the substituted dibenzofuranyl group and the substituted dibenzothiophenyl group may be bonded to form a fused ring, the groups may contain a hetero atom such as a nitrogen atom, an oxygen atom, a sulfur atom, a silicon atom, and a selenium atom, and the bonding position may be any one of 1- to 8-positions.

Specific examples of such the substituted dibenzofuranyl group and substituted dibenzothiophenyl group include groups shown below.

[Chem. 5]

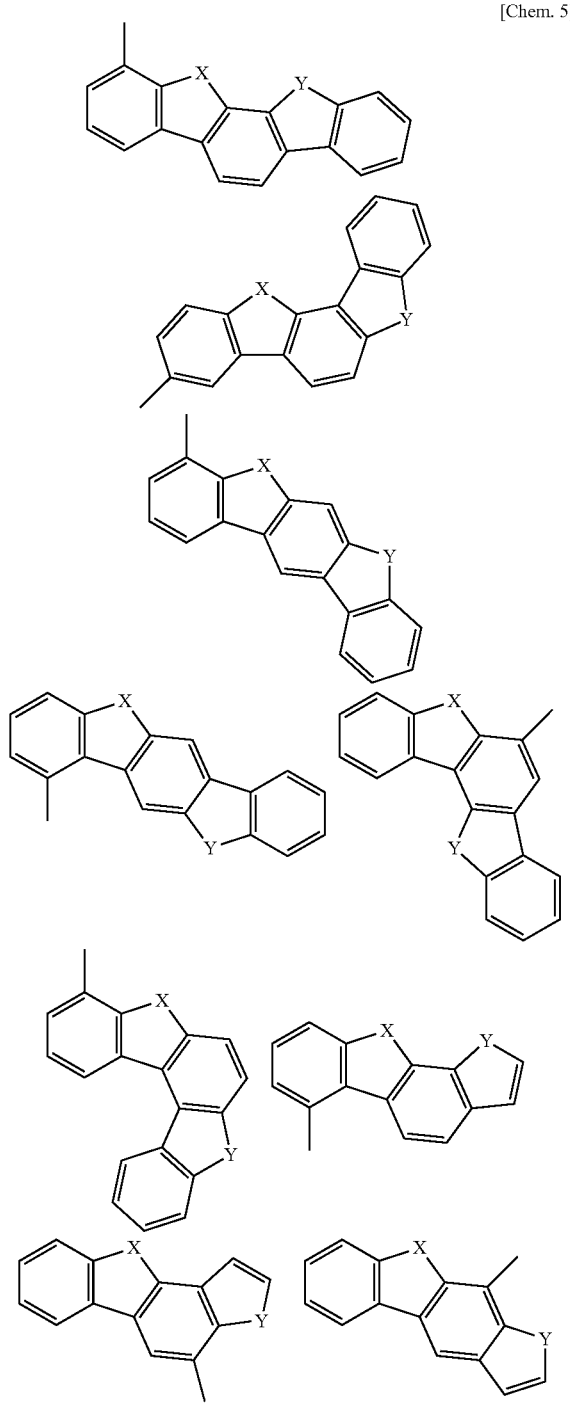

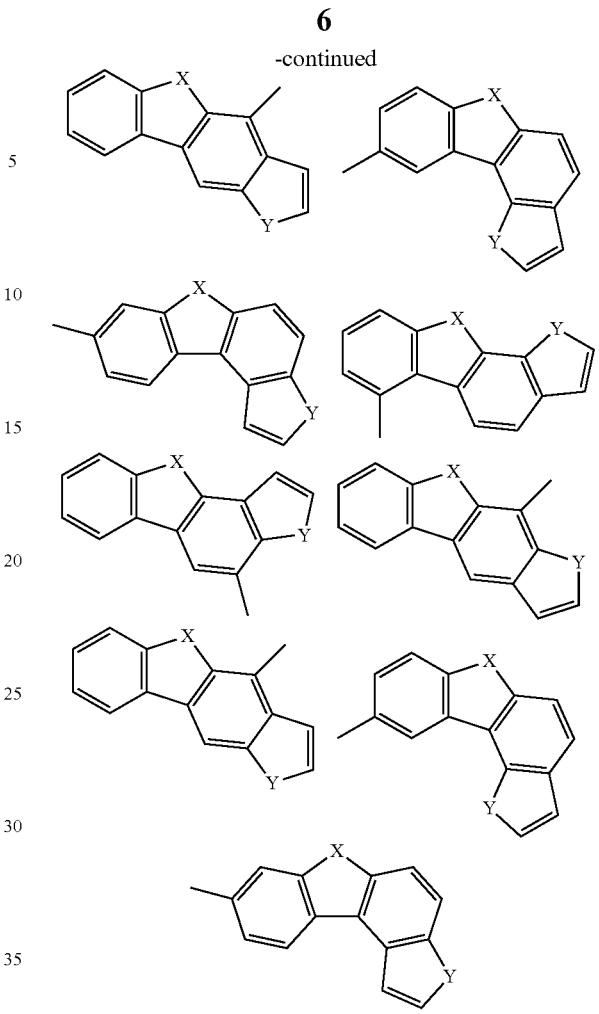

In the formulae, X represents an oxygen atom or a sulfur atom, Y represents an oxygen atom, a sulfur atom, NH, NR$^a$ (R$^a$ is an alkyl group or an aryl group), CH$_2$, or CR$^b_2$ (R$^b$ is an alkyl group or an aryl group).

Moreover, a substituent, or the substituent referred to by "substituted or unsubstituted" is preferably selected from the group consisting of an alkyl group having 1 to 50 carbon atoms (preferably 1 to 18 carbon atoms, and more preferably 1 to 8 carbon atoms); a cycloalkyl group having 3 to 50 ring carbon atoms (preferably 3 to 10 ring carbon atoms, more preferably 3 to 8 ring carbon atoms, and still more preferably 5 or 6 ring carbon atoms); an aryl group having 6 to 50 ring carbon atoms (preferably 6 to 25 ring carbon atoms, and more preferably 6 to 18 ring carbon atoms); an aralkyl group having 7 to 51 carbon atoms (preferably 7 to 30 carbon atoms, and more preferably 7 to 20 carbon atoms), which contains an aryl group having 6 to 50 ring carbon atoms (preferably 6 to 25 ring carbon atoms, and more preferably 6 to 18 ring carbon atoms); an alkoxy group containing an alkyl group having 1 to 50 carbon atoms (preferably 1 to 18 carbon atoms, and more preferably 1 to 8 carbon atoms); an aryloxy group having 6 to 50 ring carbon atoms (preferably 6 to 25 ring carbon atoms, and more preferably 6 to 18 ring carbon atoms); a di-substituted amino group having a substituent selected from an alkyl group having 1 to 50 carbon atoms (preferably 1 to 18 carbon atoms, and more preferably 1 to 8 carbon atoms) and an aryl group having 6 to 50 ring carbon atoms (preferably 6 to 25 ring carbon atoms, and more preferably 6 to 18 ring carbon atoms); a mono-, di-, or tri-substituted silyl group having a substituent selected from an alkyl group having 1 to 50 carbon atoms (preferably 1 to 18 carbon atoms, and more preferably 1 to 8 carbon atoms) and an aryl group having 6 to 50 ring carbon atoms (preferably 6 to 25 ring carbon atoms, and more preferably 6 to 18 ring carbon atoms); a heteroaryl group having 5 to 50 ring atoms (preferably 5 to 24 ring atoms, and more preferably 5 to 13 ring atoms); a haloalkyl group having 1 to 50 carbon atoms (preferably 1 to 18 carbon atoms, and more preferably 1 to 8 carbon atoms); a halogen atom (a fluorine atom, a chlorine atom, a bromine atom, or an iodine atom); a cyano group; a nitro group; a sulfonyl group having a substituent selected from an alkyl group having 1 to 50 carbon atoms (preferably 1 to 18 carbon atoms, and more preferably 1 to 8 carbon atoms) and an aryl group having 6 to 50 ring carbon atoms (preferably 6 to 25 ring carbon atoms, and more preferably 6 to 18 ring carbon atoms); a di-substituted phosphoryl group having a substituent selected from an alkyl group having 1 to 50 ring carbon atoms (preferably 1 to 18 carbon atoms, and more preferably 1 to 8 carbon atoms), and an aryl group having 6 to 50 ring carbon atoms (preferably 6 to 25 ring carbon atoms, and more preferably 6 to 18 ring carbon atoms); an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

These substituents may further be substituted with the above-described arbitrary substituents. In addition, these substituents which are present in plural numbers are optionally bonded to each other to form a ring.

In addition, the term of "unsubstituted" referred to by "substituted or unsubstituted" means that these substituents are not substituted and a hydrogen atom is bonded.

Among these substituents, more preferred are a substituted or unsubstituted alkyl group having 1 to 50 carbon atoms (preferably 1 to 18 carbon atoms, and more preferably 1 to 8 carbon atoms), a substituted or unsubstituted aryl group having 6 to 50 ring carbon atoms (preferably 6 to 25 ring carbon atoms, and more preferably 6 to 18 ring carbon atoms), a substituted or unsubstituted heteroaryl group having 5 to 50 ring atoms (preferably 5 to 24 ring atoms, and more preferably 5 to 13 ring atoms), a halogen atom, a cyano group, a substituted or unsubstituted fluoroalkyl group having 1 to 50 carbon atoms (preferably 1 to 20 carbon atoms, more preferably 1 to 10 carbon atoms, and still more preferably 1 to 5 carbon atoms), a substituted or unsubstituted alkoxy group having 1 to 50 carbon atoms (preferably 1 to 20 carbon atoms, more preferably 1 to 10 carbon atoms, and still more preferably 1 to 5 carbon atoms), a substituted or unsubstituted fluoroalkoxy group having 1 to 50 carbon atoms (preferably 1 to 20 carbon atoms, more preferably 1 to 10 carbon atoms, and still more preferably 1 to 5 carbon atoms), a substituted or unsubstituted aryloxy group having 6 to 50 ring carbon atoms (preferably 6 to 25 ring carbon atoms, more preferably 6 to 18 ring carbon atoms, and still more preferably 6 to 12 ring carbon atoms), a di-substituted amino group having a substituent selected from an alkyl group having 1 to 50 carbon atoms (preferably 1 to 18 carbon atoms, and more preferably 1 to 8 carbon atoms) and an aryl group having 6 to 50 ring carbon atoms (preferably 6 to 25 ring carbon atoms, and more preferably 6 to 18 ring carbon atoms), and a tri-substituted silyl group having a substituent selected from an alkyl group having 1 to 50 carbon atoms (preferably 1 to 18 carbon atoms, and more preferably 1 to 8 carbon atoms) and an aryl group having 6 to 50 ring carbon atoms (preferably 6 to 25 ring carbon atoms, and more preferably 6 to 18 ring carbon atoms).

Among these substituents, still more preferred are a substituted or unsubstituted aryl group having 6 to 50 ring carbon atoms (preferably 6 to 25 ring carbon atoms, and more preferably 6 to 18 ring carbon atoms), a substituted or unsubstituted heteroaryl group having 5 to 50 ring atoms (preferably 5 to 24 ring atoms, and more preferably 5 to 13 ring atoms), a halogen atom, a cyano group, a substituted or unsubstituted fluoroalkyl group having 1 to 50 carbon atoms (preferably 1 to 20 carbon atoms, more preferably 1 to 10 carbon atoms, and still more preferably 1 to 5 carbon atoms), a substituted or unsubstituted alkoxy group having 1 to 50 carbon atoms (preferably 1 to 20 carbon atoms, more preferably 1 to 10 carbon atoms, and still more preferably 1 to 5 carbon atoms), a substituted or unsubstituted fluoroalkoxy group having 1 to 50 carbon atoms (preferably 1 to 20 carbon atoms, more preferably 1 to 10 carbon atoms, and still more preferably 1 to 5 carbon atoms), or a substituted or unsubstituted aryloxy group having 6 to 50 ring carbon atoms (preferably 6 to 25 ring carbon atoms, more preferably 6 to 18 ring carbon atoms, and still more preferably 6 to 12 ring carbon atoms).

Specific Examples of Substituent

Examples of the alkyl group having 1 to 50 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups).

Examples of the aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl group, an anthryl group, a benzoanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a heptacenyl group, a picenyl group, a pentaphenyl group, a pyrenyl group, a chrysenyl group, a benzochrysenyl group, an s-indacenyl group, an as-indacenyl group, and a perylenyl group.

The heteroaryl group having 5 to 50 ring atoms includes at least one, and preferably 1 to 3 hetero atoms (for example, a nitrogen atom, a sulfur atom, and an oxygen atom) which are the same as or different from each other.

Examples of the heteroaryl group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzthiazolyl group, an indazolyl group, a benzisoxazolyl group, a benzisothiazolyl group, a dibenzofuranyl group, a dibenzothiophenyl group, a carbazolyl group, a phenanthridinyl group, an acridinyl group, a phenanthrolinyl group, a phenazinyl group, a phenothiazinyl group, a phenoxazinyl group, and a xanthenyl group.

Examples of the fluoroalkyl group having 1 to 50 carbon atoms include groups obtained by substituting at least one hydrogen atom, and preferably 1 to 7 hydrogen atoms, or all hydrogen atoms in the above-described alkyl groups having 1 to 50 carbon atoms with fluorine atoms.

Specific examples of the fluoroalkyl group include a heptafluoropropyl group, a pentafluoroethyl group, a 2,2,2-trifluoroethyl group, and a trifluoromethyl group.

The alkoxy group having 1 to 50 carbon atoms is a group represented by $-OR^X$, and $R^X$ represents the above-described alkyl group having 1 to 50 carbon atoms.

Specific examples of the alkoxy group include a t-butoxy group, a propoxy group, an ethoxy group, and a methoxy group.

The fluoroalkoxy group having 1 to 50 carbon atoms is a group represented by $-OR^Y$, and $R^Y$ represents the above-described fluoroalkyl group having 1 to 50 carbon atoms.

Specific examples of the fluoroalkoxy group include a heptafluoropropoxy group, a pentafluoroethoxy group, a 2,2,2-trifluoroethoxy group, and a trifluoromethoxy group.

The aryloxy group having 6 to 50 ring carbon atoms is a group represented by $-OR^Z$, and $R^Z$ represents the above-described aryl group having 6 to 50 ring carbon atoms.

Specific examples of the aryloxy group include a phenyloxy group, a 1-naphthyloxy group, a 2-naphthyloxy group, a 4-biphenylyloxy group, a p-terphenyl-4-yloxy group, and a p-tolyloxy group.

Examples of the alkyl group and the aryl group of the di-substituted amino group having a substituent selected from an alkyl group having 1 to 50 carbon atoms and an aryl group having 6 to 50 ring carbon atoms include the above-described alkyl groups having 1 to 50 carbon atoms and aryl groups having 6 to 50 ring carbon atoms.

Examples of the di-substituted amino group include dialkylamino groups such as a dimethylamino group, a diethylamino group, a diisopropylamino group, and a di-t-butylamino group; a diphenylamino group, a di(methylphenyl)amino group, a dinaphthylamino group, and a dibiphenylylamino group.

Examples of the alkyl group and the aryl group of the tri-substituted silyl group having a substituent selected from an alkyl group having 1 to 50 carbon atoms and an aryl group having 6 to 50 ring carbon atoms include the above-described alkyl groups having 1 to 50 carbon atoms and aryl groups having 6 to 50 ring carbon atoms.

As the tri-substituted silyl group, a trialkylsilyl group (the alkyl group is as described above), or a triarylsilyl group (the aryl group is as described above) is preferable. Examples of the trialkylsilyl group include a trimethylsilyl group, a triethylsilyl group, a triisopropylsilyl group, a tri-t-butylsilyl group, and a tri-n-butylsilyl group. Examples of the triarylsilyl group include a triphenylsilyl group and a tri(methylphenyl)silyl group.

Hereinafter, the present invention will be described in detail.

Furthermore, in this description, those which are defined as being preferred can be selected arbitrarily and an arbitrary combination thereof is available.

[Compound]

In one embodiment of the present invention, a compound represented by the following general formula (1) (hereinafter also referred to as a "compound (1)") is provided. The compound is useful as a material for organic electroluminescence devices.

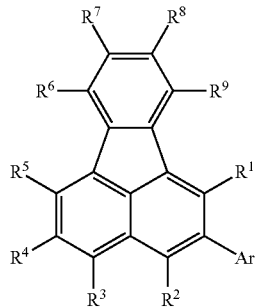

(1)

In the general formula (1), Ar represents a substituted or unsubstituted aryl group having 6 to 50 ring carbon atoms, a substituted or unsubstituted heteroaryl group having 5 to 50 ring atoms, or a group formed by a combination of these groups.

$R^1$ to $R^9$ each independently represent a hydrogen atom or a substituent, provided that $R^2$ and $R^3$, $R^3$ and $R^4$, $R^4$ and $R^5$, $R^6$ and $R^7$, $R^7$ and $R^8$, and $R^8$ and $R^9$ are optionally bonded to each other to form a benzene ring.

<Regarding $R^1$ to $R^9$ in the General Formula (1)>

The substituents represented by W to $R^9$ are as mentioned above, and preferred examples thereof are also the same.

Furthermore, $R^2$ and $R^3$, $R^3$ and $R^4$, $R^4$ and $R^5$, $R^6$ and $R^7$, $R^7$ and $R^8$, and $R^8$ and $R^9$ are optionally bonded to each other to form a benzene ring. For example, the compound in which $R^3$ and $R^4$ are bonded to each other to form a benzene ring is represented by the following general formula (1-1).

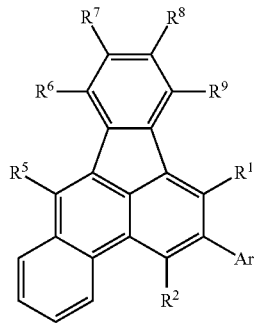

(1-1)

In the general formula (1-1), Ar, $R^1$, $R^2$, and $R^5$ to $R^9$ are as defined above.

It is preferable that $R^2$ and $R^3$, $R^3$ and $R^4$, $R^4$ and $R^5$, $R^6$ and $R^7$, $R^7$ and $R^8$, and $R^8$ and $R^9$ are not bonded to each other to form a benzene ring from the viewpoint of emission efficiency.

It is preferable that $R^1$ to $R^9$ are all hydrogen atoms from the viewpoint of emission efficiency.

Furthermore, it is preferable that the compound of the present invention has only one fluoranthene skeleton within one molecule from the viewpoint of emission efficiency. Here, the fluoranthene skeleton mentioned herein also includes a structure in which $R^2$ and $R^3$, $R^3$ and $R^4$, $R^4$ and $R^5$, $R^6$ and $R^7$, $R^7$ and $R^8$, or $R^8$ and $R^9$ are bonded to each other to form a benzene ring. In other words, it is preferable that all of Ar and $R^1$ to $R^9$ do not have a fluoranthene skeleton.

<Regarding Ar in General Formula (1)>

Ar represents a substituted or unsubstituted aryl group having 6 to 50 ring carbon atoms, a substituted or unsubstituted heteroaryl group having 5 to 50 ring atoms, or a group formed by a combination of these groups.

Examples of the aryl group represented by Ar include a phenyl group, a naphthyl group (a 1-naphthyl group and a 2-naphthyl group), an anthryl group (a 1-anthryl group, a 2-anthryl group, and the like), a benzoanthryl group, a phenanthryl group (a 1-phenanthryl group, a 2-phenanthryl group, a 3-phenanthryl group, a 9-phenanthryl group, and the like), a benzophenanthryl group, a fluorenyl group, a 9,9-di-substituted fluorenyl group (a 9,9-dimethyl-2-fluorenyl group, a 9,9-diphenyl-2-fluorenyl group, and the like), a spirobifluorenyl group, a benzofluorenyl group, a dibenzofluorenyl group, a picenyl group, a tetracenyl group, a heptacenyl group, a pyrenyl group, a chrysenyl group, a benzochrysenyl group, an s-indacenyl group, an as-indacenyl group, a triphenylenyl group, a benzotriphenylenyl group, a perylenyl group, a coronyl group, and a dibenzoanthryl group. As the aryl group, a substituted or unsubstituted aryl group having 6 to 40 ring carbon atoms is preferable, and a substituted or unsubstituted aryl group having 6 to 30 ring carbon atoms is more preferable from the viewpoint of emission efficiency.

Examples of the heteroaryl group represented by Ar include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzthiazolyl group, an indazolyl group, a benzisoxazolyl group, a benzisothiazolyl group, a dibenzofuranyl group, a dibenzothiophenyl group, a phenanthridinyl group, an acridinyl group, a carbazolyl group, a phenanthrolinyl group, a phenazinyl group, a phenothiazinyl group, a phenoxazinyl group, and a xanthenyl group. As the heteroaryl group, from the viewpoints of emission efficiency and lifetime, a substituted or unsubstituted heteroaryl group having 5 to 30 ring atoms is preferable, and a substituted or unsubstituted heteroaryl group having 5 to 20 ring atoms is more preferable.

As the heteroaryl group, from the viewpoints of emission efficiency and lifetime, specifically, a substituted or unsubstituted, furyl group, a thienyl group, a pyridyl group, an imidazopyridyl group, a pyridazinyl group, a pyrimidinyl group, a pyrazinyl group, a triazinyl group, a benzimidazolyl group, a dibenzofuranyl group, a dibenzothiophenyl group, a carbazolyl group, a phenanthrolinyl group, or the like is preferable, a substituted or unsubstituted pyrimidinyl group, a substituted or unsubstituted triazinyl group, or a substituted or unsubstituted carbazolyl group is more preferable, a substituted pyrimidinyl group, a substituted triazinyl group, or a substituted carbazolyl group is still more preferable, and a di-substituted pyrimidinyl group, a di-substituted triazinyl group, a mono-substituted carbazolyl group, or a di-substituted carbazolyl group is particularly preferable. As the carbazolyl group, an N-carbazolyl group, an N-aryl-2-carbazolyl group (the number of ring carbon atoms of the aryl group is preferably 6 to 25, more preferably 6 to 18, still more preferably 6 to 10, and particularly preferably 6), or an N-aryl-3-carbazolyl group (the number of ring carbon atoms of the aryl group is preferably 6 to 25, more preferably 6 to 18, still more preferably 6 to 10, and particularly preferably 6) is preferable.

As Ar, from the viewpoint of emission efficiency, a group formed by a substituted or unsubstituted aryl group having 6 to 50 ring carbon atoms and a substituted or unsubstituted heteroaryl group having 5 to 50 ring atoms is also preferable. The descriptions of the aryl group and the heteroaryl group are as described above. Further, in the case of a group formed by the combination, the groups other than the terminal groups are divalent or higher. For example, "-aryl group-heteroaryl group" is strictly directed to "-arylene group-heteroaryl group", and "-heteroaryl group-aryl group" is strictly directed to "-heteroarylene group-aryl group". The arylene group corresponds to a group obtained by removing one hydrogen atom from the aryl group, and the heteroarylene group corresponds to a group obtained by removing one hydrogen atom from the heteroaryl group.

Examples of the group formed by the combination include "-arylene group-heteroaryl group," "-heteroarylene group-aryl group," "-arylene group-heteroarylene group-aryl group," "-heteroarylene group-arylene group-heteroaryl group," "-arylene group-heteroarylene group-arylene group-heteroaryl group," and "-heteroarylene group-arylene group-heteroarylene group-aryl group". The number of ring carbon atoms of each of the aryl group and the arylene group is preferably 6 to 30, more preferably 6 to 20, still more preferably 6 to 18, and particularly preferably 6 to 12. Further, the number of ring atoms of each of the heteroaryl group and the heteroarylene group is preferably 5 to 30, more preferably 5 to 20, and still more preferably 5 to 13.

Here, specific examples of the arylene group include a phenylene group (a 1,2-phenylene group, a 1,3-phenylene group, a 1,4-phenylene group, and the like), a naphthylene group (a 1,4-naphthylene group, a 1,5-naphthylene group, and the like), a biphenylene group, a fluorenylene group (a 2,7-fluorenylene group and the like), a 9,9-di-substituted fluorenylene group (a 9,9-dimethyl-2,7-fluorenylene group, a 9,9-diphenyl-2,7-fluorenylene group, and the like), a benzofluorenylene group, a dibenzofluorenylene group, a picenylene group, a tetracenylene group, a pentacenylene group, a pyrenylene group, a chrysenylene group, a benzochrysenylene group, an s-indacenylene group, an as-indacenylene group, a triphenylenylene group, a benzotriphenylenylene group, a perylenylene group, a coronylene group, and a dibenzoanthrylene group.

Furthermore, specific examples of the heteroarylene group include a pyrrolylene group, a furylene group, a thienylene group, a pyridylene group, an imidazopyridylene group, a pyridazinylene group, a pyrimidinylene group, a pyrazinylene group, a triazinylene group, an imidazolylene group, an oxazolylene group, a thiazolylene group, a pyrazolylene group, an isoxazolylene group, an isothiazolylene group, an oxadiazolylene group, a thiadiazolylene group, a triazolylene group, a tetrazolylene group, an indolylene group, an isoindolylene group, a benzofuranylene group, an isobenzofuranylene group, a benzothiophenylene group, an isobenzothiophenylene group, an indolizinylene group, a quinolizinylene group, a quinolylene group, an isoquinolylene group, a cinnolylene group, a phthalazinylene group, a quinazolinylene group, a quinoxalinylene group, a benzimidazolylene group, a benzoxazolylene group, a benzthiazolylene group, an indazolylene group, a benzisoxazolylene group, a benzisothiazolylene group, a dibenzofuranylene group, a dibenzothiophenylene group, a carbazolediyl group, a phenanthridinylene group, an acridinylene group, a phenanthrolinylene group, a phenazinylene group, a phenothiazinylene group, a phenoxazinylene group, and a xanthenylene group. Here, the carbazolediyl group is preferably bonded to a 2-position and N (9-position), and more preferably bonded to a 3-position and N (9-position).

Preferred Embodiments of Compound (1)

From the viewpoint of emission efficiency, one preferred embodiment of the compound (1) includes a compound represented by the following general formula (2).

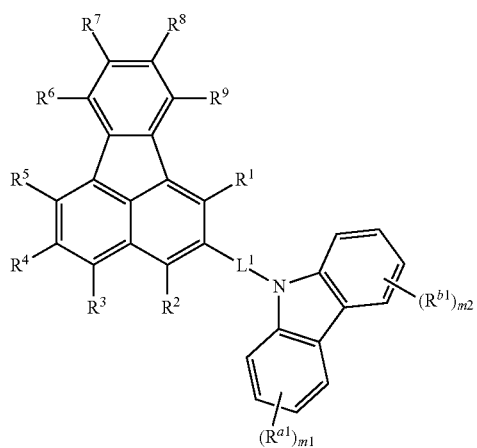

(2)

In the general formula (2), $R^1$ to $R^9$ are the same as those described above in the general formula (1).

$L^1$ represents a single bond, a substituted or unsubstituted arylene group having 6 to 18 ring carbon atoms or a substituted or unsubstituted heteroarylene group having 5 to 20 ring atoms.

$R^{a1}$ and $R^{b1}$ each independently represent a substituent. m1 represents an integer of 0 to 4. m2 represents an integer of 0 to 3. In the case where plural $R^{a1}$'s or plural $R^{b1}$'s are present, plural $R^{a1}$'s or plural $R^{b1}$'s are the same as or different from each other and are optionally bonded to each other to form a ring.

Examples of the arylene group represented by $L^1$ include a phenylene group (a 1,2-phenylene group, a 1,3-phenylene group, and a 1,4-phenylene group), a naphthylene group (a 1,4-naphthylene group, a 1,5-naphthylene group, and the like), a biphenylene group, a fluorenylene group (a 2,7-fluorenylene group and the like), a 9,9-di-substituted fluorenylene group (a 9,9-dimethyl-2,7-fluorenylene group, a 9,9-diphenyl-2,7-fluorenylene group, and the like), a benzofluorenylene group, a tetracenylene group, a pyrenylene group, a chrysenylene group, an s-indacenylene group, an as-indacenylene group, and a triphenylenylene group. The number of ring carbon atoms of the arylene group is preferably 6 to 14, more preferably 6 to 12, and still more preferably 6 to 10.

Examples of the heteroarylene group represented by $L^1$ include a pyrrolylene group, a furylene group, a thienylene group, a pyridylene group, an imidazopyridylene group, a pyridazinylene group, a pyrimidinylene group, a pyrazinylene group, a triazinylene group, an imidazolylene group, an oxazolylene group, a thiazolylene group, a pyrazolylene group, an isoxazolylene group, an isothiazolylene group, an oxadiazolylene group, a thiadiazolylene group, a triazolylene group, a tetrazolylene group, an indolylene group, an isoindolylene group, a benzofuranylene group, an isobenzofuranylene group, a benzothiophenylene group, an isobenzothiophenylene group, an indolizinylene group, a quinolizinylene group, a quinolylene group, an isoquinolylene group, a cinnolylene group, a phthalazinylene group, a quinazolinylene group, a quinoxalinylene group, a benzimidazolylene group, a benzoxazolylene group, a benzthiazolylene group, an indazolylene group, a benzisoxazolylene group, a benzisothiazolylene group, a phenanthridinylene group, an acridinylene group, a phenanthrolinylene group, a phenazinylene group, a phenothiazinylene group, a phenoxazinylene group, and a xanthenylene group. The number of ring carbon atoms of the heteroarylene group is preferably 5 to 14, more preferably 5 to 12, and still more preferably 5 to 10.

From the viewpoint of emission efficiency, $L^1$ is preferably a single bond or an arylene group, more preferably a single bond, a phenylene group, a naphthylene group, or a biphenylene group, still more preferably a single bond or a phenylene group, and particularly preferably a single bond. The phenylene group may be either a 1,3-phenylene group or a 1,4-phenylene group, and is preferably a 1,4-phenylene group.

The substituents represented by $R^{a1}$ and $R^{b1}$ are as defined above, and preferred examples thereof are also the same. Among these, a substituted or unsubstituted alkyl group having 1 to 8 carbon atoms, a substituted or unsubstituted aryl group having 6 to 18 ring carbon atoms (more preferably 6 to 12 ring carbon atoms), a substituted or unsubstituted heteroaryl group having 5 to 13 ring atoms, a substituted or unsubstituted alkoxy group having 1 to 10 carbon atoms (more preferably 1 to 5 carbon atoms), and a substituted or unsubstituted aryloxy group having 6 to 12 ring carbon atoms are particularly preferred, a substituted or unsubstituted aryl group having 6 to 18 ring carbon atoms (more preferably 6 to 12 ring carbon atoms) and a substituted or unsubstituted heteroaryl group having 5 to 13 ring atoms are the most preferred, and specific examples thereof include a phenyl group, a biphenylyl group, a naphthyl group, and a carbazolyl group. As the carbazolyl group, an N-carbazolyl group, an N-aryl-2-carbazolyl group (the number of ring carbon atoms of the aryl group is preferably 6 to 25, more preferably 6 to 18, still more preferably 6 to 10, and particularly preferably 6), and an N-aryl-3-carbazolyl group (the number of ring carbon atoms of the aryl group is preferably 6 to 25, more preferably 6 to 18, still more preferably 6 to 10, and particularly preferably 6) are preferred.

m1 is preferably an integer of 0 to 2, and more preferably 0 or 1, and it may be either 0 or 1. m2 is preferably an integer of 0 to 2, and more preferably 0 or 1, and it may be either 0 or 1.

In the case where plural $R^{a1}$'s or plural $R^{a1}$'s are present, plural $R^{a1}$'s or plural $R^{b1}$'s are the same as or different from each other and are optionally bonded to each other to form a ring, and a compound which does not form a ring is also preferred. Examples of the formed ring include a partially unsaturated hydrocarbon ring and an aromatic ring. As the aromatic ring, an aromatic ring having 6 to 10 ring carbon atoms is preferred, and a benzene ring is more preferred. Examples of the compound in which the plurality of $R^{a1}$'s and the plurality of $R^{a1}$'s are bonded to each other to form a ring include the following compounds.

[Chem. 9]
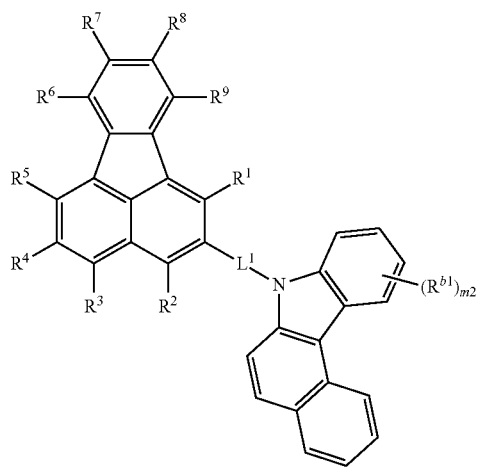
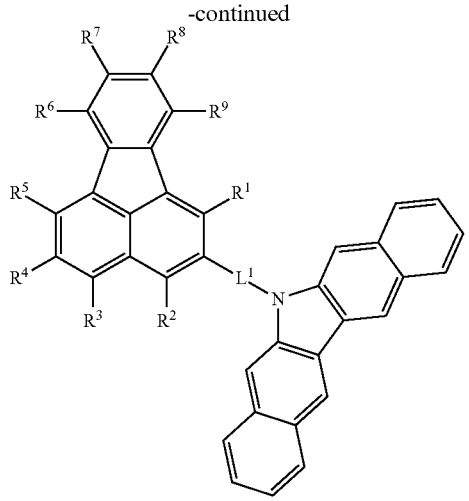
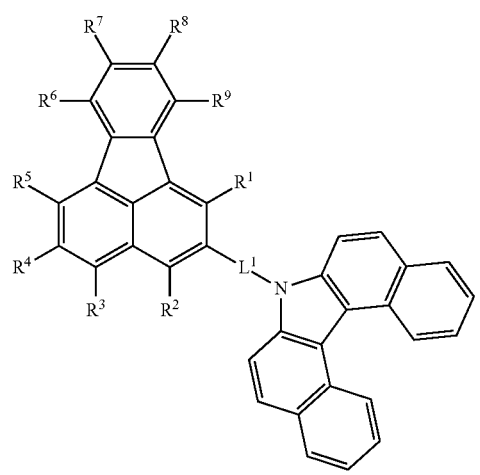
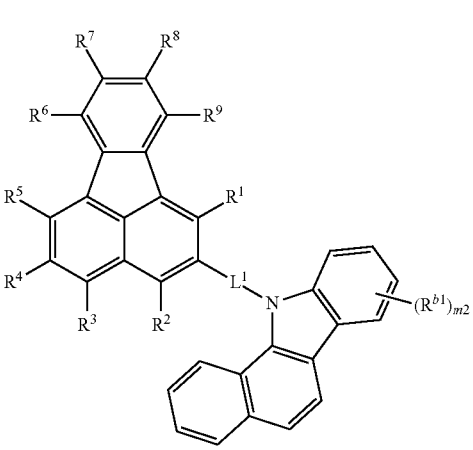
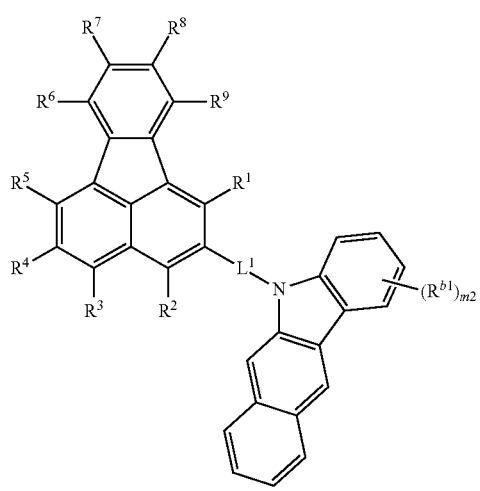
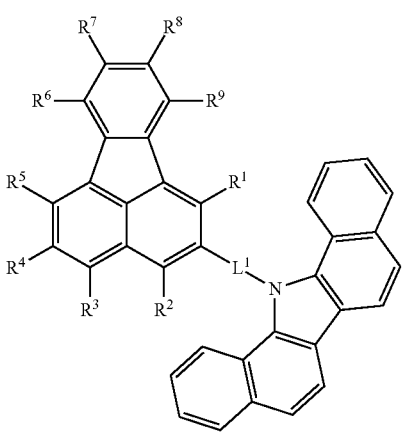

-continued

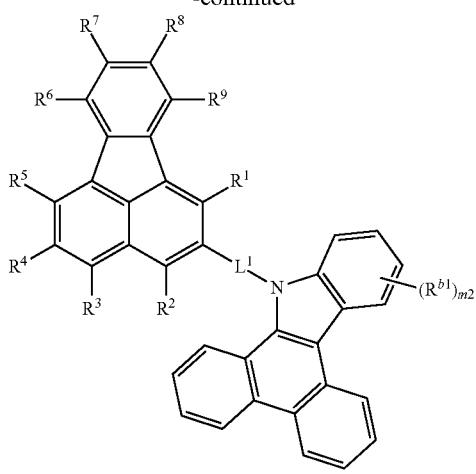

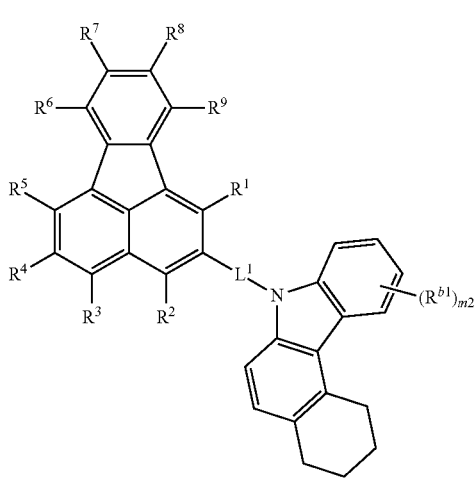

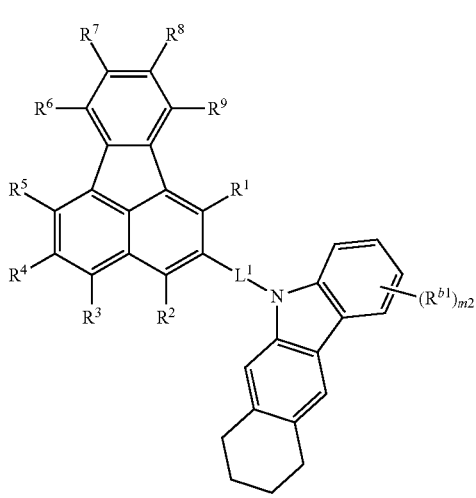

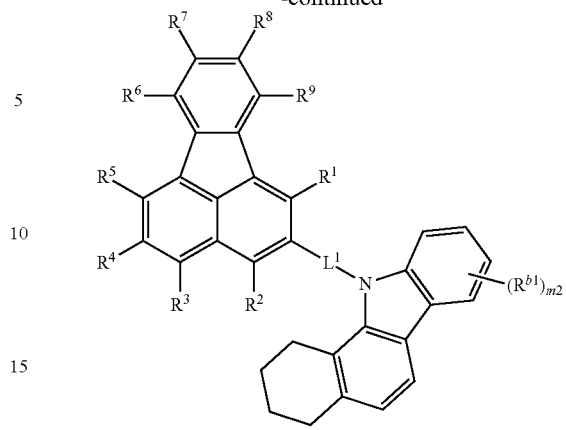

(The definitions of the respective groups in the formulae are the same as those in the general formula (2).)

From the viewpoint of emission efficiency, one preferred embodiment of the compound (2) includes a compound represented by the following general formula (2-1).

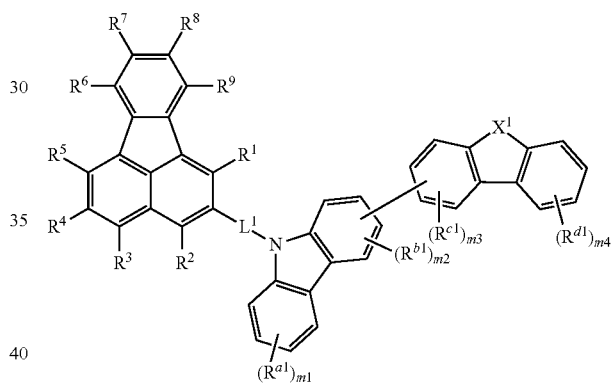

(2-1)

In the general formula (2-1), $R^1$ to $R^9$, and $L^1$ are the same as those described above in the general formula (1). $R^{a1}$, $R^{b1}$, m1, and m2 are the same as those described above in the general formula (2).

$R^{c1}$ and $R^{d1}$ each independently represent a substituent. m3 represents an integer of 0 to 3. m4 represents an integer of 0 to 4. In the case where plural $R^{c1}$'s or plural $R^{d1}$'s are present, plural $R^{c1}$'s or plural $R^{d1}$'s are the same as or different from each other and are optionally bonded to each other to form a ring.

$X^1$ represents —N($R^{A1}$)—, —C($R^{B1}$)($R^{C1}$)—, an oxygen atom, or a sulfur atom. $R^{A1}$ represents a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, or a substituted or unsubstituted fluoroalkyl group having 1 to 20 carbon atoms. $R^{B1}$ and $R^{C1}$ each independently represent a hydrogen atom, a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a substituted or unsubstituted fluoroalkyl group having 1 to 20 carbon atoms, or a cyano group, or may be bonded to form a ring structure.

In the present invention, a compound in which $X^1$ is —N($R^{A1}$)—, a compound in which $X^1$ is —C($R^{B1}$)($R^{C1}$)—, a compound in which $X^1$ is an oxygen atom, and a compound in which $X^1$ is a sulfur atom are each also preferable.

Examples of the alkyl group having 1 to 20 carbon atoms represented by $R^{A1}$ include a methyl group, an ethyl group, an n-propyl group, an isopropyl group, an n-butyl group, an isobutyl group, an s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups). The alkyl group is preferably an alkyl group having 1 to 10 carbon atoms, more preferably an alkyl group having 1 to 8 carbon atoms, still more preferably an alkyl group having 1 to 5 carbon atoms, and particularly preferably an alkyl group having 1 to 3 carbon atoms.

Examples of the aryl group having 6 to 50 ring carbon atoms represented by $R^{A1}$ include the same as the aryl groups of Ar in the general formula (1). Among these, an aryl group having 6 to 30 ring carbon atoms is preferred, an aryl group having 6 to 20 ring carbon atoms is more preferred, an aryl group having 6 to 13 ring carbon atoms is still more preferred, a phenyl group, a biphenylyl group (a 3-biphenylyl group, a 4-biphenylyl group, and the like), a naphthyl group, and a 9,9-dimethylfluorenyl group are particularly preferred, and a phenyl group and a biphenylyl group (a 3-biphenylyl group, a 4-biphenylyl group, and the like) are the most preferred.

Examples of the heteroaryl group having 5 to 50 ring atoms represented by $R^{A1}$ include the same those as the heteroaryl group of Ar in the general formula (1). Among these, a heteroaryl group having 5 to 30 ring atoms is preferred, a heteroaryl group having 5 to 20 ring atoms is more preferred, a heteroaryl group having 5 to 13 ring atoms is still more preferred, and a dibenzofuranyl group and a dibenzothiophenyl group are particularly preferred.

Examples of the fluoroalkyl group having 1 to 20 carbon atoms, represented by $R^{A1}$, include the fluoroalkyl group having 1 to 20 carbon atoms among the fluoroalkyl groups in the description of the substituent.

Among these, $R^{A1}$ is preferably a substituted or unsubstituted aryl group having 6 to 50 ring carbon atoms, or a substituted or unsubstituted heteroaryl group having 5 to 50 ring atoms, more preferably a biphenylyl group (for example, a 3-biphenylyl group and a 4-biphenylyl group), more preferably a phenyl group or a 3-biphenylyl group, and still more preferably a phenyl group.

The alkyl group having 1 to 20 carbon atoms, the aryl group having 6 to 50 ring carbon atoms, the heteroaryl group having 5 to 50 ring atoms, the fluoroalkyl group having 1 to 20 carbon atoms, and the cyano group, represented by $R^{B1}$ and $R^{C1}$, are described in the same manner as $R^{A1}$, but in particular, as the alkyl group, a methyl group is preferred, and as the aryl group, a phenyl group is preferred. $R^{B1}$ and the $R^{C1}$ are both preferably an alkyl group having 1 to 20 carbon atoms or an aryl group having 6 to 50 ring carbon atoms.

Furthermore, in the case of forming a ring structure by the mutual bonding of $R^{B1}$ and $R^{C1}$ of —C($R^{B1}$)($R^{C1}$)— include the following ring structures.

[Chem. 11]

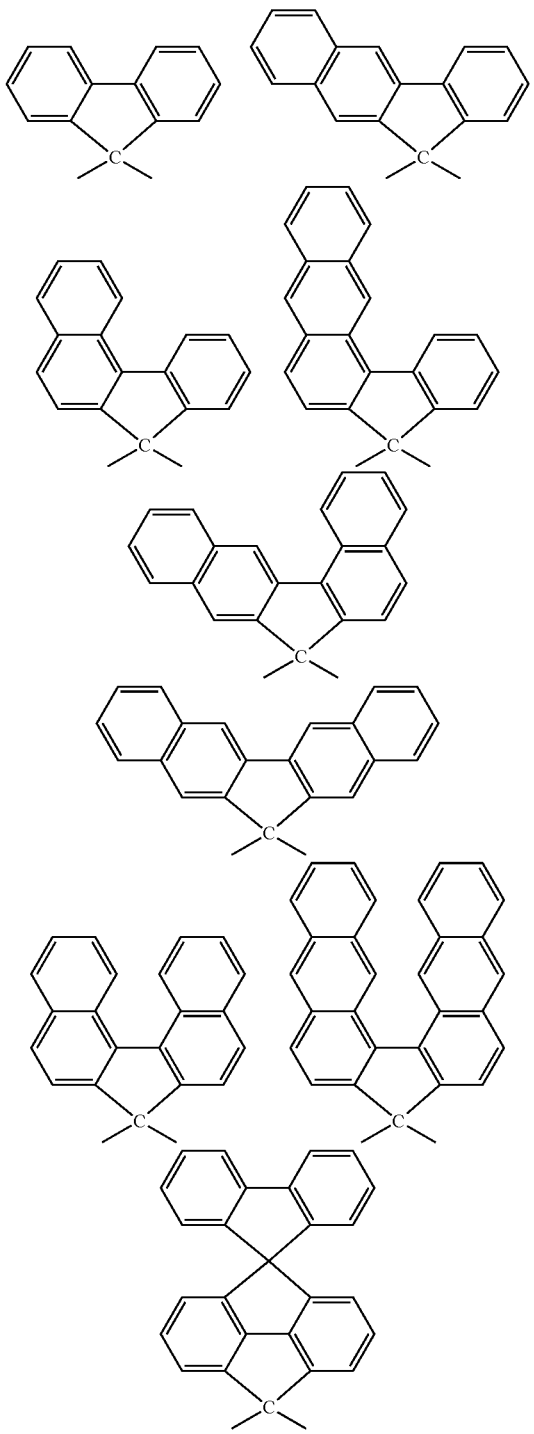

The substituents represented by $R^{c1}$ and $R^{d1}$ are as defined above, and preferred examples thereof are also the same. Among these, particularly preferred examples of the substituent include the same ones as in the case of $R^{a1}$ and $R^{b1}$.

m3 is preferably an integer of 0 to 2, more preferably 0 or 1, and still more preferably 0. m4 is preferably an integer of 0 to 2, more preferably 0 or 1, and still more preferably 0.

In the case where plural $R^{c1}$'s or plural $R^{d1}$'s are present, plural $R^{c1}$'s or plural $R^{d1}$'s are the same as or different from each other and are optionally bonded to each other to form a ring, and a compound which does not form a ring is also preferred. Examples of the formed ring include a partially unsaturated hydrocarbon ring and an aromatic ring. As the aromatic ring, an aromatic ring having 6 to 10 ring carbon atoms is preferred, and a benzene ring is more preferred. Further, it is preferable that the plurality of $R^{c1}$'s are not bonded to each other to form a ring. Examples of the compound in which the plurality of $R^{d1}$'s are bonded to each other to form a ring include the following compounds.

[Chem. 12]

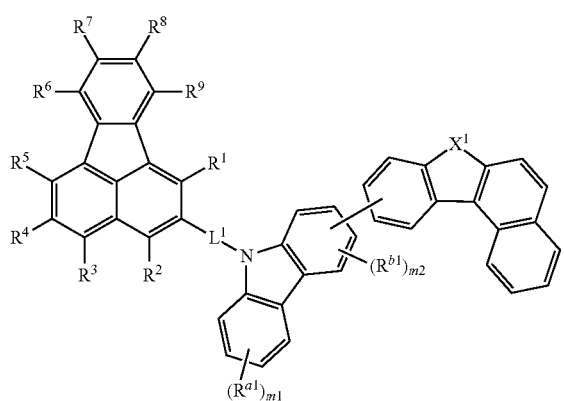

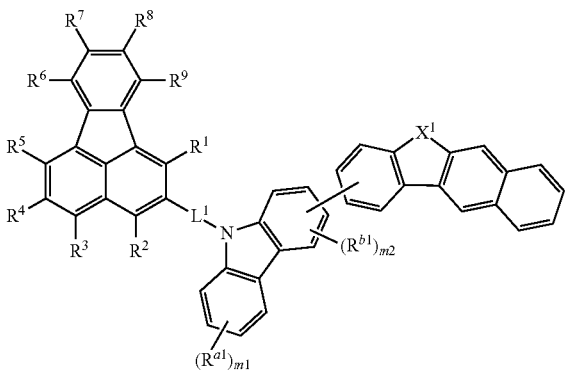

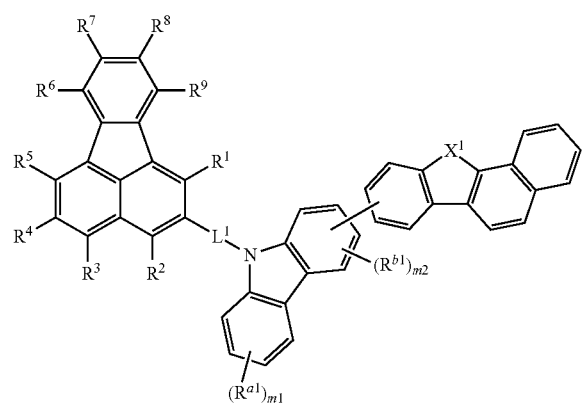

[Chem. 13]

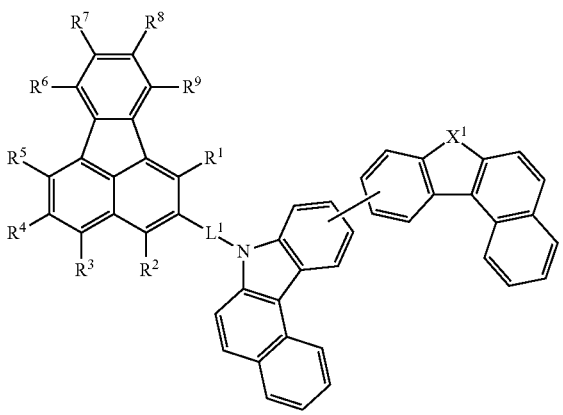

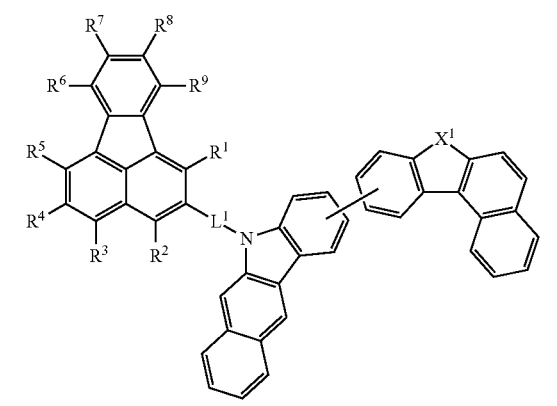

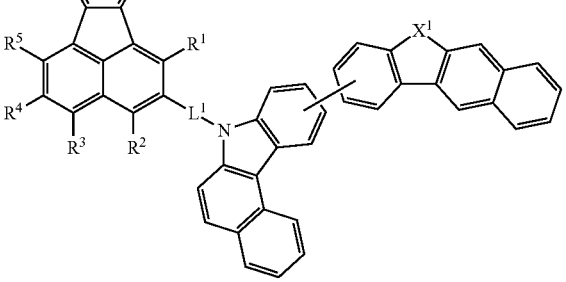

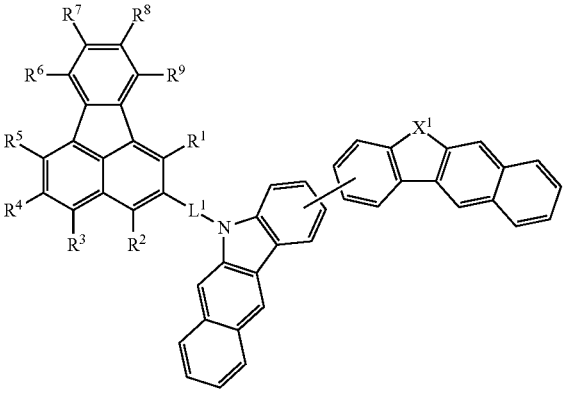

(The definitions of the respective groups in the formulae are the same as those in the general formula (2-1), and preferred examples are also the same.)

-continued

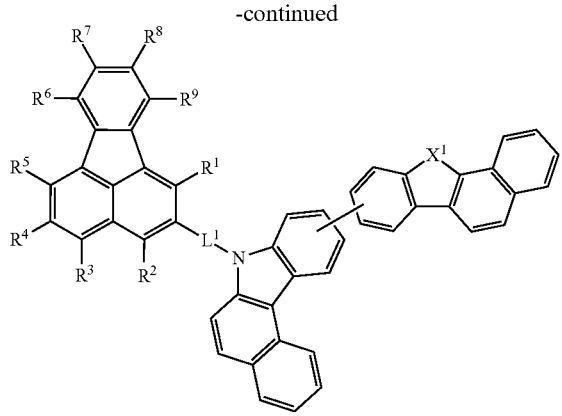

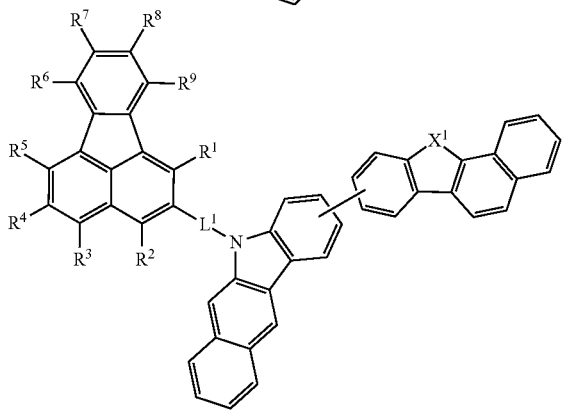

(The definitions of the respective groups in the formulae are the same as those in the general formula (2-1), and preferred examples are also the same.)

[Chem. 14]

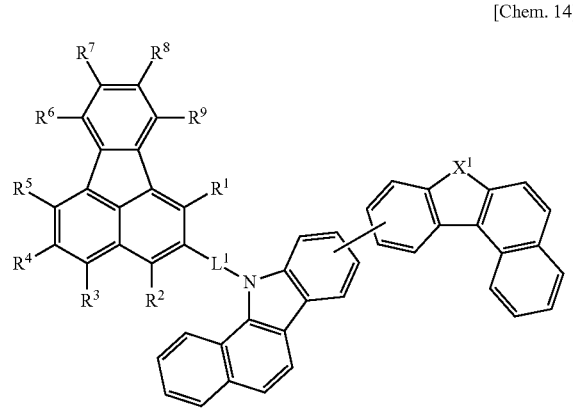

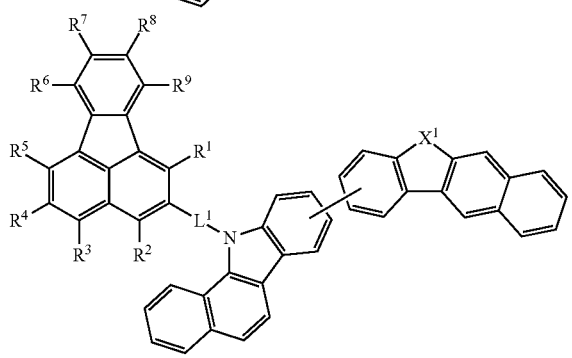

-continued

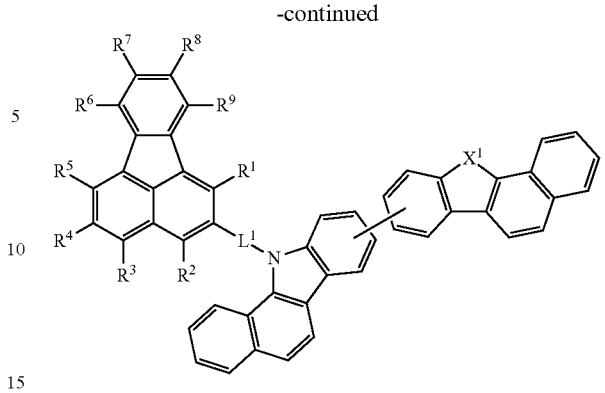

(The definitions of the respective groups in the formulae are the same as those in the general formula (2-1), and preferred examples are also the same.)

From the viewpoint of emission efficiency, one preferred embodiment of the compound (2-1) includes a compound represented by any one of the following general formulae (2-1-1) to (2-1-3).

(2-1-1)

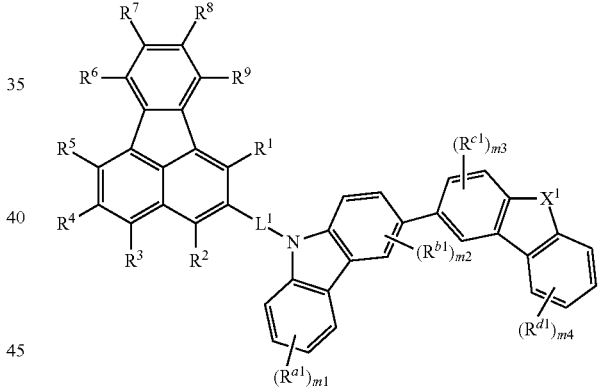

(2-1-2)

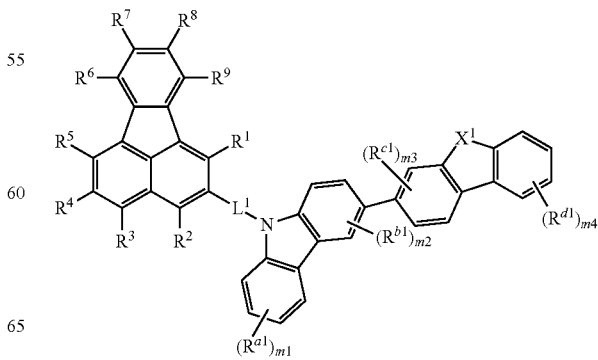

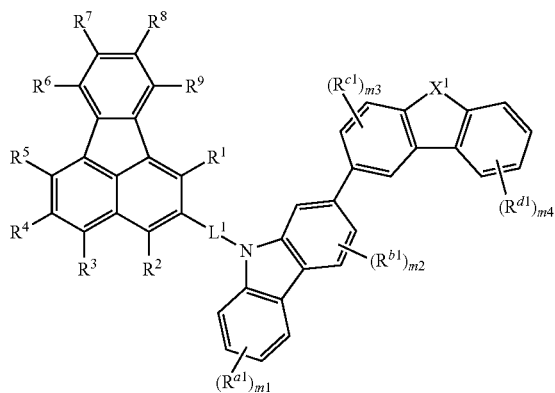

(2-1-3)

In the general formulae (2-1-1) to (2-1-3), $R^1$ to $R^9$ and $L^1$ are the same as those in the general formula (1), and preferred examples are also the same. $R^{a1}$, $R^{b1}$, m1, and m2 are the same as those in the general formula (2), and preferred examples are also the same. $R^{c1}$, $R^{d1}$, m3, m4, and $X^1$ are the same as those in the general formula (2-1), and preferred examples are also the same.

From the viewpoint of emission efficiency, one preferred embodiment of the compound (2) includes a compound represented by the following general formula (2-2)

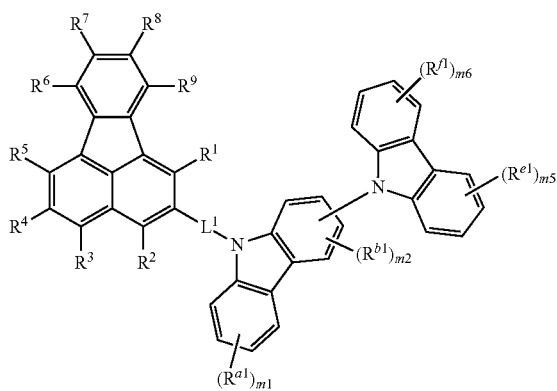

(2-2)

In the general formula (2-2), $R^1$ to $R^9$ and $L^1$ are the same as those in the general formula (1), and preferred examples are also the same. $R^{a1}$, $R^{b1}$, m1, and m2 are the same as those in the general formula (2), and preferred examples are also the same.

$R^{e1}$ and $R^{f1}$ each independently represent a substituent. m5 and m6 each independently represent an integer of 0 to 4. In the case where plural $R^{e1}$'s or plural $R^{f1}$'s are present, plural $R^{1e1}$'s or plural $R^{f1}$'s are the same as or different from each other and are optionally bonded to each other to form a ring.

The substituents represented by $R^{c1}$ and $R^{f1}$ are as defined above, and preferred examples thereof are also the same. Among these, particularly preferred examples of the substituent include the same ones as in the case of $R^{a1}$ and $R^{b1}$, and in addition, a substituted or unsubstituted heteroaryl group having 5 to 13 ring atoms (for example, a carbazolyl group and the like).

m5 is preferably an integer of 0 to 2, more preferably 0 or 1, and still more preferably 0. m6 is preferably an integer of 0 to 2, more preferably 0 or 1, and still more preferably 0.

In the case where plural $R^{e1}$'s or plural Re's are present, plural $R^{e1}$'s or plural $R^{f1}$'s are the same as or different from each other and are bonded to each other to form a ring, and a compound which does not form a ring is also preferred. Examples of the formed ring include a partially unsaturated hydrocarbon ring and an aromatic ring. As the aromatic ring, an aromatic ring having 6 to 10 ring carbon atoms is preferred, and a benzene ring is more preferred. Examples of the compound in which the plurality of Rees and the plurality of Re's are bonded to each other to form a ring include the following compounds, from which any one can also be selected.

[Chem. 17]

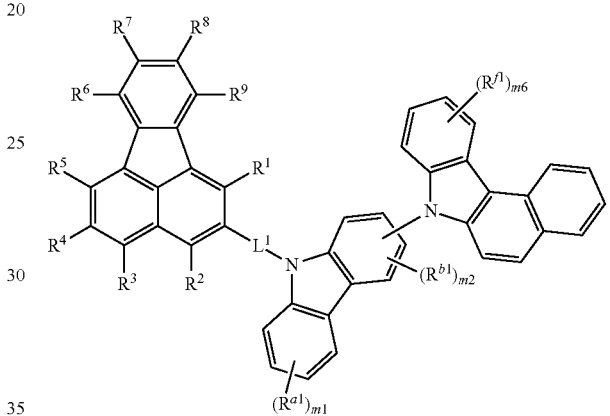

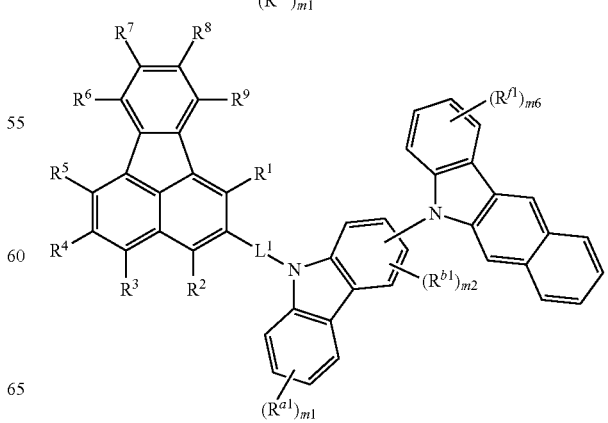

-continued

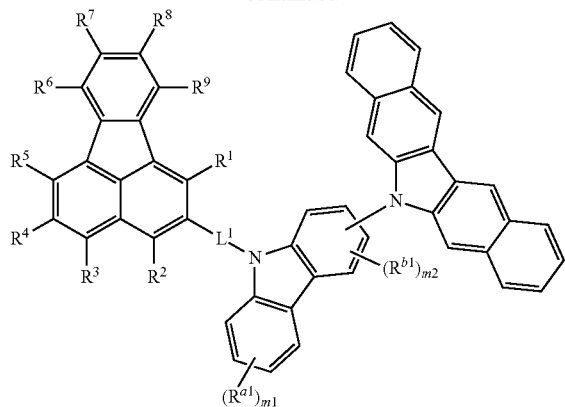

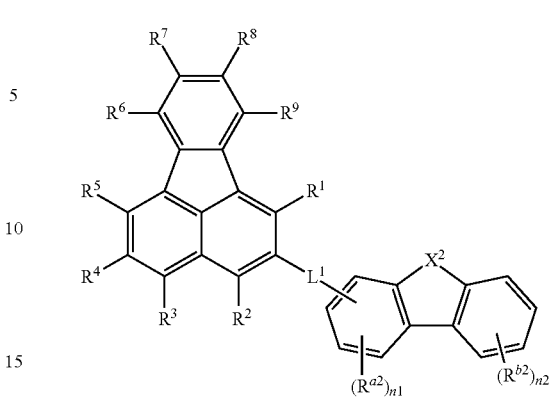

(3)

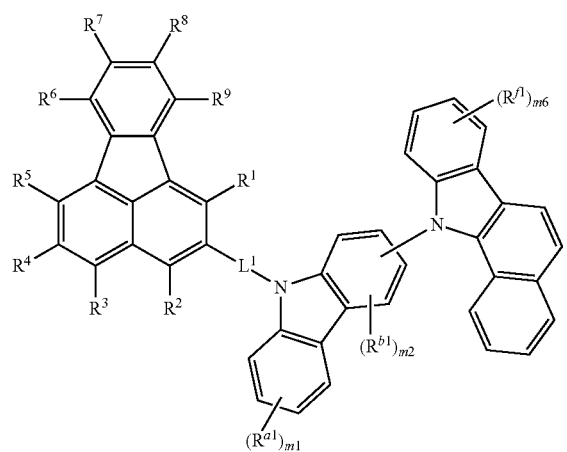

In the general formula (3), $R^1$ to $R^9$, and $L^1$ are the same as those described above in the general formula (1), and preferred examples are also the same.

$X^2$ represents $-N(R^{A2})-$, $-C(R^{B2})(R^{C2})-$, an oxygen atom, or a sulfur atom. $R^{A2}$ represents a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, or a substituted or unsubstituted fluoroalkyl group having 1 to 20 carbon atoms. $R^{B2}$ and $R^{C2}$ each independently represent a hydrogen atom, a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a substituted or unsubstituted fluoroalkyl group having 1 to 20 carbon atoms, or a cyano group, or may be bonded to form a ring structure.

$R^{a2}$ and $R^{b2}$ each independently represent a substituent. n1 and n2 each independently represents an integer of 0 to 3. In the case where plural $R^{a2}$'s or plural $R^{b2}$'s are present, plural $R^{a2}$'s or plural $R^{b2}$'s are the same as or different from each other and are optionally bonded to each other to form a ring, and in this case, may be bonded to $L^1$ via the ring.

In the present invention, a compound in which $X^2$ is $-N(R^{A2})-$, a compound in which $X^2$ is $-C(R^{B2})(R^{C2})-$, a compound in which $X^2$ is an oxygen atom, and a compound in which $X^2$ is a sulfur atom are each also preferable.

$R^{A2}$ is the same as described above as $R^{A1}$ (refer to the descriptions with regard to $X^1$ in the general formula (2-1)). $R^{B2}$ and $R^{C2}$ are each the same as described above as $R^{B1}$ and $R^{C1}$ (refer to the descriptions with regard to $X^1$ in the general formula (2-1)).

The substituents represented by $R^{a2}$ and $R^{b2}$ are as defined above, and preferred examples thereof are also the same. Among these, particularly preferred examples of the substituent include the same ones as in the case of $R^{a1}$ and $R^{b1}$.

n1 is preferably an integer of 0 to 2, more preferably 0 or 1, and still more preferably 0. n2 is preferably an integer of 0 to 2, more preferably 0 or 1, and still more preferably 0.

In the case where plural $R^{a2}$'s or plural $R^{b2}$'s are present, plural $R^{a2}$'s or plural $R^{b2}$'s are the same as or different from each other and are optionally bonded to each other to form a ring, and a compound which does not form a ring is also preferred. Examples of the formed ring include a partially unsaturated hydrocarbon ring and an aromatic ring. As the aromatic ring, an aromatic ring having 6 to 10 ring carbon atoms is preferred, and a benzene ring is more preferred. Examples of the compound in which the plurality of $R^{a2}$'s and the plurality of $R^{b2}$'s are bonded to each other to form a ring include the following compounds.

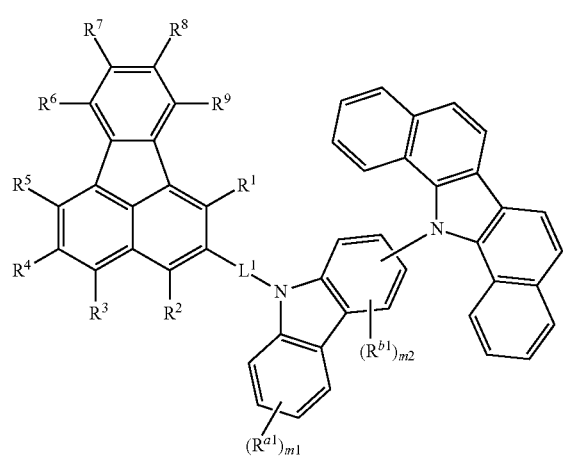

(The definitions of the respective groups in the formulae are the same as those in the general formula (2-2), and preferred examples are also the same.)

From the viewpoint of emission efficiency, one preferred embodiment of the compound (1) includes a compound represented by the following general formula (3).

[Chem. 19]

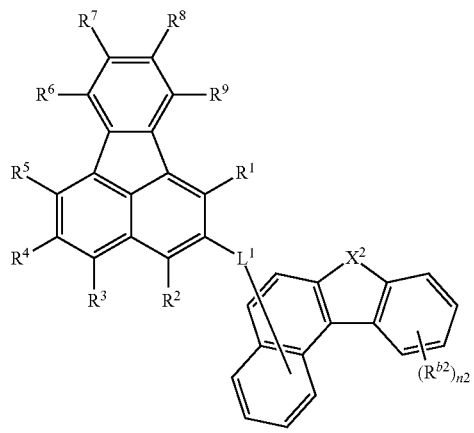

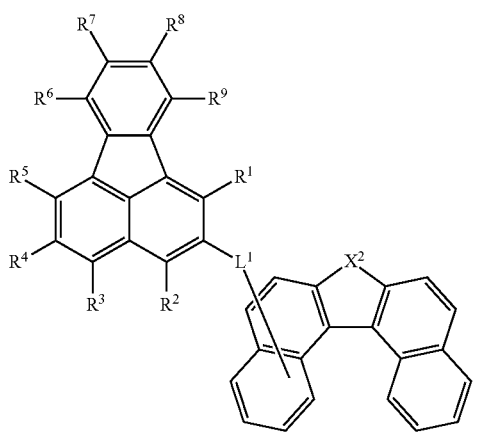

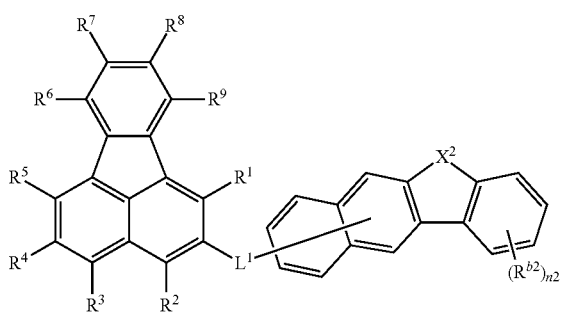

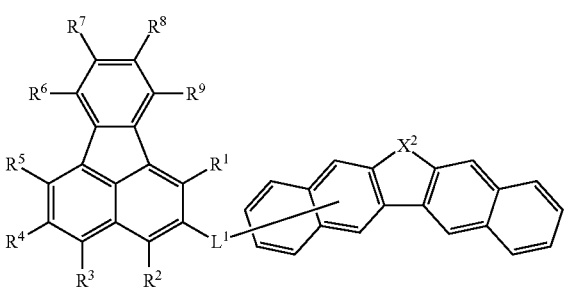

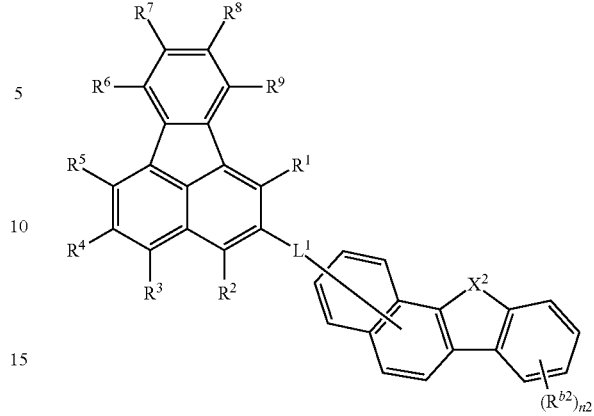

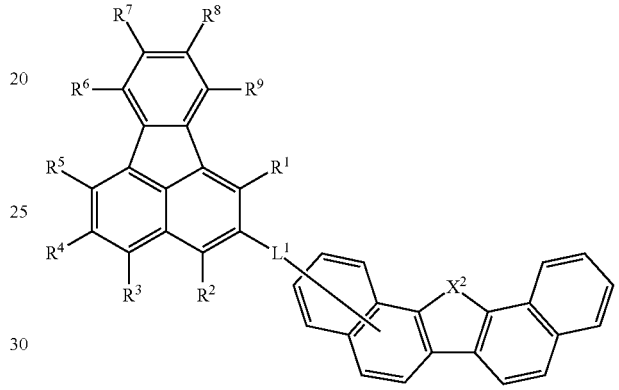

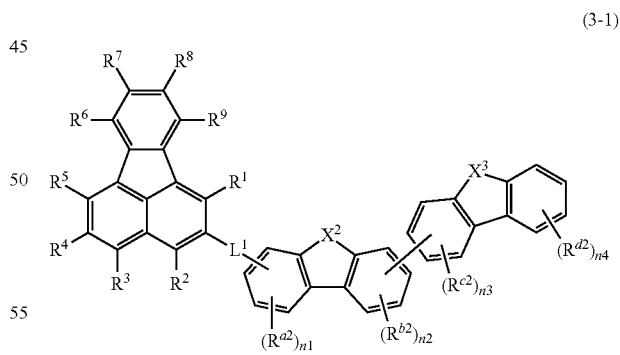

(The definitions of the respective groups in the formulae are the same as those in the general formula (3), and preferred examples are also the same. Further, in the formulae, L' represents a bonding at an arbitrary position of the naphthalene ring.)

From the viewpoint of emission efficiency, one preferred embodiment of the compound (3) includes a compound represented by the following general formula (3-1).

(3-1)

In the general formula (3-1), $R^1$ to $R^9$, and $L^1$ are the same as those described above in the general formula (1), and preferred examples are also the same. $R^{a2}$, $R^{b2}$, $X^2$, n1, and n2 are the same as those in the general formula (3), and preferred examples are also the same.

$X^3$ represents —N($R^{A3}$)—, —C($R^{B3}$)($R^{C3}$)—, an oxygen atom, or a sulfur atom. $R^{A3}$ represents a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, or a substituted or unsubstituted fluoroalkyl group having 1 to 20 carbon atoms. $R^{B3}$ and $R^{C3}$ each independently represent a hydrogen atom, a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a substituted or unsubstituted fluoroalkyl group having 1 to 20 carbon atoms, or a cyano group, or may be bonded to form a ring structure.

$R^{c2}$ and $R^{d2}$ each independently represent a substituent. n3 represents an integer of 0 to 3. n4 represents an integer of 0 to 4. In the case where plural $R^{c2}$'s or plural $R^{d2}$'s are present, plural $R^{c2}$'s or plural $R^{d2}$'s are the same as or different from each other and are optionally bonded to each other to form a ring.

In the present invention, a compound in which $X^3$ is —N($R^{A3}$)—, a compound in which $X^3$ is —C($R^{B3}$)($R^{C3}$)—, a compound in which $X^3$ is an oxygen atom, and a compound in which $X^3$ is a sulfur atom are each also preferable.

$R^{A3}$ is the same as described above as $R^{A1}$ (refer to the descriptions with regard to $X^1$ in the general formula (2-1)). $R^{B3}$ and $R^{C3}$ are each the same as described above as $R^{B1}$ and $R^{C1}$ (refer to the descriptions with regard to $X^1$ in the general formula (2-1)).

The substituents represented by $R^{c2}$ and $R^{d2}$ are as defined above, and preferred examples thereof are also the same. Among these, particularly preferred examples of the substituent include the same ones as in the case of $R^{a1}$ and $R^{b1}$.

n3 is preferably an integer of 0 to 2, more preferably 0 or 1, and still more preferably 0. n4 is preferably an integer of 0 to 2, more preferably 0 or 1, and still more preferably 0.

In the case where plural $R^{c2}$'s or plural $R^{d2}$'s are present, plural $R^{c2}$'s or plural $R^{d2}$'s are the same as or different from each other and are optionally bonded to each other to form a ring, and a compound which does not form a ring is also preferred. Examples of the formed ring include a partially unsaturated hydrocarbon ring and an aromatic ring. As the aromatic ring, an aromatic ring having 6 to 10 ring carbon atoms is preferred, and a benzene ring is more preferred. Further, it is preferable that the plurality of $R^{c2}$'s are not bonded to each other to form a ring. Examples of the compound in which the plurality of $R^{d2}$'s are bonded to each other to form a ring include the following compounds.

[Chem. 21]

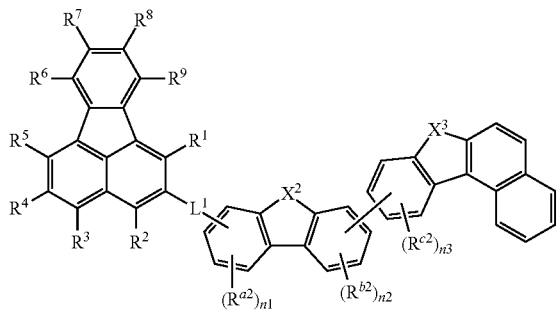

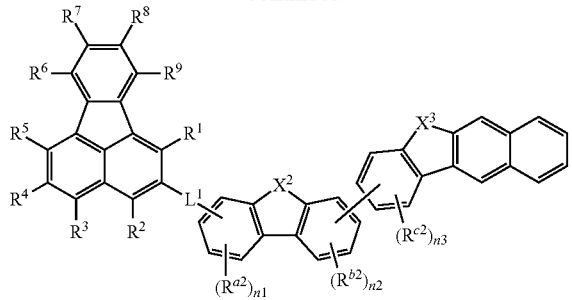

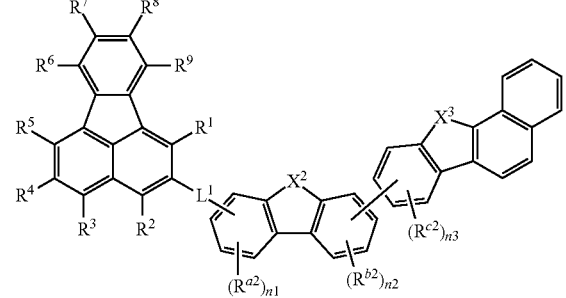

(The definitions of the respective groups in the formulae are the same as those in the general formula (3-1), and preferred examples are also the same.)

From the viewpoint of emission efficiency, one preferred embodiment of the compound (3) includes a compound represented by the following general formula (3-2).

(3-2)

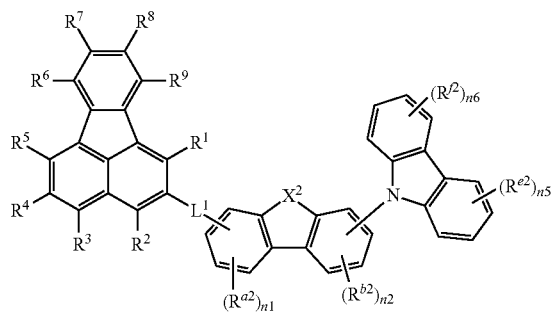

In the general formula (3-2), $R^1$ to $R^9$ and $L^1$ are the same as those in the general formula (1), and preferred examples are also the same. $R^{a2}$, $R^{b2}$, $X^2$, n1, and n2 are the same as those in the general formula (3), and preferred examples are also the same.

$R^{c2}$ and $R^{f2}$ each independently represent a substituent. n5 and n6 each independently represent an integer of 0 to 4. In the case where plural $R^{c2}$'s or plural $R^{f2}$'s are present, plural $R^{c2}$'s or plural $R^{f2}$'s are the same as or different from each other and are optionally bonded to each other to form a ring.

The substituents represented by $R^{c2}$ and $R^{f2}$ are as defined above, and preferred examples thereof are also the same. Among these, particularly preferred examples of the substituent include the same ones as in the case of $R^{a1}$ and $R^{b1}$.

n5 is preferably an integer of 0 to 2, more preferably 0 or 1, and still more preferably 0. n6 is preferably an integer of 0 to 2, more preferably 0 or 1, and still more preferably 0.

In the case where plural $R^{e2}$'s or plural $R^{f2}$'s are present, plural $R^{e2}$'s or plural $R^{f2}$'s are the same as or different from each other and are optionally bonded to each other to form a ring, and a compound which does not form a ring is also preferred. Examples of the formed ring include a partially unsaturated hydrocarbon ring and an aromatic ring. As the aromatic ring, an aromatic ring having 6 to 10 ring carbon atoms is preferred, and a benzene ring is more preferred. Examples of the compound in which the plurality of $R^{e2}$'s and the plurality of $R^{f2}$'s are bonded to each other to form a ring include the following compounds.

[Chem. 23]

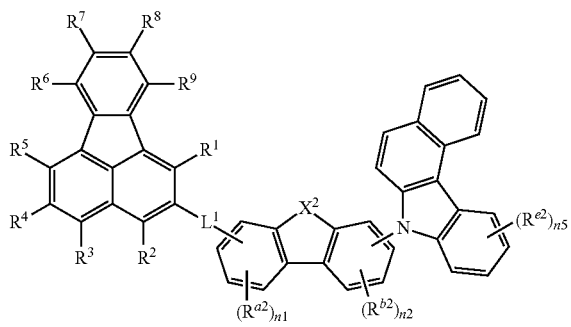

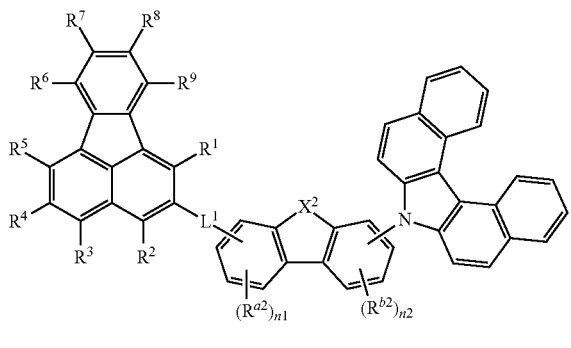

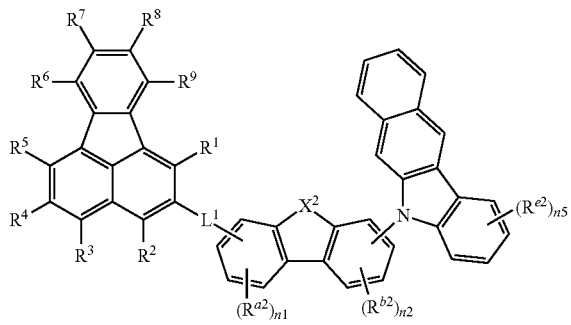

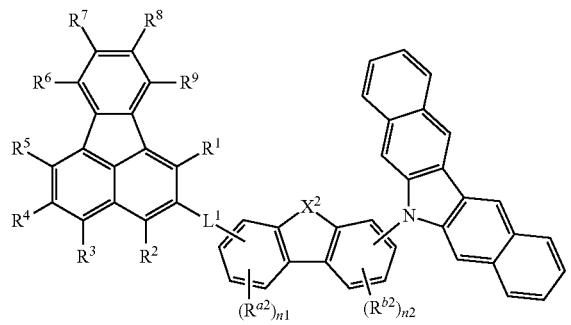

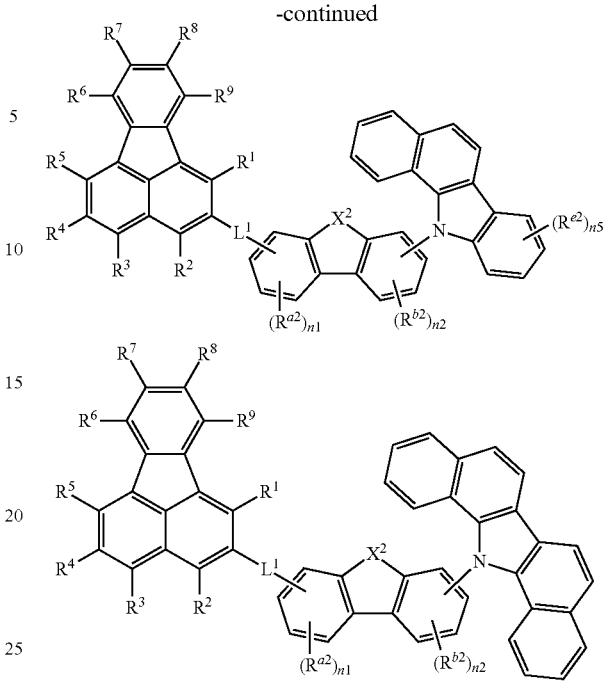

(The definitions of the respective groups in the formulae are the same as those in the general formula (3-2).)

From the viewpoint of emission efficiency, one preferred embodiment of the compound (1) includes a compound represented by the following general formula (4).

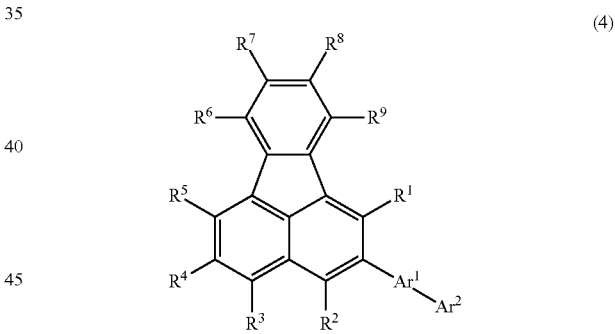

(4)

In the general formula (4), $R^1$ to $R^9$ are the same as those in the general formula (1).

$Ar^1$ represents a substituted or unsubstituted arylene group, $Ar^2$ represents a substituted or unsubstituted aryl group, and the total number of ring carbon atoms of the arylene group of $Ar^1$ and the aryl group of $Ar^2$ is 12 to 50.

The total number of ring carbon atoms of the arylene group of $Ar^1$ and the aryl group of $Ar^2$ is not particularly limited as long as it is from 12 to 50 (preferably from 12 to 40, more preferably from 12 to 30, and still more preferably from 12 to 20), but $Ar^1$ is preferably an arylene group having 6 to 18 ring carbon atoms. Further, $Ar^2$ is preferably an aryl group having 6 to 40 ring carbon atoms, more preferably an aryl group having 6 to 30 ring carbon atoms, and still more preferably an aryl group having 6 to 20 ring carbon atoms.

Examples of the arylene group include a phenylene group (a 1,2-phenylene group, a 1,3-phenylene group, and a 1,4-phenylene group), a naphthylene group (a 1,4-naphthylene group, a 1,5-naphthylene group, and the like), a biphenylene group, a fluorenylene group (a 2,7-fluorenylene group and the like), a 9,9-di-substituted fluorenylene group (a 9,9-dimethyl-2,7-fluorenylene group, a 9,9-diphenyl-2,7-fluorenylene group, and the like), a benzofluorenylene group, a dibenzofluorenylene group, a picenylene group, a tetracenylene group, a pentacenylene group, a pyrenylene group, a chrysenylene group, a benzochrysenylene group, an s-indacenylene group, an as-indacenylene group, a triphenylenylene group, a benzotriphenylenylene group, a perylenylene group, a coronylene group, and a dibenzoanthrylene group.

Examples of the aryl group include a phenyl group, a naphthyl group (a 1-naphthyl group and a 2-naphthyl group), an anthryl group (a 1-anthryl group, a 2-anthryl group, and the like), a benzoanthryl group, a phenanthryl group (a 1-phenanthryl group, a 2-phenanthryl group, a 3-phenanthryl group, a 9-phenanthryl group, and the like), a benzophenanthryl group, a fluorenyl group, a 9,9-di-substituted fluorenyl group (a 9,9-dimethyl-2-fluorenyl group, a 9,9-diphenyl-2-fluorenyl group, and the like), a spirobifluorenyl group, a benzofluorenyl group, a dibenzofluorenyl group, a picenyl group, a tetracenyl group, a pentacenyl group, a pyrenyl group, a chrysenyl group, a benzochrysenyl group, an s-indacenyl group, an as-indacenyl group, a triphenylenyl group, a benzotriphenylenyl group, a perylenyl group, a coronyl group, and a dibenzoanthryl group.

Specific examples of the combination of $Ar^1$ and $Ar^2$ include $(Ar^1, Ar^2)$=(a phenylene group, a phenyl group), (a phenylene group, a naphthyl group), (a phenylene group, a phenanthryl group), (a phenylene group, a triphenylenyl group), (a phenylene group, a benzo[c]phenanthryl group), (a phenylene group, a 9,9-dimethylfluorenyl group), (a phenylene group, a 9,9-diphenylfluorenyl group), (a naphthylene group, a phenanthryl group), (a naphthylene group, a benzo[c]phenanthryl group), and (an anthrylene group, a naphthyl group).

From the viewpoint of emission efficiency, one preferred embodiment of the compound (1) includes a compound represented by the following general formula (5).

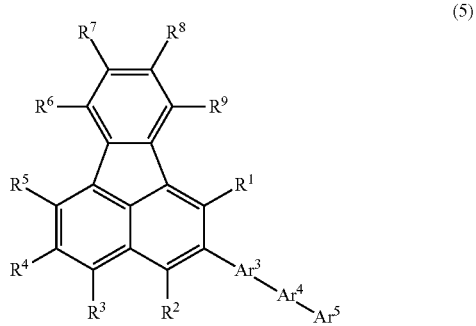

(5)

In the general formula (5), $R^4$ to $R^9$ are the same as those in the general formula (1), and preferred examples are also the same.

$Ar^3$ and $Ar^4$ each independently represent a substituted or unsubstituted arylene group, $Ar^5$ represents a substituted or unsubstituted aryl group, and further, the total numbers of ring carbon atoms of the arylene groups of $Ar^3$ and $Ar^4$, and the aryl group of $Ar^5$ is from 18 to 50.

The arylene groups represented by $Ar^3$ and $Ar^4$, and the aryl group represented by $Ar^5$ are not particularly limited as long as the total number of the ring carbon atoms is from 18 to 50 (preferably from 18 to 40, and more preferably from 18 to 30). $Ar^3$ and $Ar^4$ each are preferably independently an arylene group having 6 to 10 ring carbon atoms. Further, $Ar^5$ is preferably an aryl group having 6 to 40 ring carbon atoms, more preferably an aryl group having 6 to 30 ring carbon atoms, still more preferably an aryl group having 6 to 20 ring carbon atoms, particularly preferably an aryl group having 6 to 14 ring carbon atoms, and most preferably an aryl group having 6 to 10 ring carbon atoms. Specific examples of the arylene group and the aryl group include the same ones as the arylene group represented by $Ar^1$ and the aryl group represented by $Ar^2$.

Specific examples of a combination of $Ar^3$, $Ar^4$, and $Ar^5$ include $(Ar^3, Ar^4, Ar^5)$=(a phenylene group, a phenylene group, a phenyl group), (a phenylene group, an anthrylene group, a naphthyl group), (a phenylene group, a naphthylene group, a phenyl group), (a phenylene group, a phenylene group, a naphthyl group), (a phenylene group, a naphthylene group, a naphthyl group), (a phenylene group, a naphthylene group, a 9,9-dimethylfluorenyl group), (a phenylene group, a naphthylene group, a 9,9-diphenylfluorenyl group), (a phenylene group, a phenylene group, a benzo[c]phenanthryl group), (a phenylene group, a phenylene group, a triphenylenyl group), (a phenylene group, a phenylene group, a 9,9-dimethylfluorenyl group), (a phenylene group, a phenylene group, a 9,9-diphenylfluorenyl group), (a naphthylene group, an anthrylene group, a naphthyl group), (a naphthylene group, a naphthylene group, a naphthyl group), (a naphthylene group, a phenylene group, a phenyl group), (a naphthylene group, a phenylene group, a triphenylyl group), (a naphthylene group, a phenylene group, a phenanthryl group), (a naphthylene group, a phenylene group, a 9,9-dimethylfluorenyl group), (a naphthylene group, a phenylene group, a 9,9-diphenylfluorenyl group), and (an anthrylene group, a phenylene group, a phenyl group).

From the viewpoint of emission efficiency, one preferred embodiment of the compound (1) includes a compound represented by the following general formula (6).

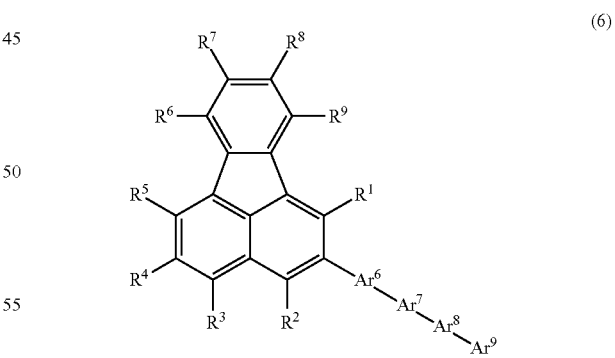

(6)

In the general formula (6), $R^1$ to $R^9$ are the same as those in the general formula (1), and preferred examples are also the same.

$Ar^6$ to $Ar^8$ each independently represent a substituted or unsubstituted arylene group, $Ar^9$ represents a substituted or unsubstituted aryl group, and further, the total number of ring carbon atoms of the arylene groups of $Ar^6$ to $Ar^8$ and the aryl group of $Ar^9$ is 24 to 50.

The arylene groups represented by $Ar^6$ to $Ar^8$, and the aryl group represented by $Ar^9$ are not particularly limited as long as the total number of the ring carbon atoms is from 24 to 50 (preferably from 24 to 40, and more preferably from 24 to 35). $Ar^6$ to Arg each are preferably independently an arylene group having 6 to 14 ring carbon atoms. Further, $Ar^9$ is preferably an aryl group having 6 to 40 ring carbon atoms, more preferably an aryl group having 6 to 30 ring carbon atoms, still more preferably an aryl group having 6 to 20 ring carbon atoms, particularly preferably an aryl group having 6 to 14 ring carbon atoms, and most preferably an aryl group having 6 to 10 ring carbon atoms. Specific examples of the arylene group and the aryl group include the same ones as the arylene group represented by $Ar^1$ and the aryl group represented by $Ar^2$.

Specific examples of a combination of $Ar^6$, $Ar^7$, Arg, and Ara include ($Ar^6$, $Ar^7$, $Ar^8$, $Ar^9$)=(a phenylene group, a phenylene group, a phenylene group, a phenyl group), (a phenylene group, a phenylene group, a naphthylene group, a phenanthryl group), (naphthylene group, an anthrylene group, a phenylene group, a phenyl group), and (a naphthylene group, a phenylene group, a phenylene group, a phenyl group).

From the viewpoint of emission efficiency, as one embodiment of the compound (1), a compound selected from the following group is also preferred.

[Chem. 27]

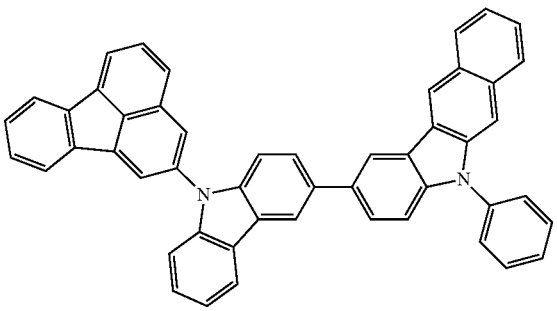

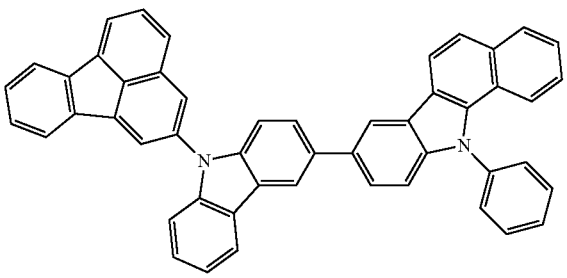

-continued

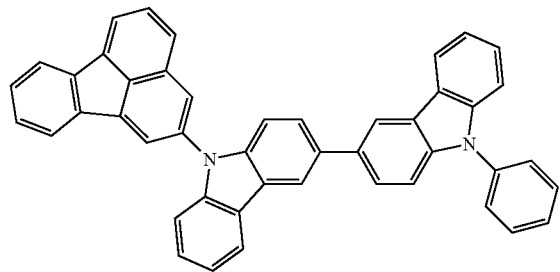

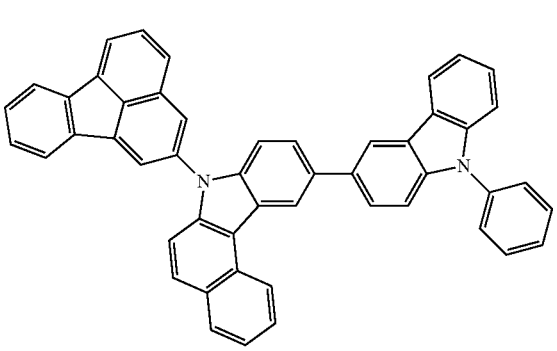

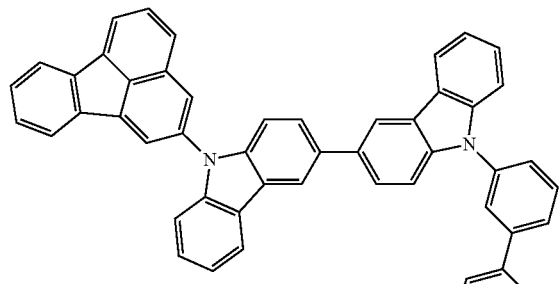

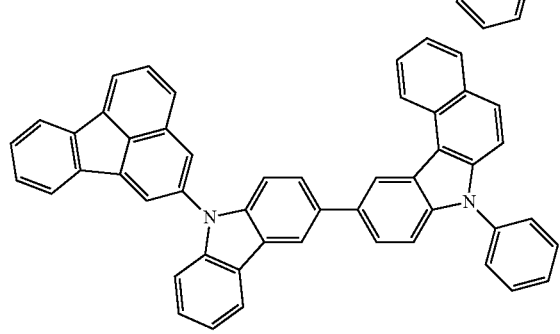

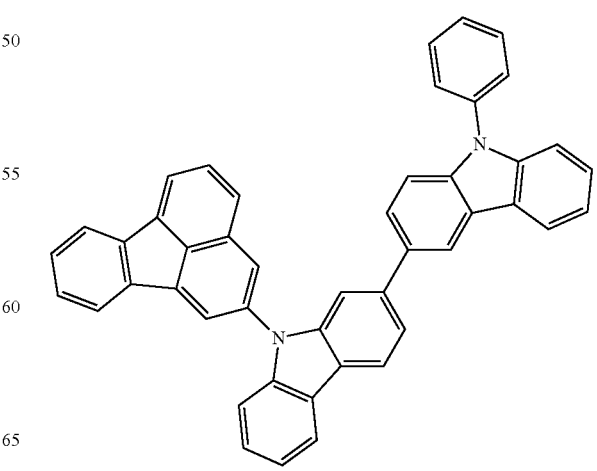

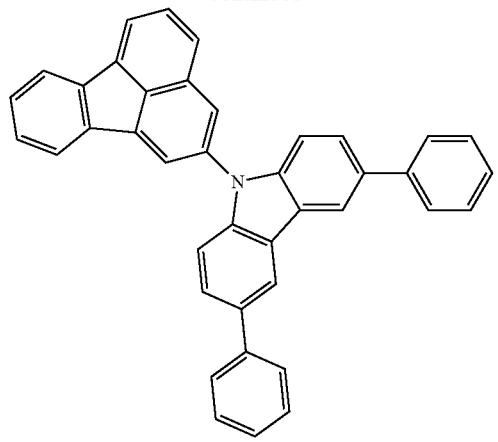
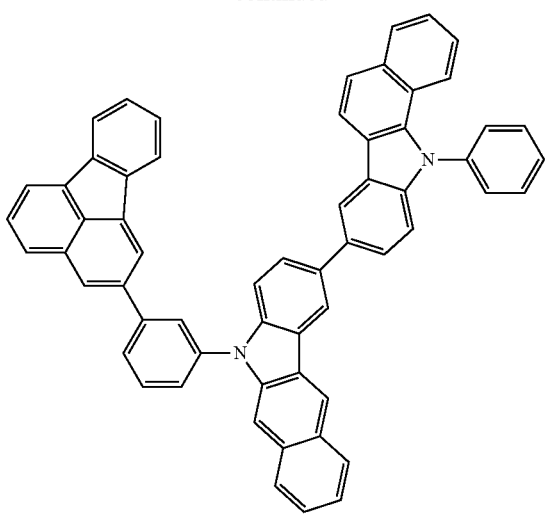
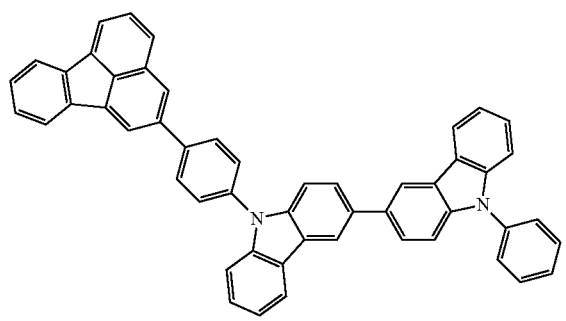
Specific examples of the compound in one embodiment of the present invention are shown below, but are not limited thereto.
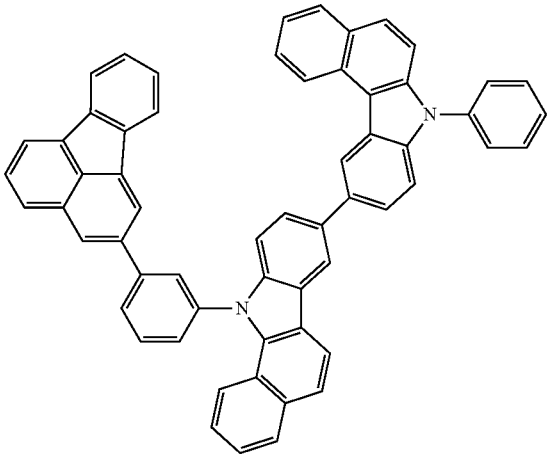
[Chem. 28]
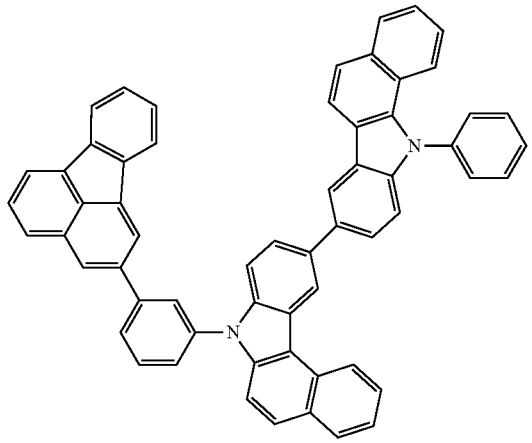
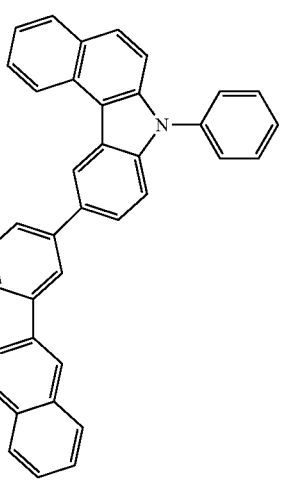

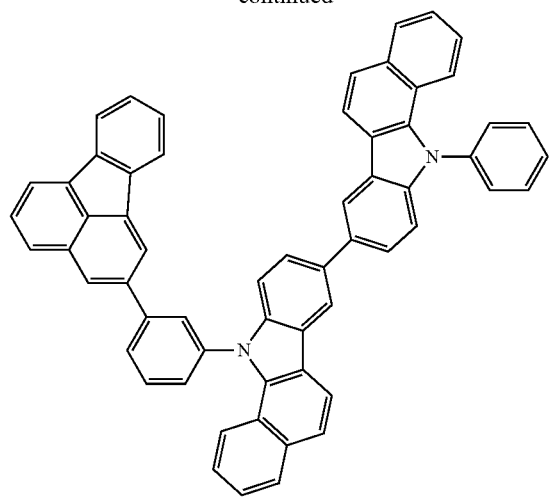
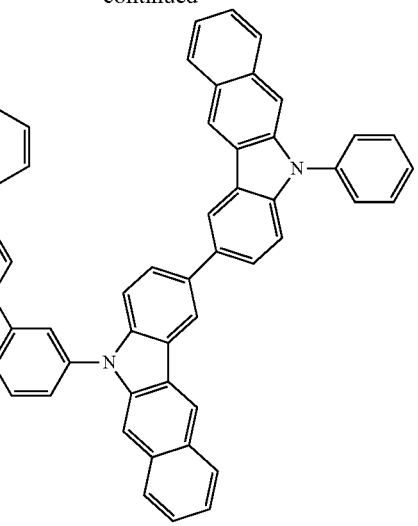
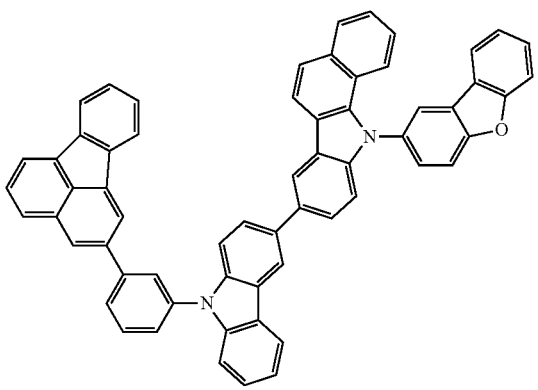
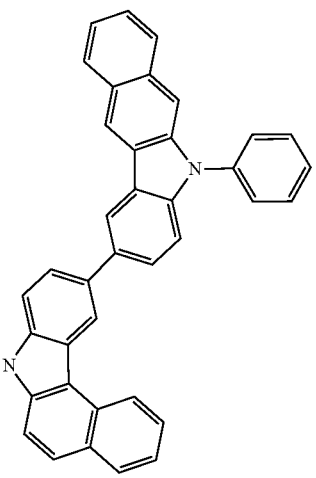
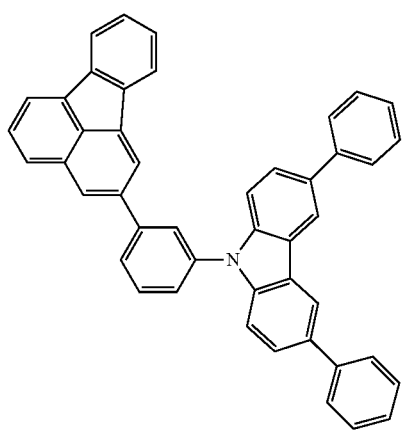
[Chem. 29]

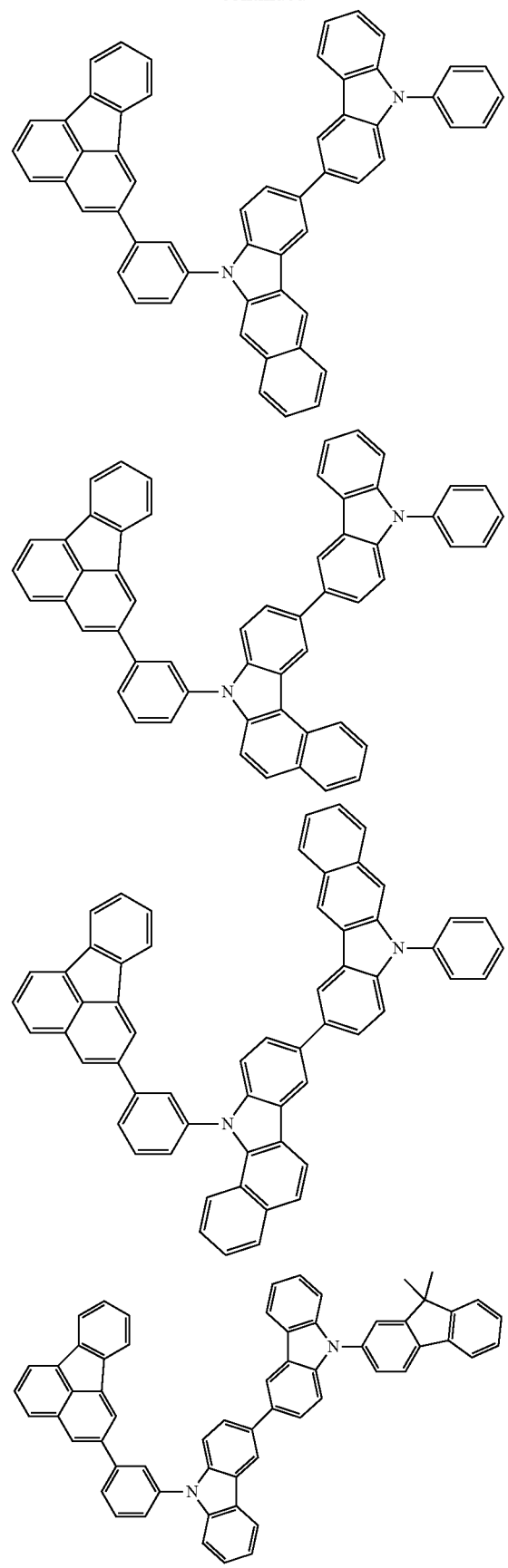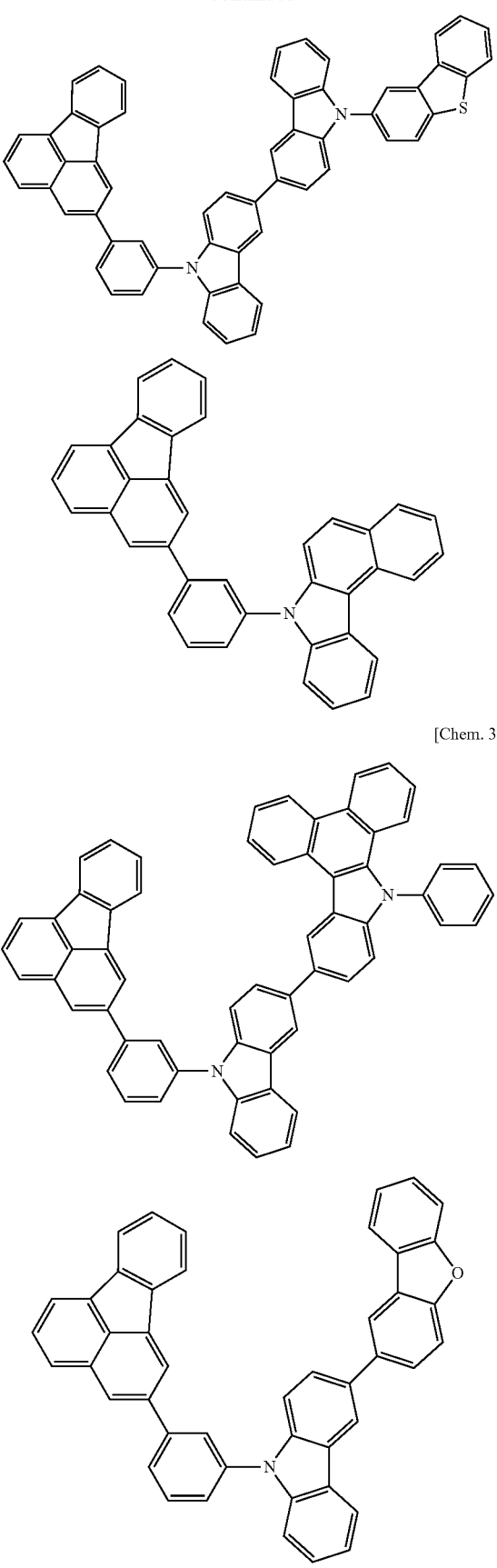
[Chem. 30]

US 10,790,449 B2
45
-continued
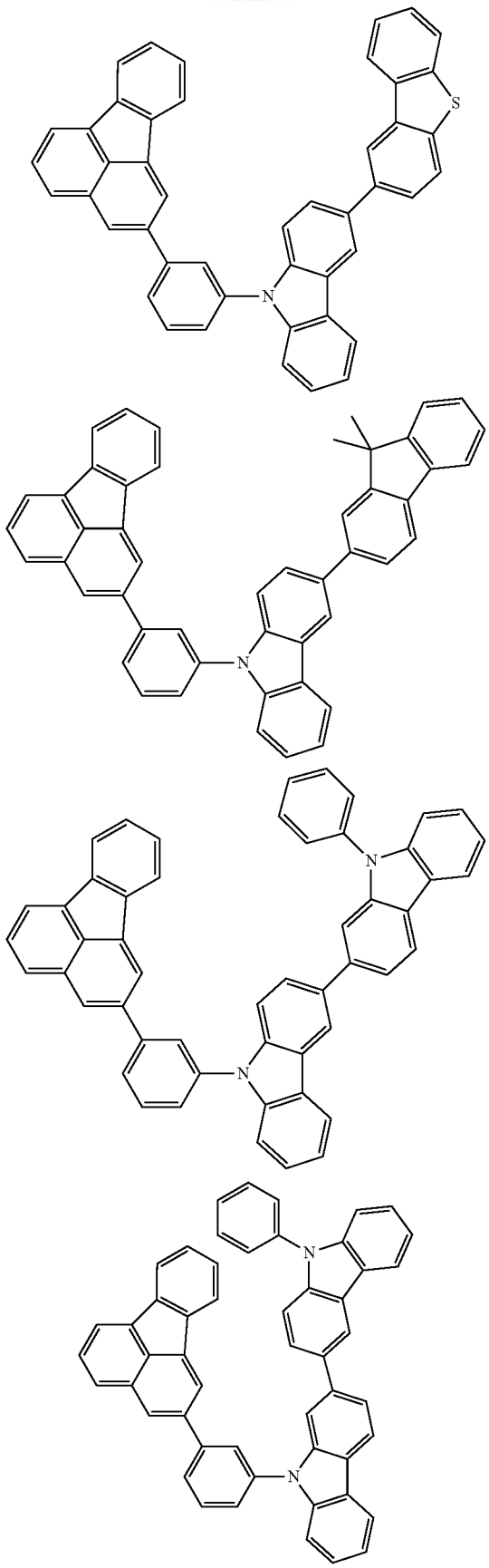
46
-continued
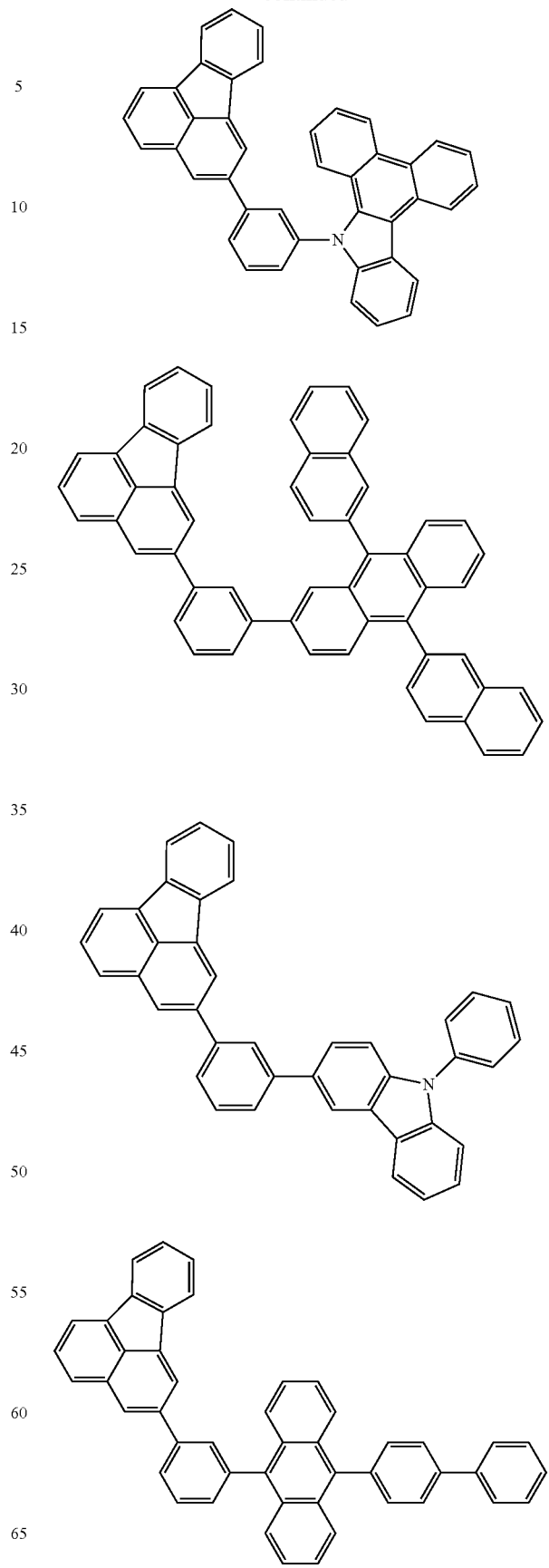

[Chem. 31]
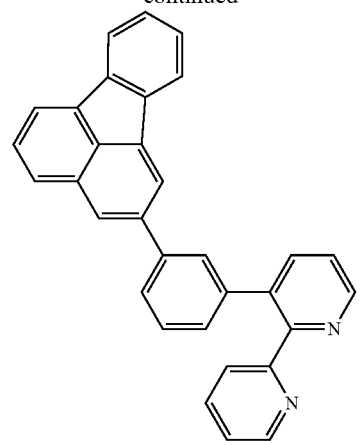
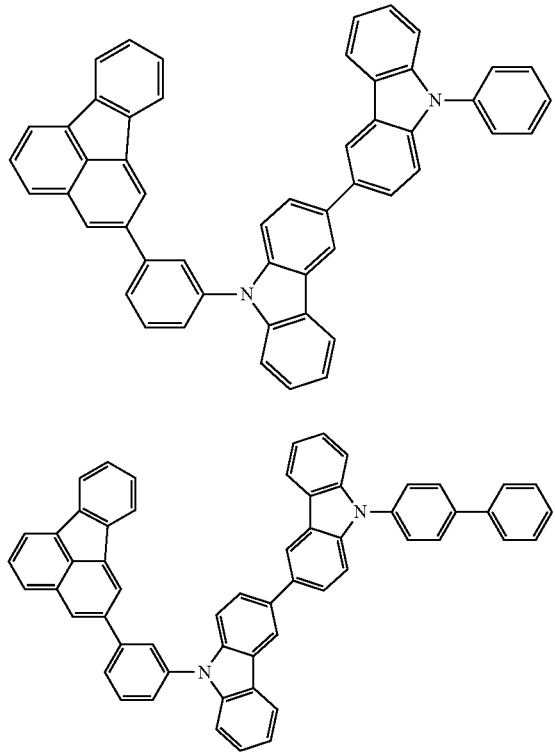
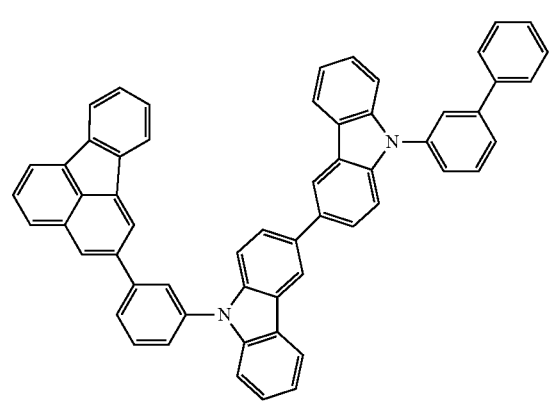
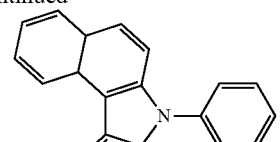
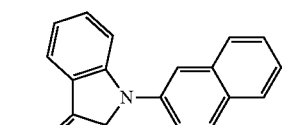
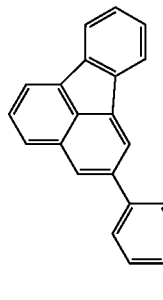
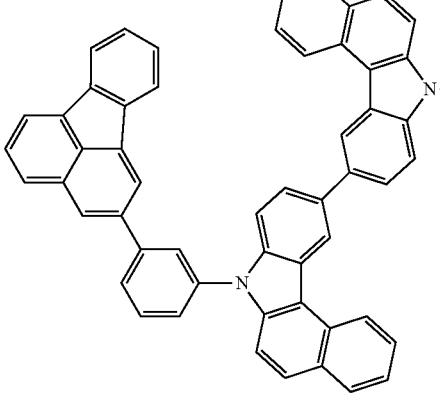
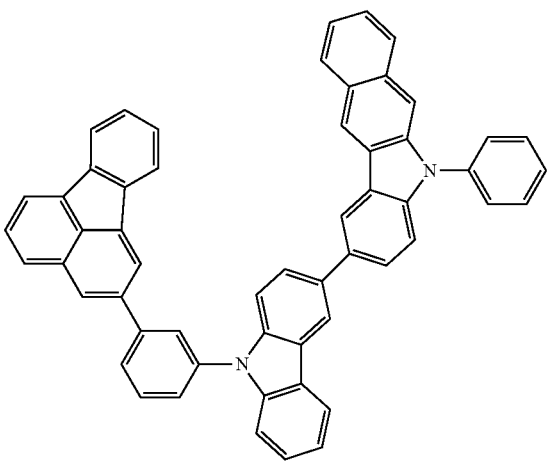

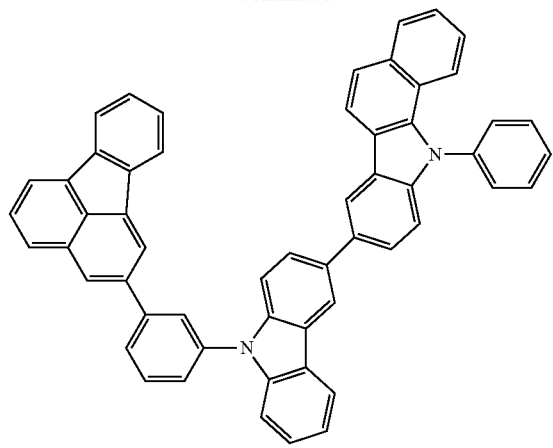
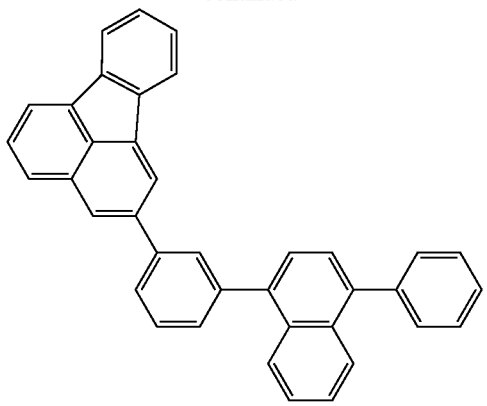
[Chem. 32]
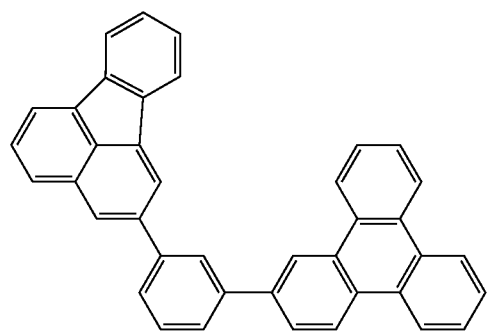
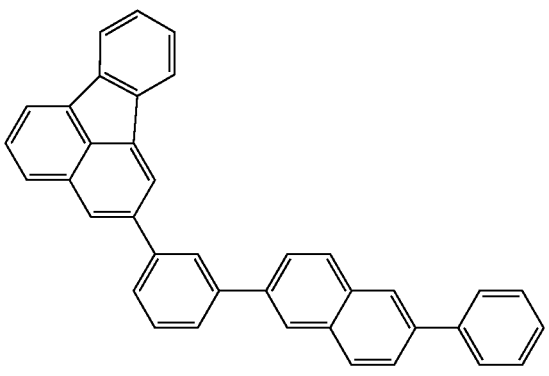
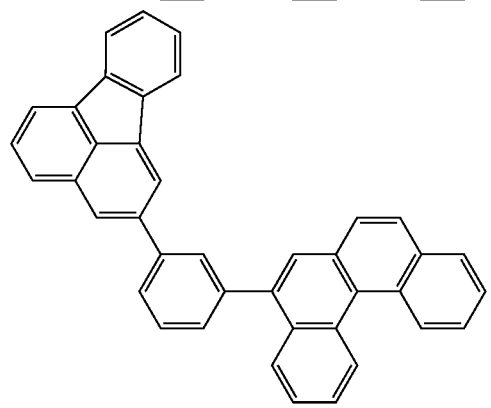
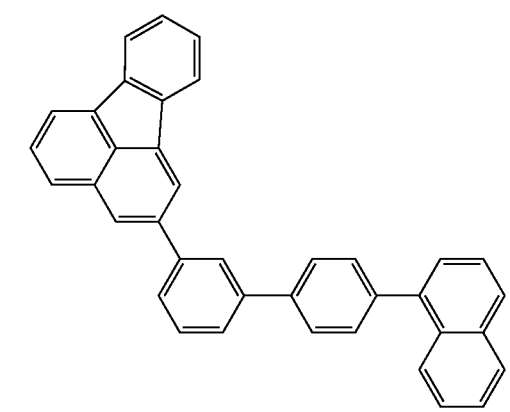
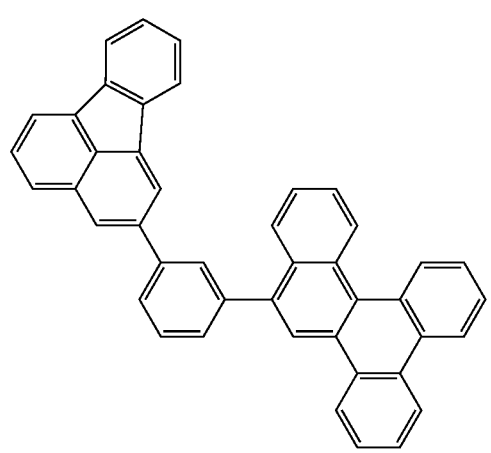
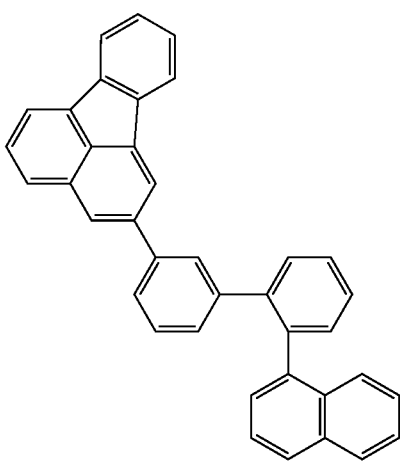

-continued
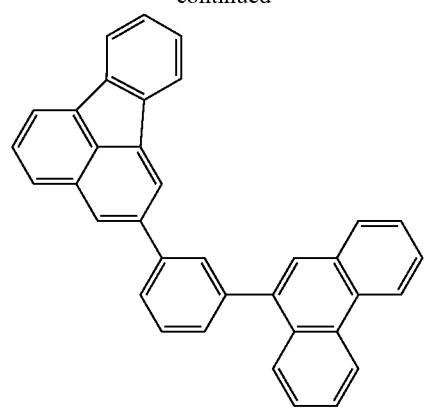
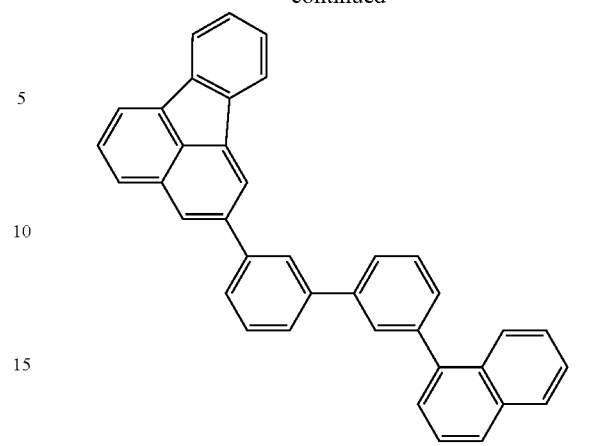
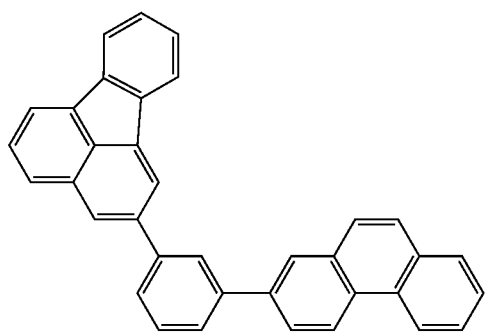
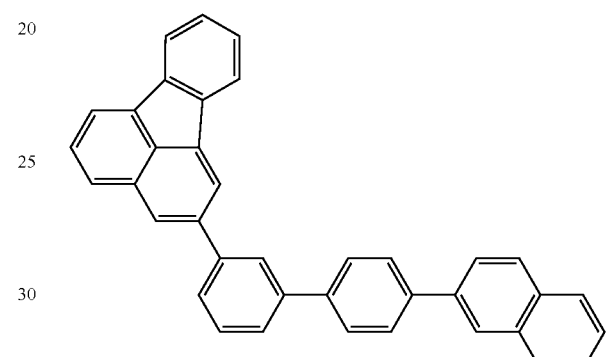
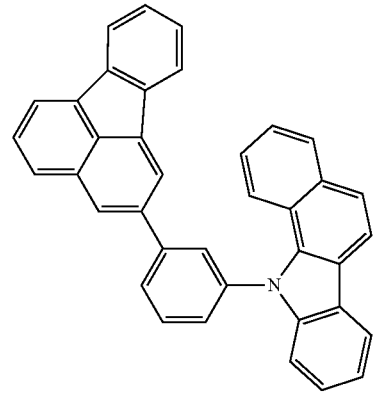
[Chem. 33]
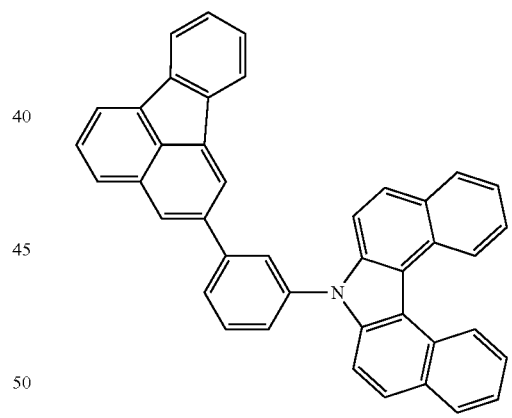
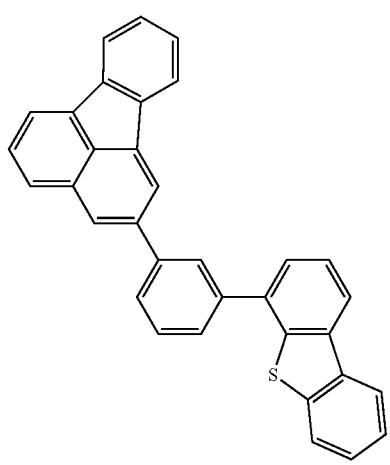
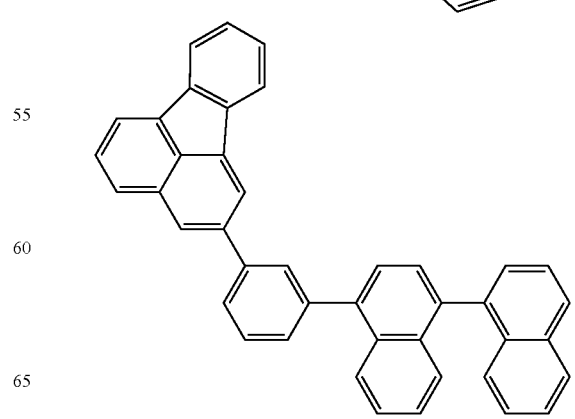

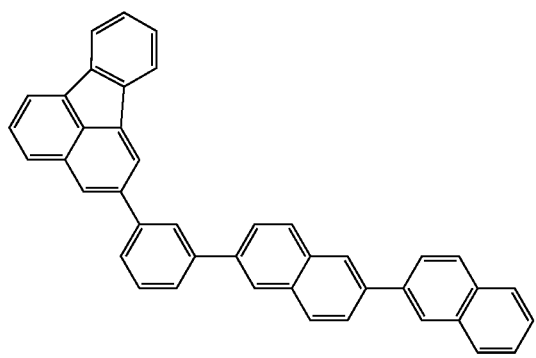
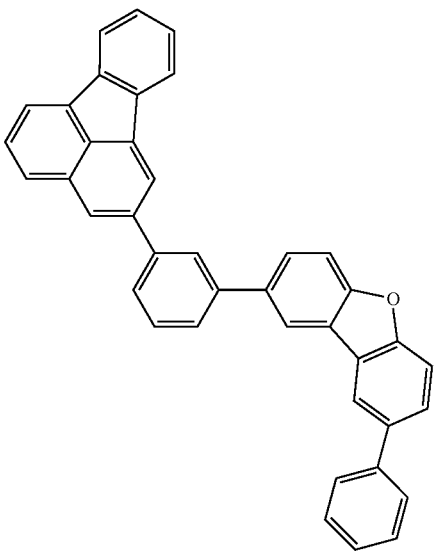
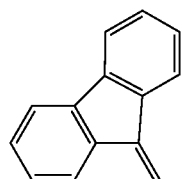
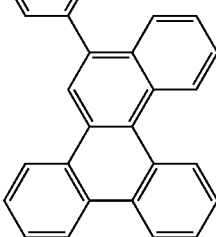
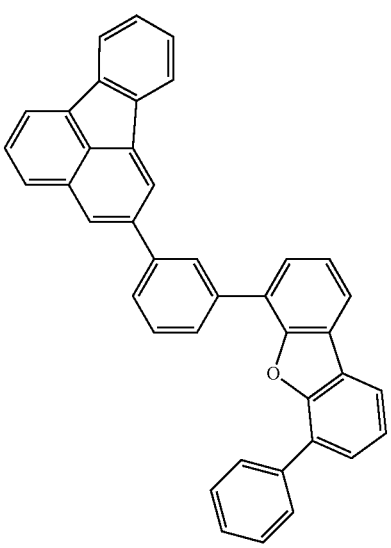
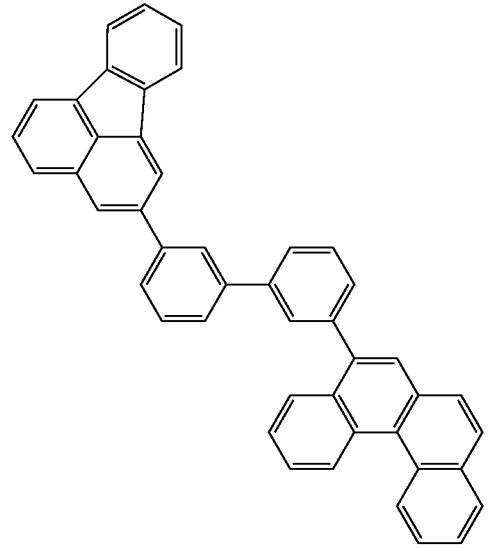

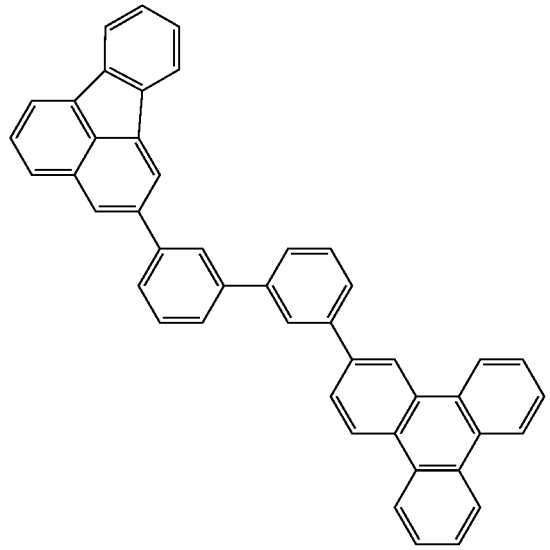
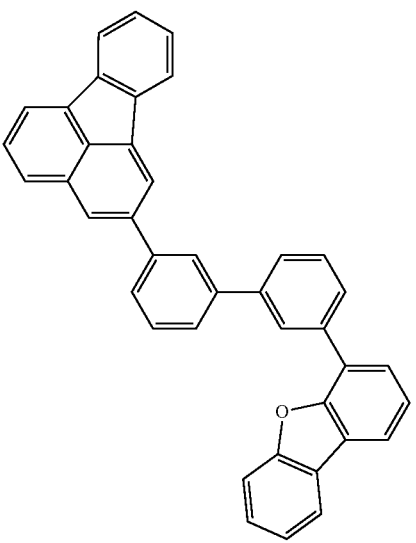
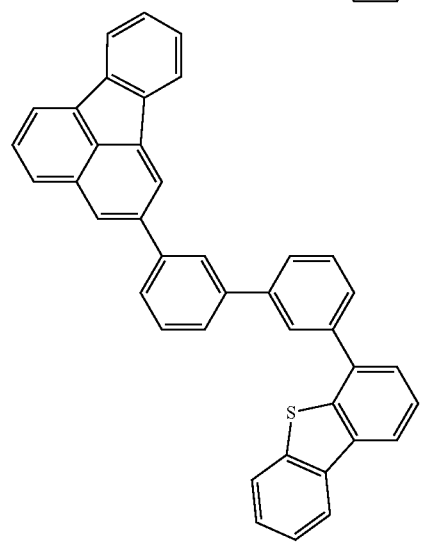
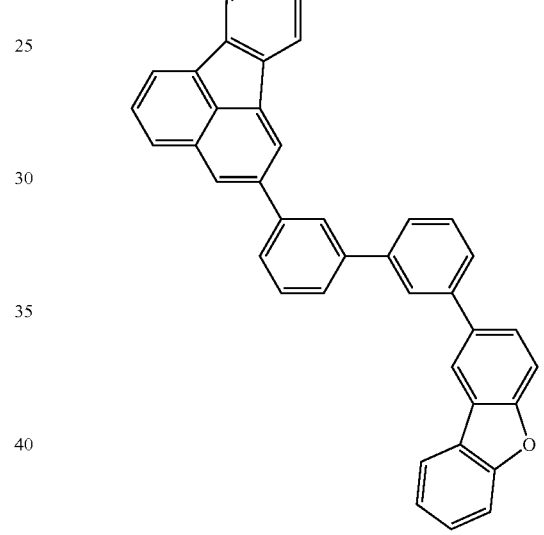
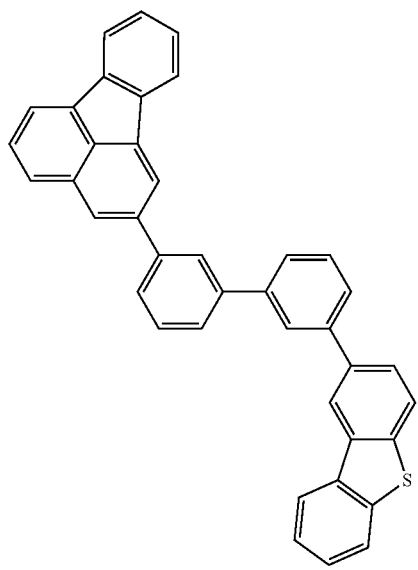
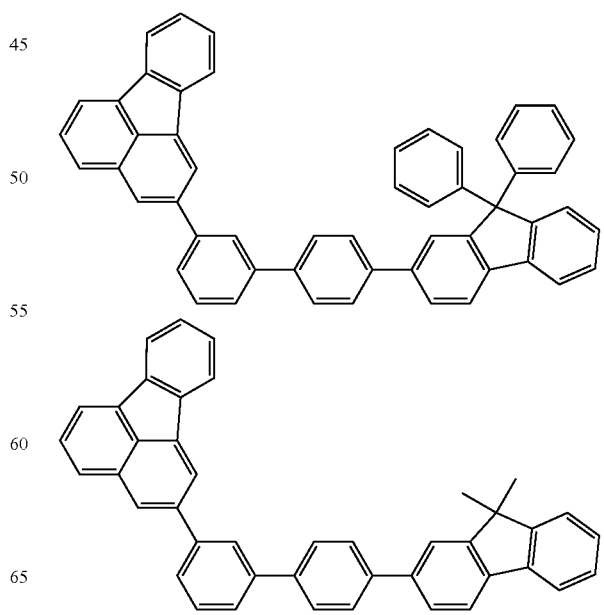
[Chem. 34]

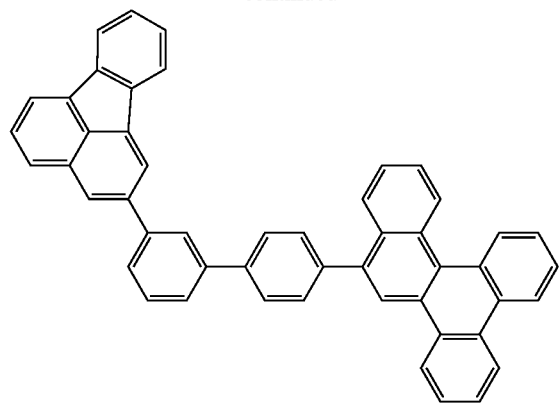
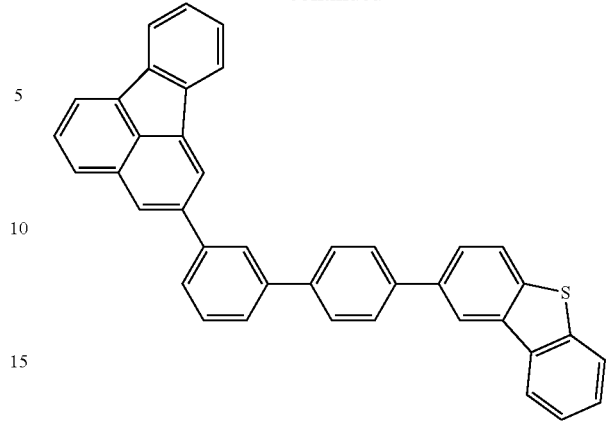
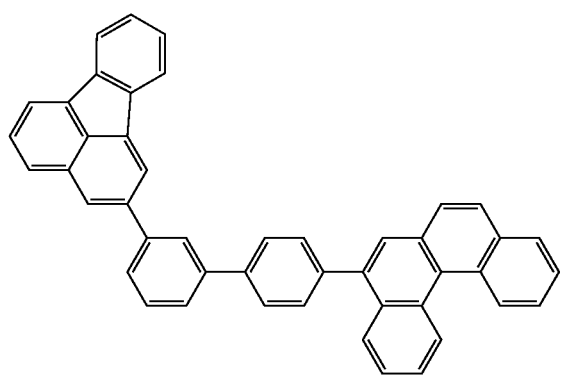
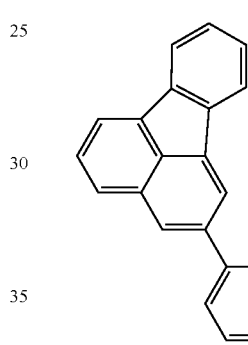
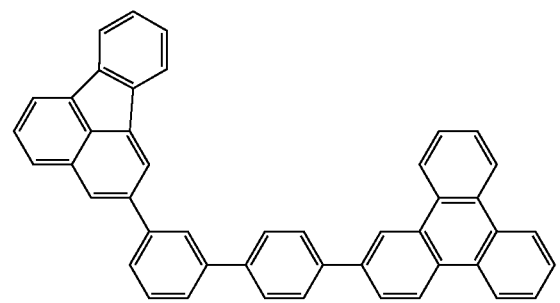
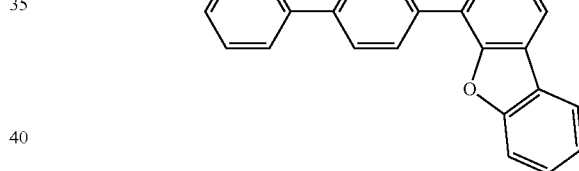
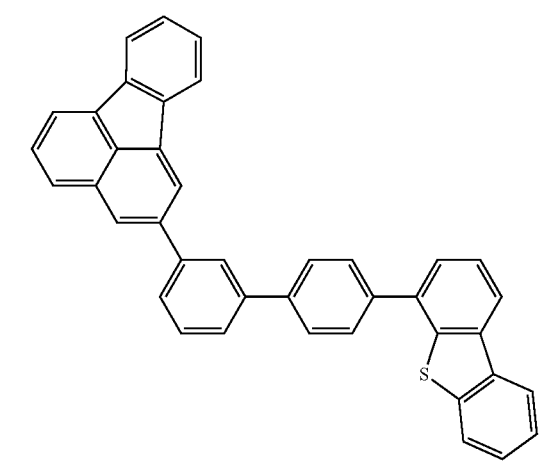
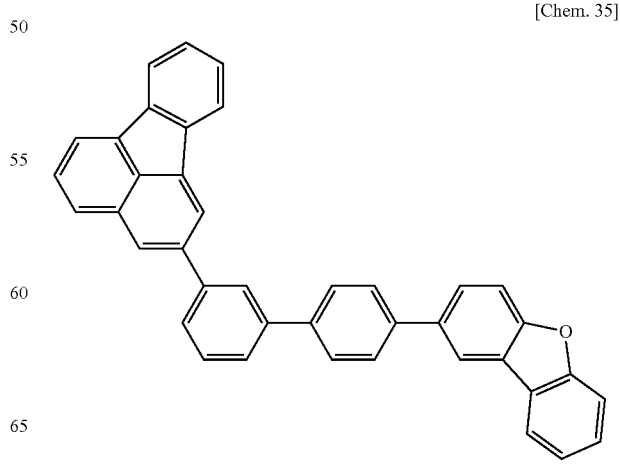
[Chem. 35]

59
-continued
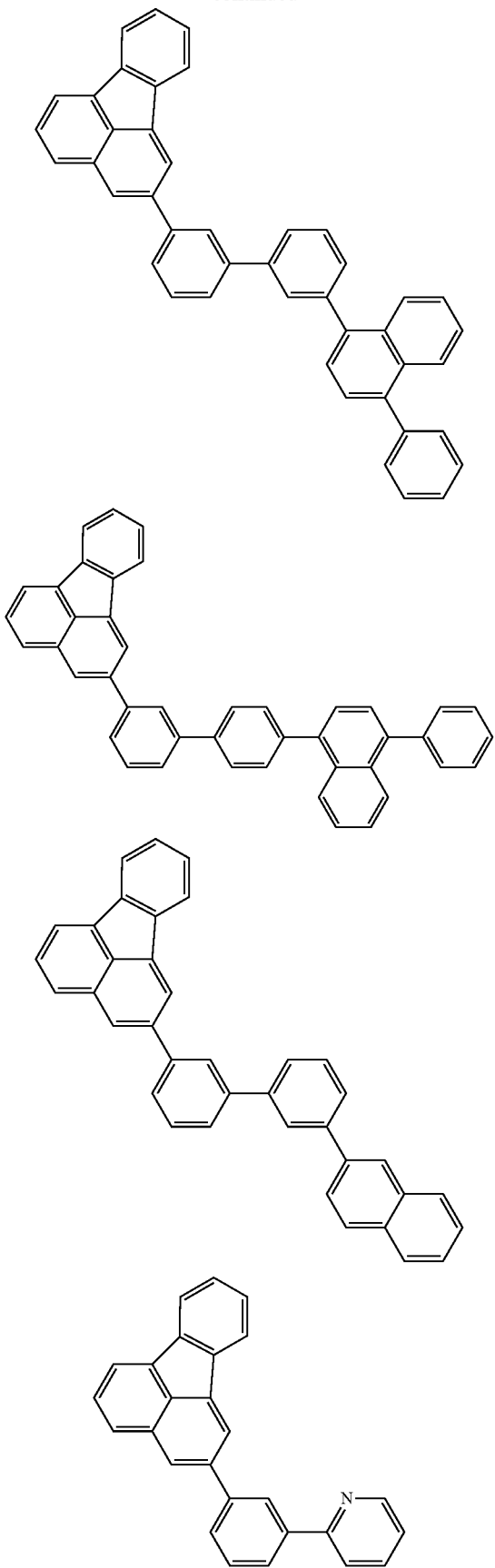
60
-continued
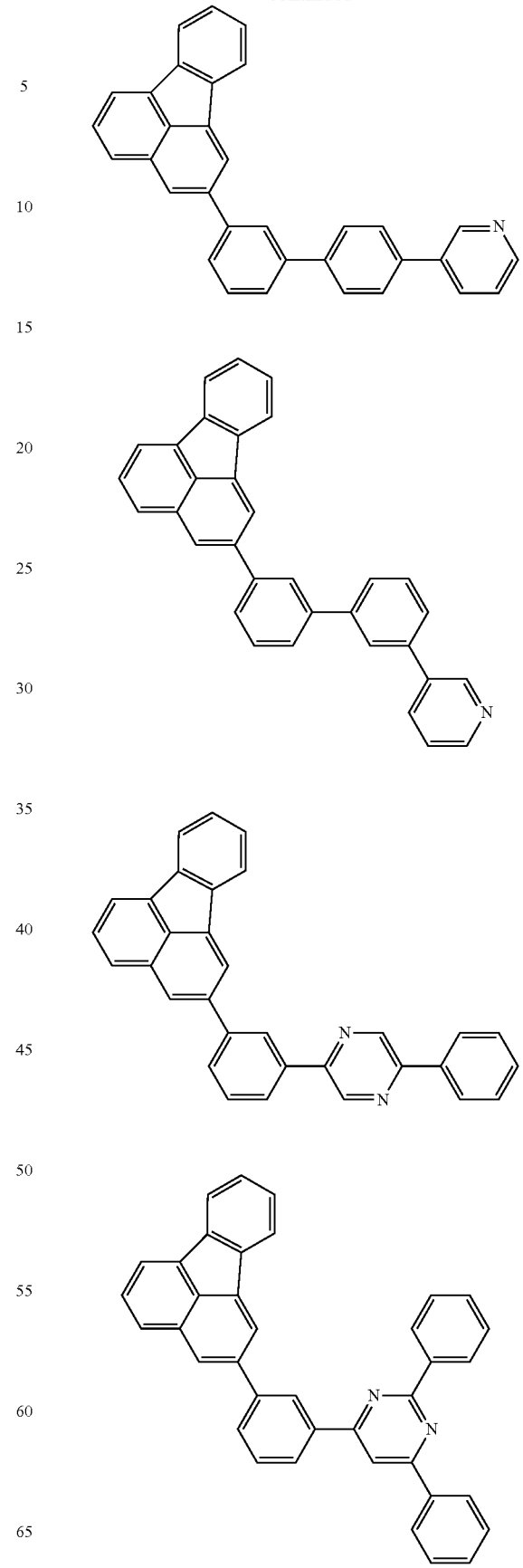

-continued
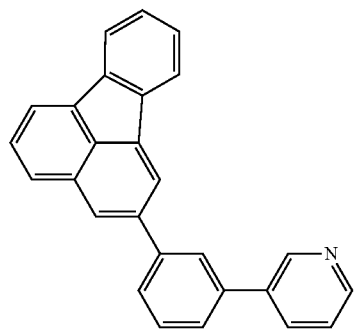
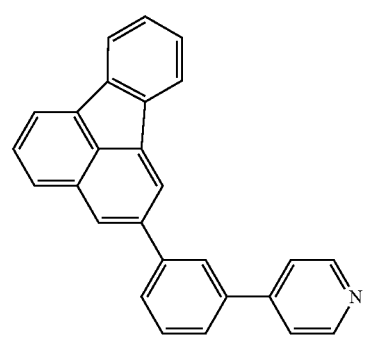
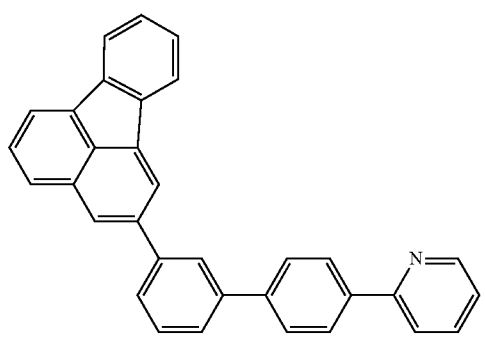
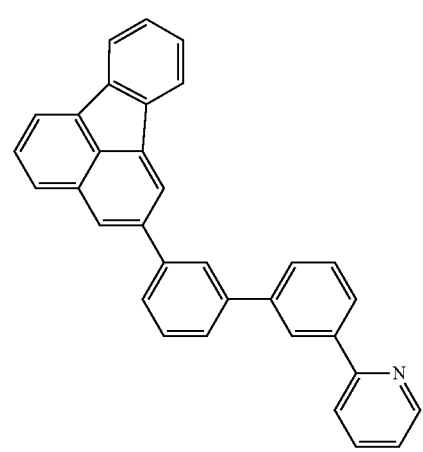
-continued
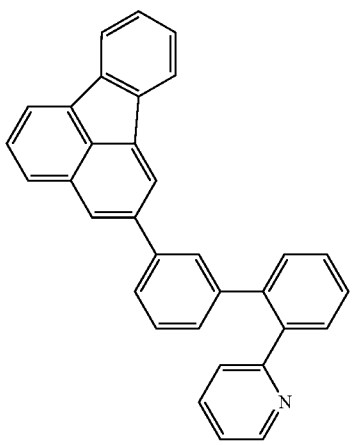
[Chem. 36]
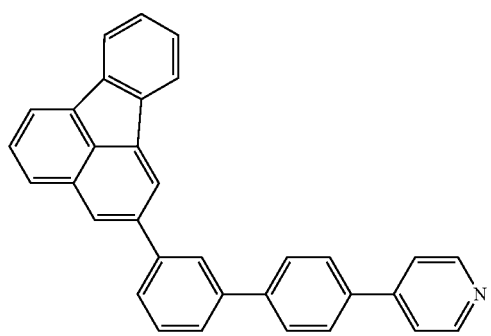
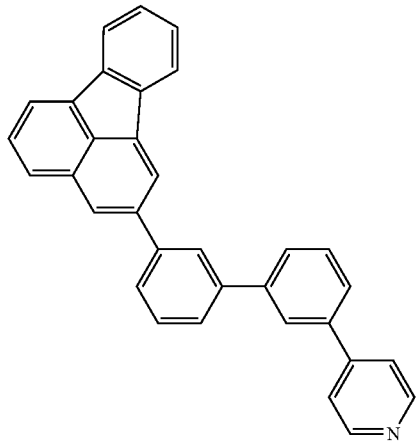
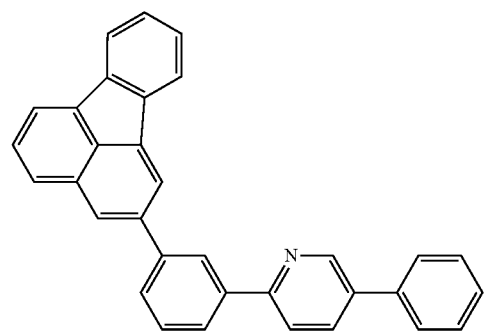

63
-continued
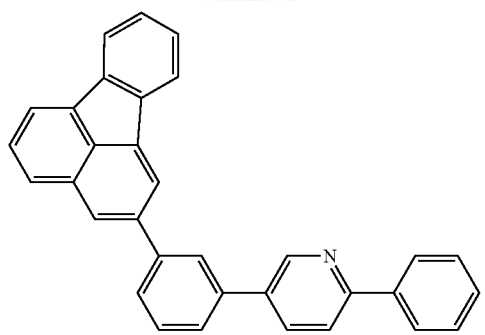
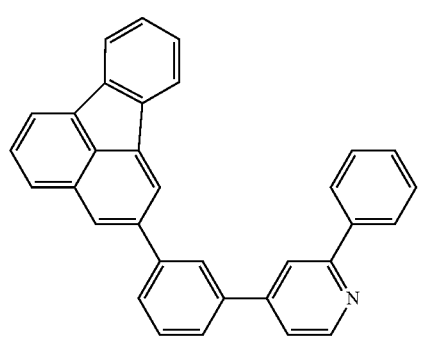
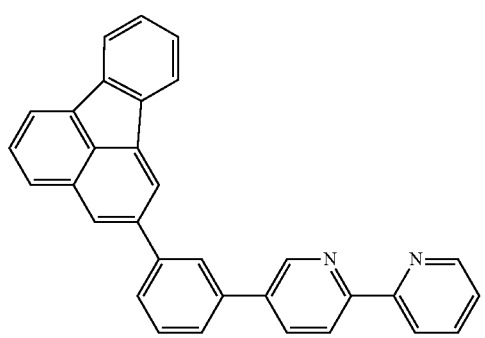
64
-continued
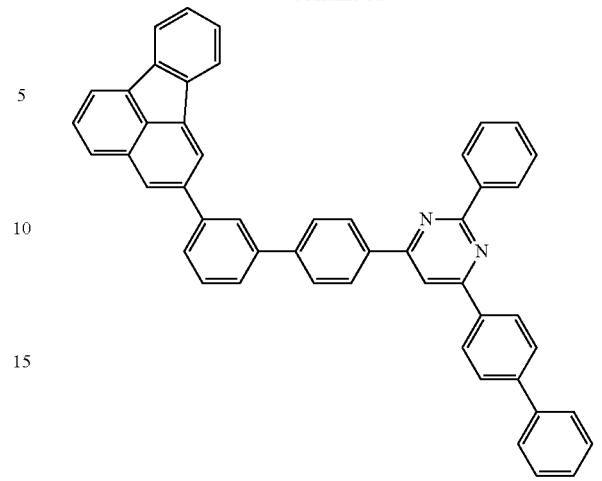
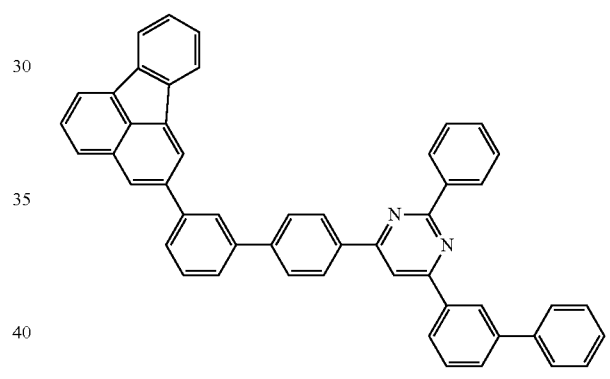
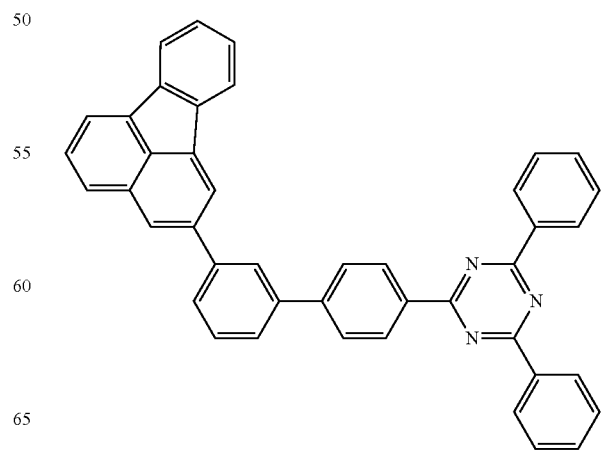

65
-continued
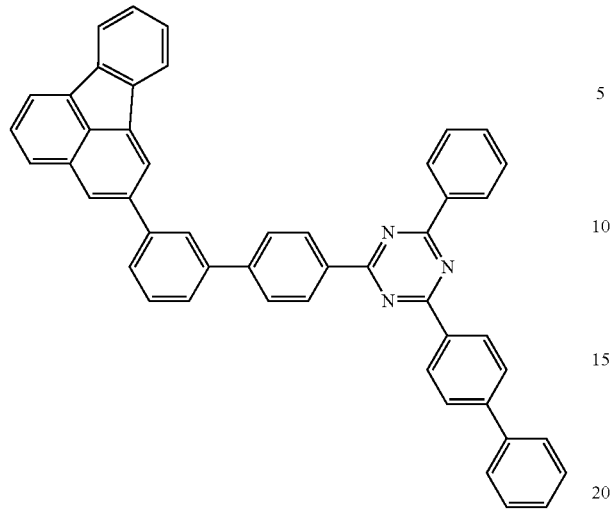
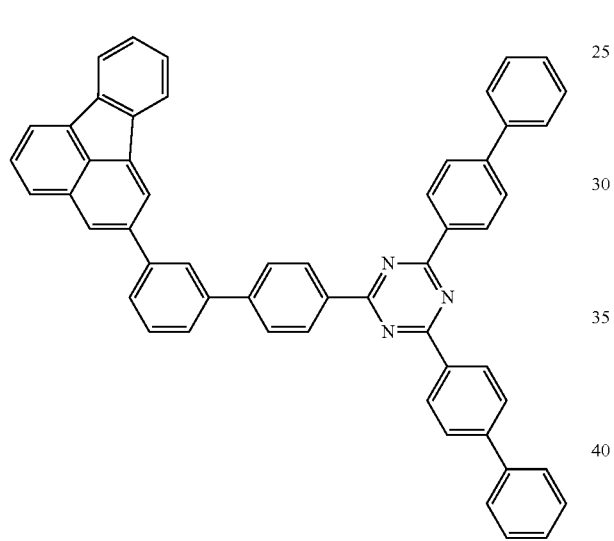
[Chem. 37]
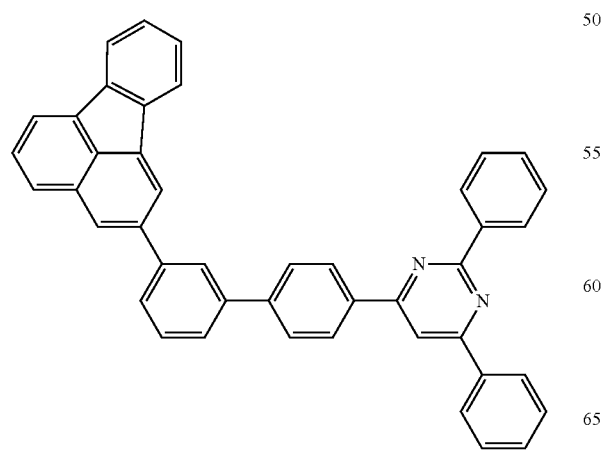
66
-continued
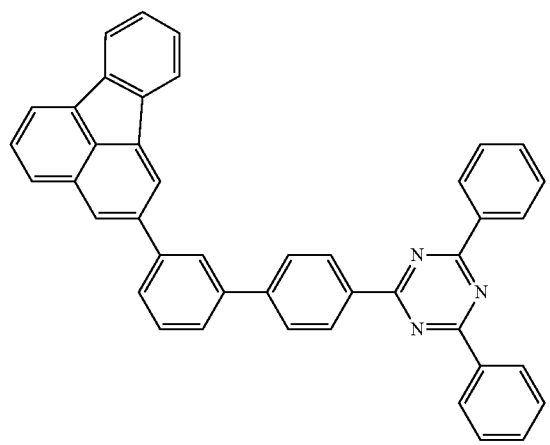
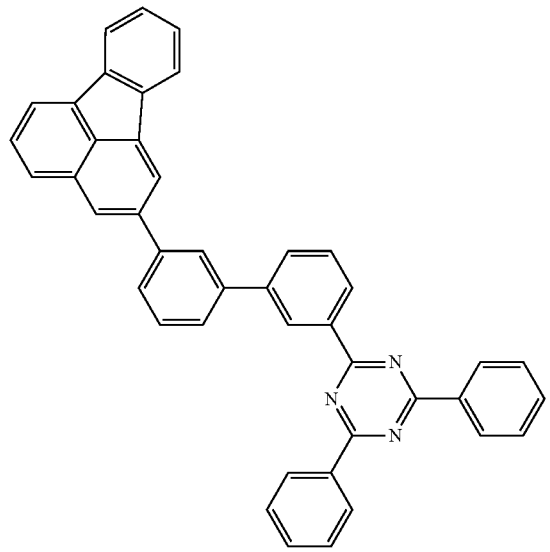
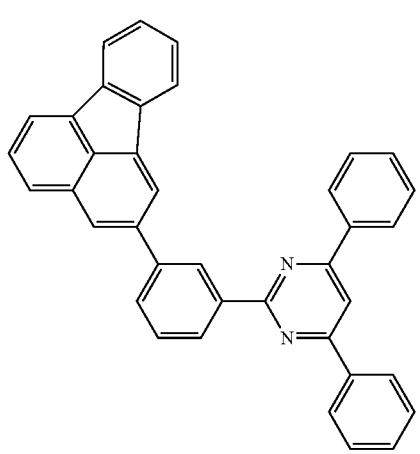

67
-continued
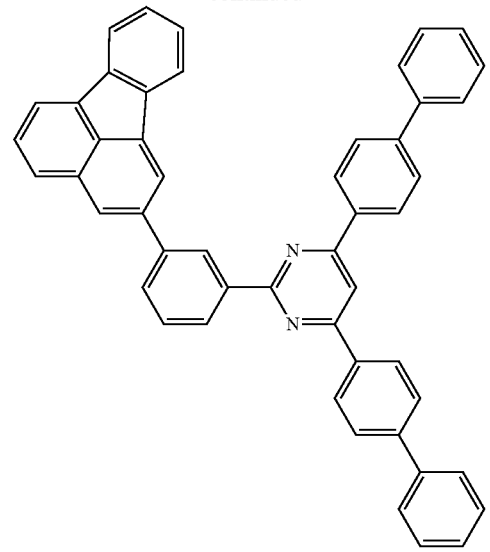
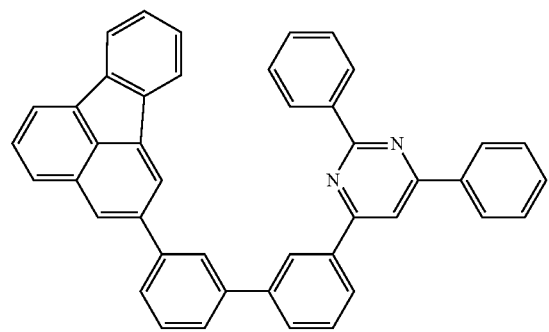
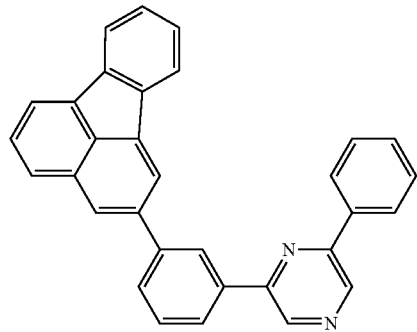
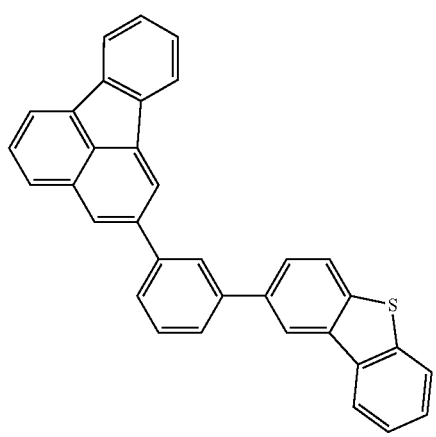
68
-continued
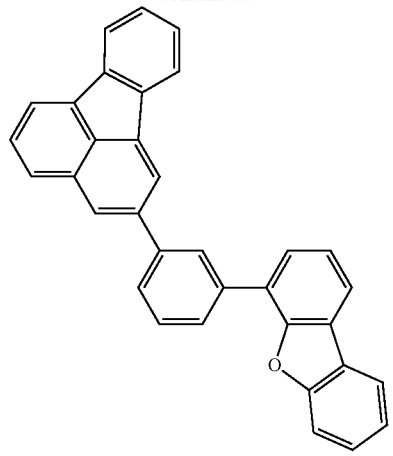
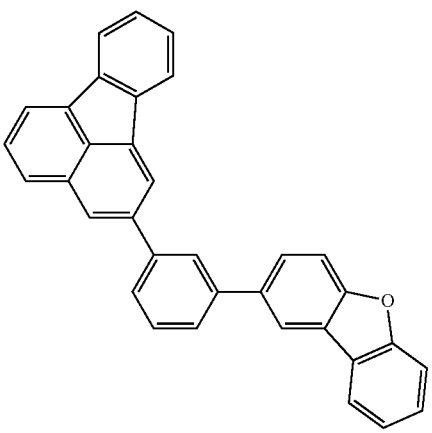
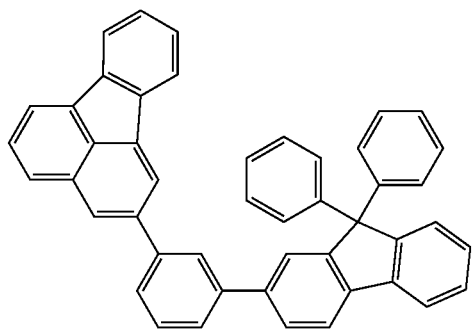
[Chem. 38]
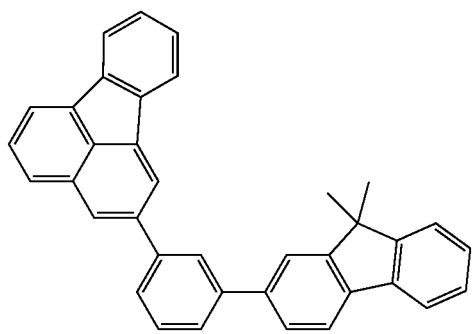

-continued
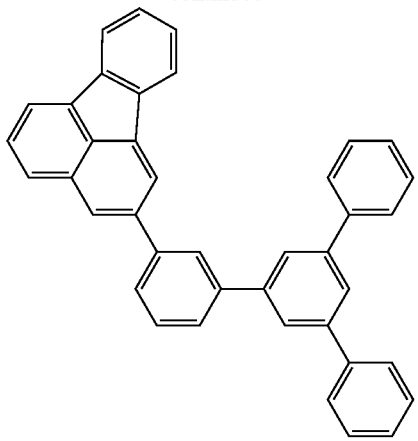
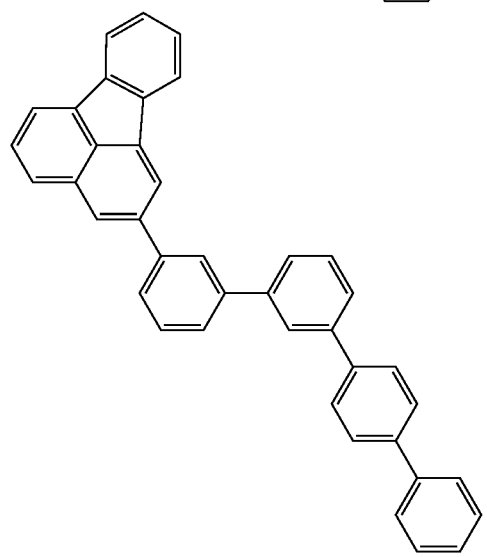
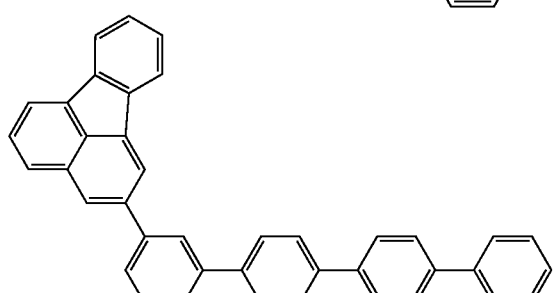
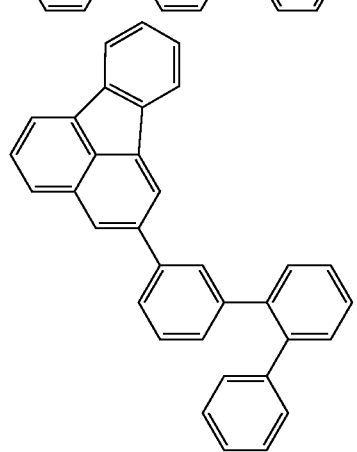
-continued
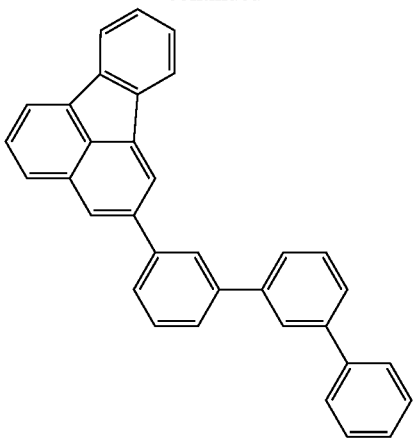
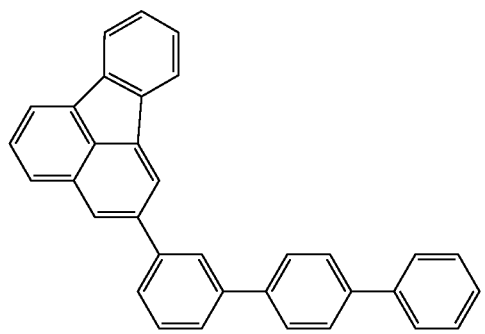
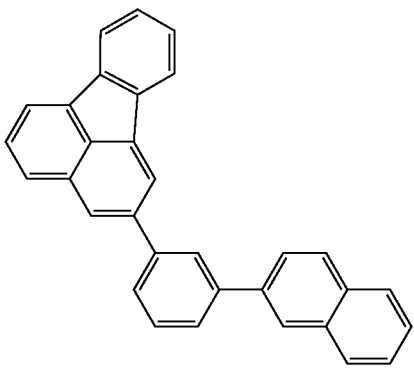
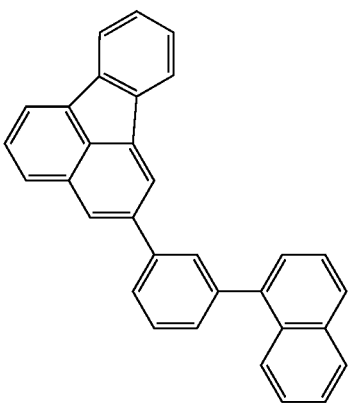

71
-continued
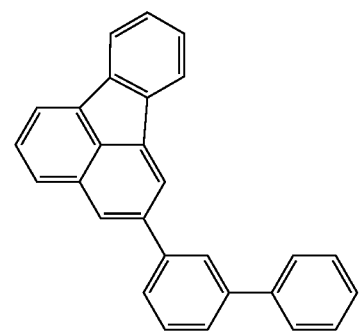
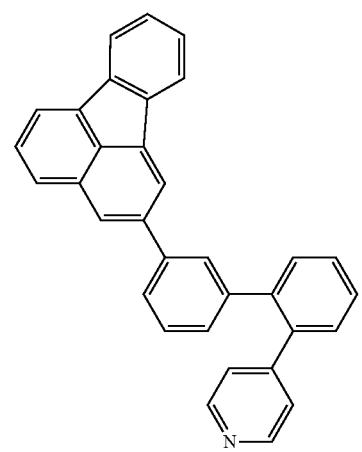
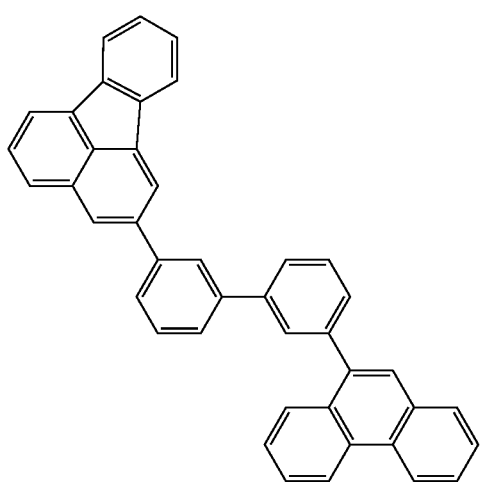
72
-continued
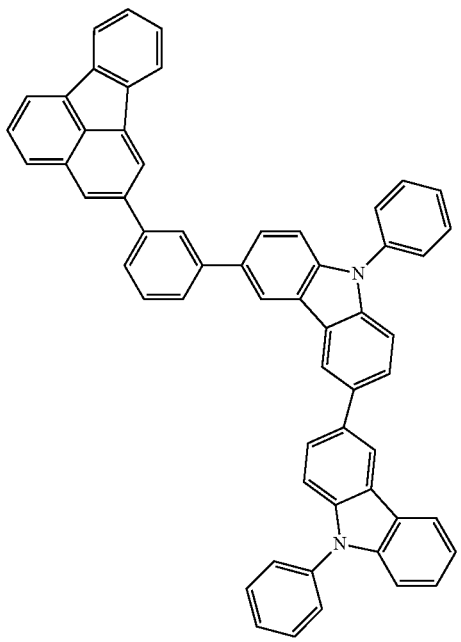
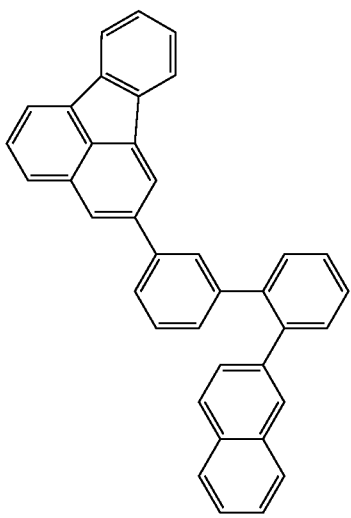
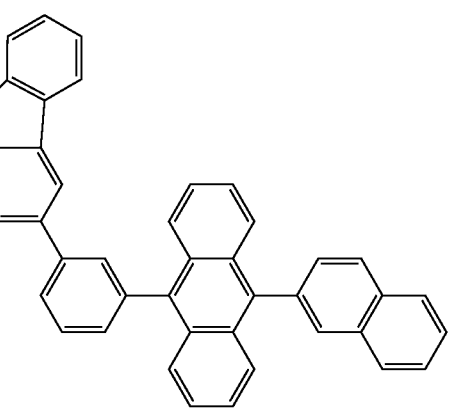

73
-continued
[Chem. 39]
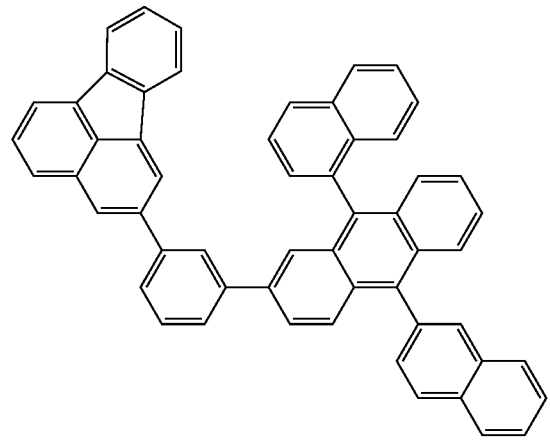
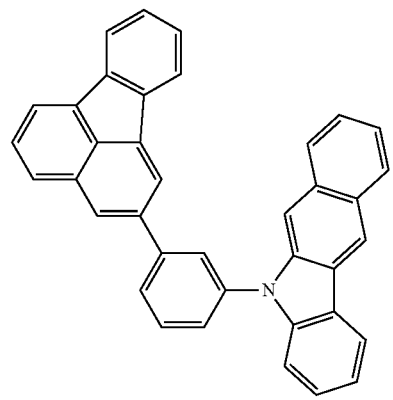
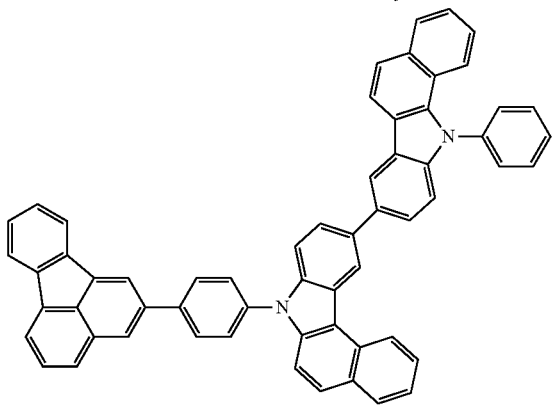
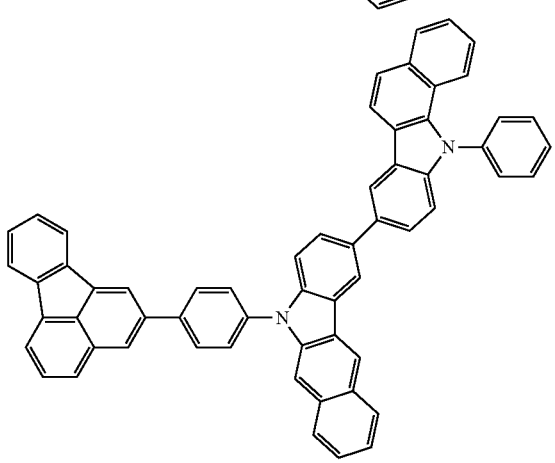
74
-continued
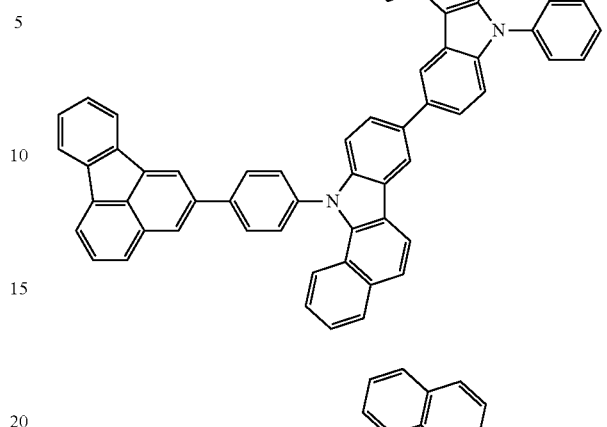
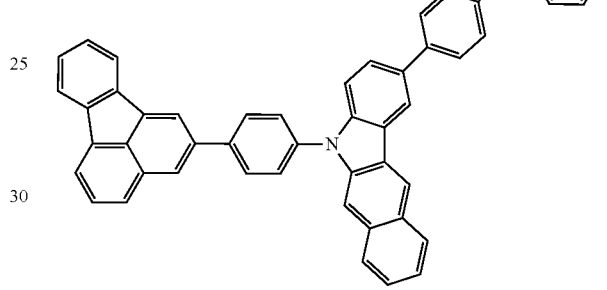
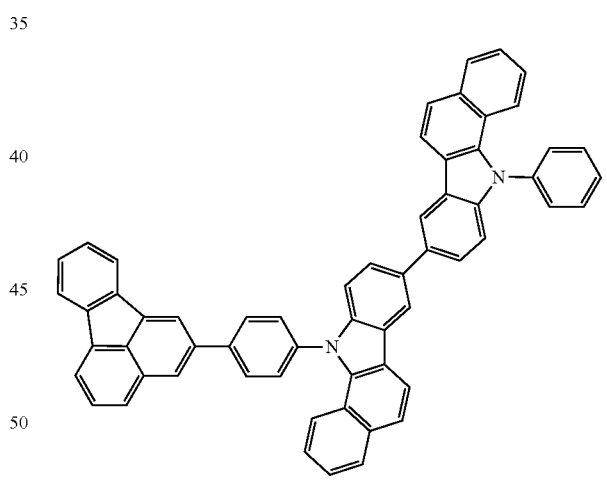
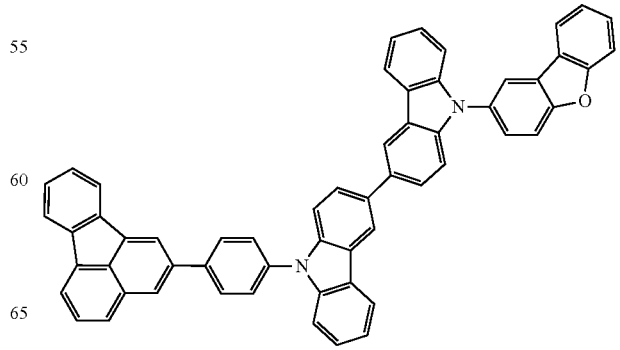

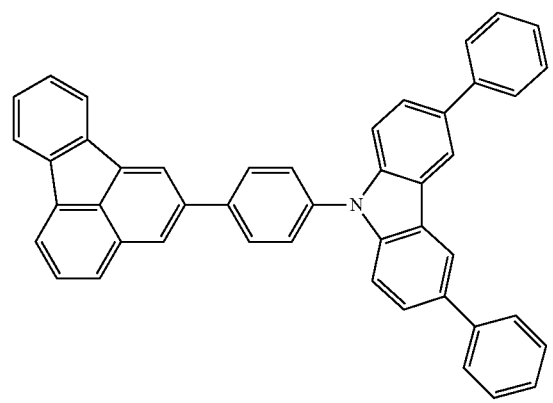
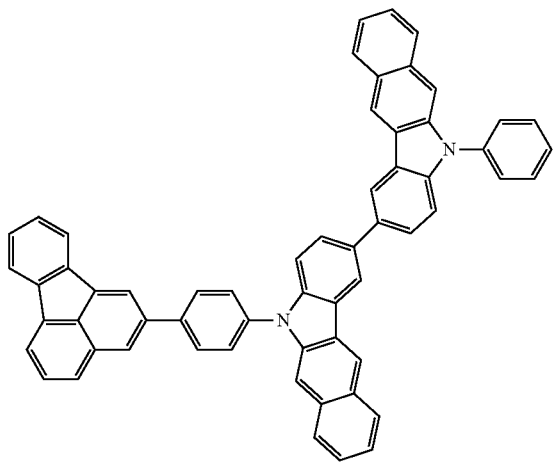
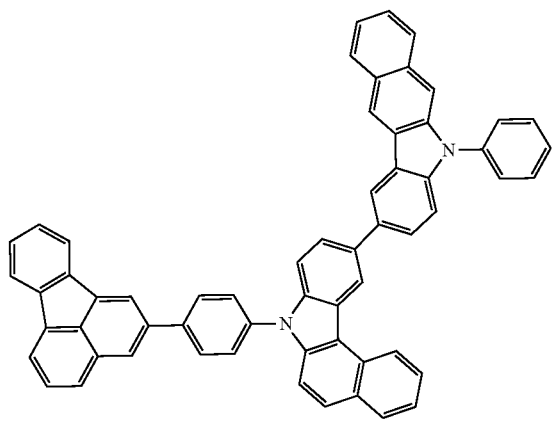
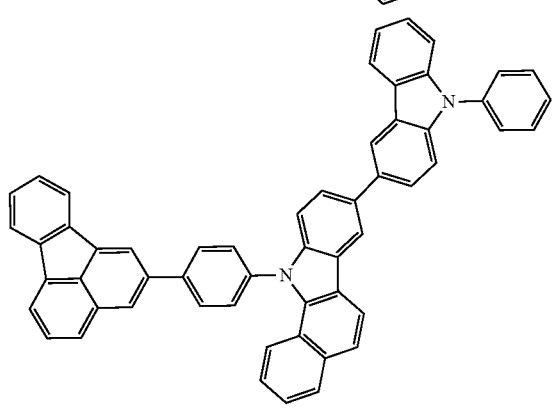
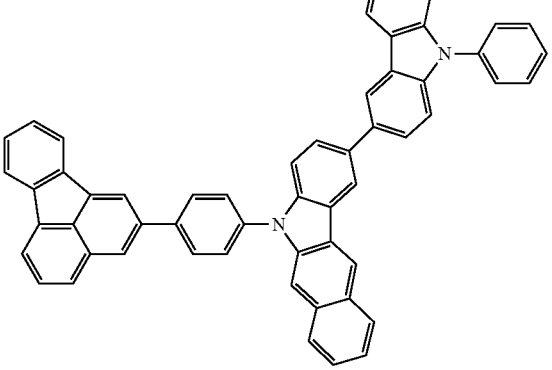
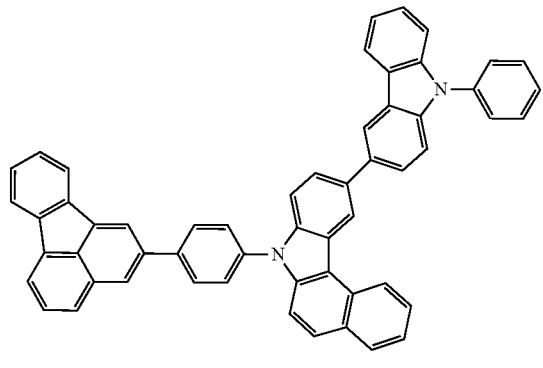
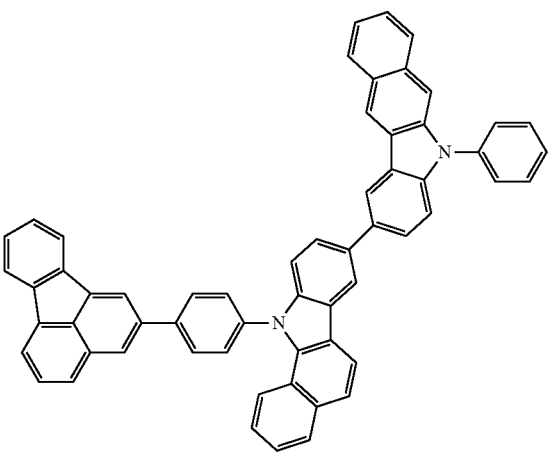
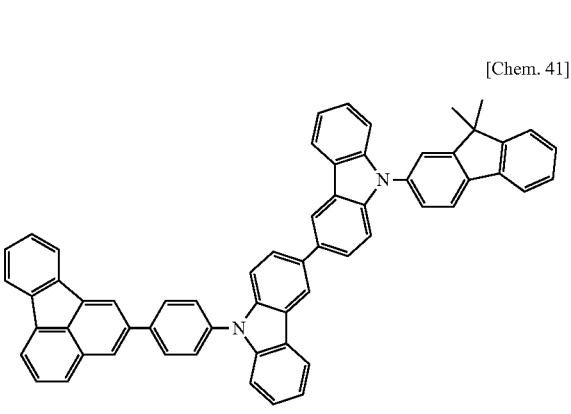

77
-continued
78
-continued
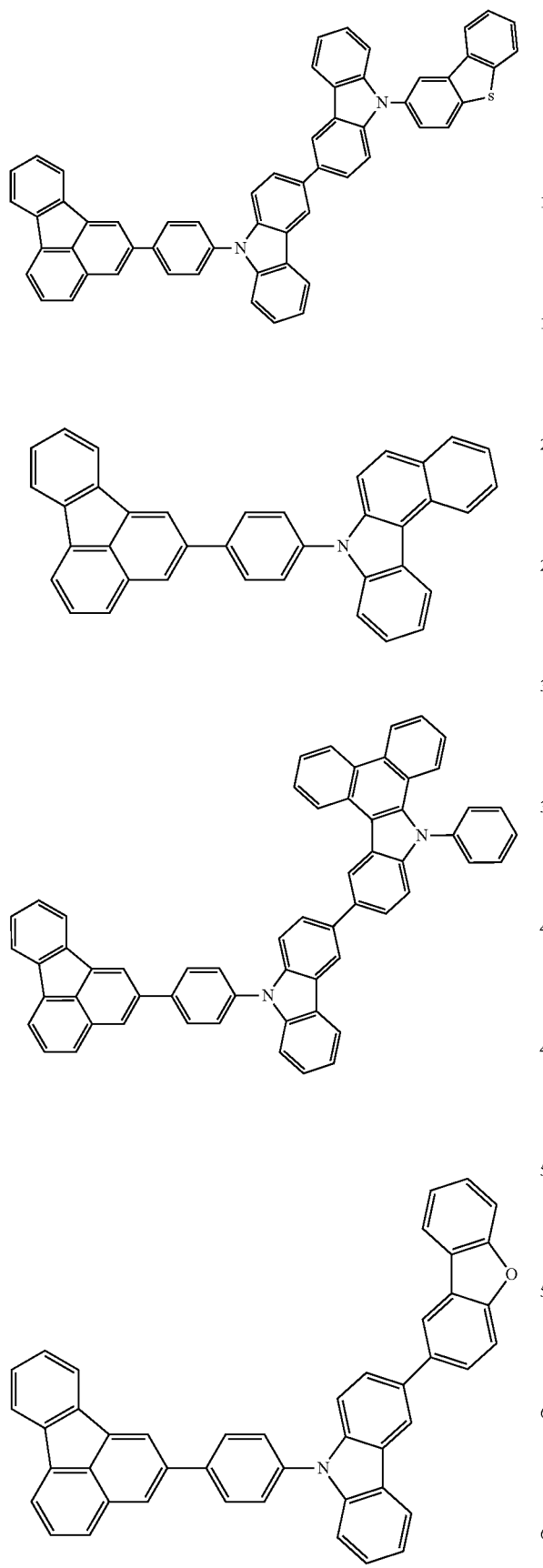
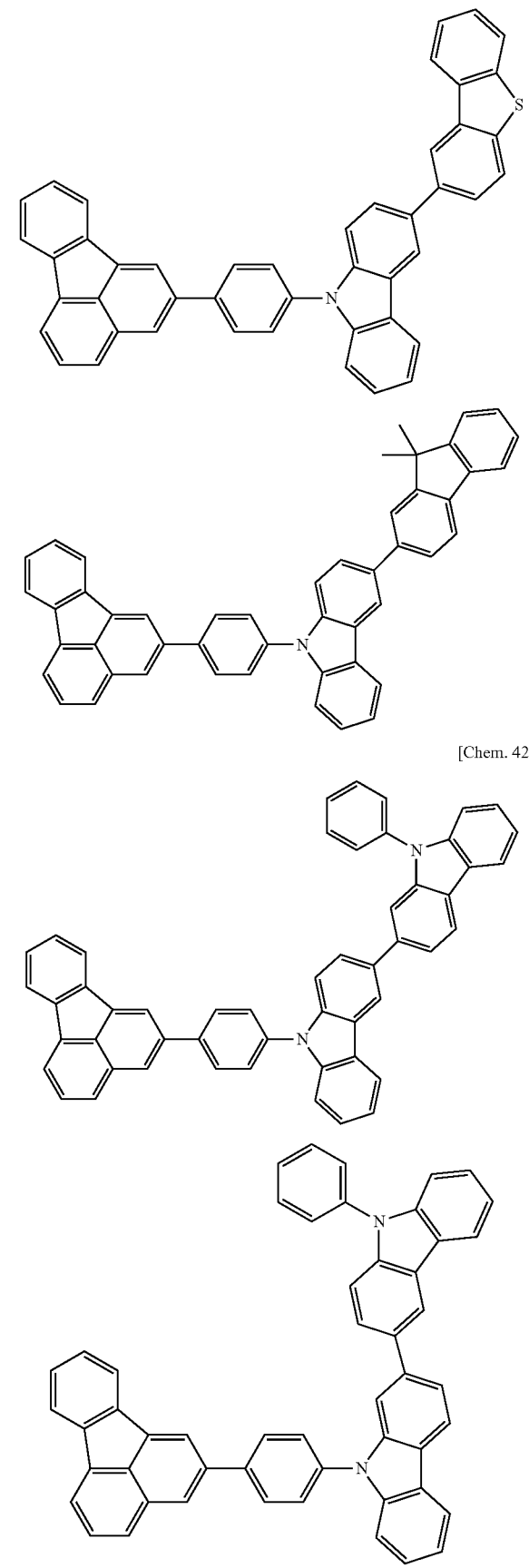
[Chem. 42]

79
-continued
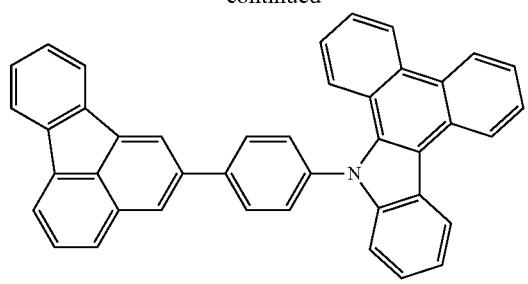
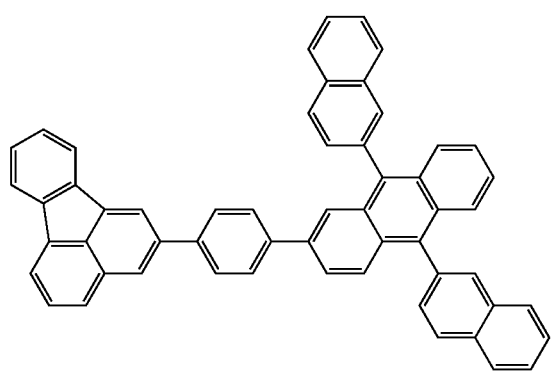
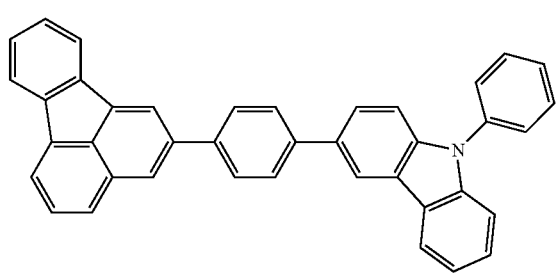
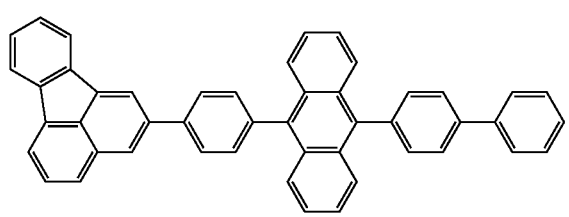
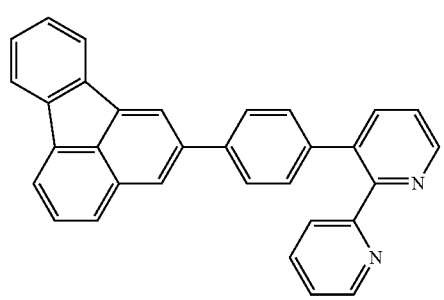
80
-continued
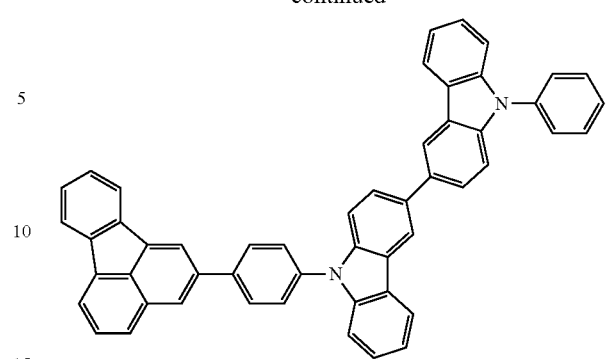
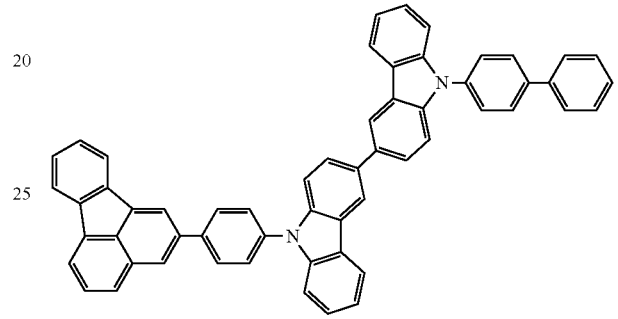
[Chem. 43]
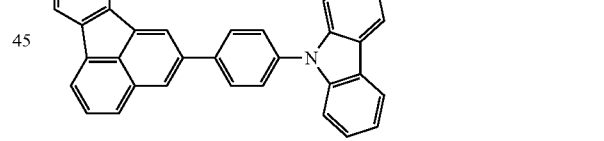
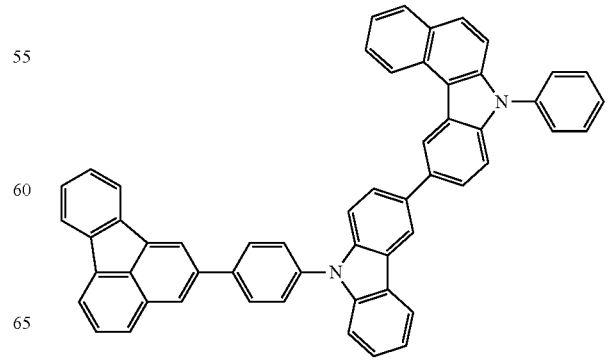

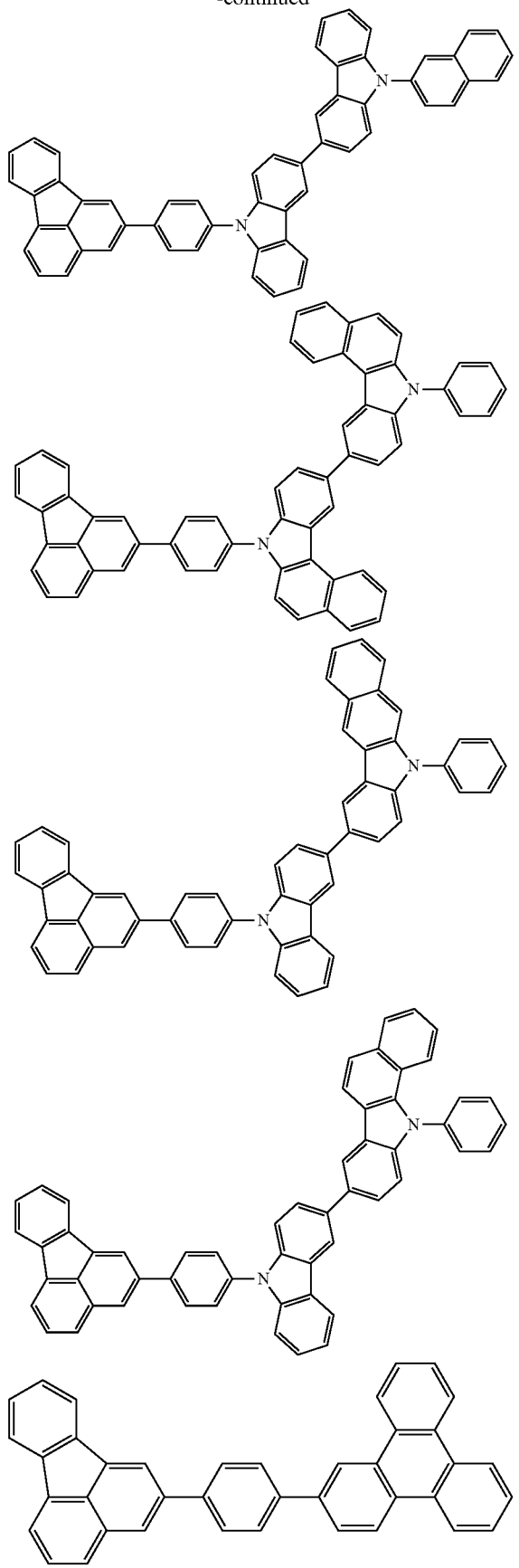
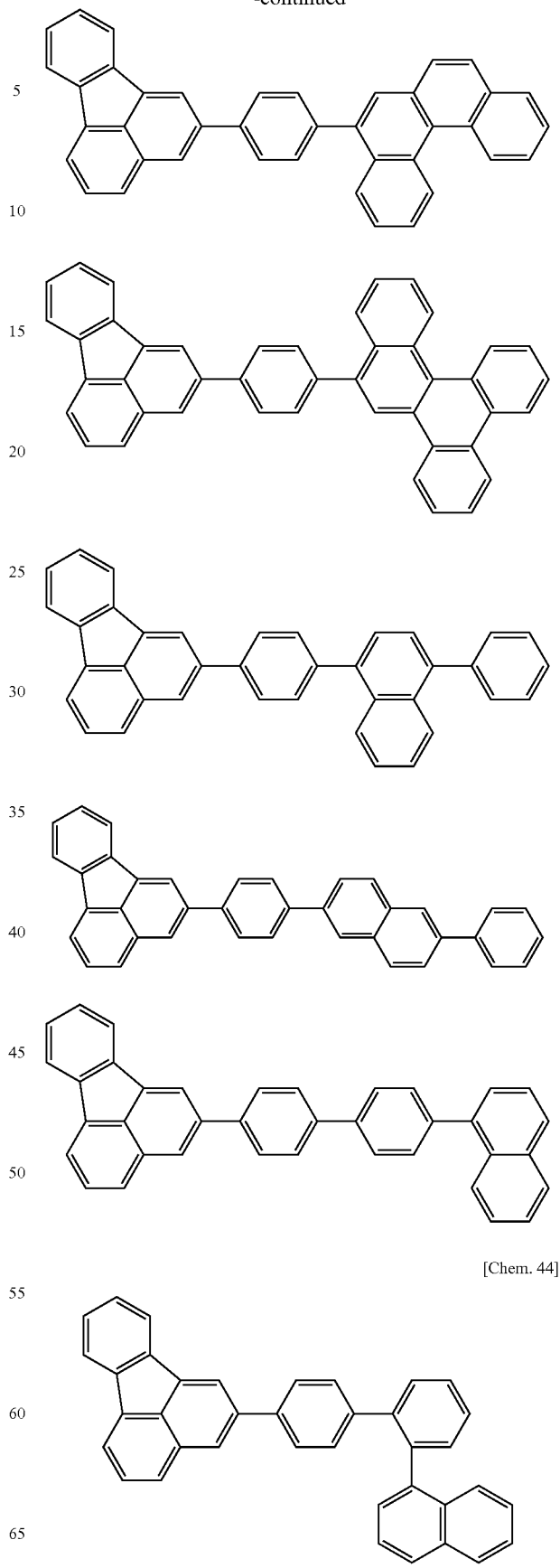
[Chem. 44]

83
-continued
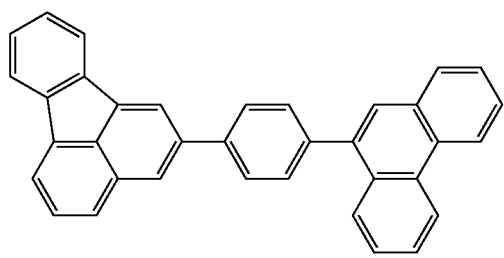
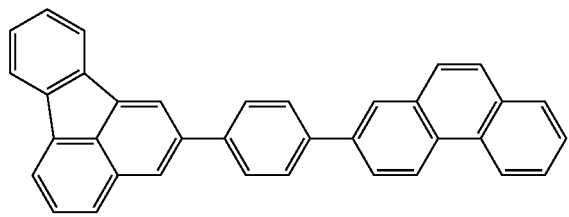
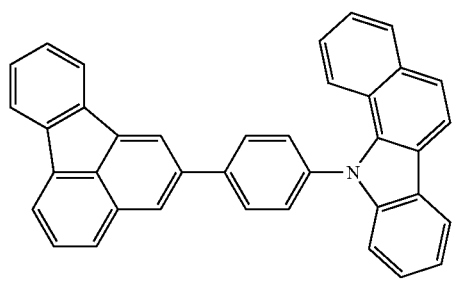
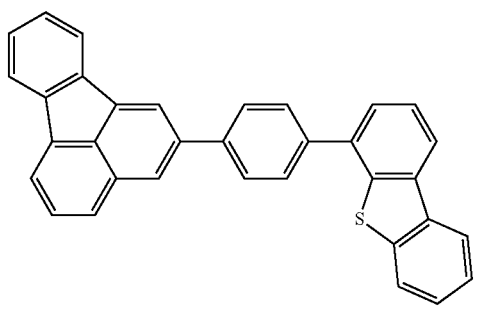
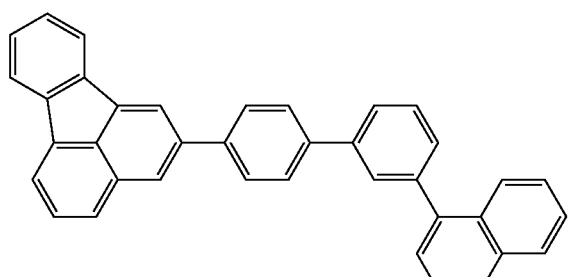
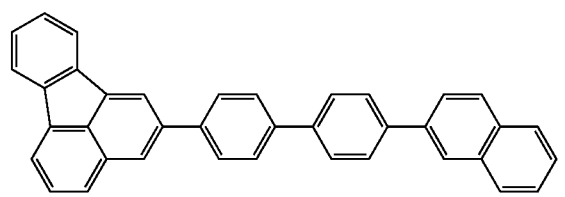
84
-continued
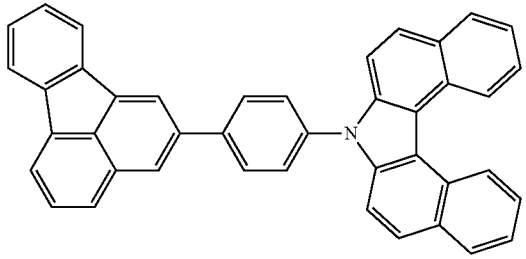
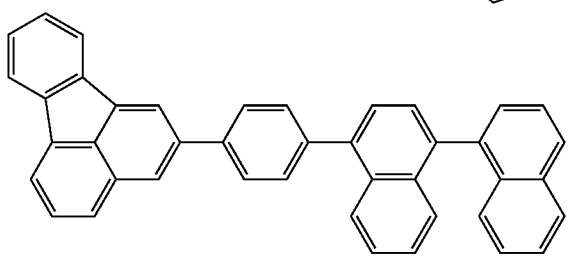
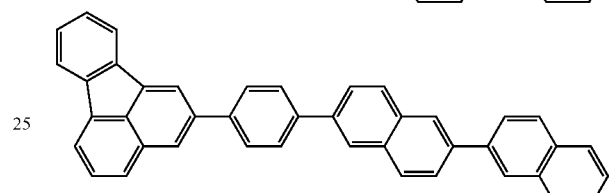
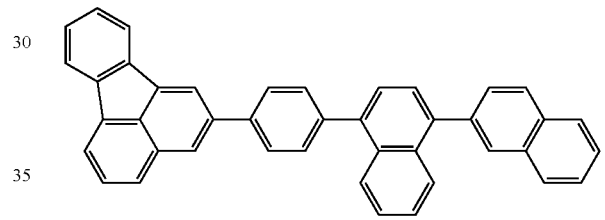
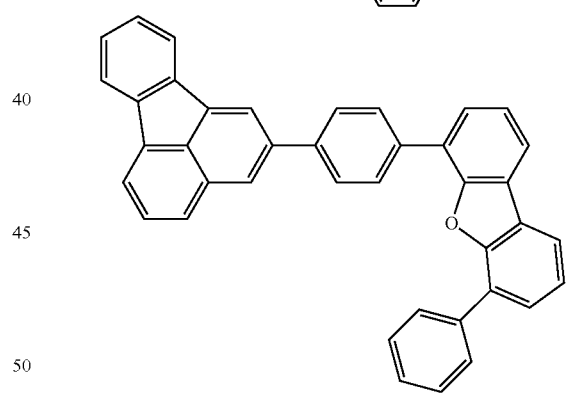
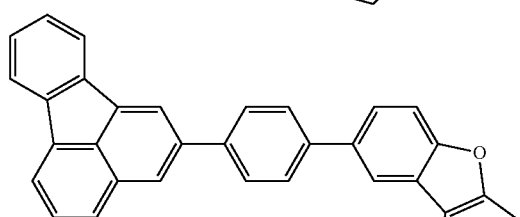

85
-continued
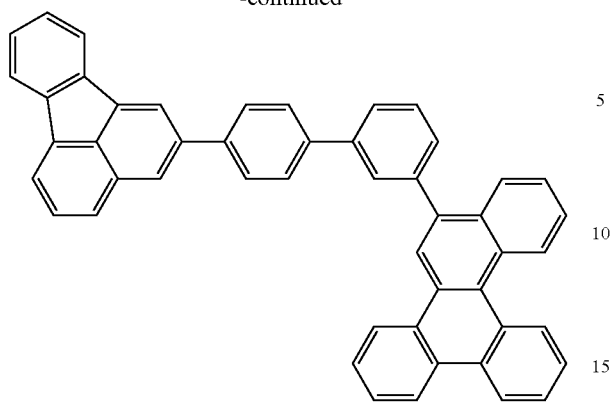
[Chem. 45]
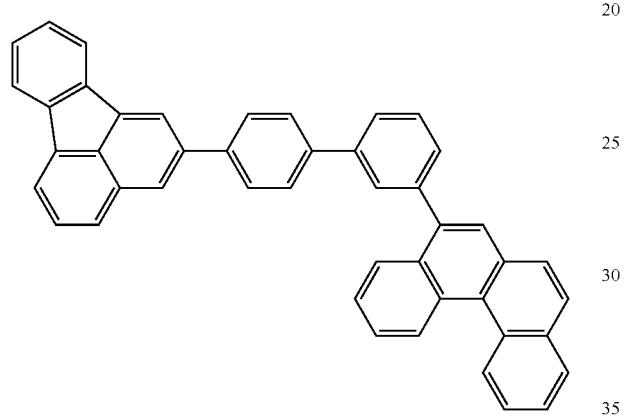
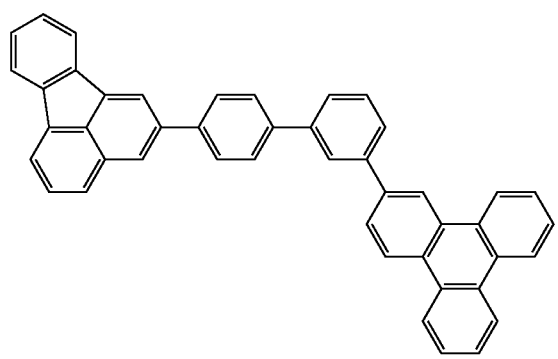
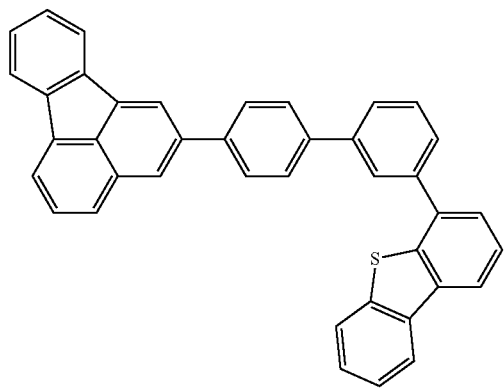
86
-continued
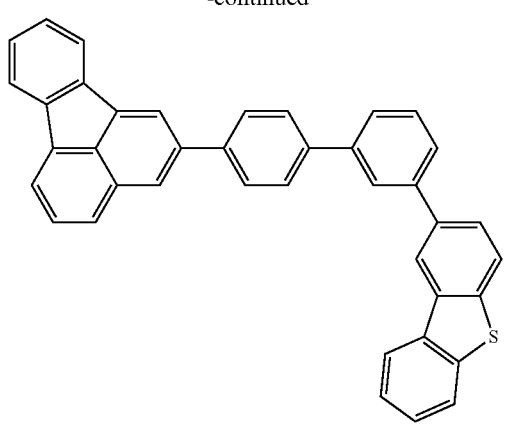
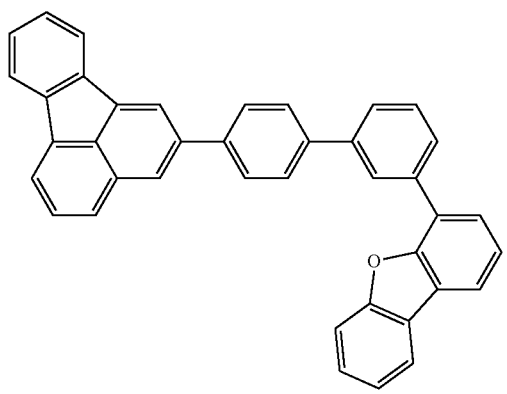
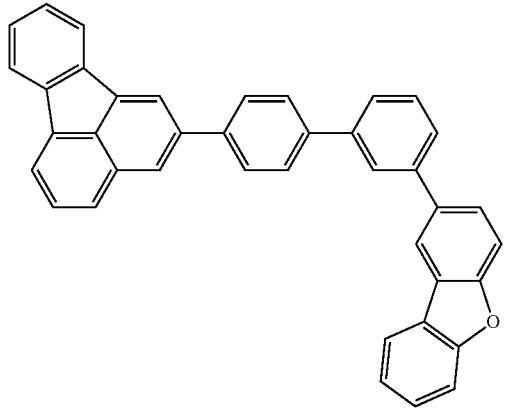
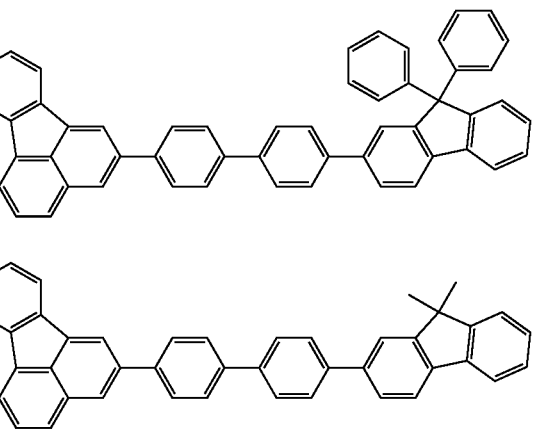

87
-continued
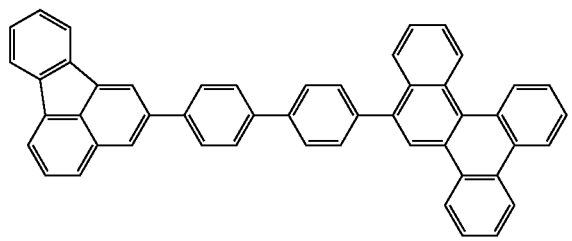
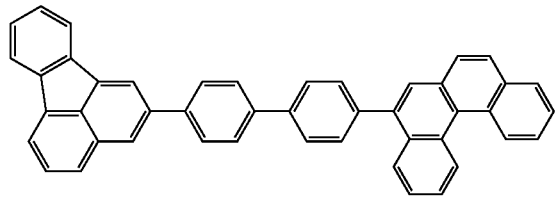
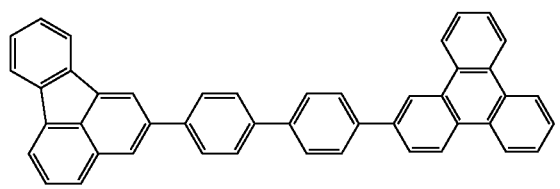
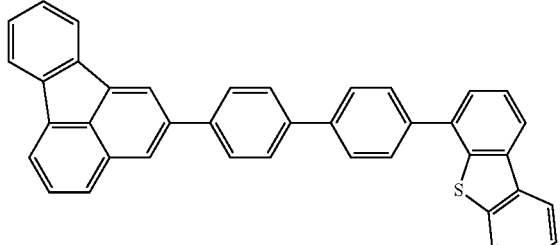
[Chem. 46]
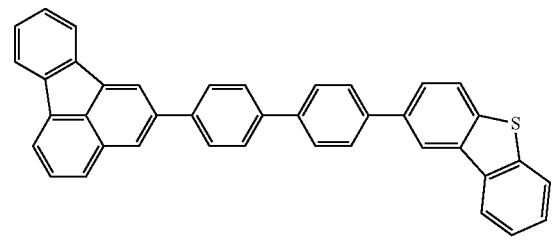
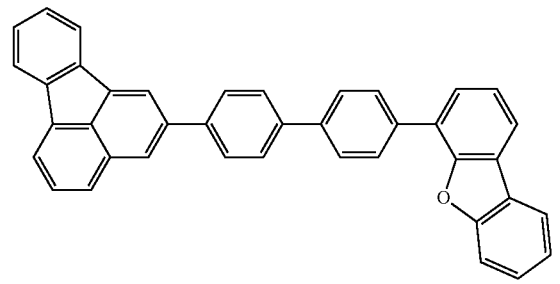
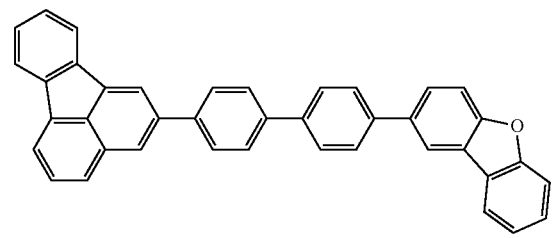
88
-continued
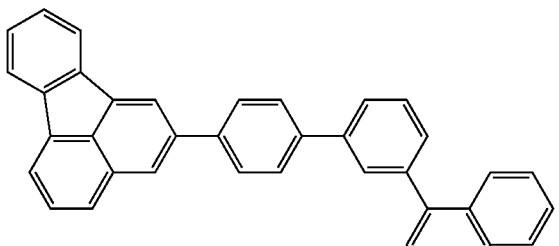
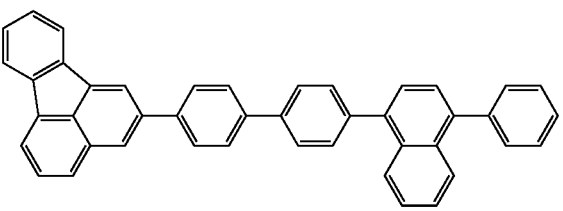
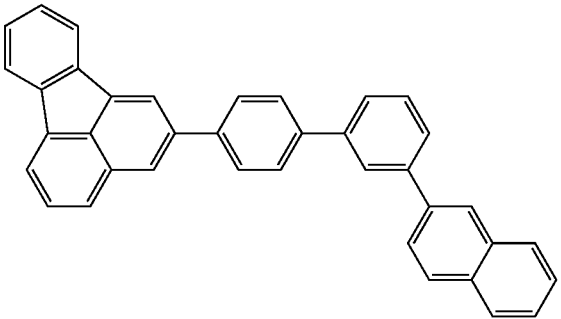
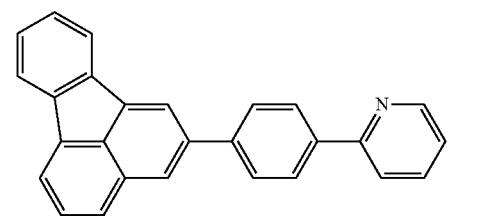
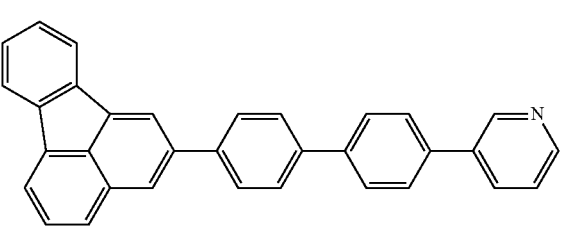
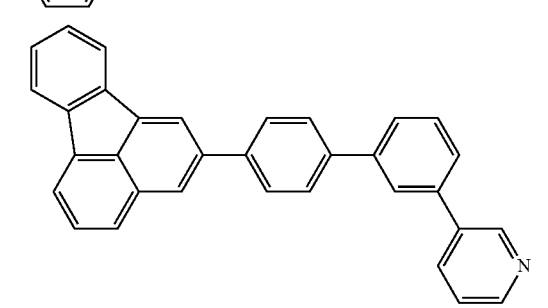

89
-continued
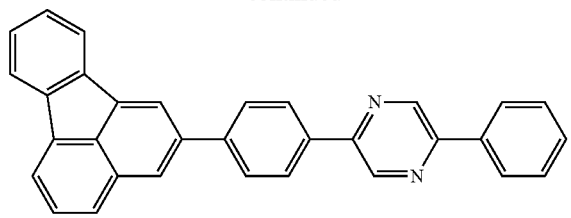
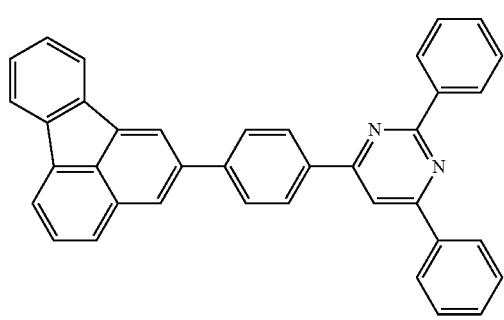
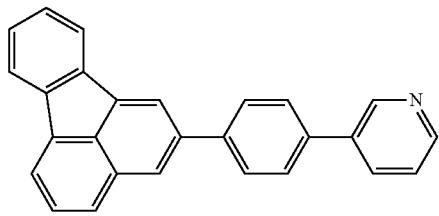
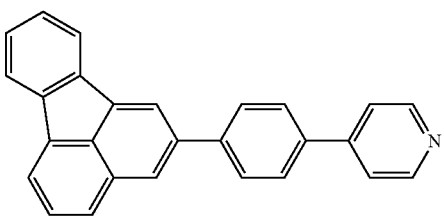
[Chem. 47]
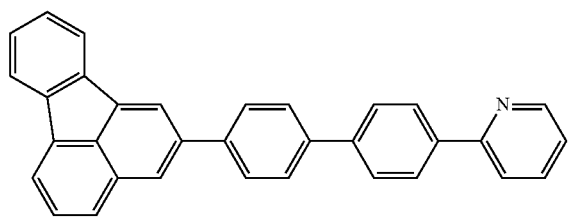
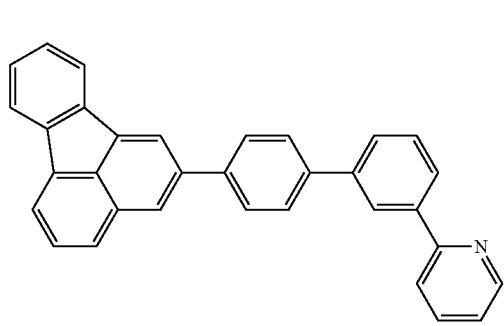
90
-continued
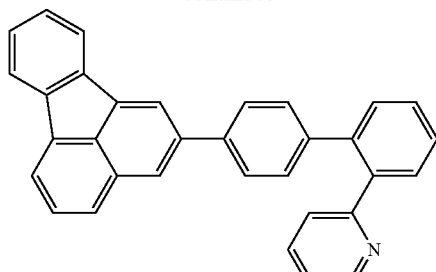
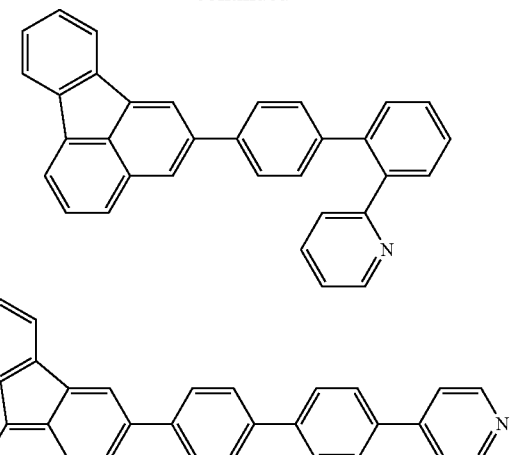
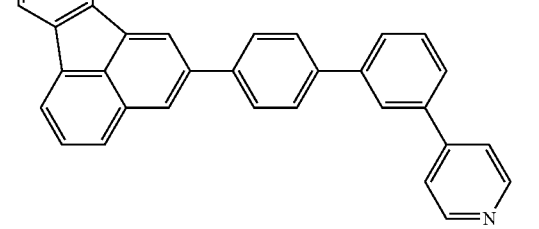
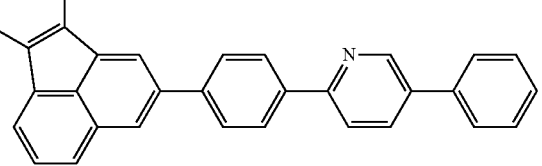
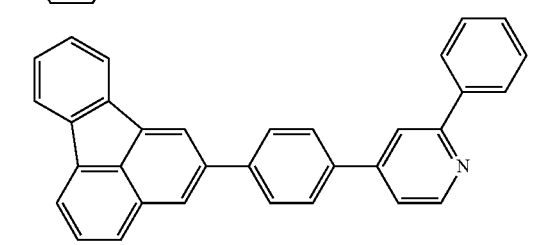
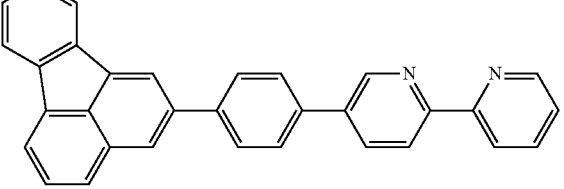

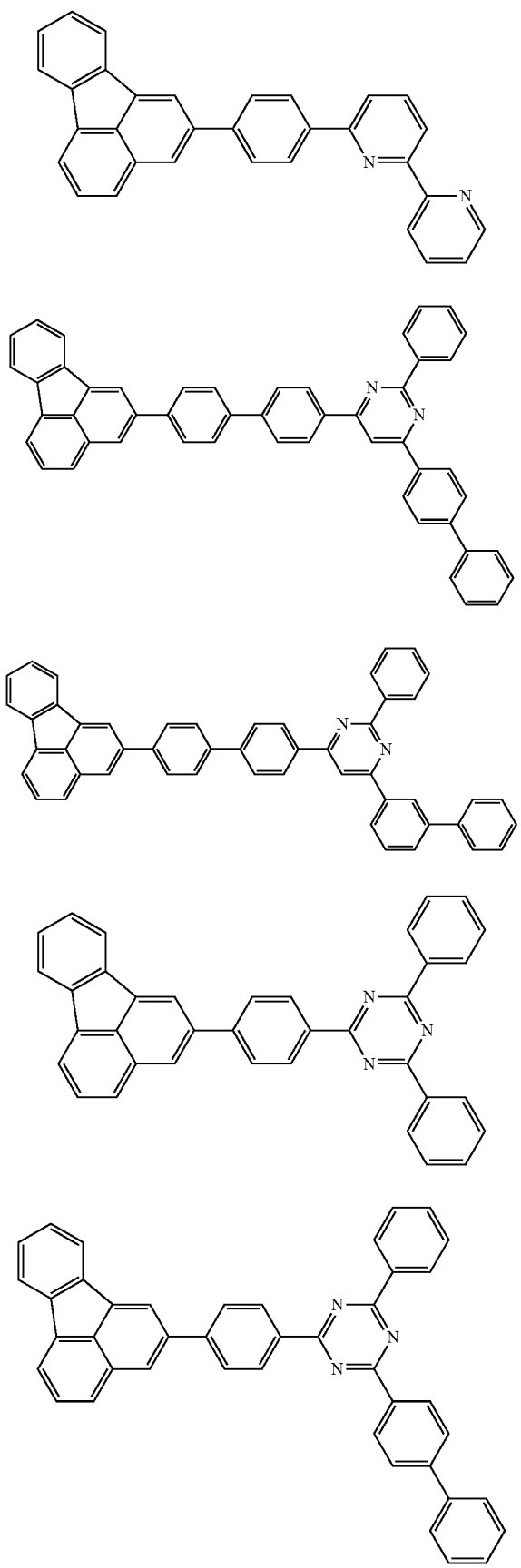
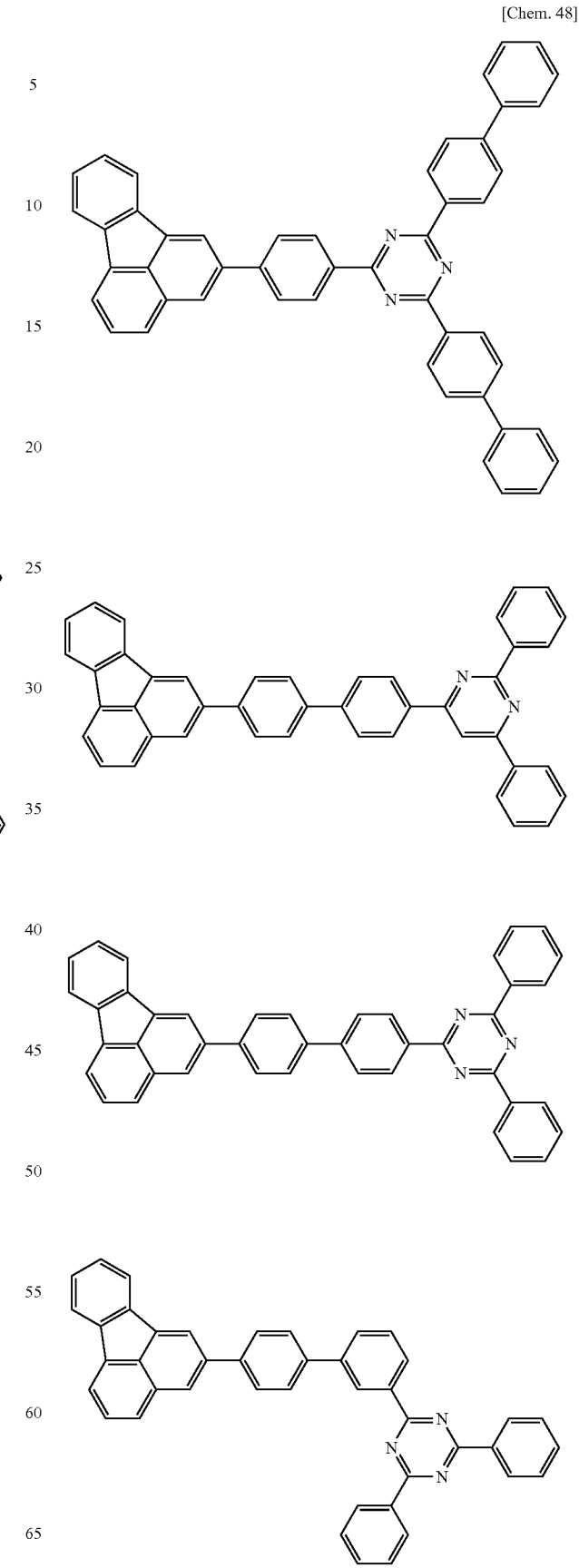

93
-continued
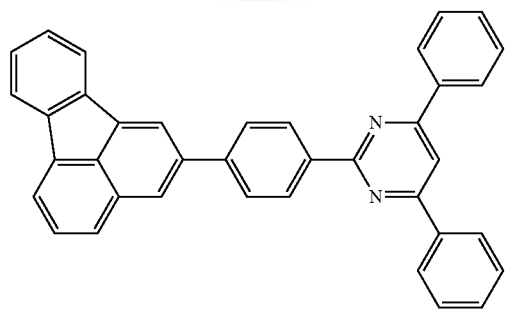
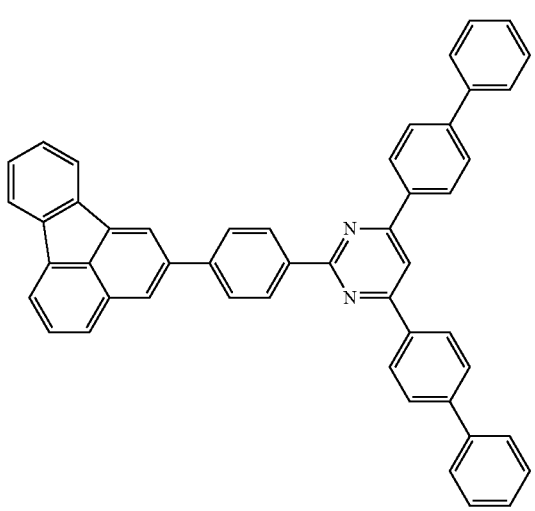
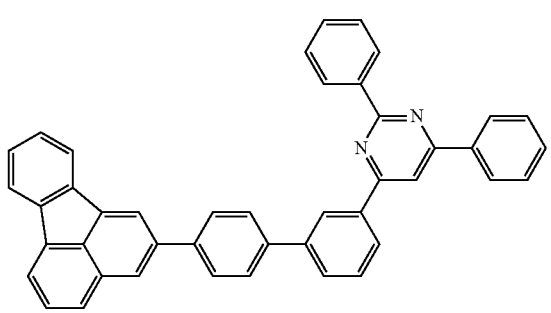
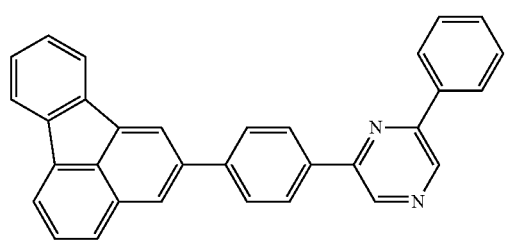
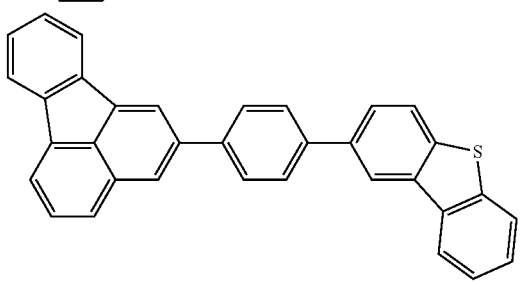
94
-continued
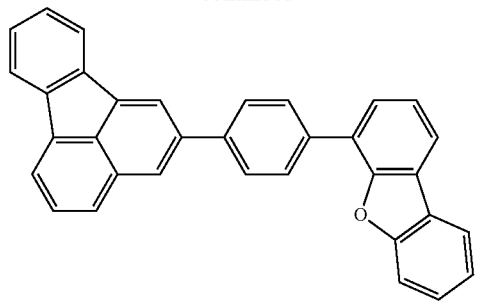
[Chem. 49]
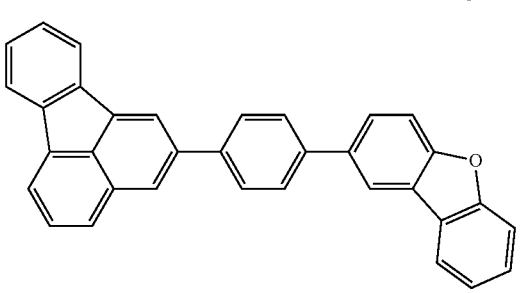
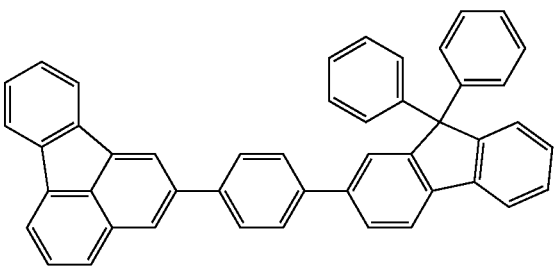
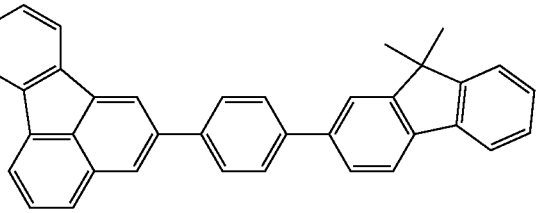
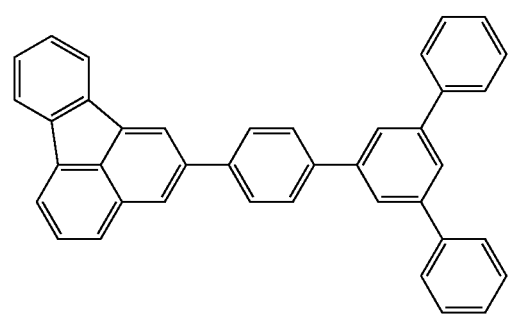

95
-continued
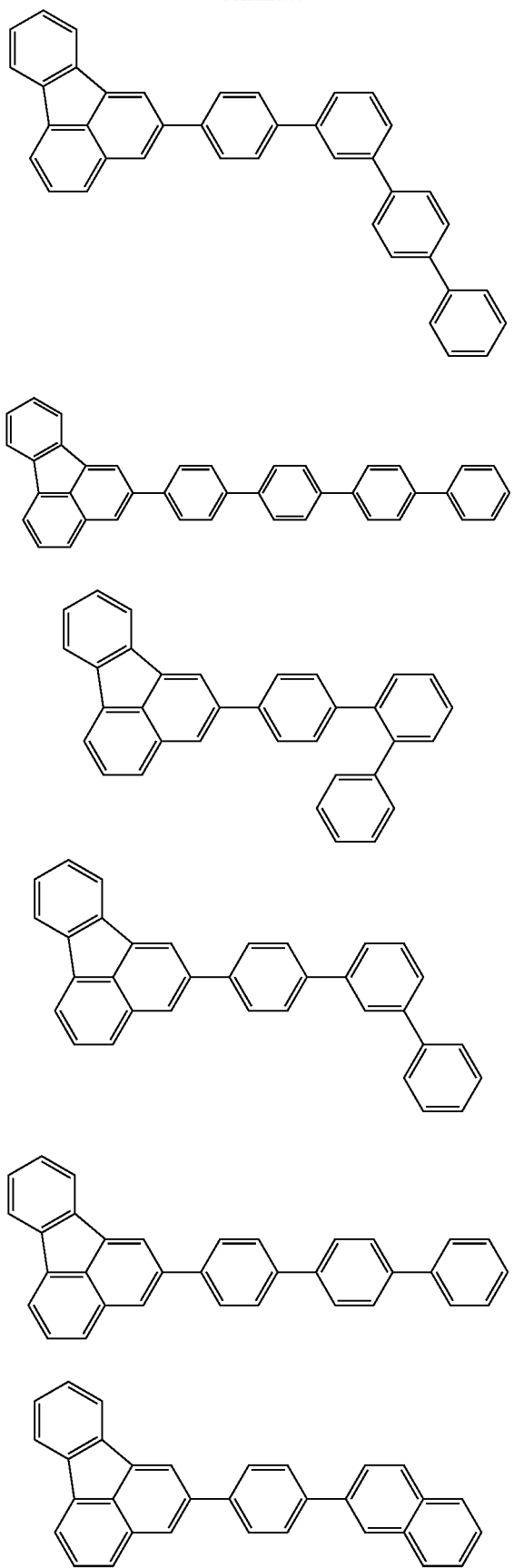
96
-continued
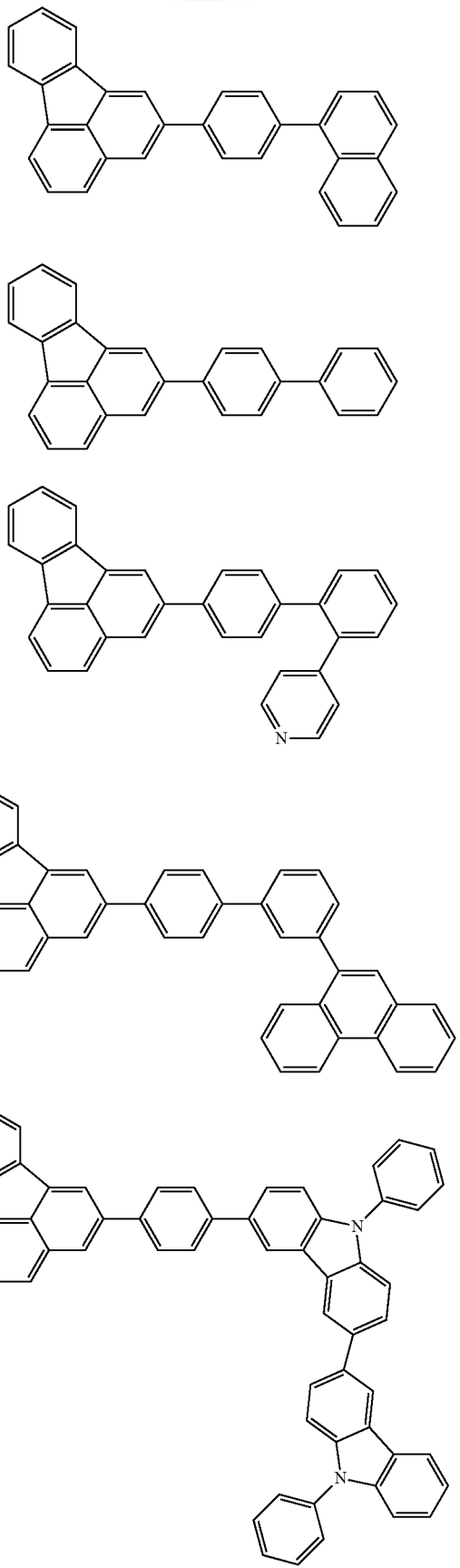

97
-continued
[Chem. 50]
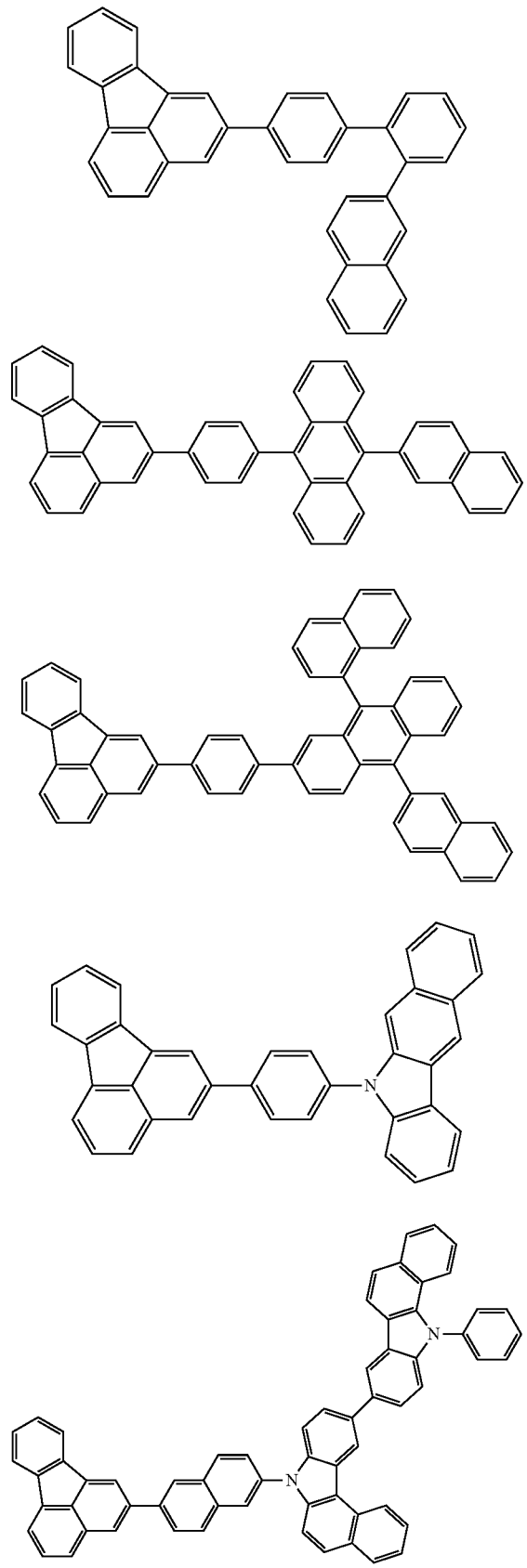
98
-continued
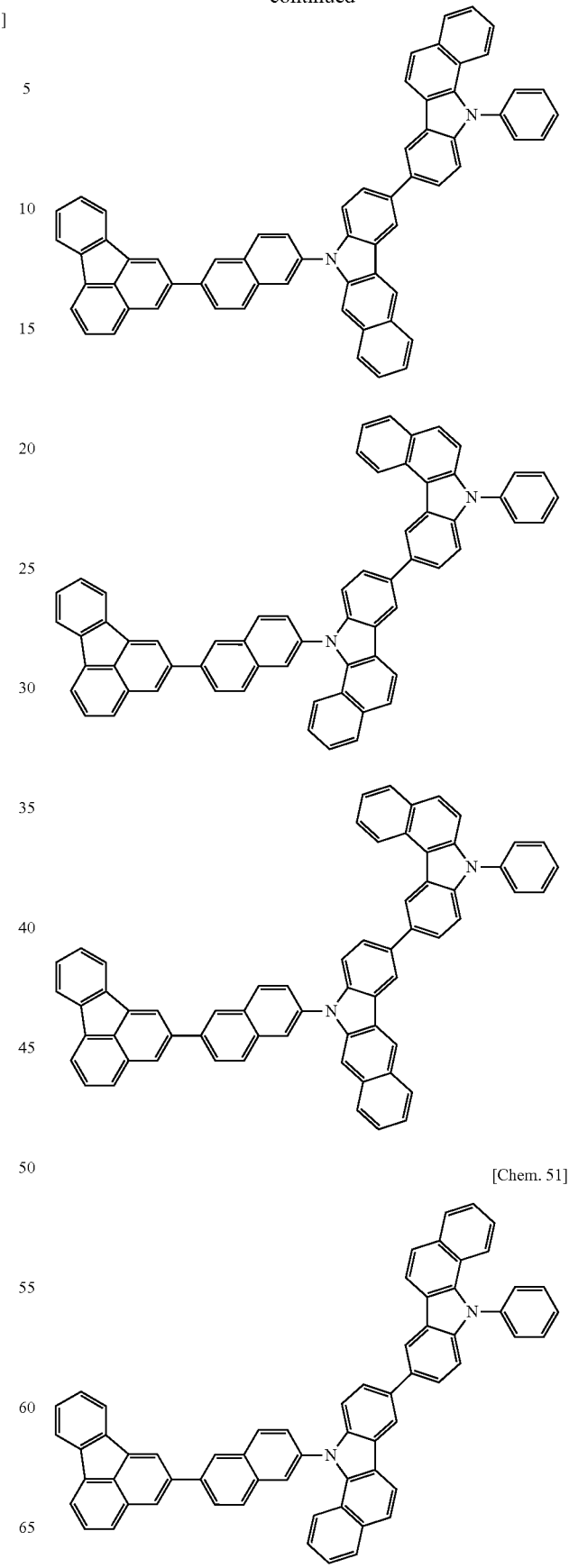
[Chem. 51]

99
-continued
100
-continued
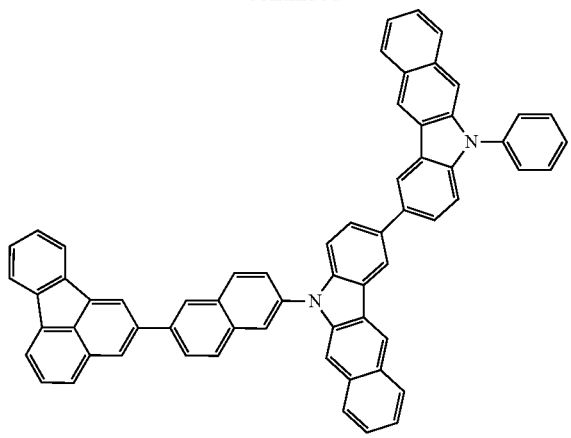
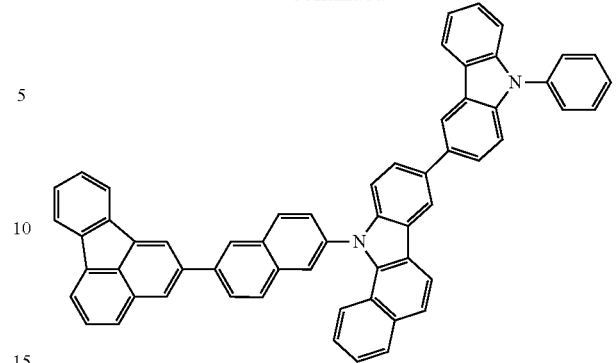
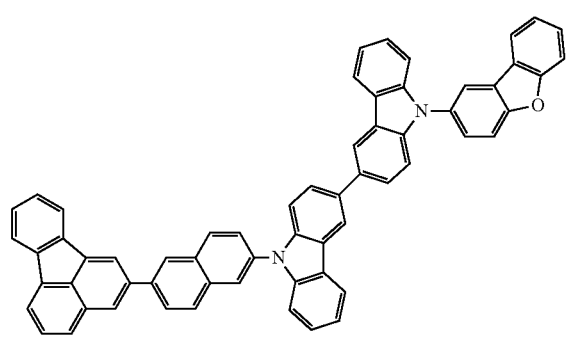
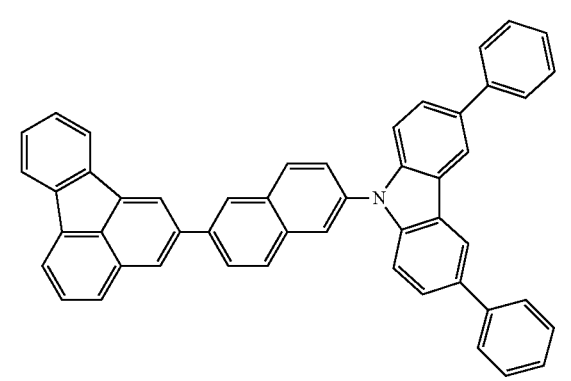
[Chem. 52]
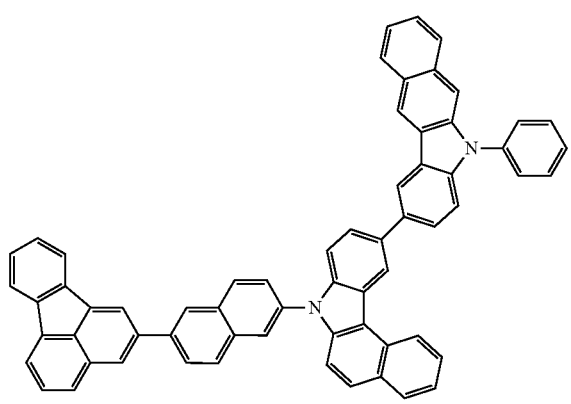

101
-continued
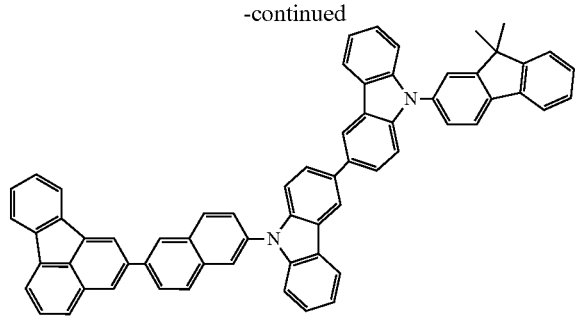
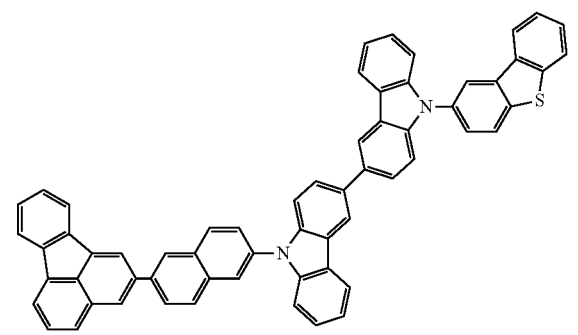
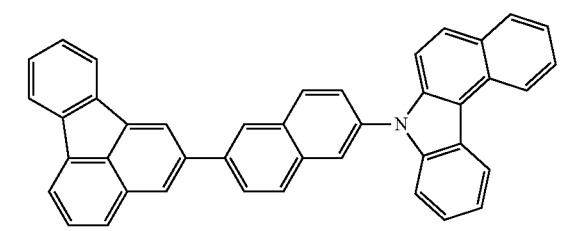
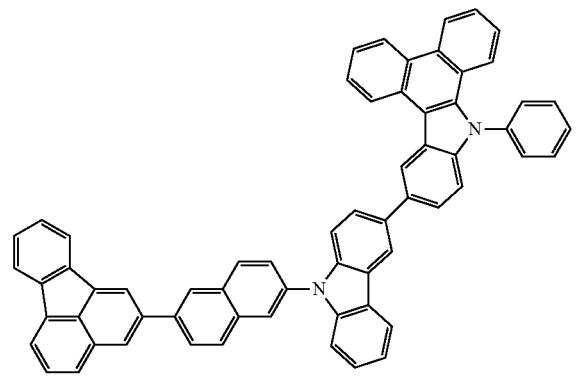
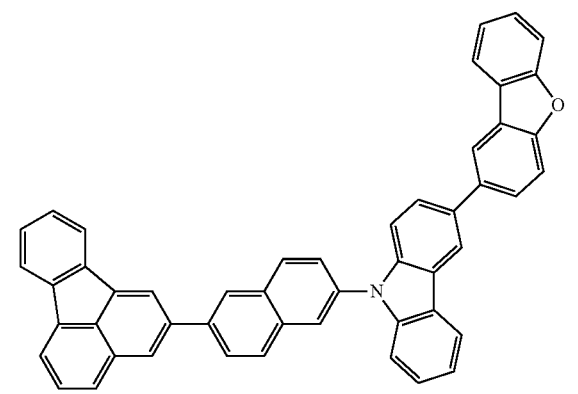
102
-continued
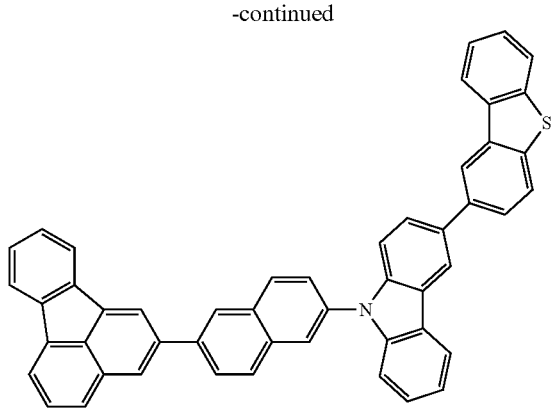
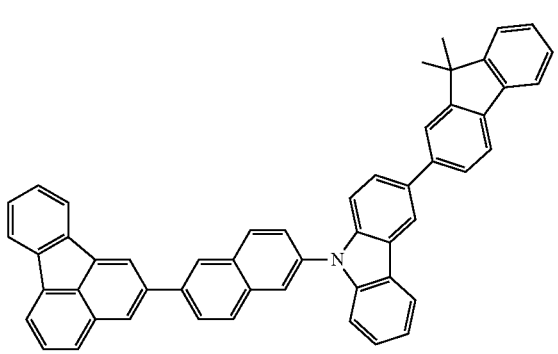
[Chem. 53]
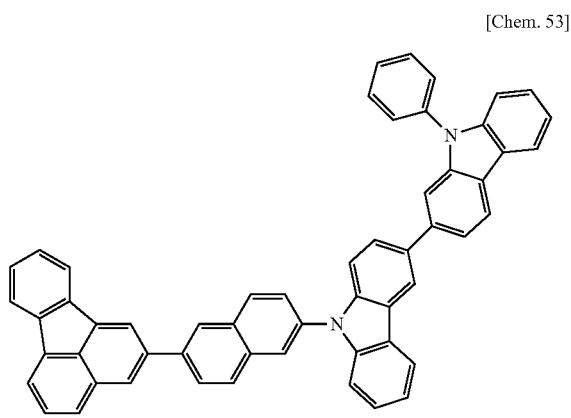
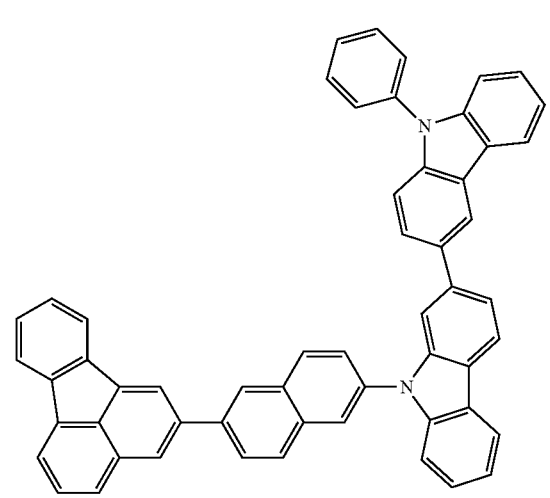

103
-continued
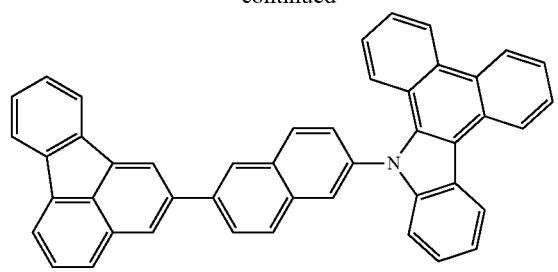
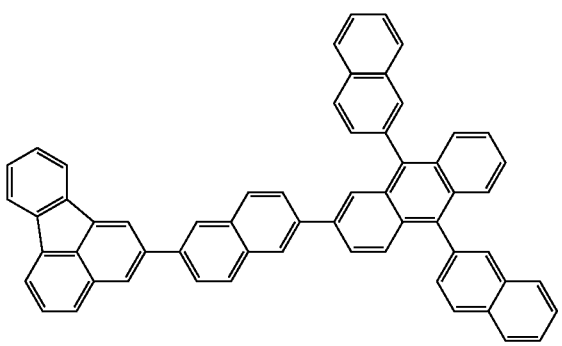
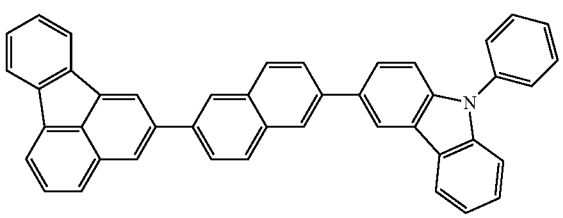
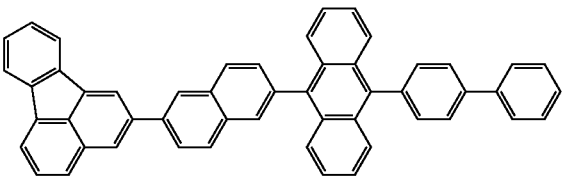
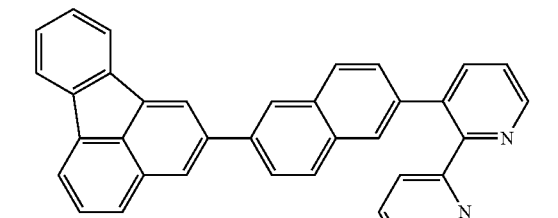
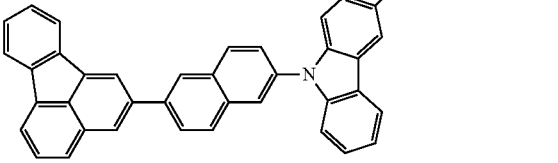
104
-continued
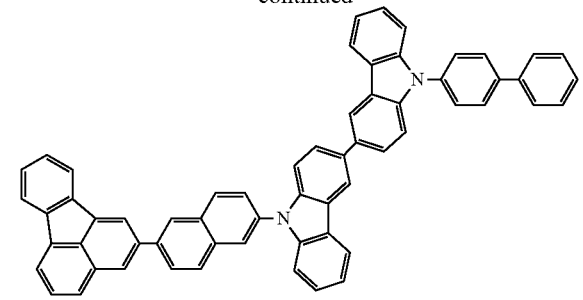
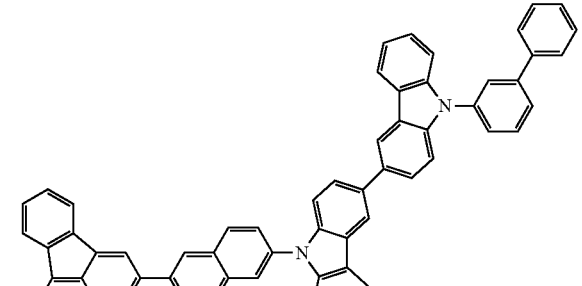
[Chem. 54]
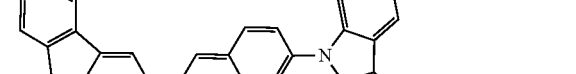
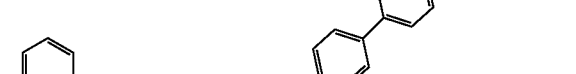
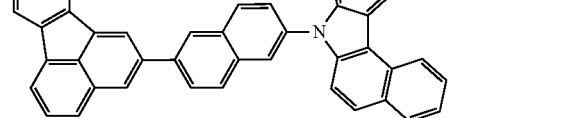

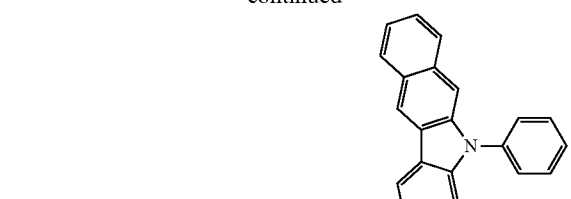
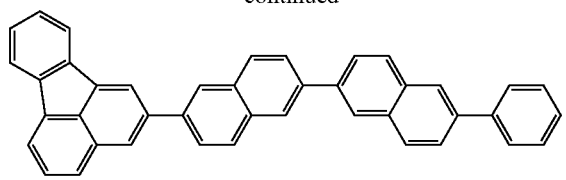
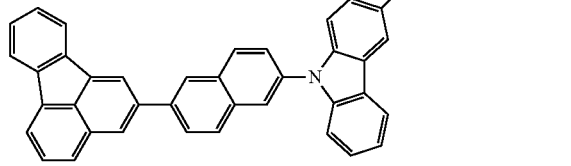
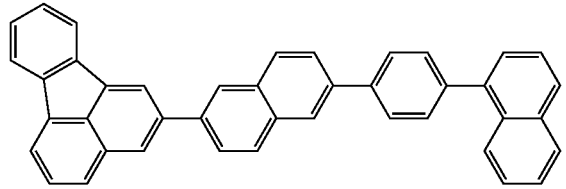
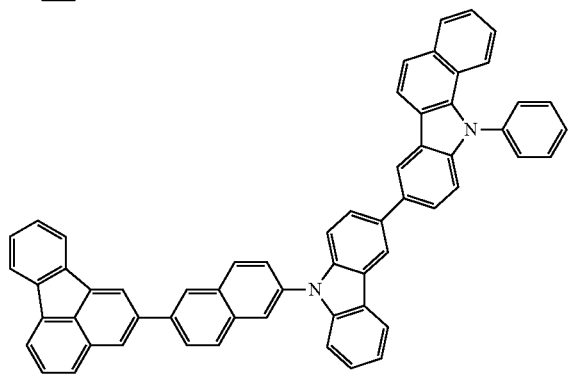
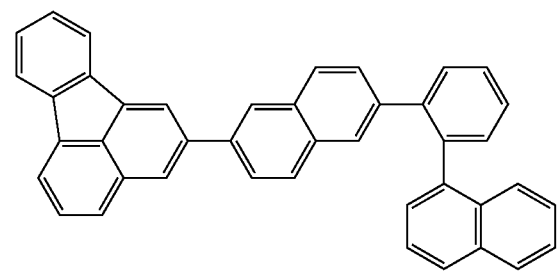
[Chem. 55]
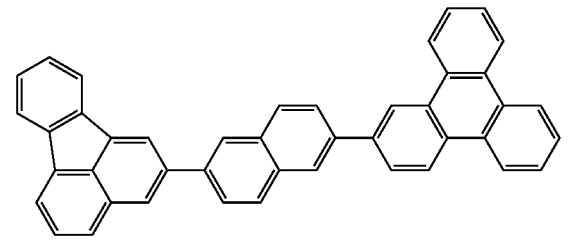
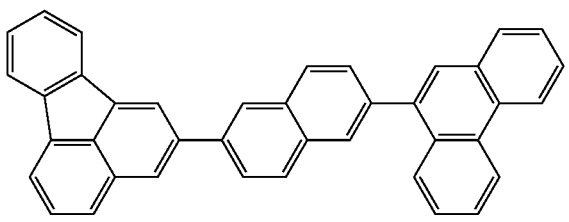
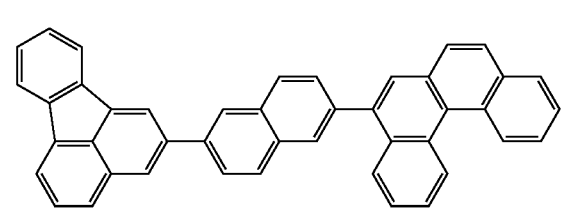
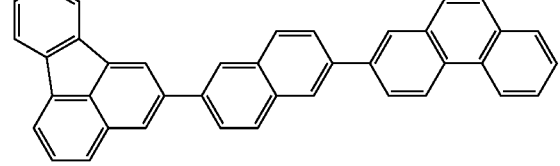
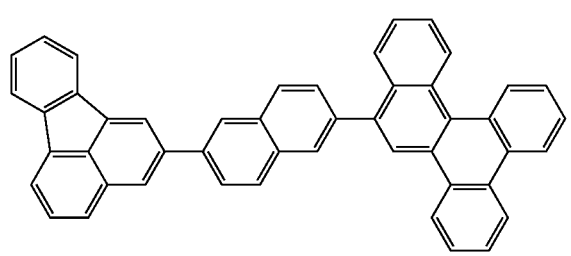
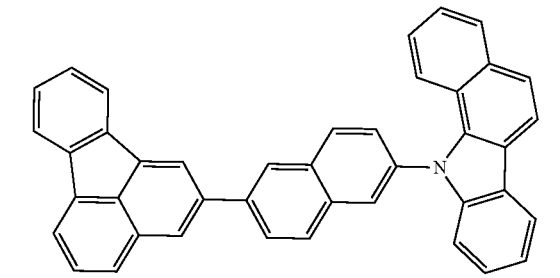
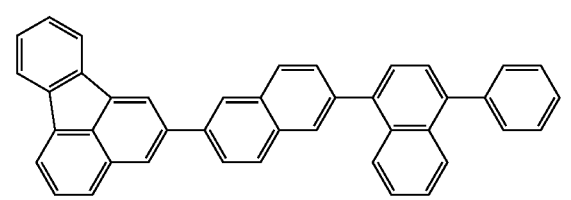
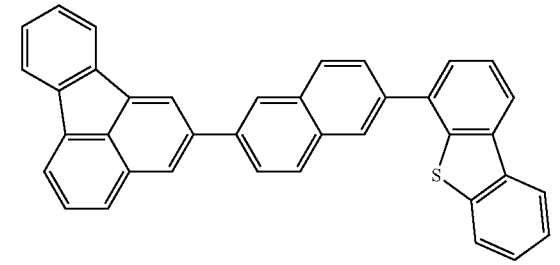

107
-continued
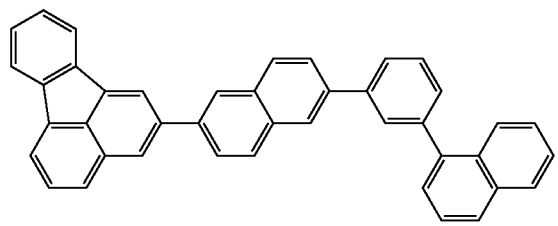
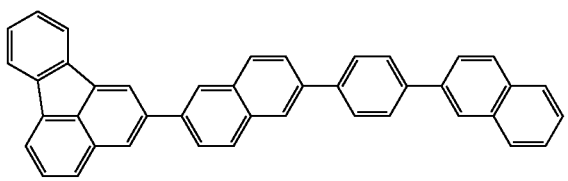
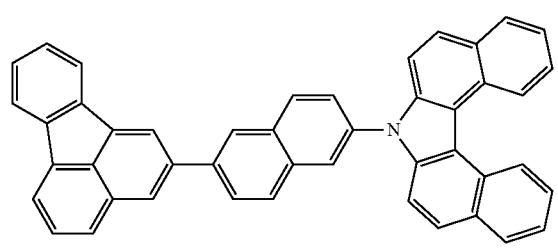
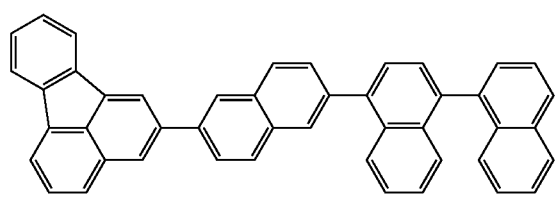
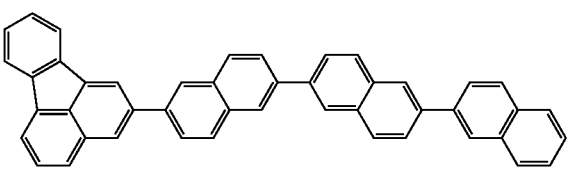
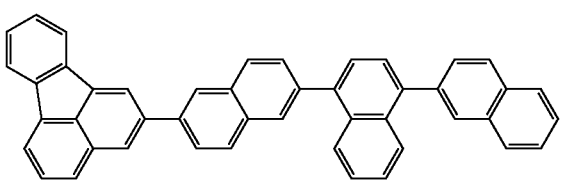
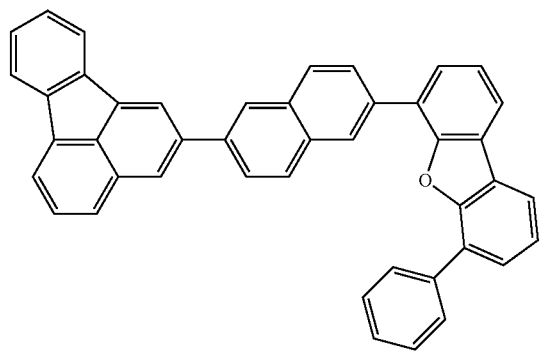
108
-continued
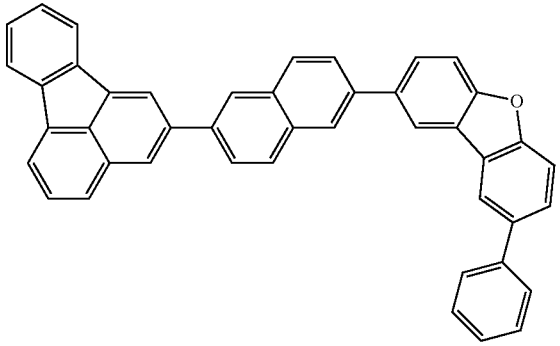
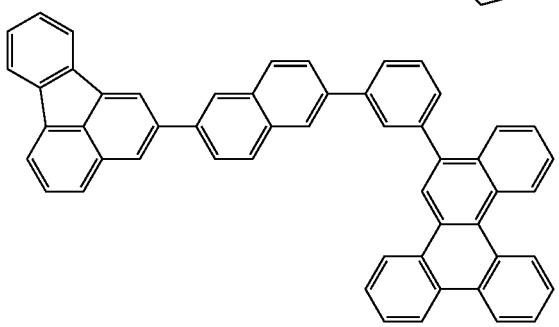
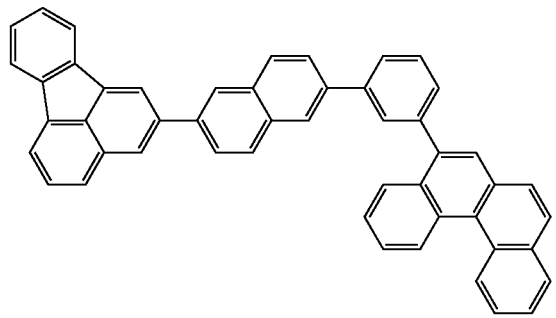
[Chem. 56]
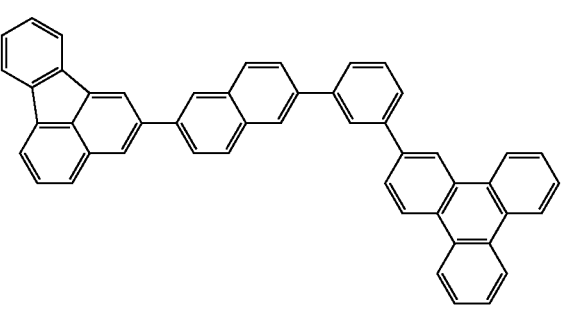
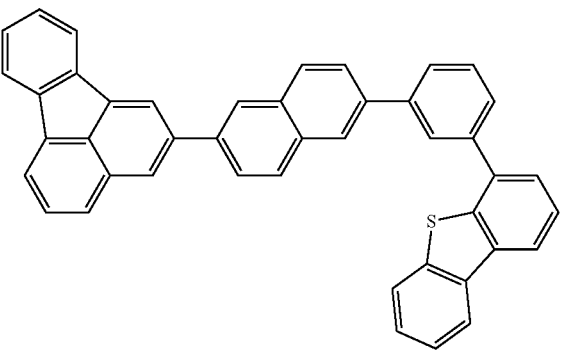

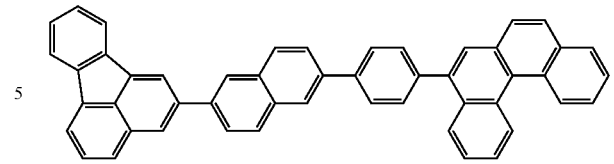
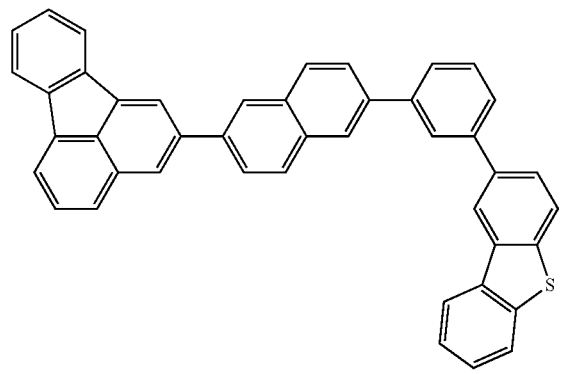
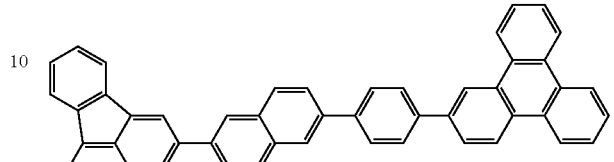
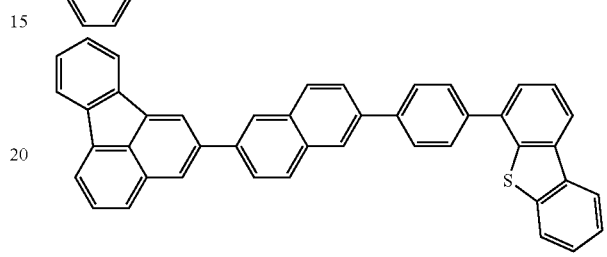
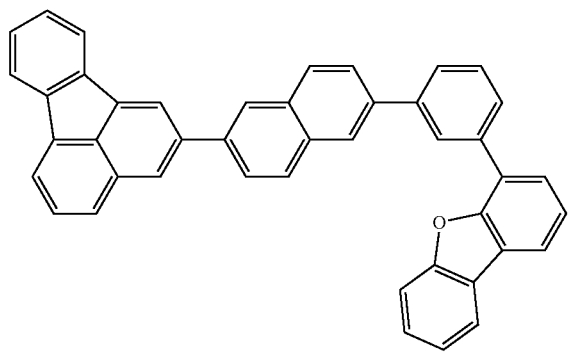
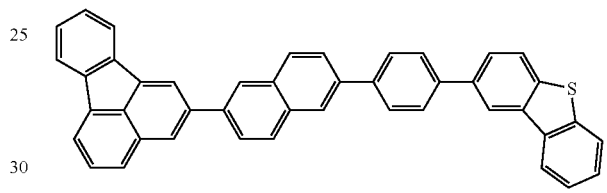
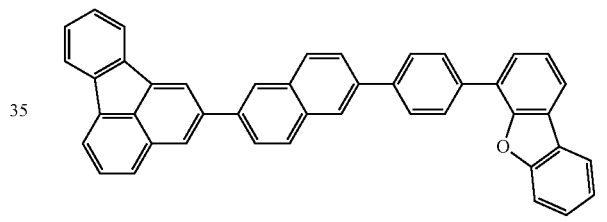
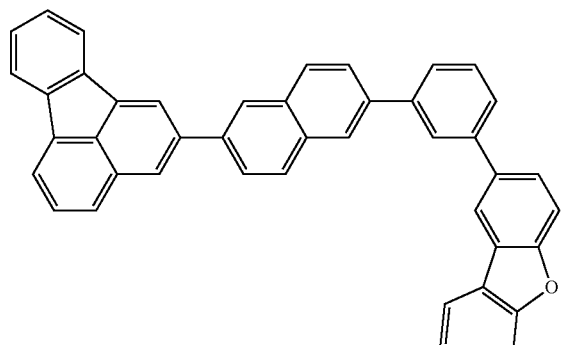
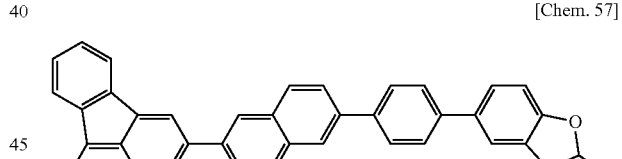
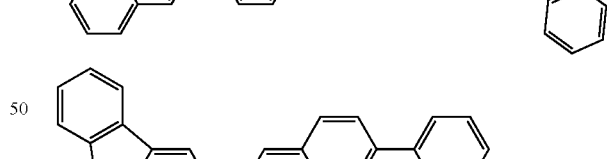
[Chem. 57]
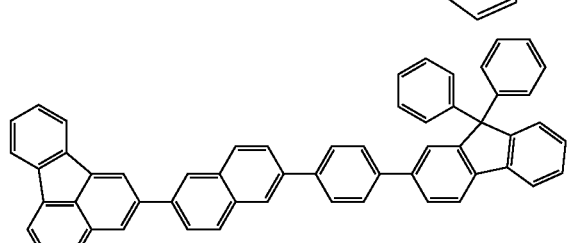
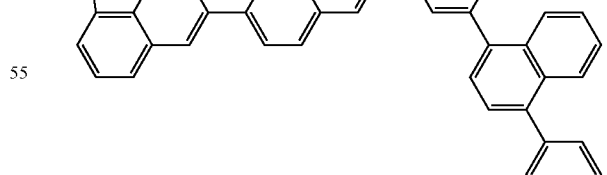
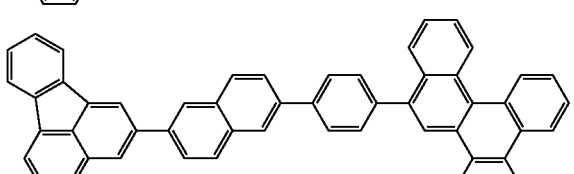
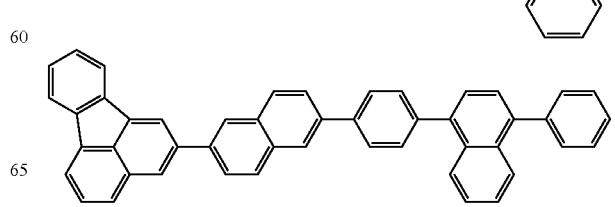
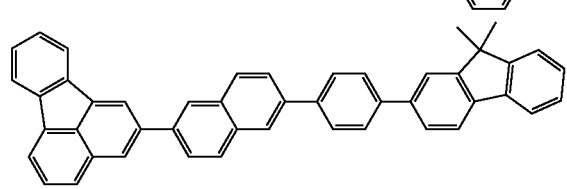

111
-continued
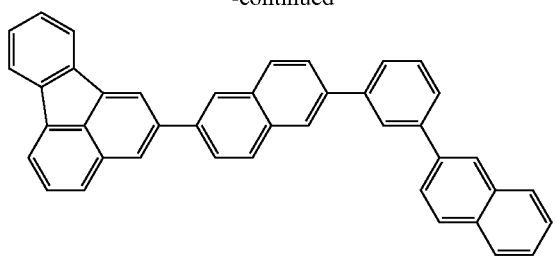
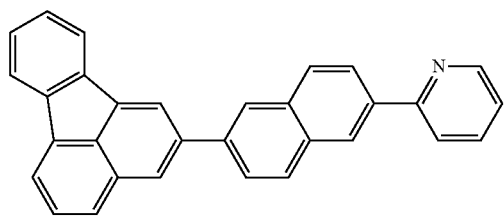
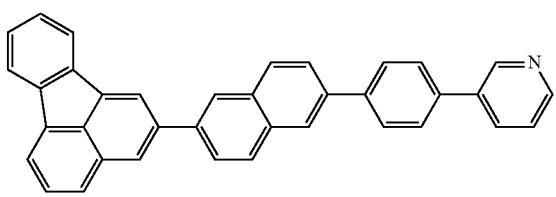
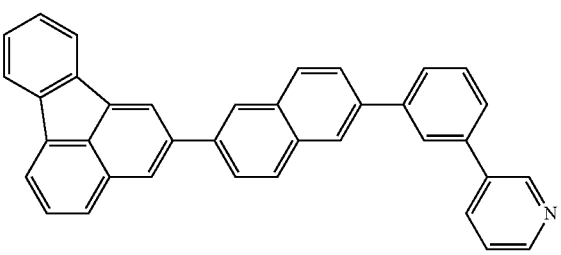
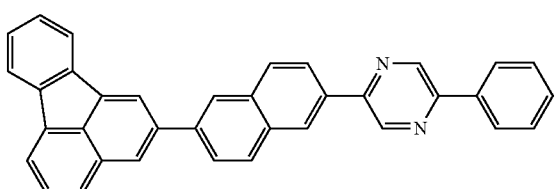
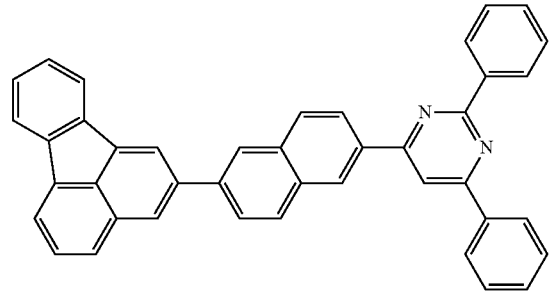
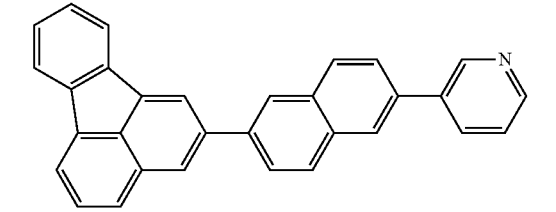
112
-continued
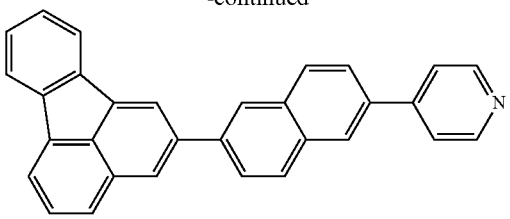
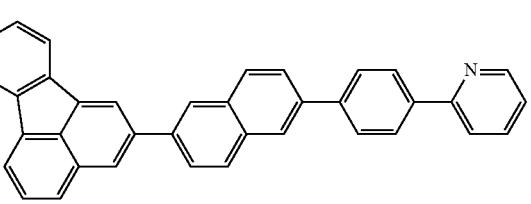
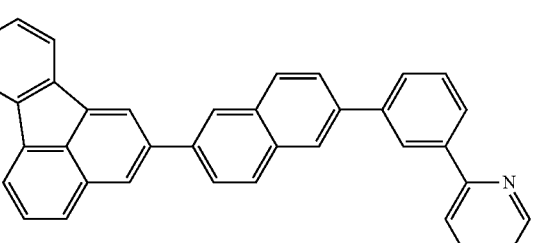
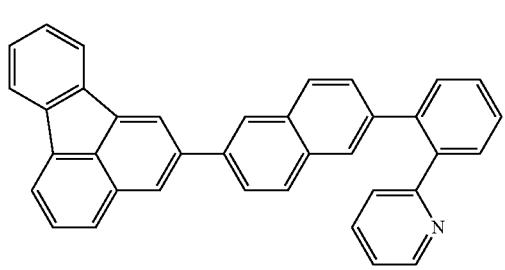
[Chem. 58]
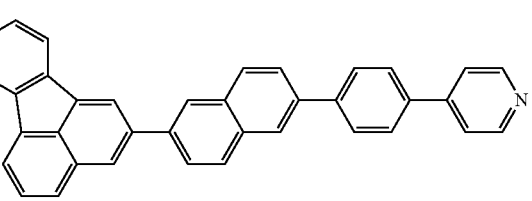
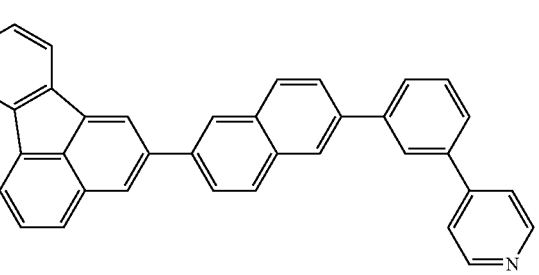
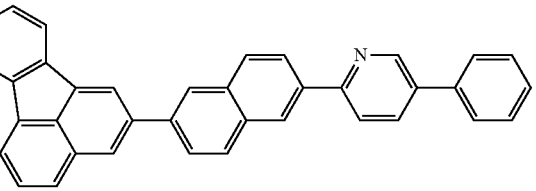

113
-continued
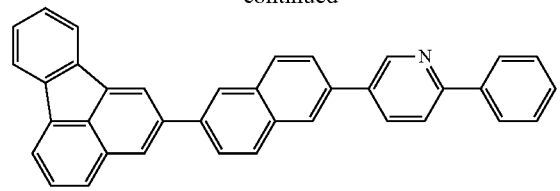
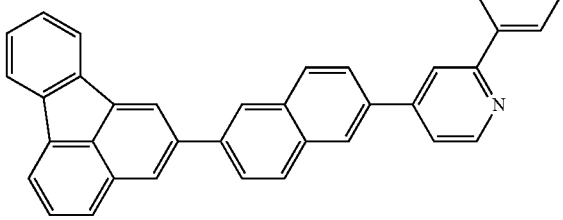
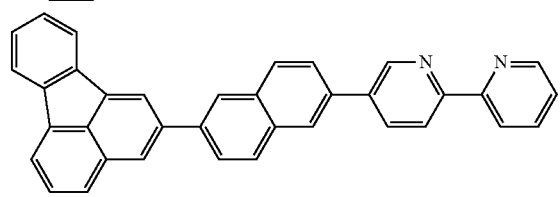
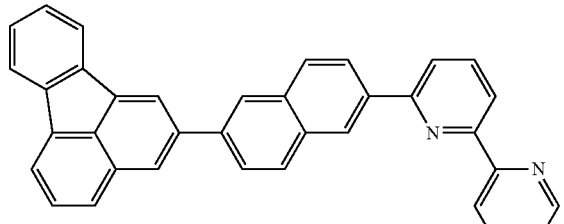
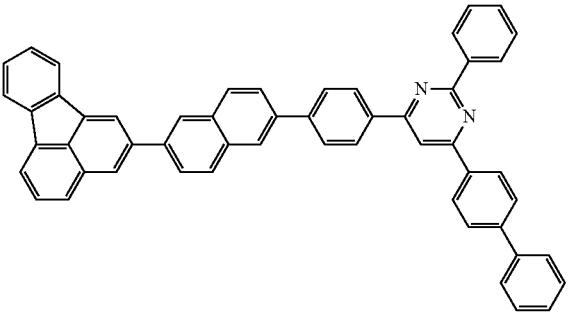
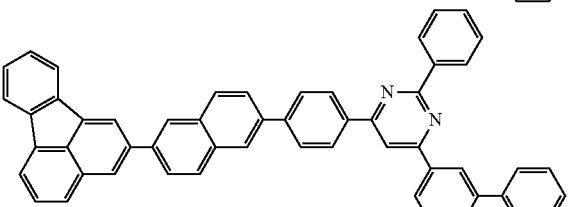
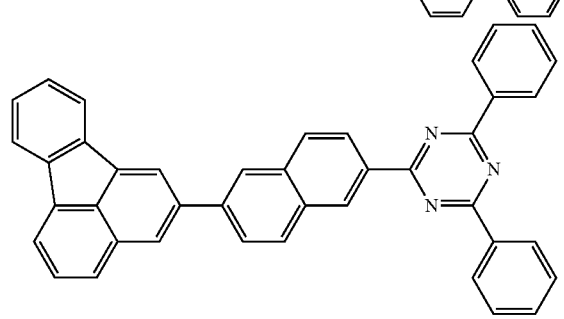
114
-continued
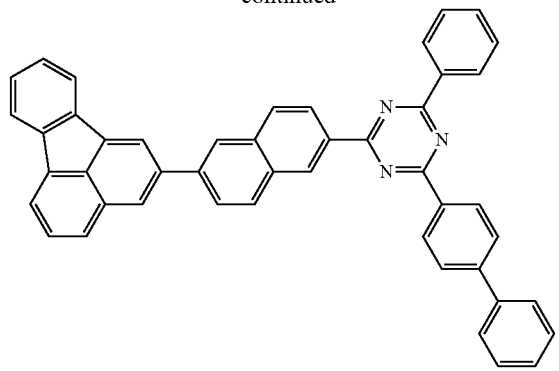
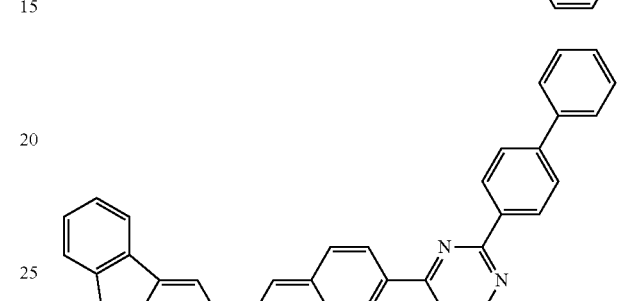
[Chem. 59]
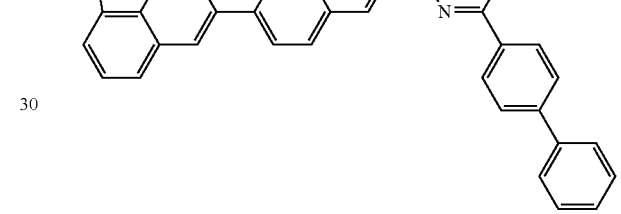
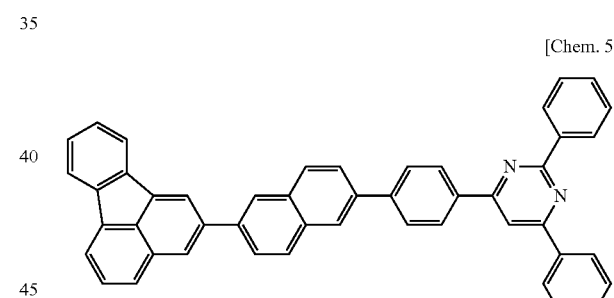
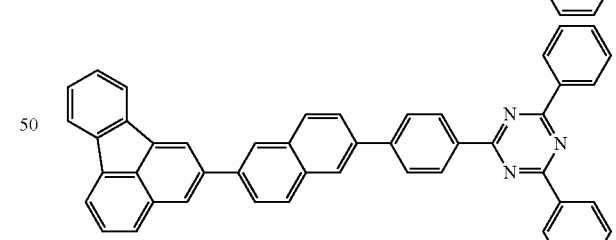
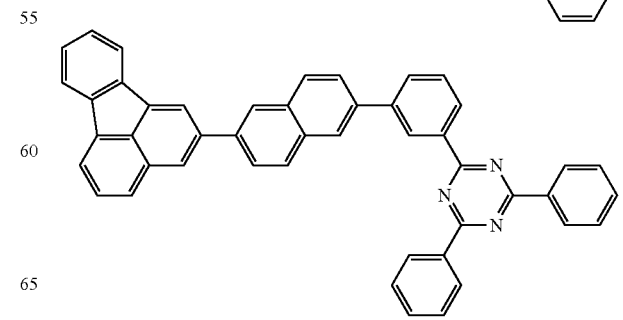

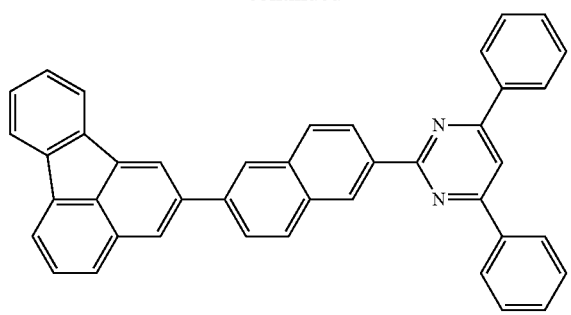
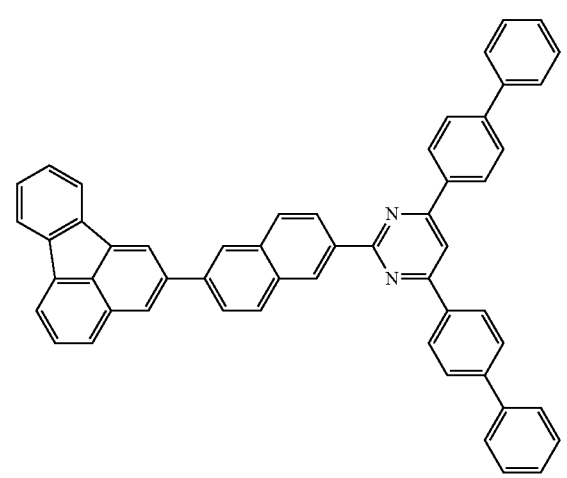
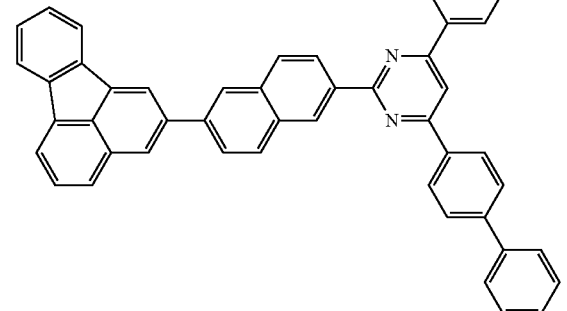
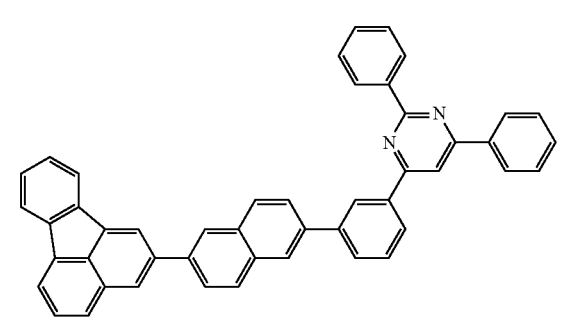
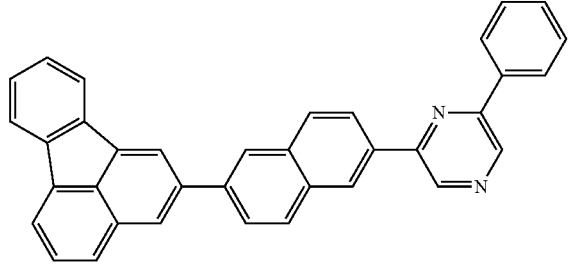
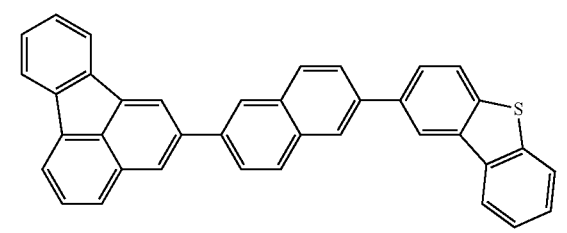
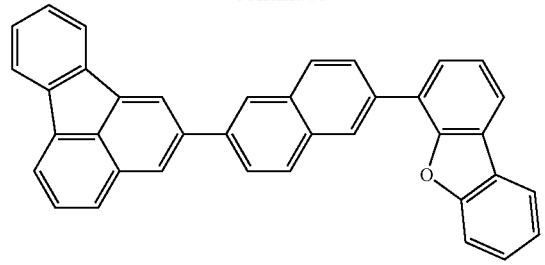
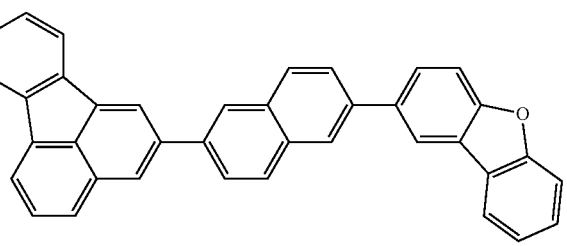
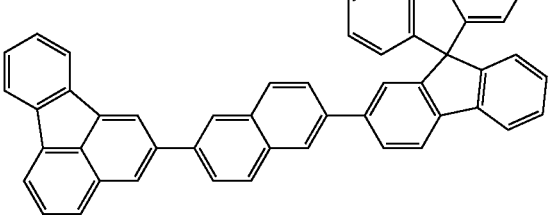
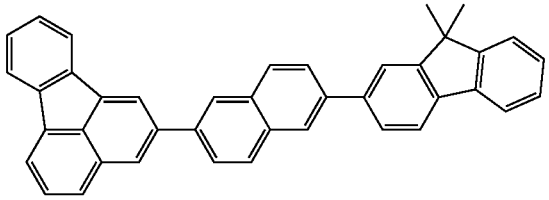
[Chem. 60]
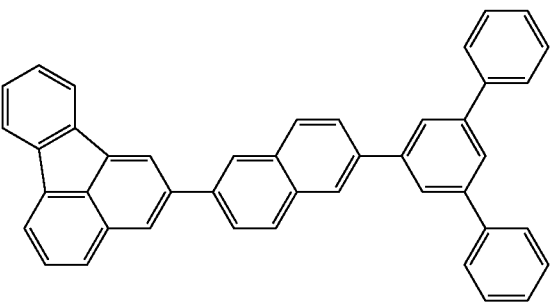
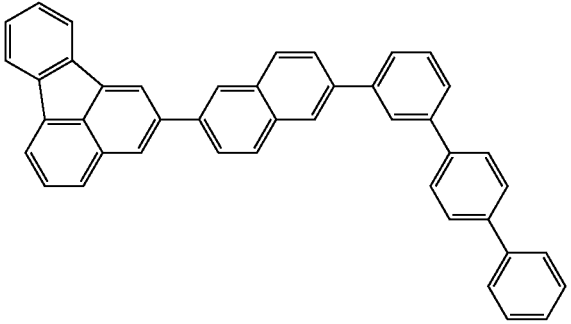

117
-continued
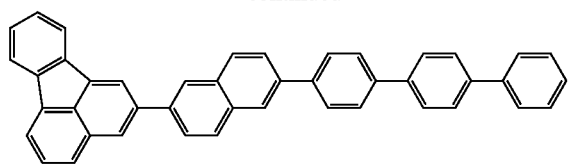
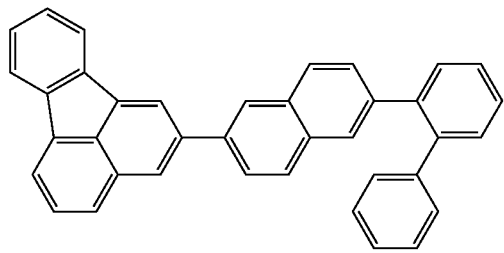
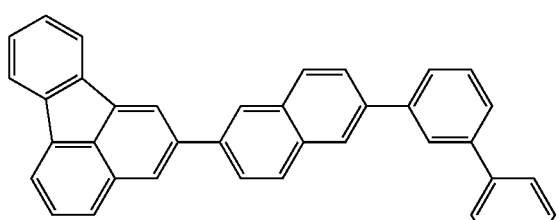
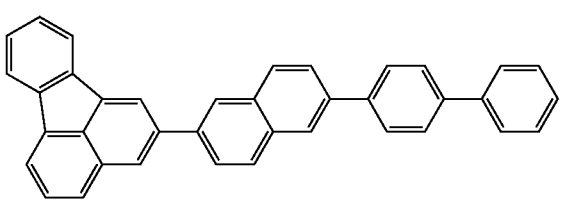
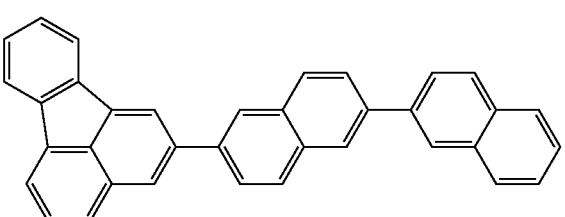
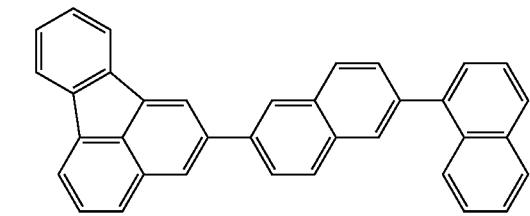
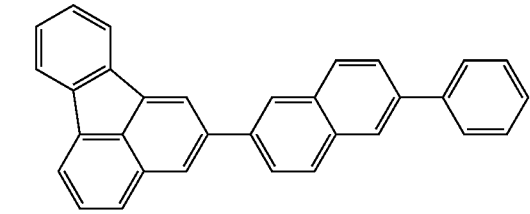
118
-continued
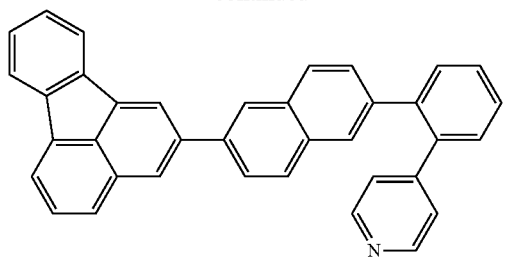
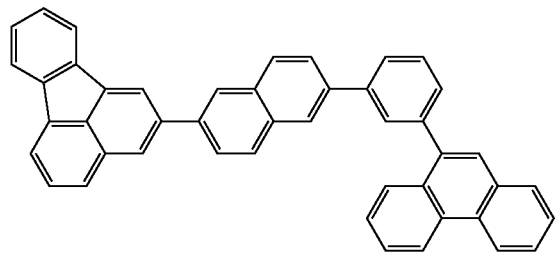
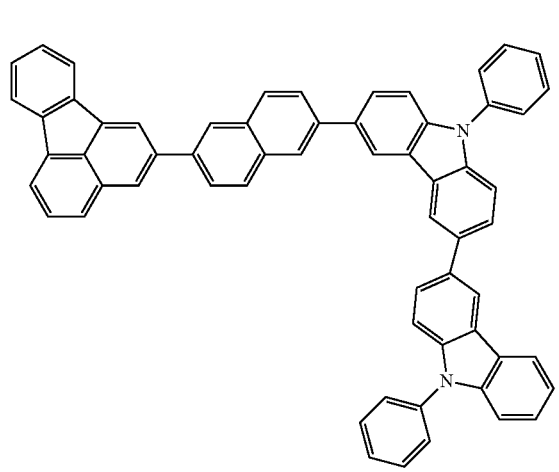
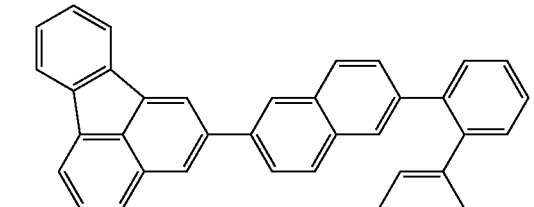
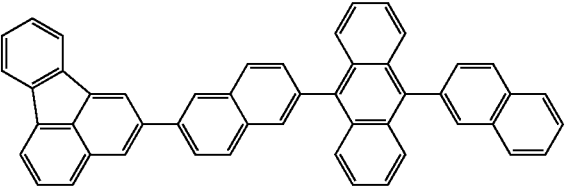

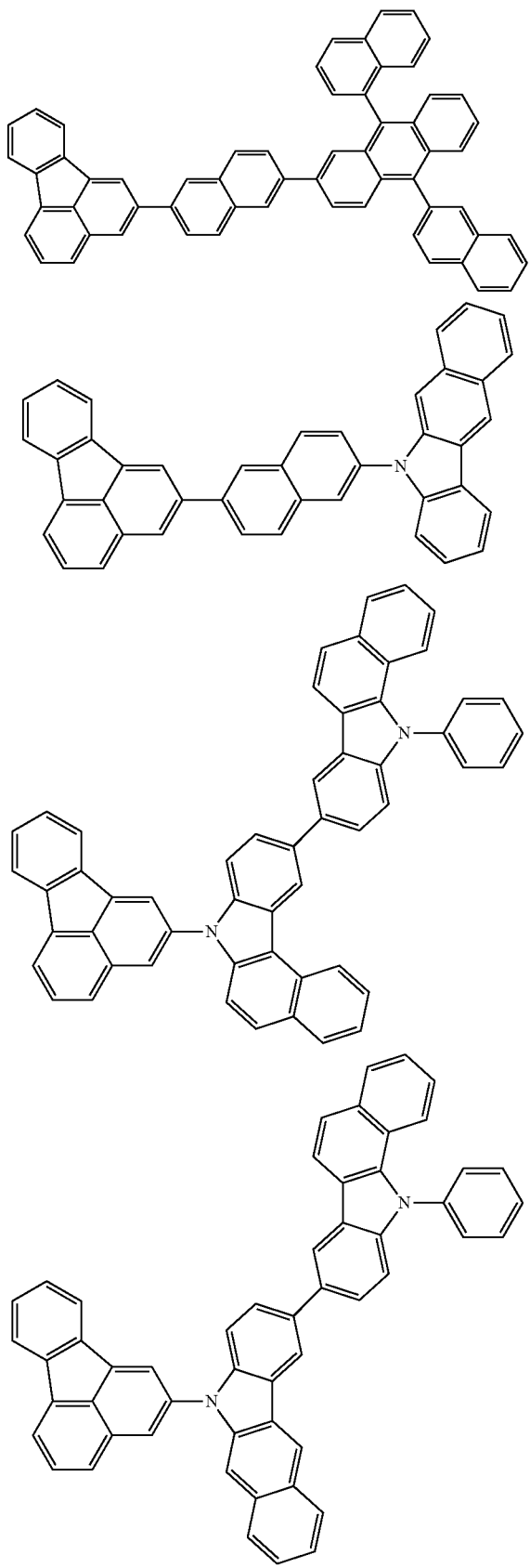
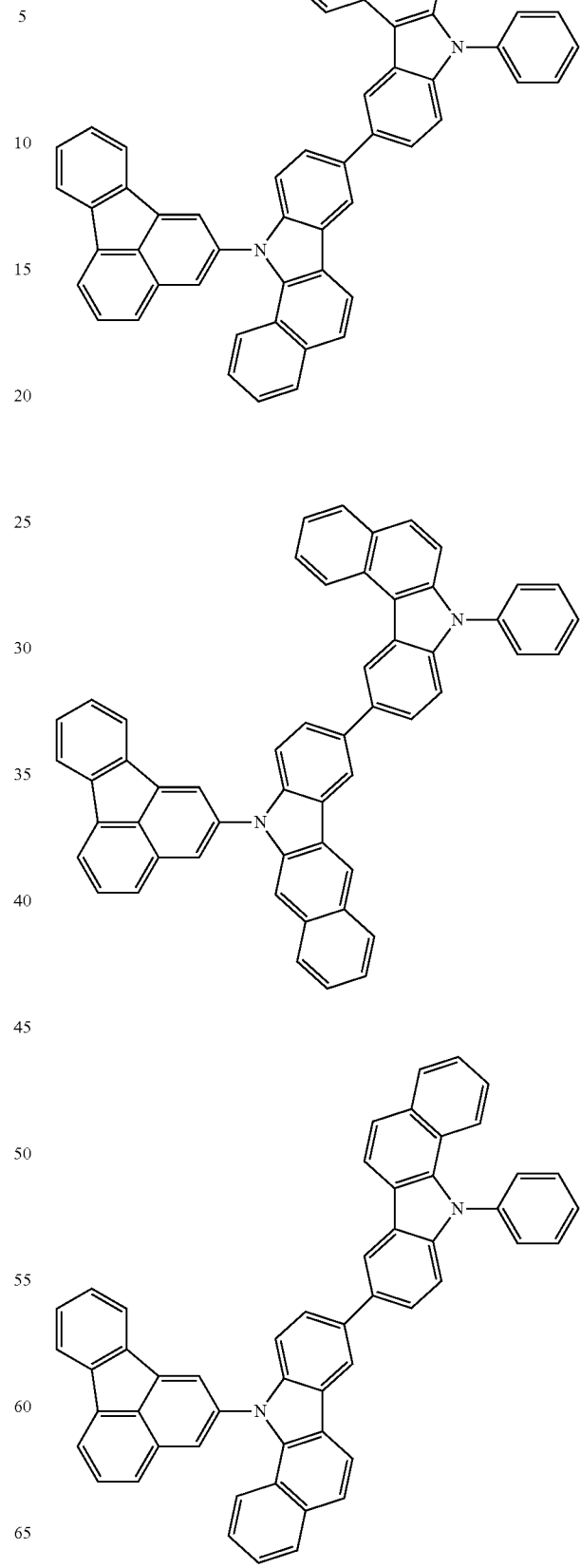

121
-continued
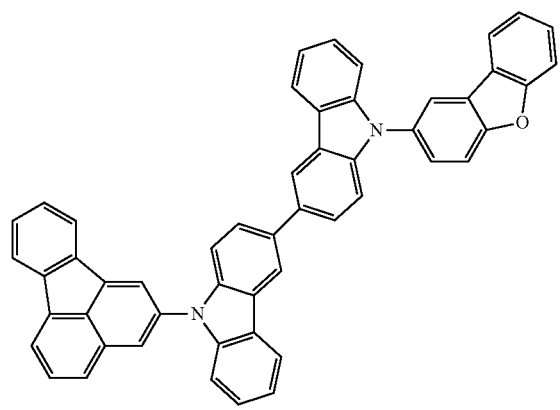
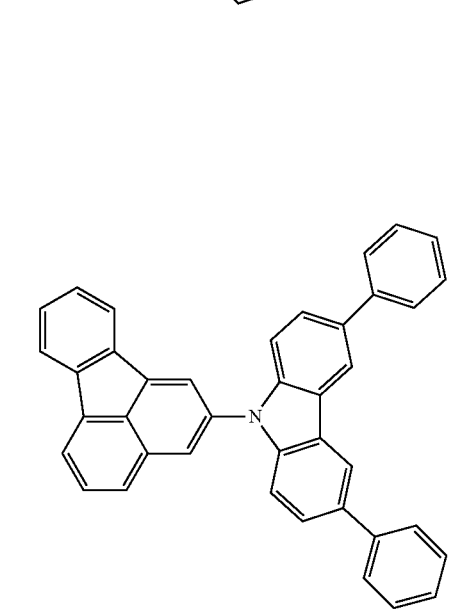
122
-continued
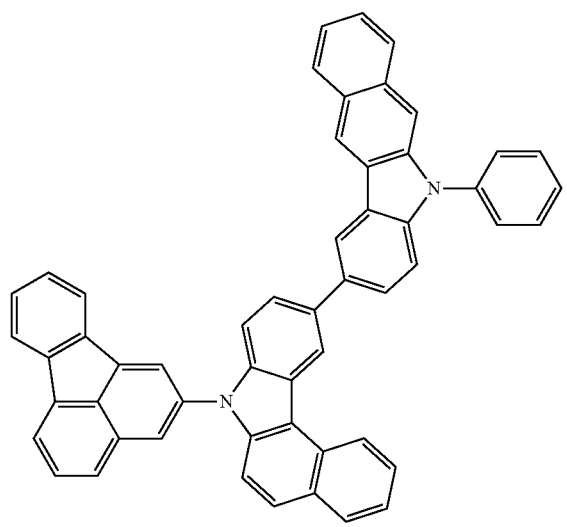
[Chem. 62]
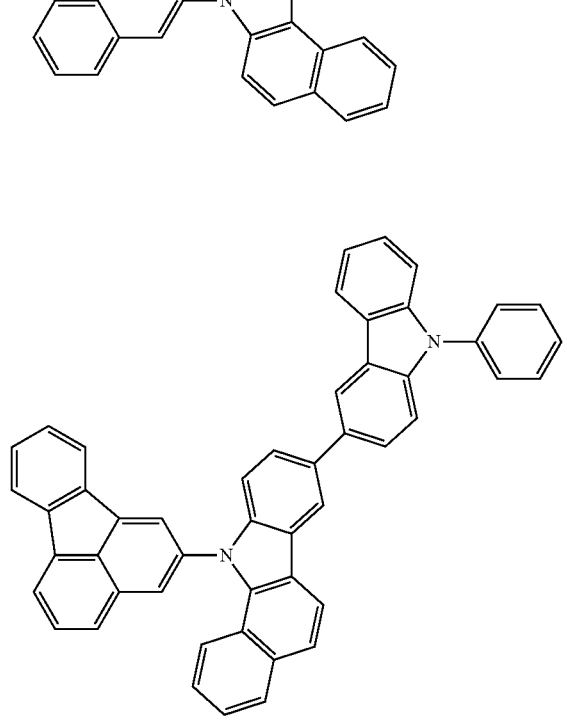
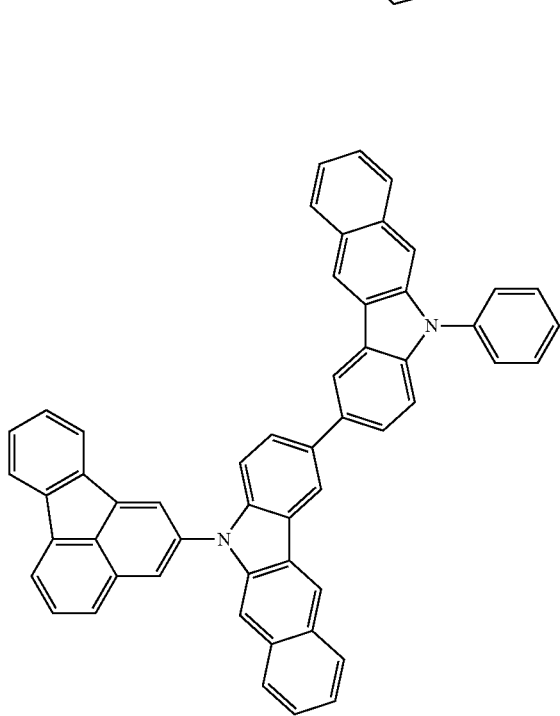

123
-continued
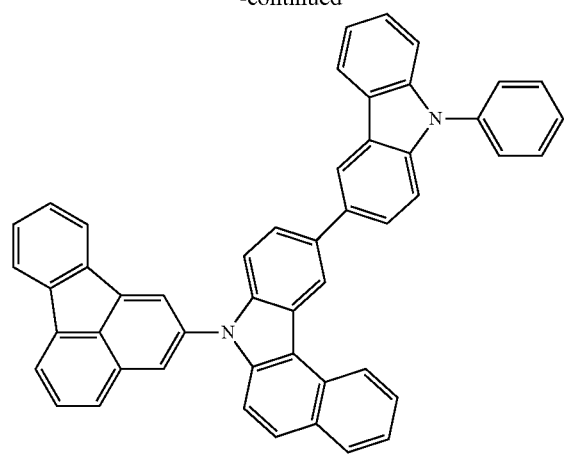
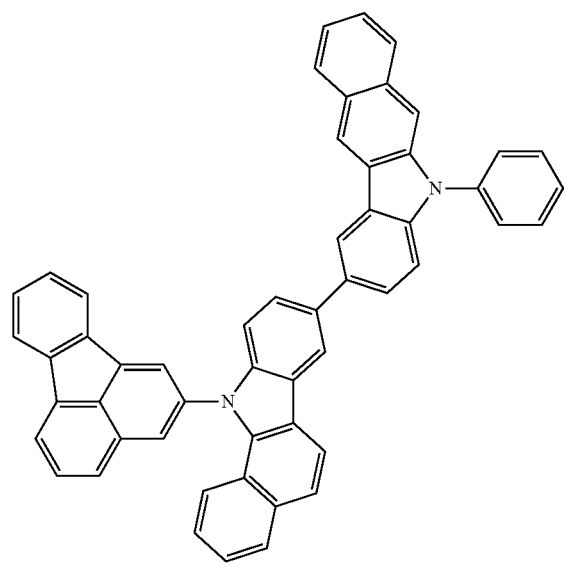
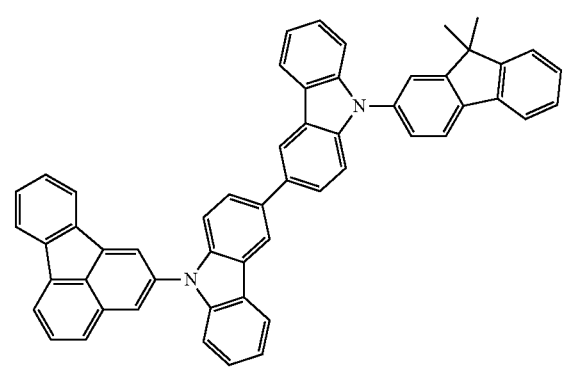
124
-continued
[Chem. 63]
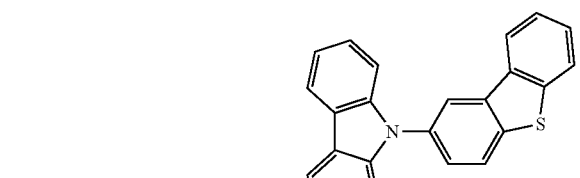
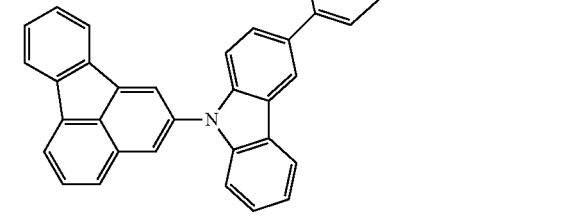
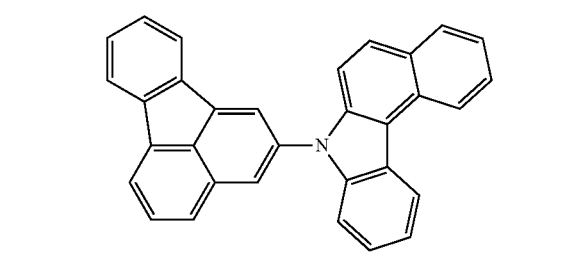
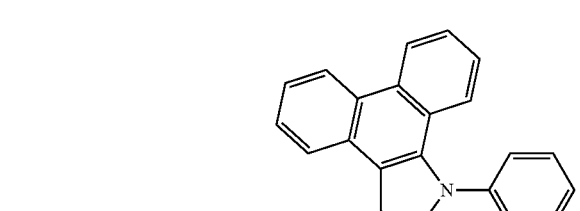
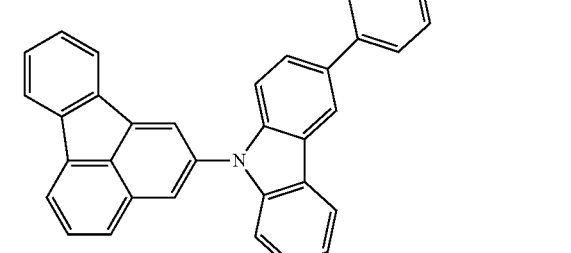
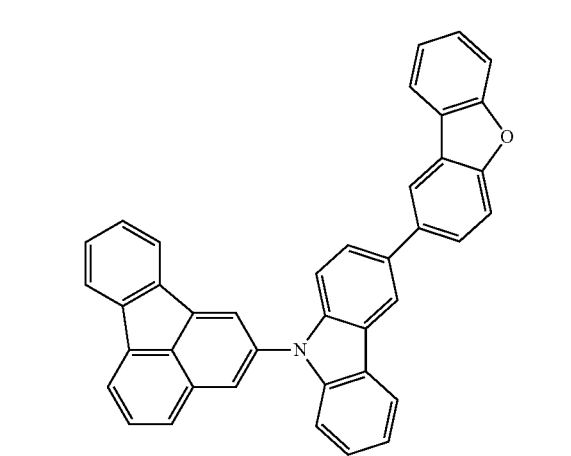

125
-continued
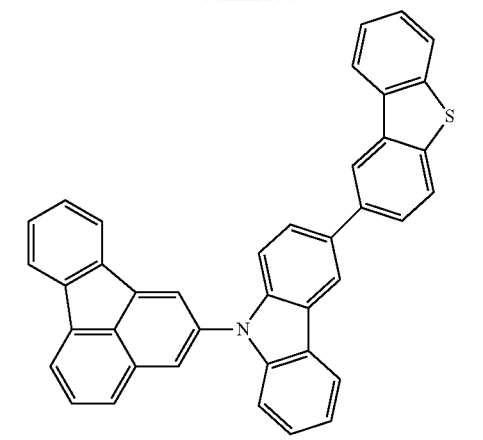
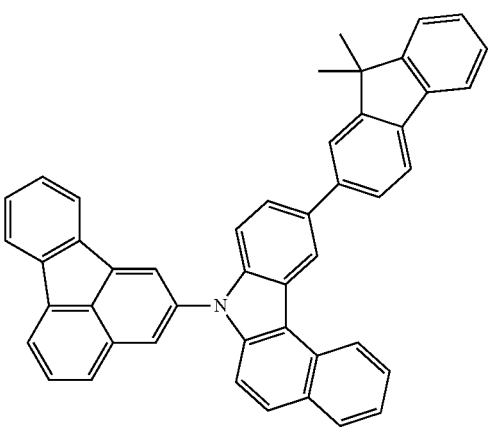
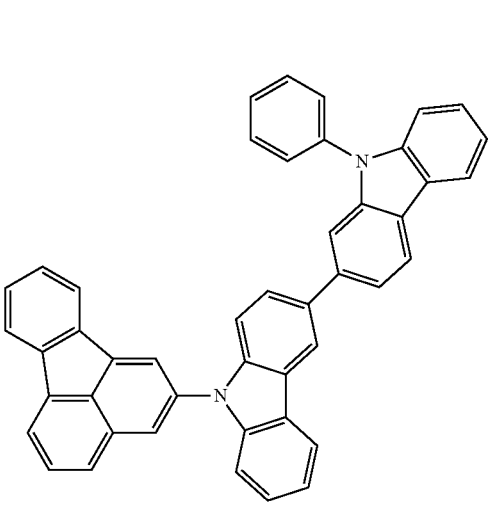
126
-continued
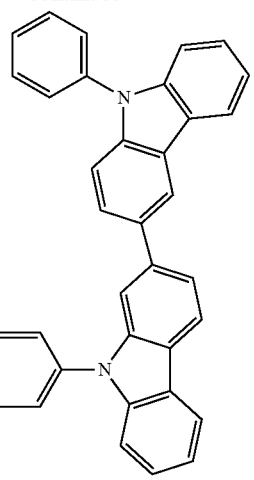
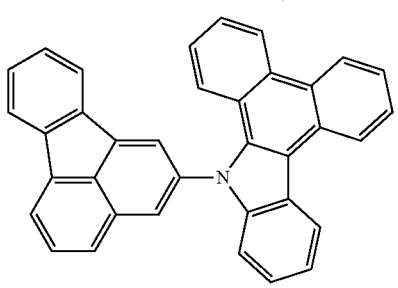
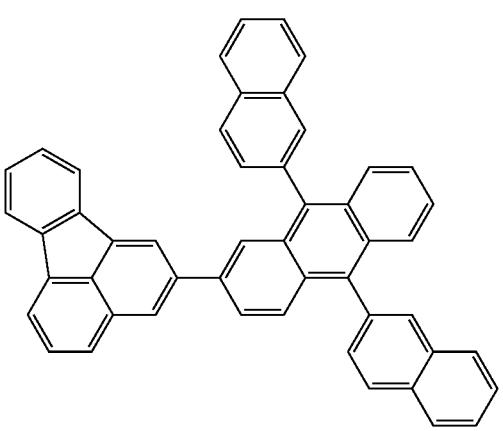
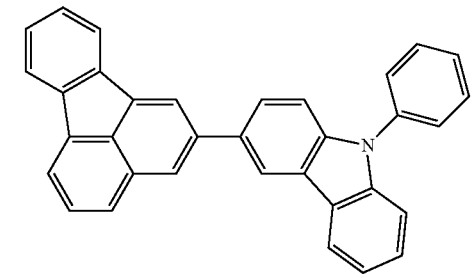
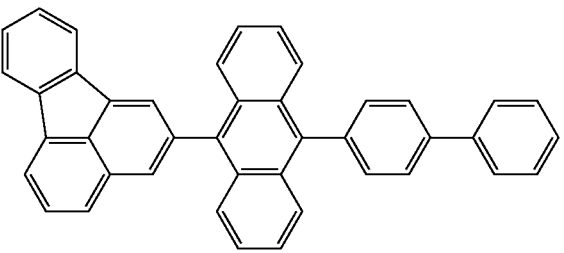

127
-continued
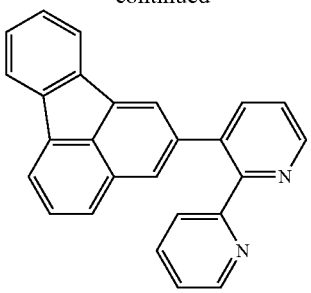
[Chem. 64]
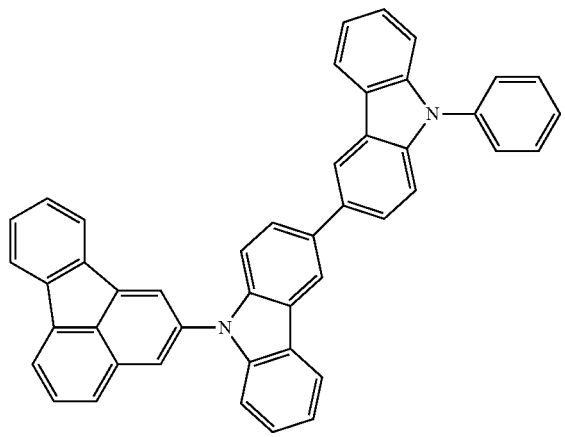
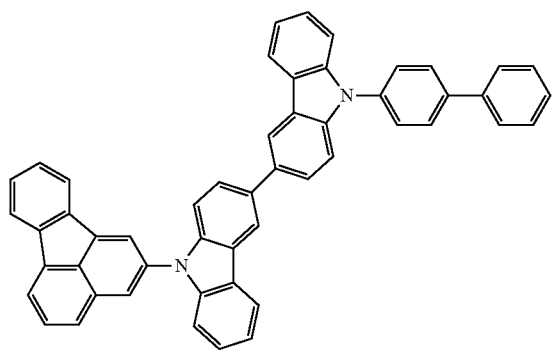
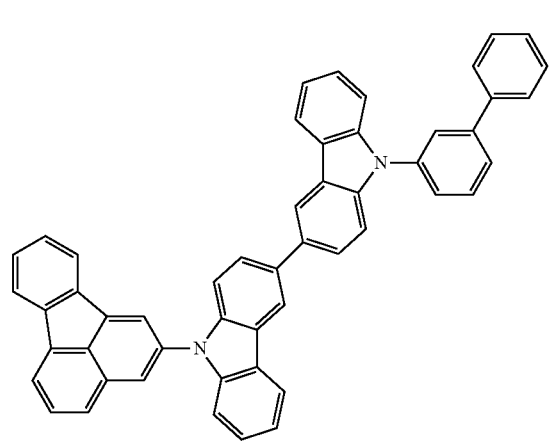
128
-continued
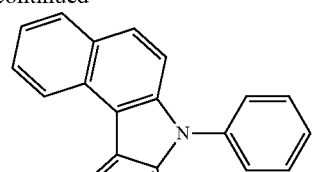
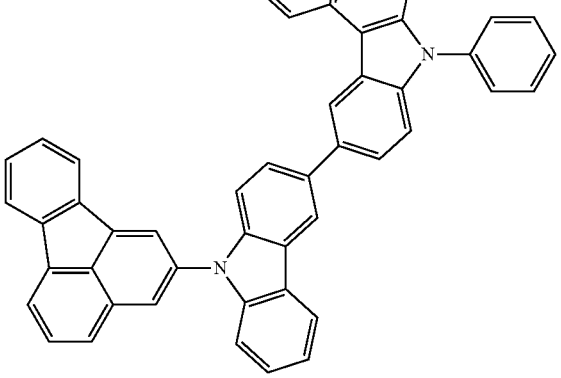
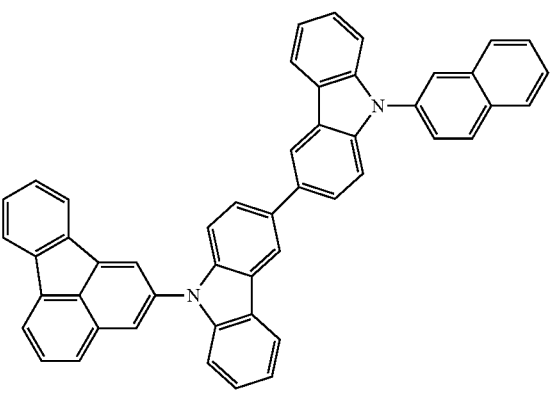
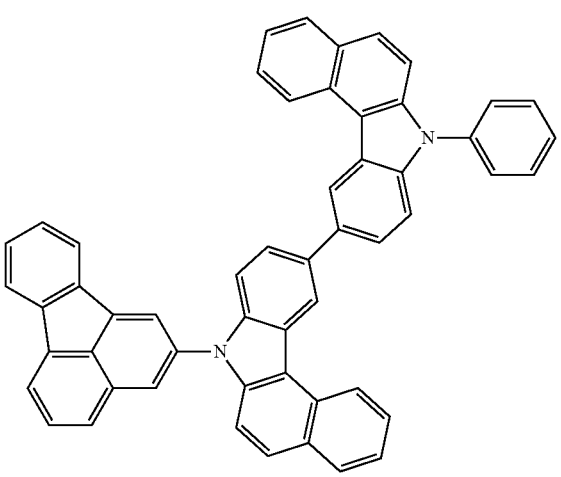

-continued
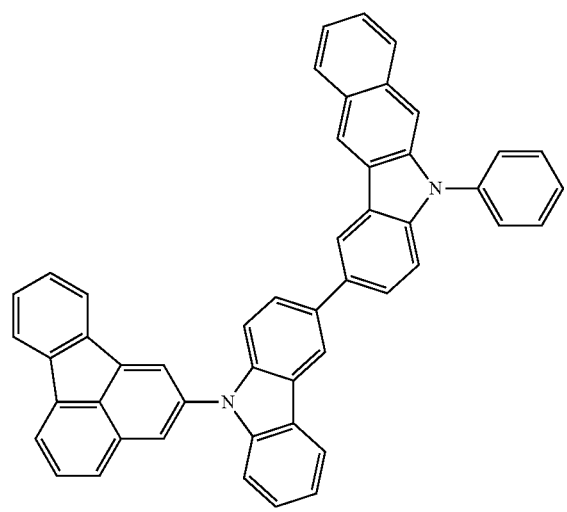
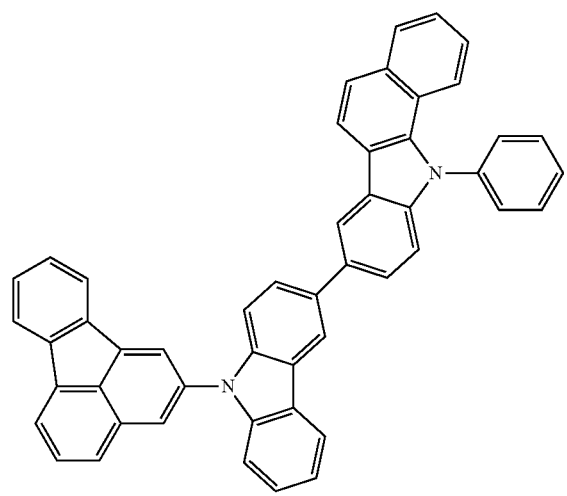
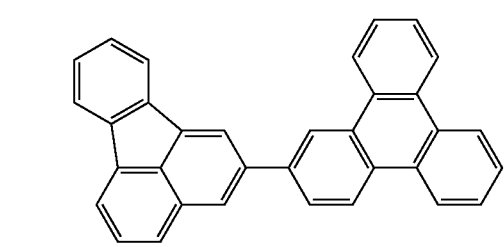
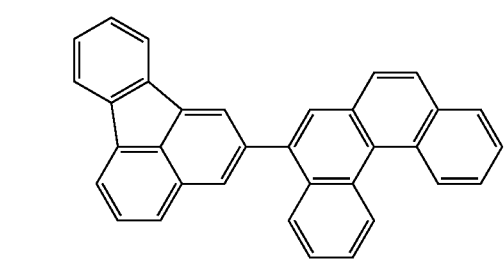
-continued
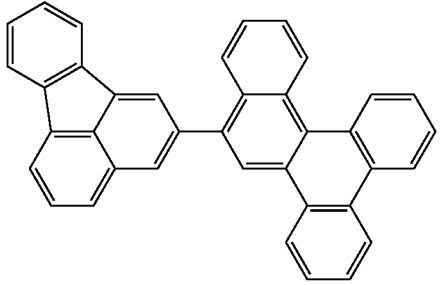
[Chem. 65]
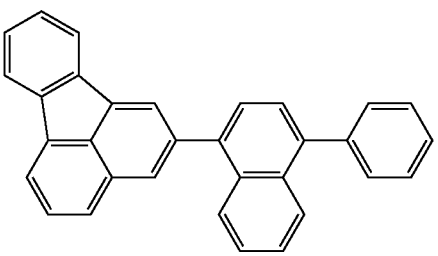
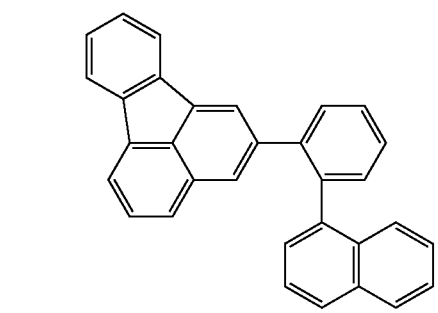
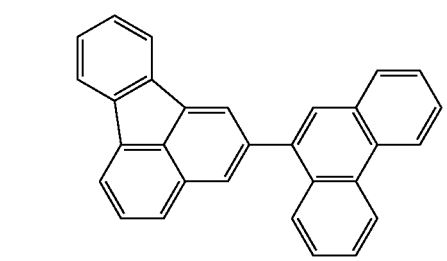
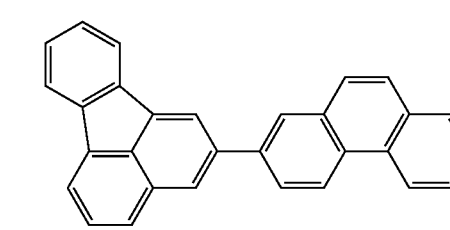
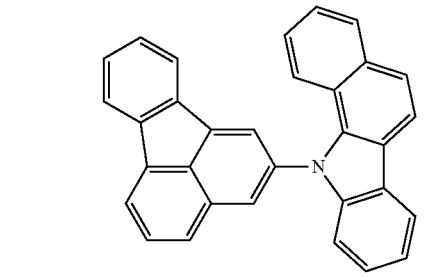

131
-continued
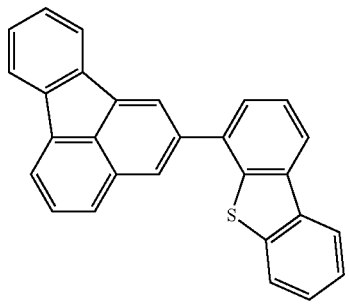
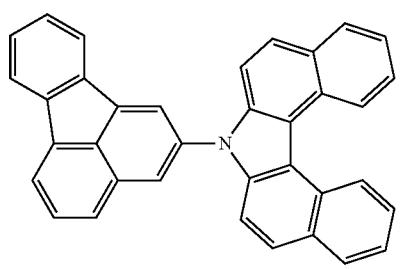
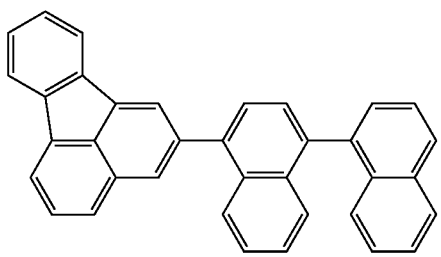
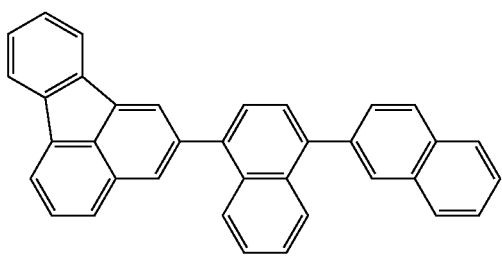
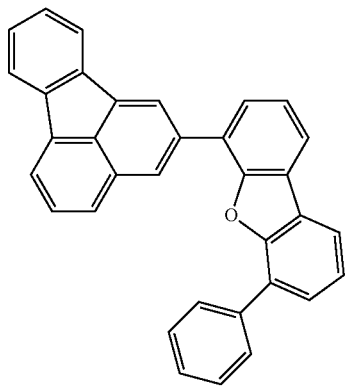
132
-continued
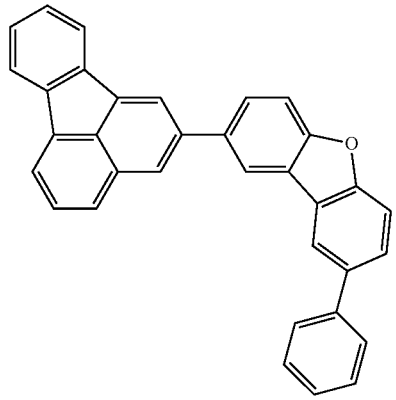
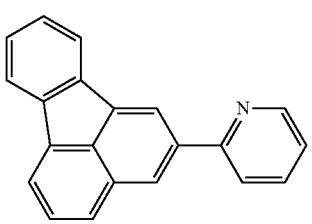
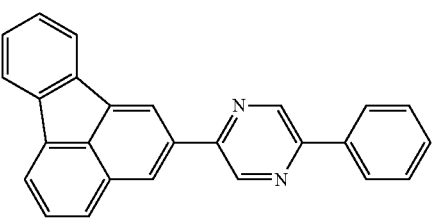
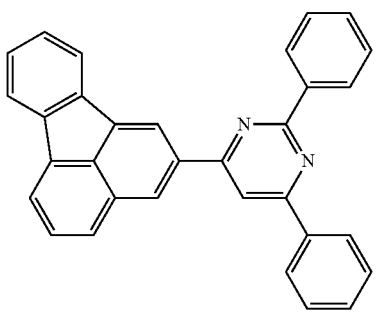
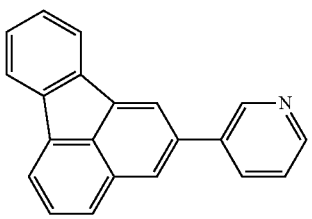
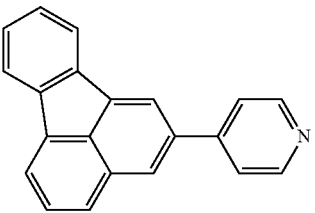

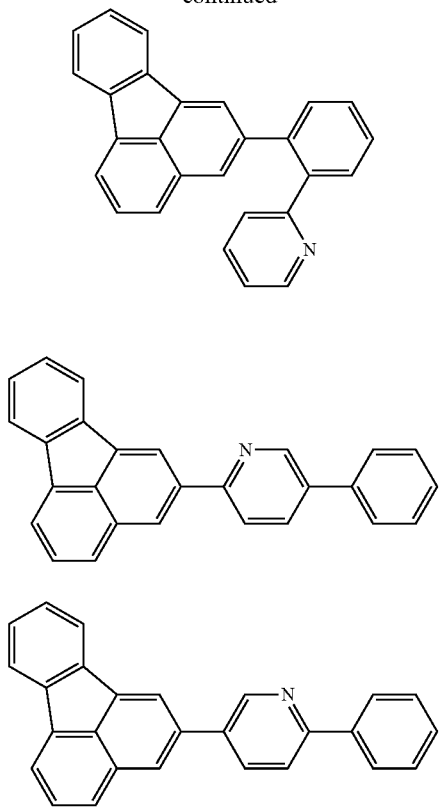
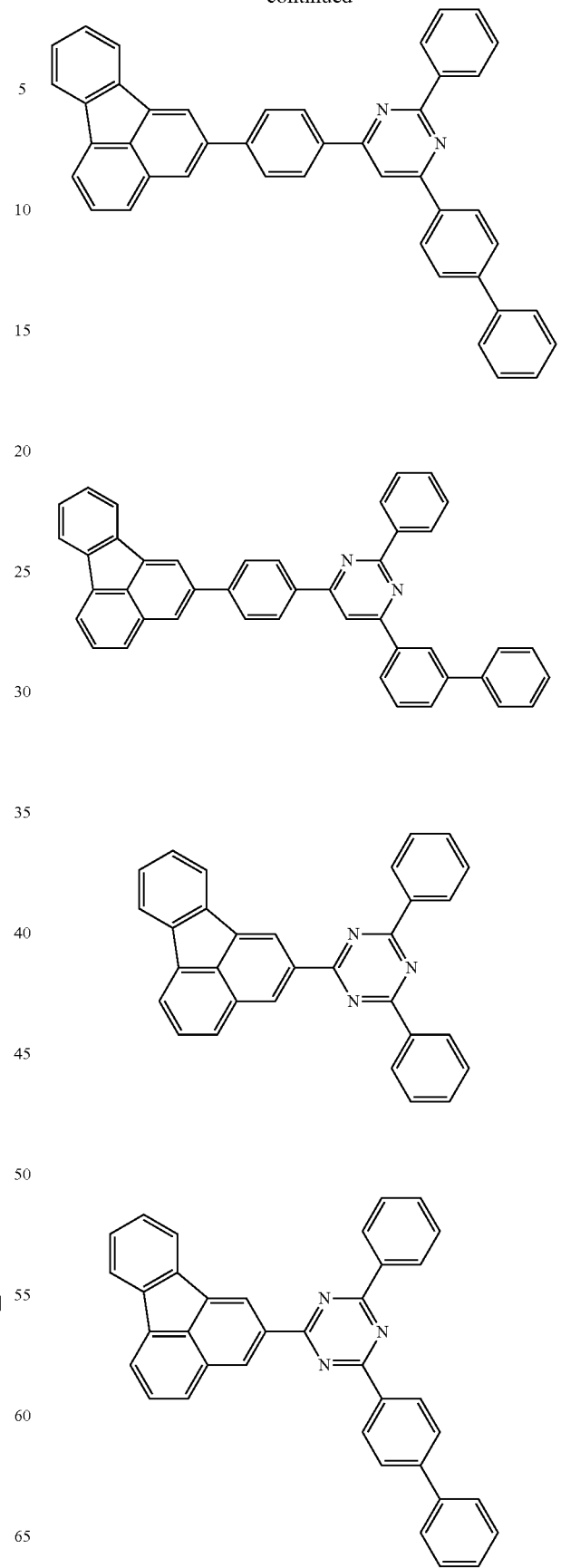
[Chem. 66]

-continued
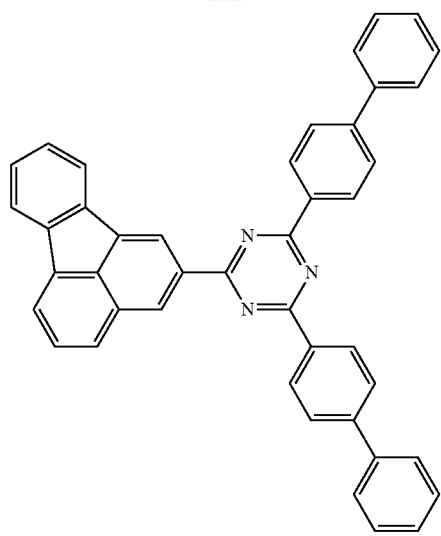
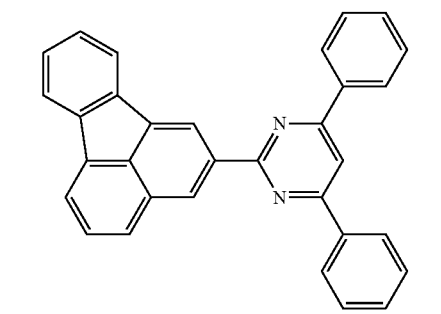
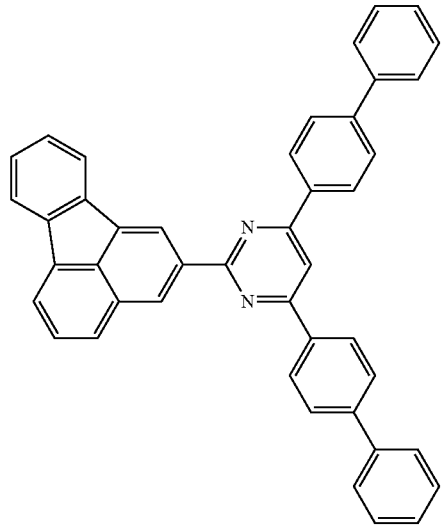
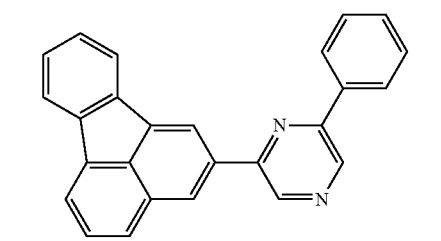
-continued
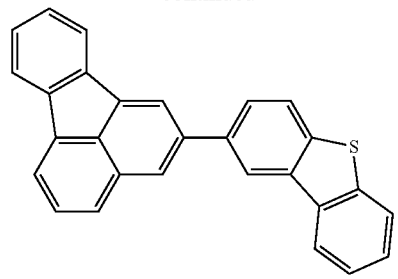
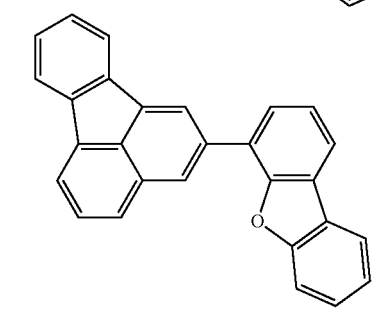
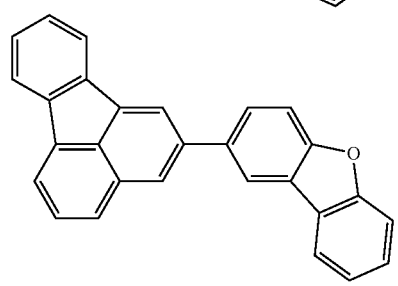
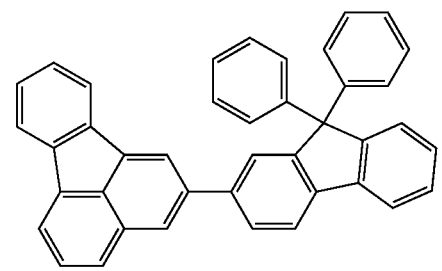
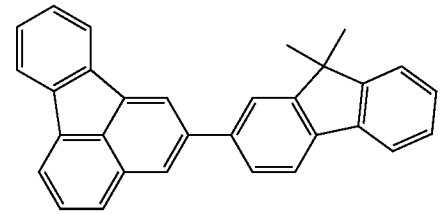
[Chem. 67]
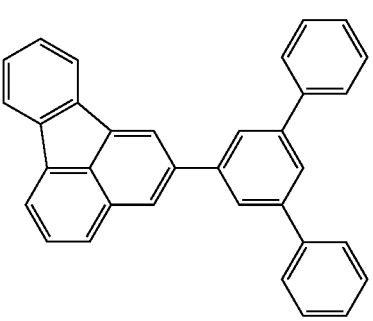

137
-continued
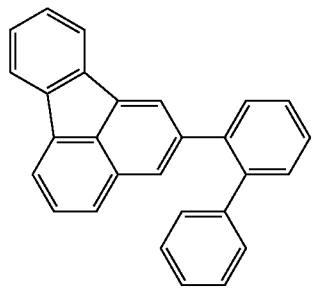
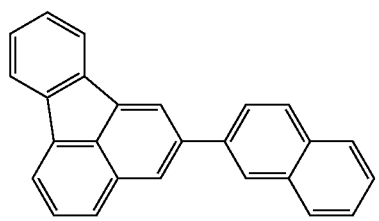
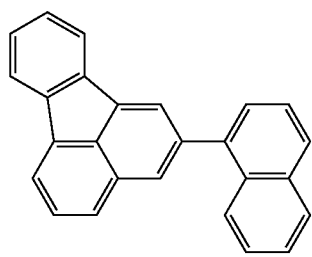
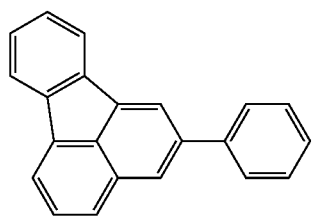
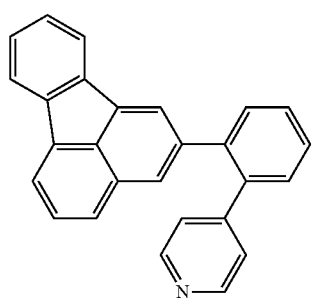
138
-continued
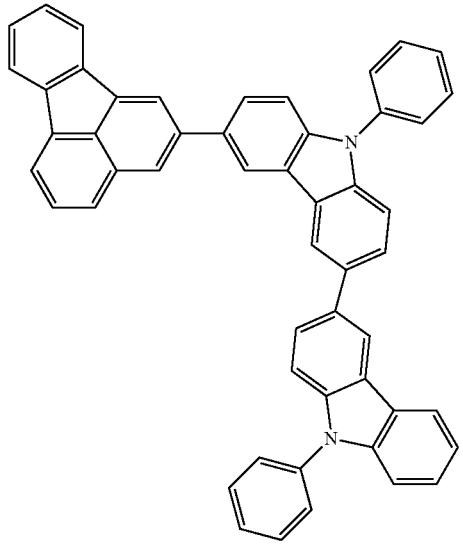
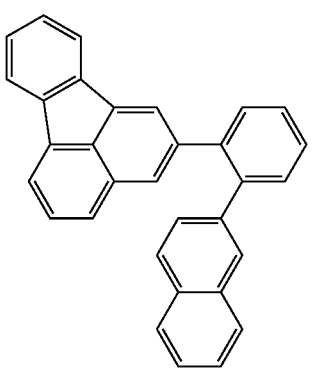
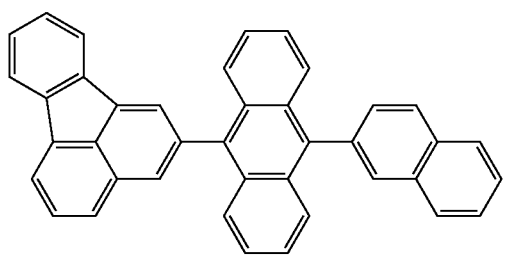
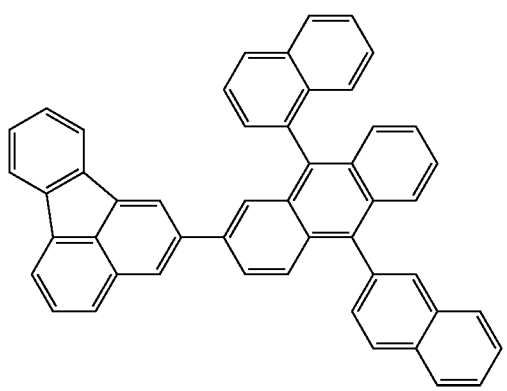

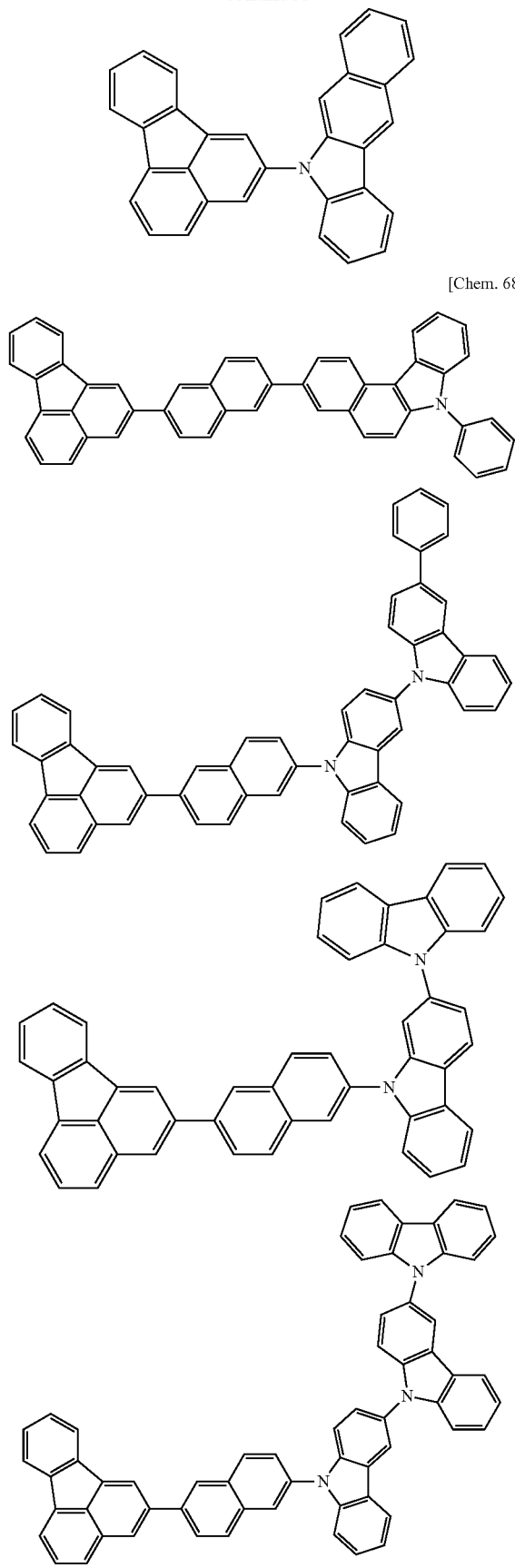
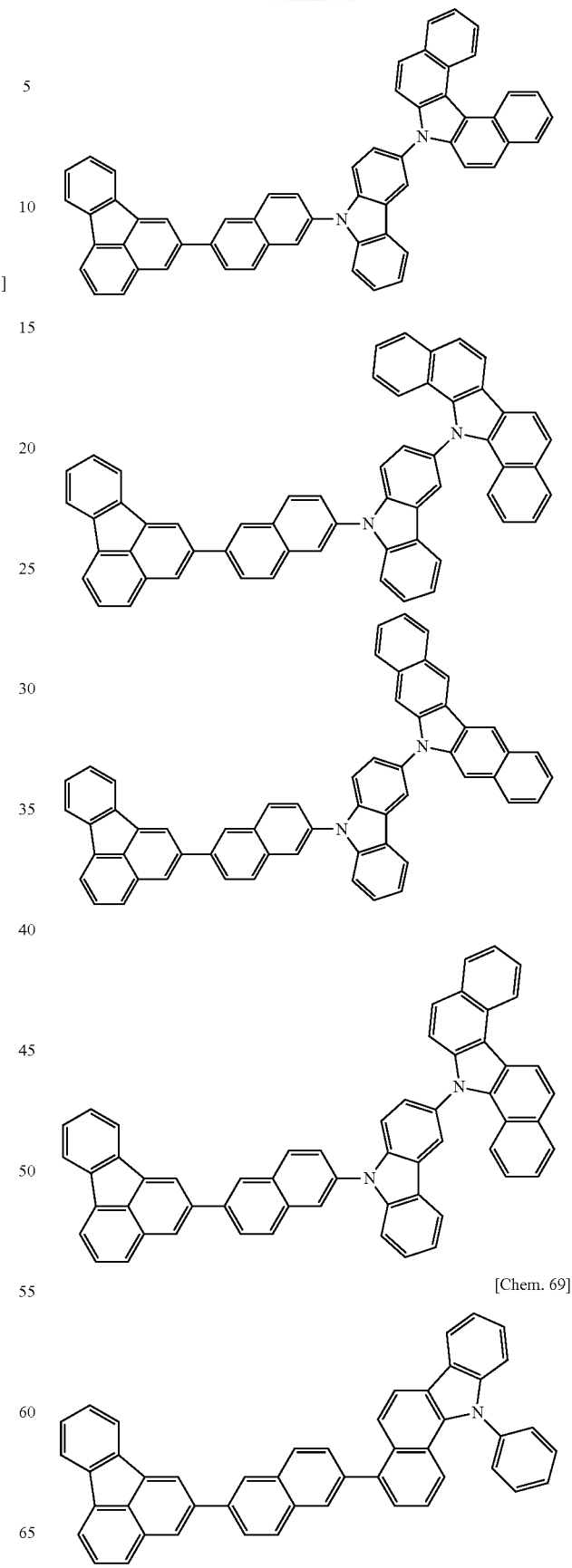

-continued
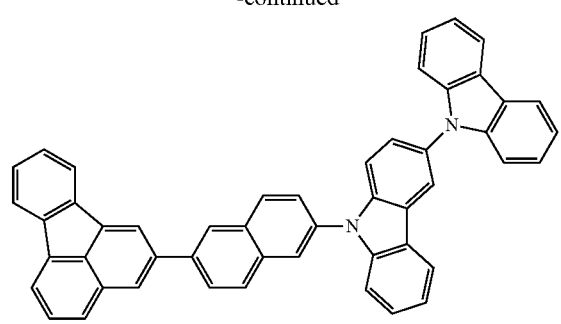
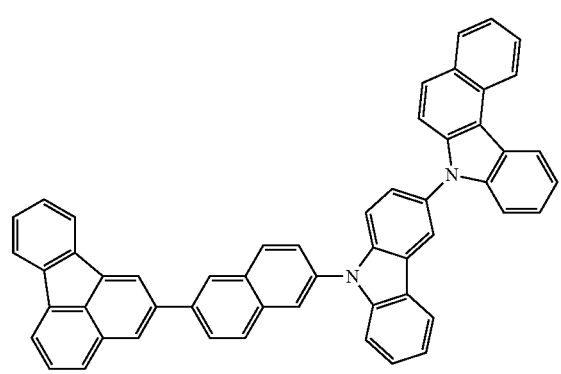
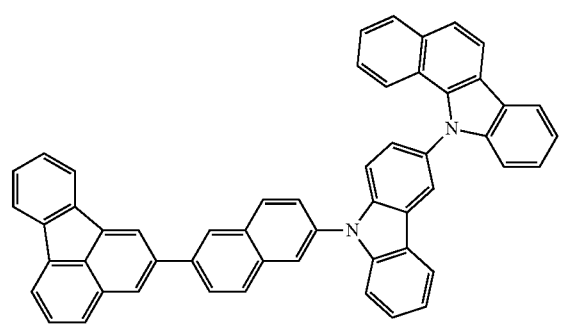
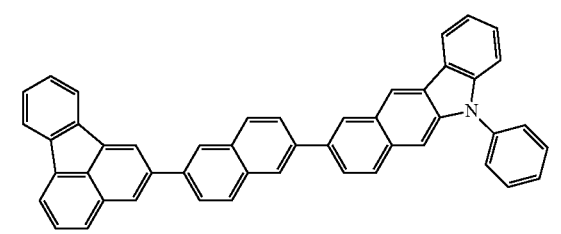
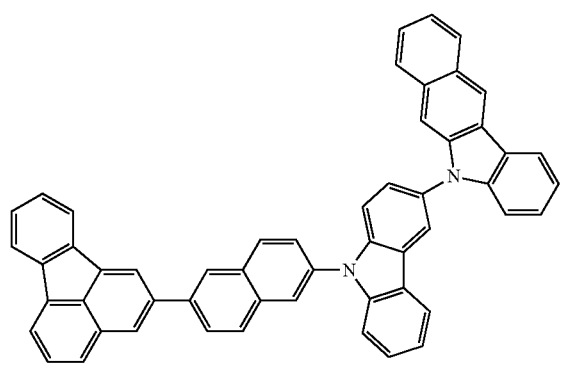
-continued
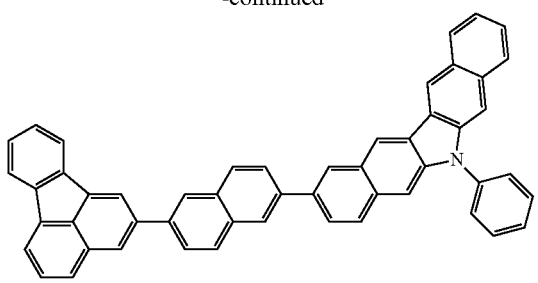
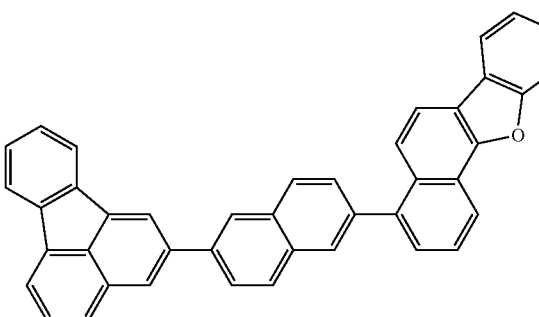
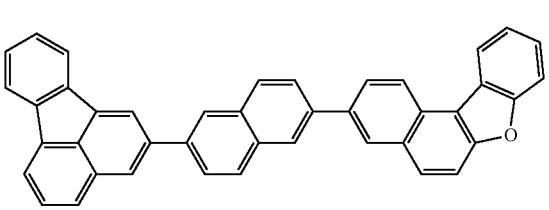
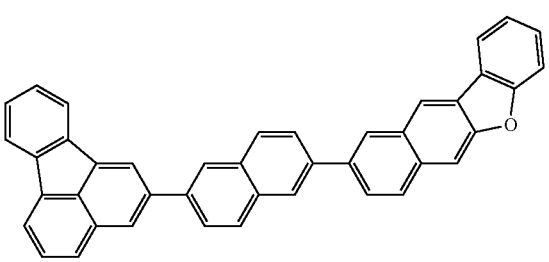
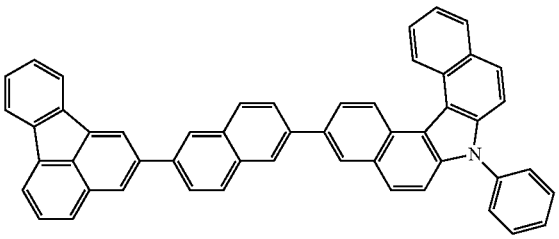
[Chem. 70]
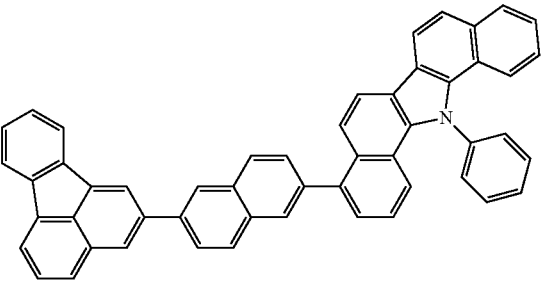

143
-continued
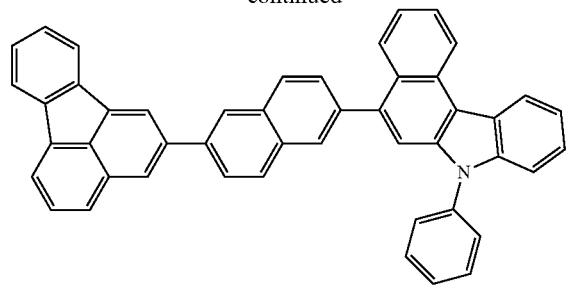
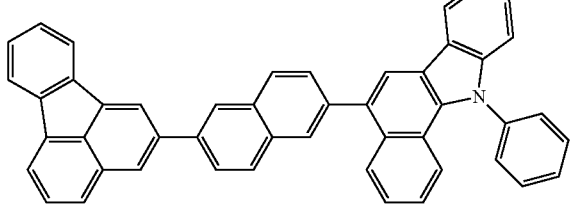
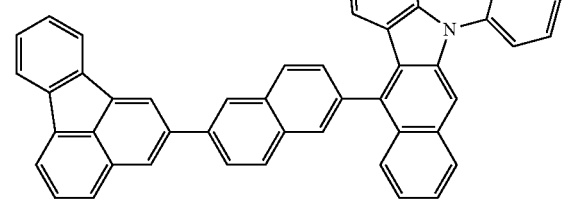
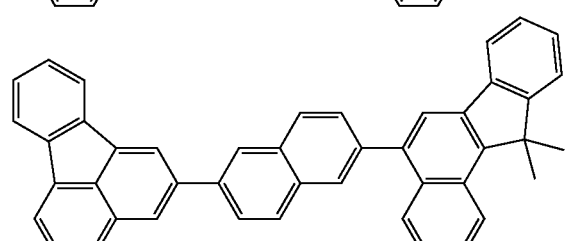
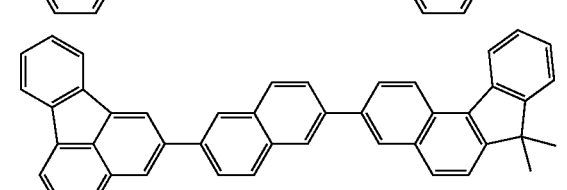
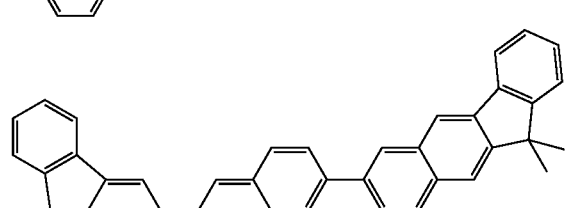
144
-continued
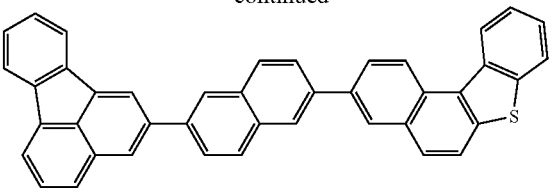
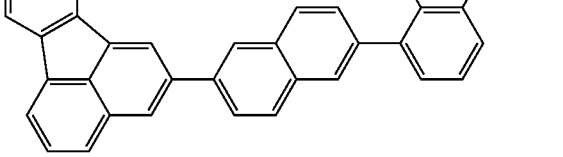
[Chem. 71]
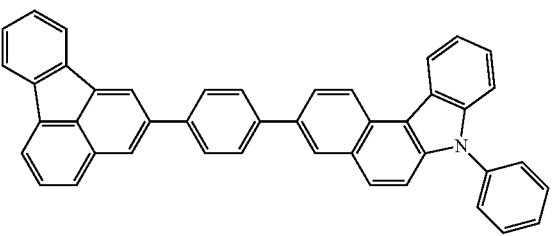

-continued
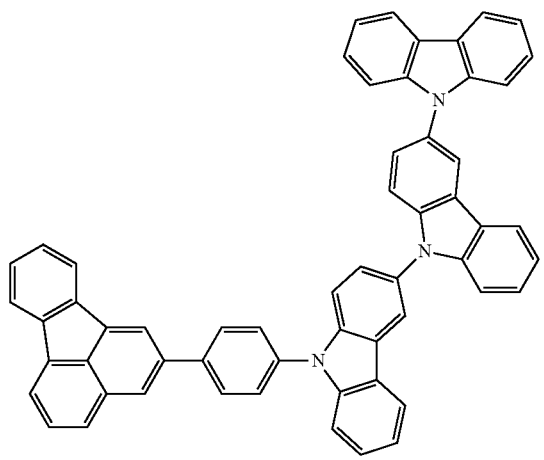
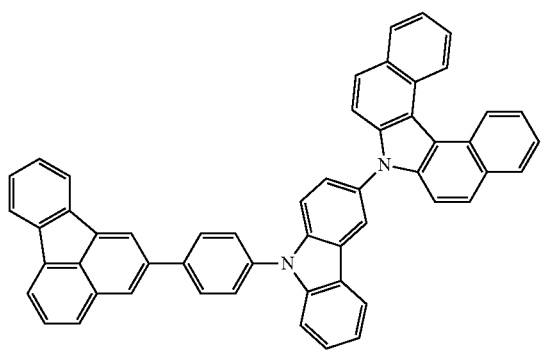
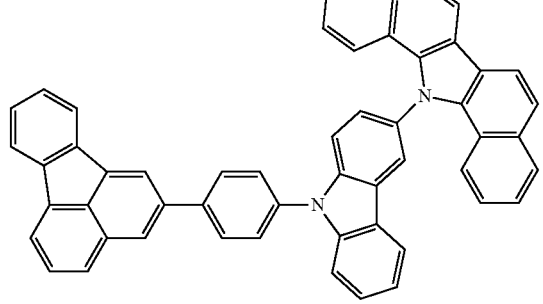
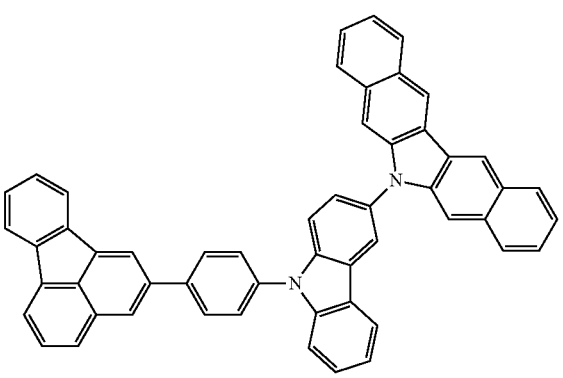
-continued
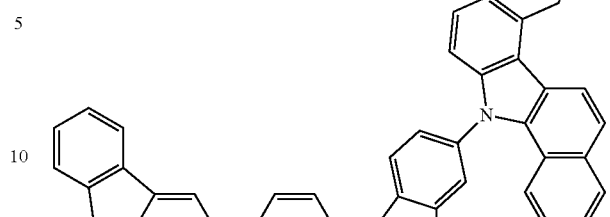
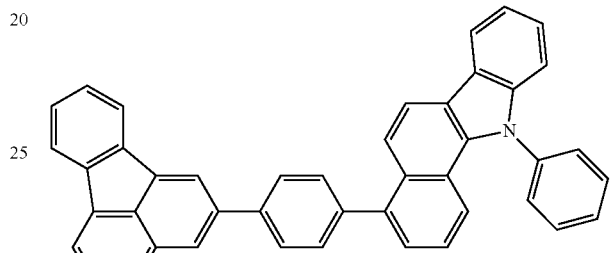
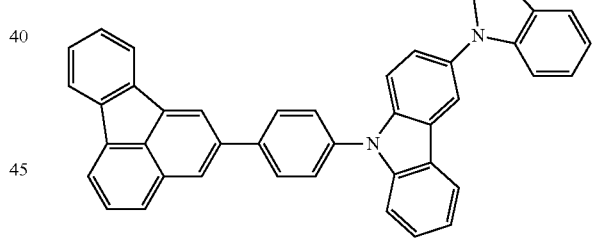
[Chem. 72]
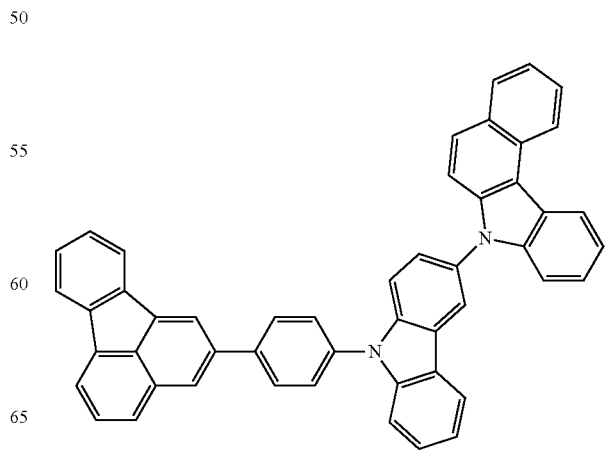

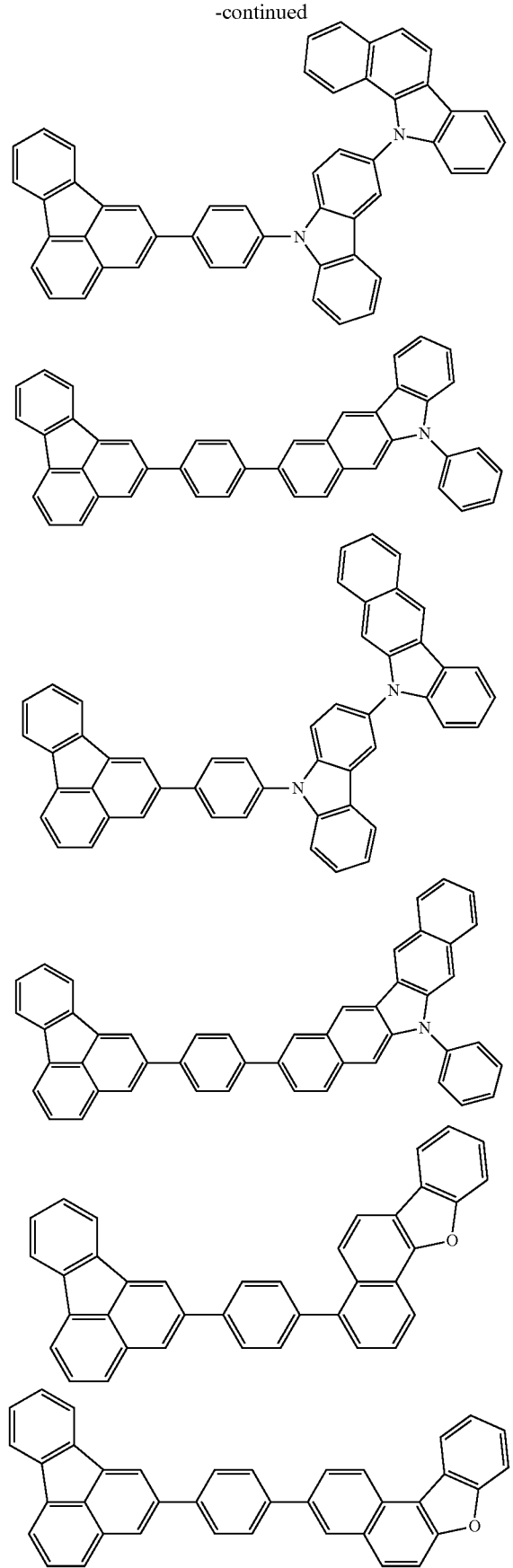
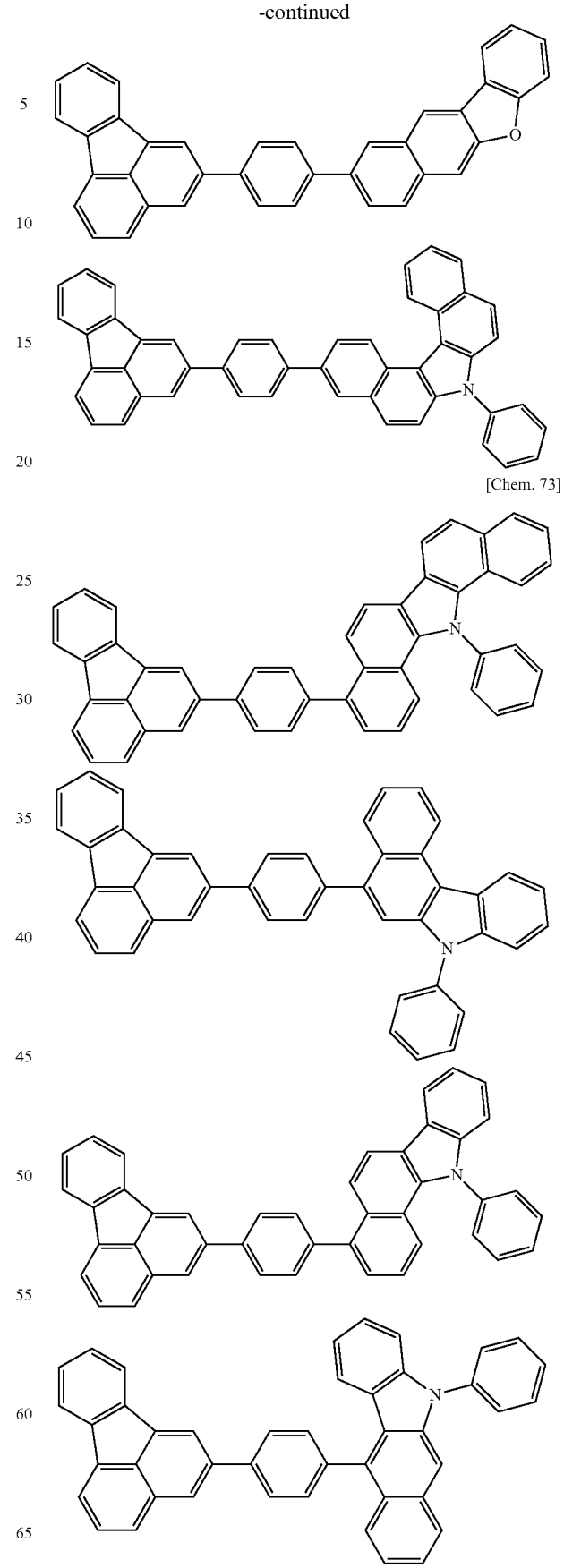
[Chem. 73]

149
-continued
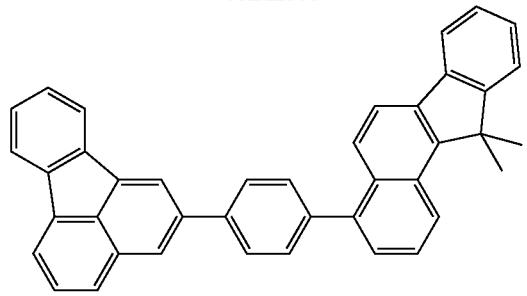
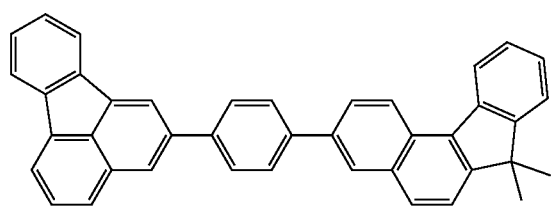
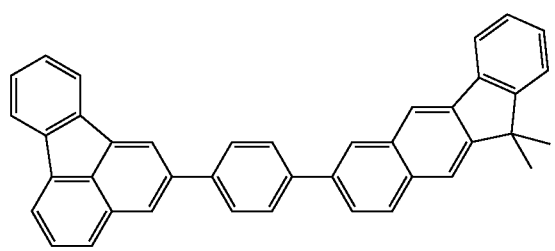
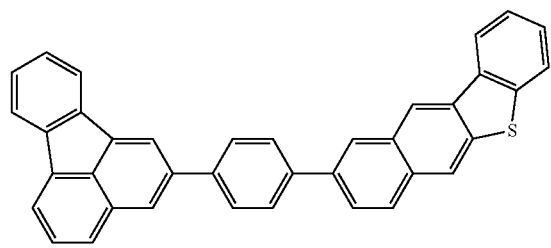
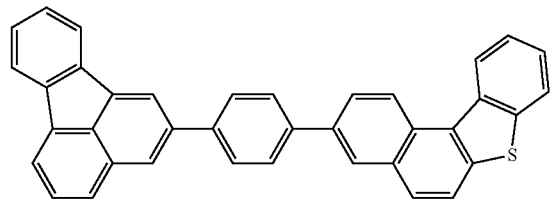
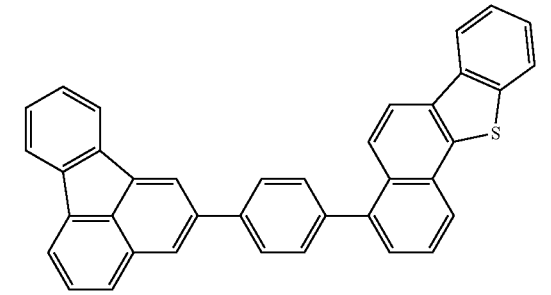
150
-continued
[Chem. 74]
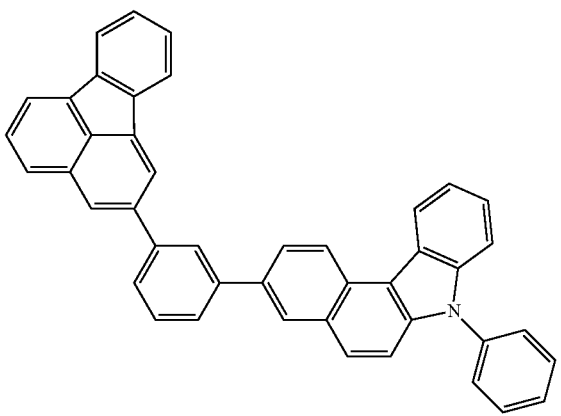
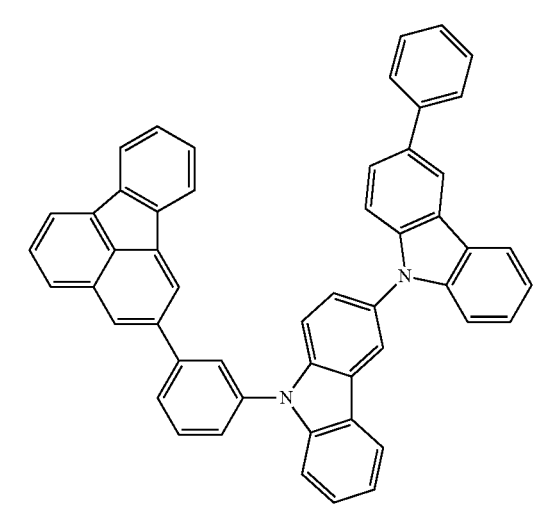
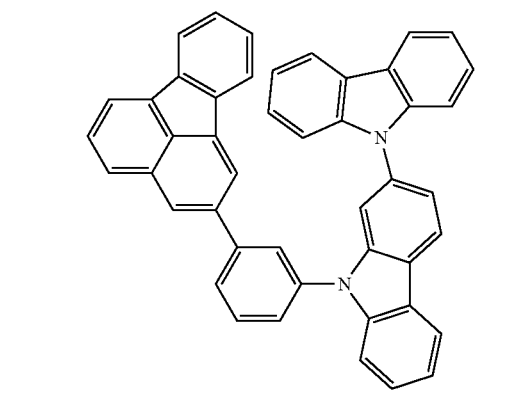

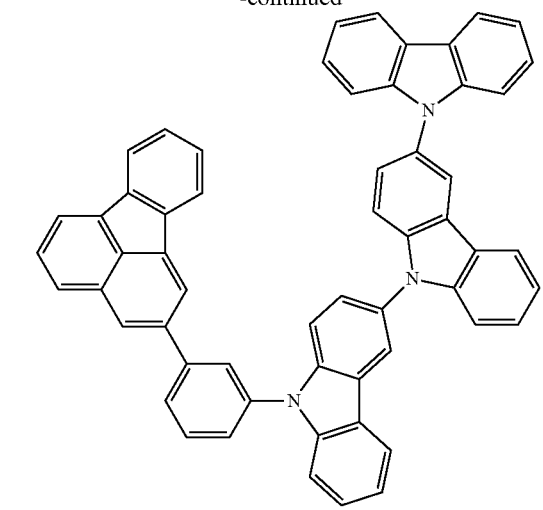
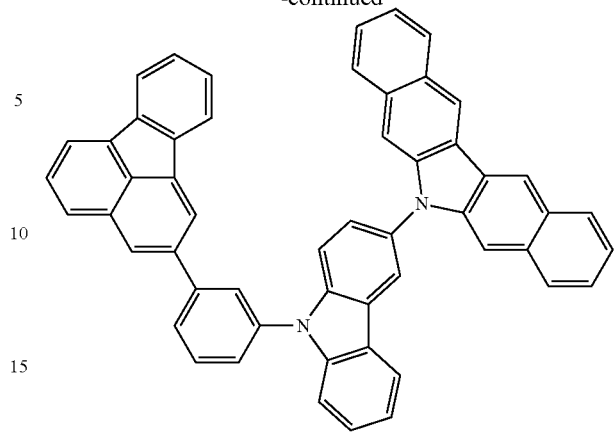
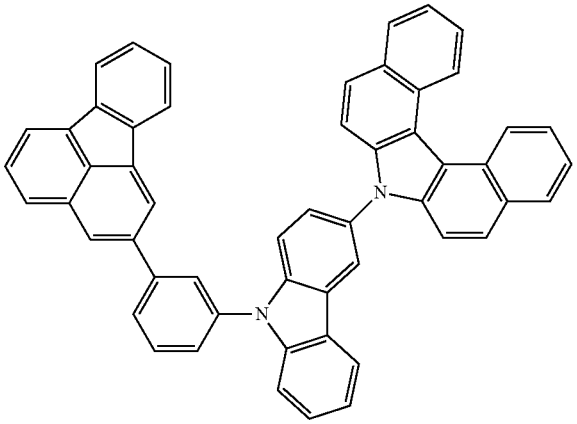
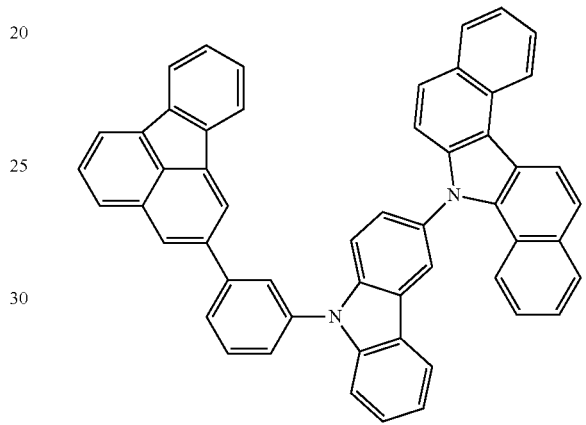
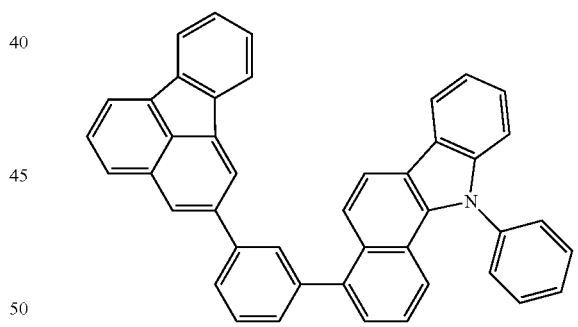
[Chem. 75]
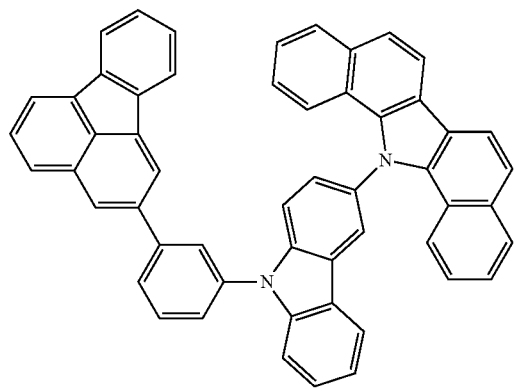
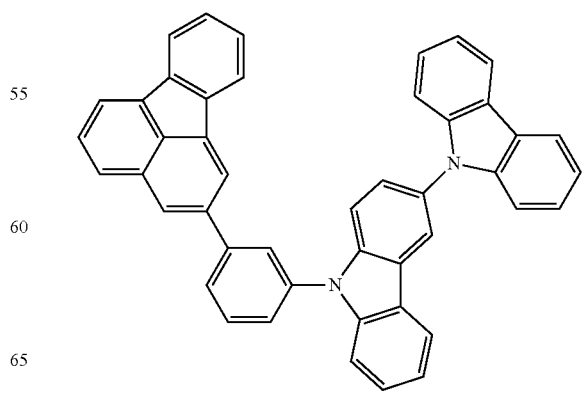

153
-continued
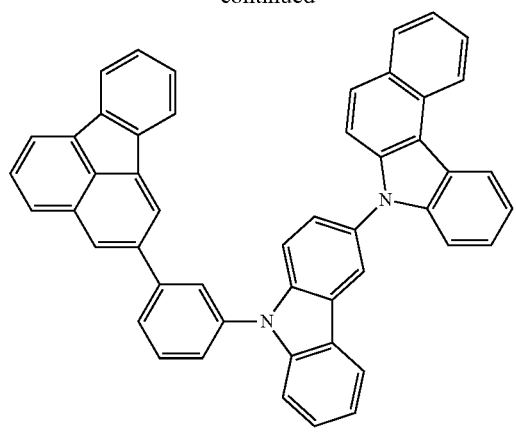
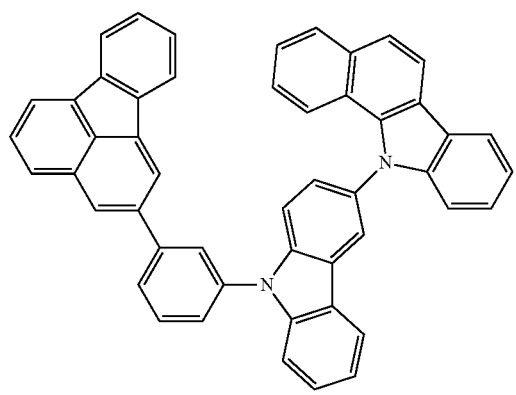
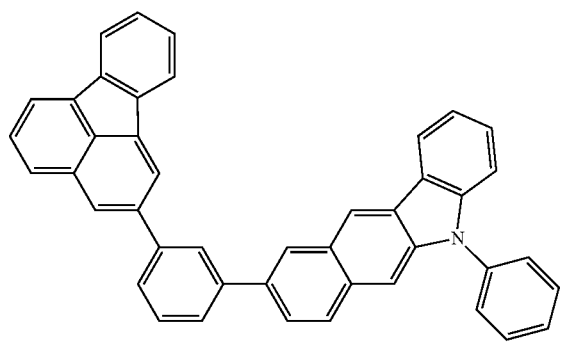
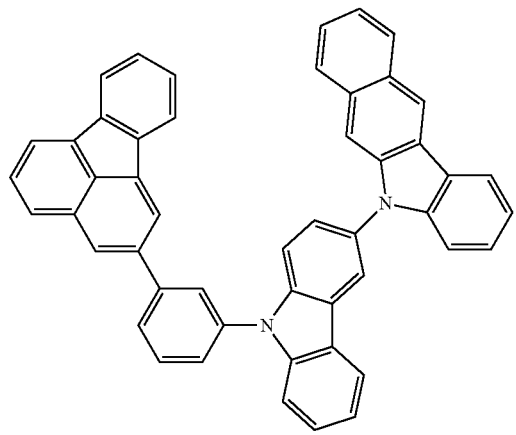
154
-continued
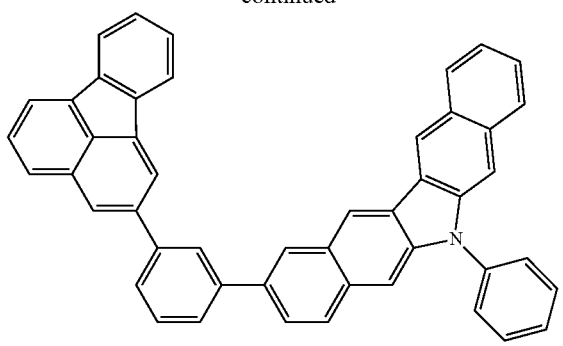
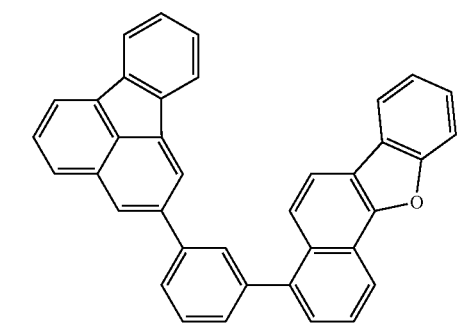
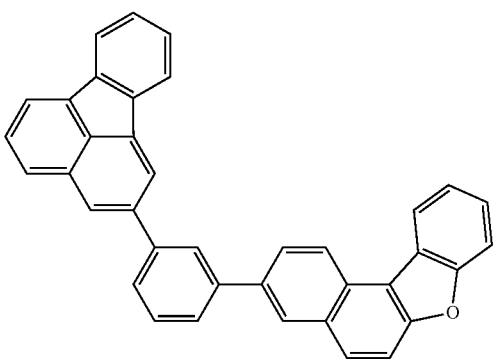
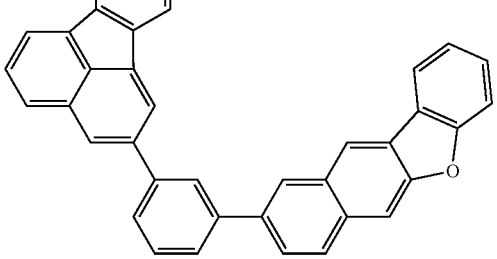

155
-continued
[Chem. 76]
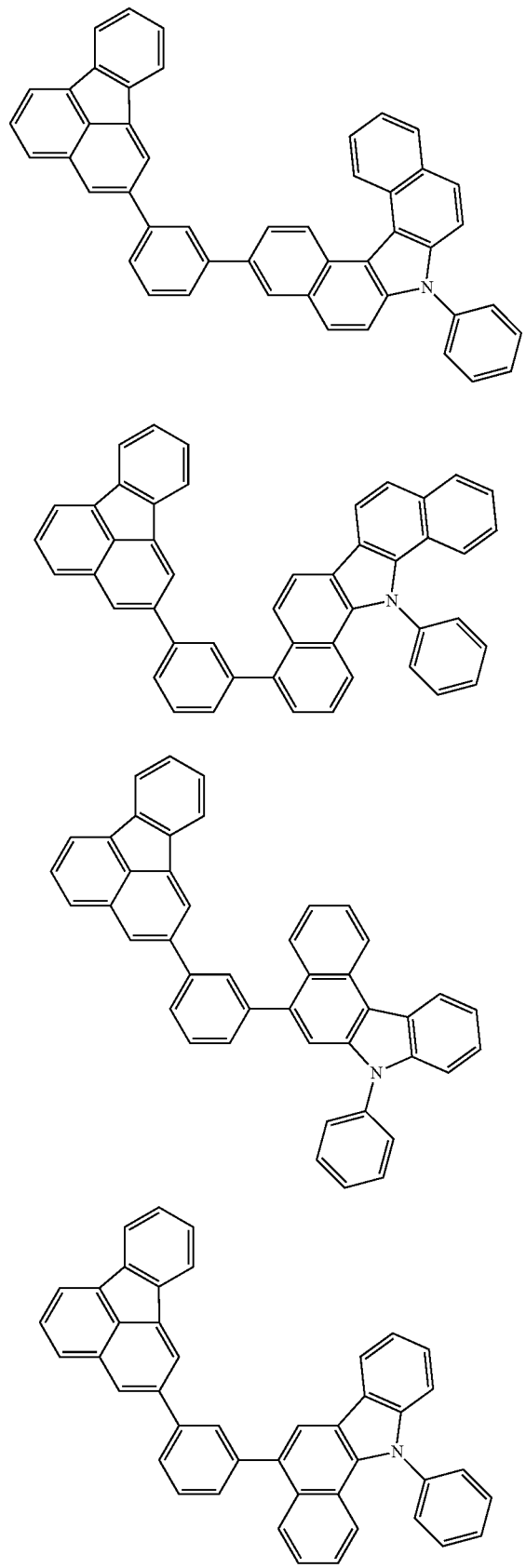
156
-continued
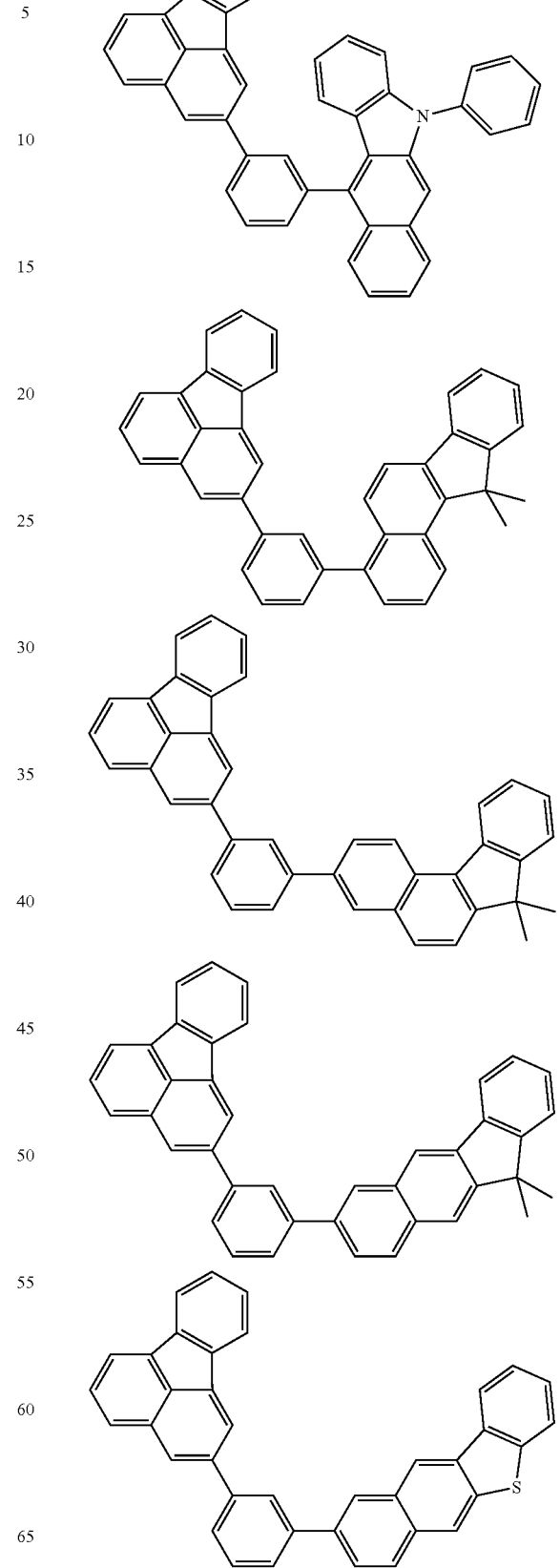

157
-continued
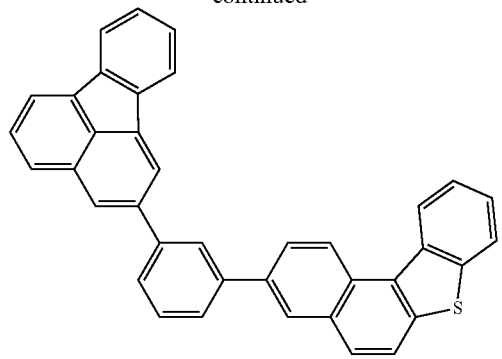
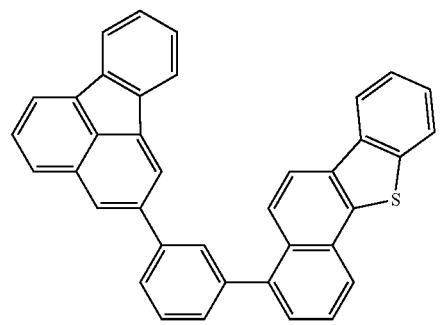
[Chem. 77]
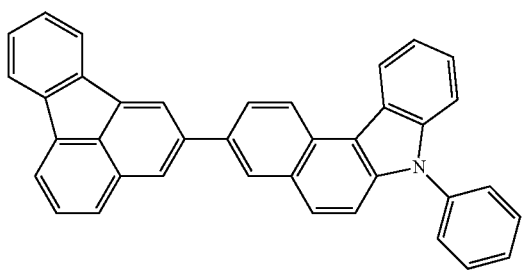
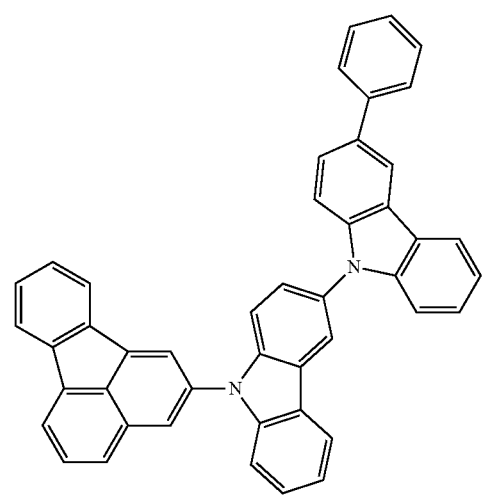
158
-continued
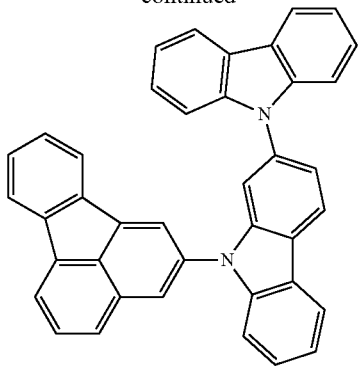
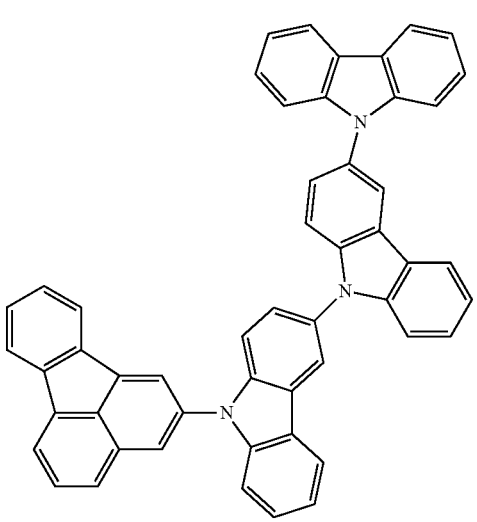
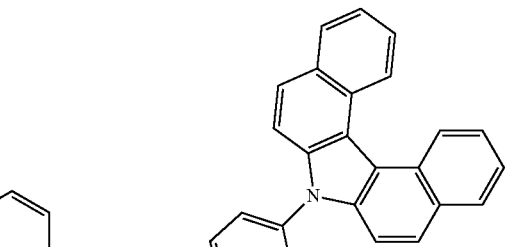
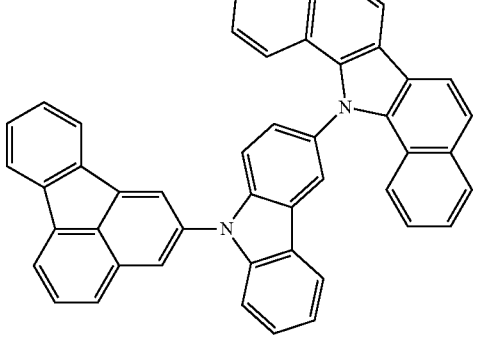

-continued
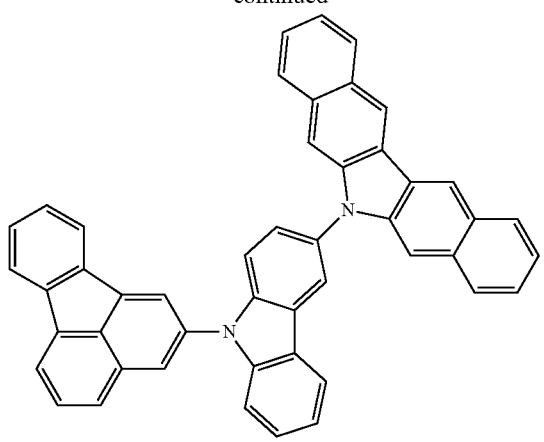
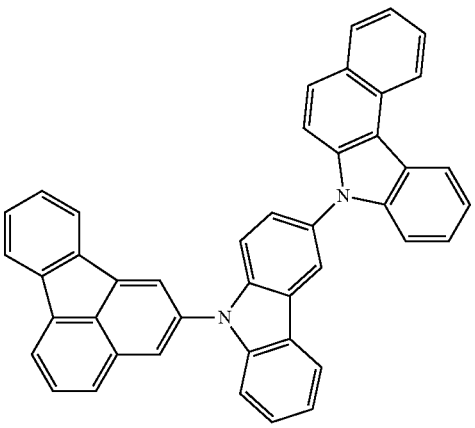
[Chem. 78]
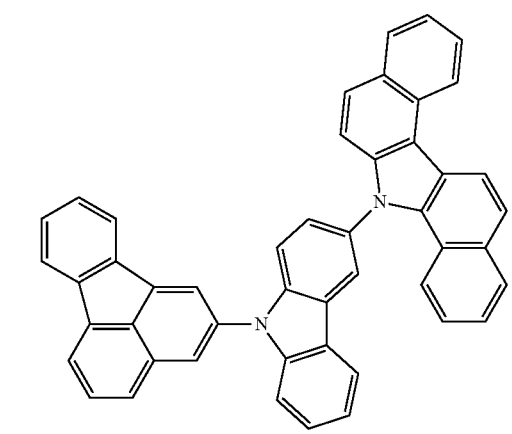
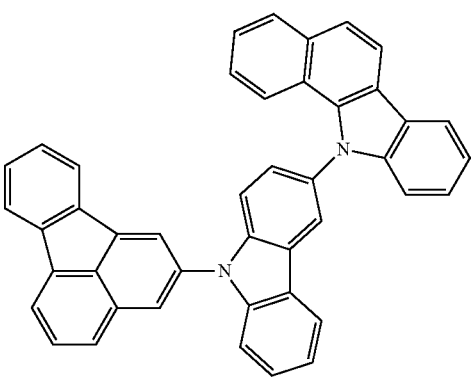
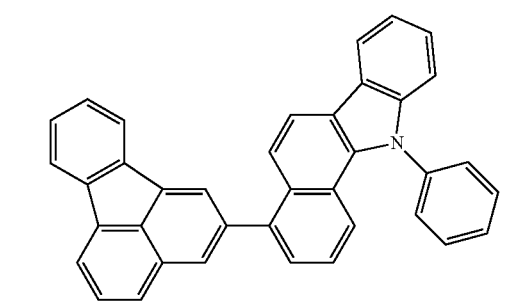
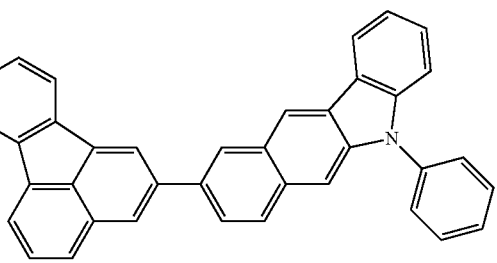
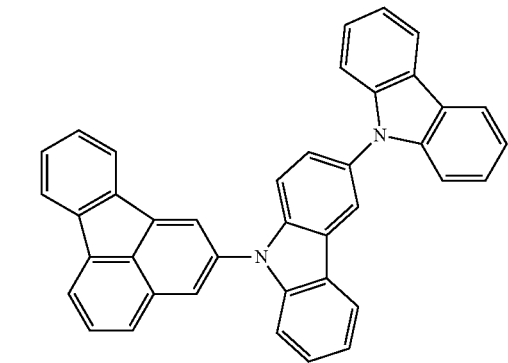
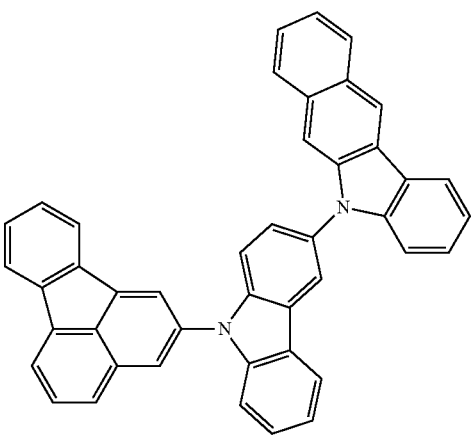

161
-continued
162
-continued
[Chem. 79]
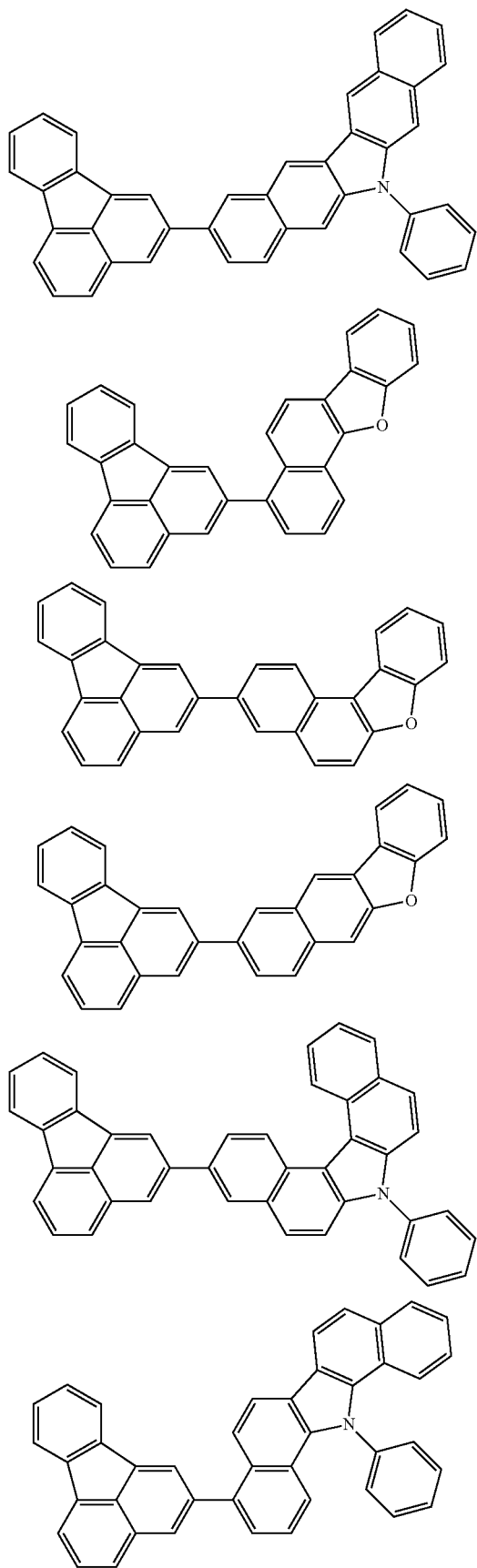
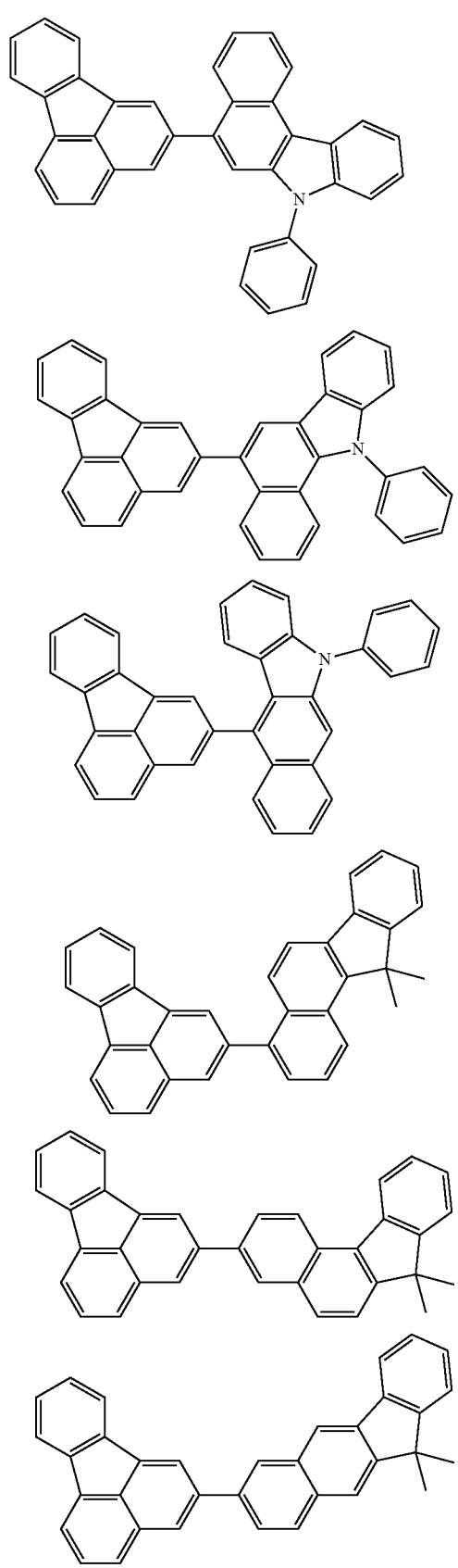

-continued

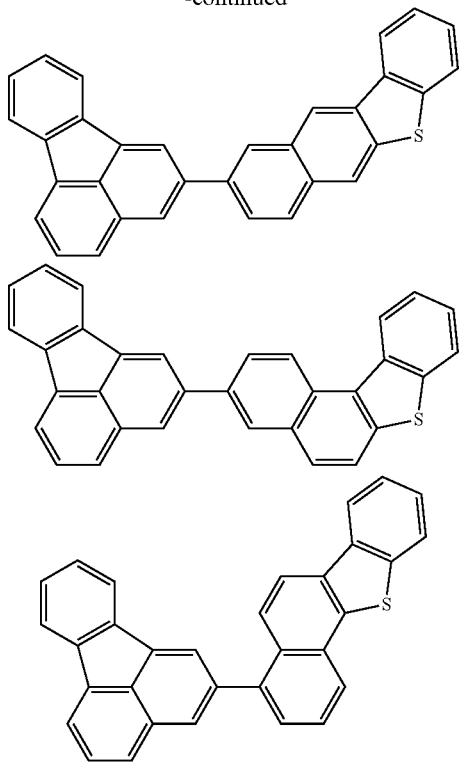

[Material for Organic EL Devices]

The material for organic EL devices in one embodiment of the present invention contains the above-described compound (1), and the content of the compound (1) is preferably 50% by mass or more, more preferably 70% by mass or more, still more preferably 80% by mass or more, and particularly preferably 90% by mass or more. The material for organic EL devices in one embodiment of the present invention may be only constituted with the above-described compound (1). The preferred compounds are as described above. Hereinbelow, the descriptions on the compound (1) can be read with replacement with the above-mentioned preferred compounds.

The material for organic EL devices in one embodiment of the present invention is useful as, for example, a material for an organic thin film layer that includes one layer or plural layers and is sandwiched between the anode and the cathode, in the organic EL device, and in particular, is more useful as a material for a hole transporting layer, a material for a hole injecting layer, or a host material (particularly a phosphorescent host material) for a light emitting layer.

[Organic EL Device]

Next, the organic EL device in one embodiment of the present invention will be described.

The organic EL device in one embodiment of the present invention is an organic electroluminescent device having a cathode, an anode, and an organic thin film layer that includes one layer or plural layers and is sandwiched between the anode and the cathode, the organic thin film layer includes a light emitting layer, at least one layer of the organic thin film layer contains a compound represented by the general formula (1) (compound (1)) [also encompassing a subconcept of the compound (1). The same applies hereinafter].

In one embodiment of the present invention, the organic EL device may be any of a fluorescent or phosphorescent type of a monochromic light emitting device, a fluorescent/phosphorescent hybrid type of a white light emitting device, a simple type of a device having a single light emitting unit, and a tandem type of a device having a plurality of light emitting units, among which the phosphorescent light emission type of a device is preferred. Here, the "light emitting unit" is the smallest unit for emitting light by the recombination of injected holes and electrons, which includes one or more organic layers in which at least one layer is a light emitting layer.

Examples of the representative configurations of a simple type of the organic EL device include (1) to (13) below, although not particularly limited thereto. Further, the device configuration of (8) is preferably used:

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/(hole injecting layer/) hole transporting layer/light emitting layer/electron transporting layer(/electron injecting layer)/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/(hole injecting layer)/hole transporting layer/light emitting layer/insulating layer/cathode; and
(13) anode/insulating layer/(hole injecting layer)/hole transporting layer/light emitting layer/electron transporting layer(/electron injecting layer)/cathode.

A schematic structure of one example of the organic EL device in one embodiment of the present invention is shown in FIG. 1.

The organic EL device 1 has a substrate 2, an anode 3, a cathode 4, and a light emitting unit 10 disposed between the anode 3 and the cathode 4. The light emitting unit 10 has a light emitting layer 5 having a host material and a dopant (light emitting material). In the light emitting unit 10, a hole injecting/transporting layer 6 (an anode-side organic thin film layer 6) and the like may be disposed between the light emitting layer 5 and the anode 3, and an electron injecting/transporting layer 7 (a cathode-side organic thin film layer 7) and the like may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the exciton generation in the light emitting layer 5.

Examples of the organic thin film layer including the compound (1) include an anode-side organic thin film layer provided between an anode and a light emitting layer (a hole transporting layer, a hole injecting layer, or the like), a light emitting layer, a cathode-side organic thin film layer provided between a cathode and a light emitting layer (an electron transporting layer, an electron injecting layer, or the like), a space layer, and a blocking layer, but are not limited thereto.

The compound (1) is used in any organic thin film layer of an organic EL device, and from the viewpoint of emission efficiency, it is preferably used in a hole injecting layer or a hole transporting layer, an electron injecting layer or an electron transporting layer, or a light emitting layer.

That is, the organic EL device in one embodiment of the present invention is more preferably an organic EL device in which the light emitting layer includes the compound (1). When the light emitting layer in the organic EL device includes the compound (1), the light emitting layer preferably further contains a phosphorescent light emitting material which will be described later. Further, in the organic EL device in one embodiment of the present invention, it is also preferable that the hole transporting layer or the electron transporting layer includes the compound (1).

In the case where the light emitting layer includes the compound (1), the content of the compound (1) in the light emitting layer is preferably 30% to 100% by mass, more preferably 50% to 100% by mass, still more preferably 80% to 100% by mass, and even still more preferably 90% to 99% by mass, with respect to the total amount of the components of the light emitting layer.

Furthermore, in the case where the organic thin film layer other than the light emitting layer includes the compound (1), the content of the compound (1) in the organic thin film layer (preferably hole transporting layer or electron transporting layer) is preferably 30% to 100% by mass, more preferably 50% to 100% by mass, still more preferably 80% to 100% by mass, and even still more preferably 95 to 100% by mass, with respect to the total amount of the components of the organic thin film layer.

In addition, preferred examples of the organic EL device in one embodiment of the present invention include a red light emitting organic EL device.

(Substrate)

The substrate is used as a support for the light emitting device. As the substrate, for example, glass, quartz, and plastics can be used. Further, a plastic substrate may also be used. The plastic substrate is a flexible substrate, and examples thereof include plastic substrates made of polycarbonate, polyarylate, polyether sulfone, polypropylene, polyester, polyvinyl fluoride, and polyvinyl chloride. In addition, an inorganic deposition film can also be used.

(Anode)

As the anode formed on the substrate, a metal, an alloy, an electrically conductive compound, and a mixture thereof, each having a large work function (specifically 4.0 eV or more) is preferably used. Specific examples thereof include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), a metal nitride (for example, titanium nitride), and the like are also included.

These materials are made into a film generally by a sputtering method. For example, a film of indium oxide-zinc oxide is formed by sputtering an indium oxide target doped with 1% to 10% by mass of zinc oxide, and a film of indium oxide doped with tungsten oxide and zinc oxide is formed by sputtering an indium oxide target doped with 0.5% to 5% by mass of tungsten oxide and 0.1% to 1% by mass of zinc oxide. In addition, a vacuum vapor deposition method, a coating method, an inkjet method, a spin coating method, and the like can be used for the formation.

Among the EL layers formed on the anode, a hole injecting layer to be formed in contact with the anode is formed from a composite material which is capable of easily injecting holes independently of the work function of the anode. Therefore a material which can be used as an electrode material (including, for example, a metal, an alloy, an electrically conductive compound, a mixture thereof, as well as the devices belonging to the group 1 or the group 2 in the periodic table) can also be used.

A material having a small work function, for example, the devices belonging to the group 1 or the group 2 in the periodic table, that is, an alkali metal such as lithium (Li) and cesium (Cs), an alkaline earth metal such as magnesium (Mg), calcium (Ca), and strontium (Sr), and an alloy including those (for example, MgAg and AlLi), rare earth metals such as europium (Eu) and ytterbium (Yb), and alloys thereof including those can also be used. Further, in the case of using the alkali metal, the alkaline earth metal, and the alloy thereof to form an anode, a vacuum vapor deposition method or a sputtering method can be employed. Incidentally, in the case of using a silver paste or the like, a coating method, an inkjet method, or the like can be employed.

(Hole Injecting Layer)

The hole injecting layer is a layer including a highly hole-transporting material.

As the highly hole-transporting material, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, or the like can be used.

Other examples thereof include aromatic amine compounds such as 4,4',4"-tris(N,N-diphenylamino)triphenylamine (abbreviation: TDATA), 4,4',4"-tris[N-(3-m ethylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), which are low molecular organic compounds.

A polymeric compound (an oligomer, a dendrimer, a polymer, and the like) can also be used. Examples thereof include polymeric compounds such as poly(N-vinylcarbazole) (abbreviation: PVK), poly(4-vinyltriphenylamine) (abbreviation: PVTPA), poly[N-(4-{N'[4-(4-diphenylamino)phenyl]phenyl-N'-phenylamino}phenyl)methacrylamid] (abbreviation: PTPDMA), and poly[N,N'-bis(4-butylphenyl)-N,N'-bis(phenyl)benzidine] (abbreviation: Poly-TPD). In addition, an acid-added polymeric compound such as poly(3,4-ethylenedioxythiophene)/poly(styrenesulfonic acid) (abbreviation: PEDOT/PSS) and polyalinine/poly(styrenesulfonic acid) (abbreviation: PAni/PSS) can also be used.

(Hole Transporting Layer)

The hole transporting layer is a layer including a highly hole-transporting material.

The organic EL device in one embodiment of the present invention may have the compound (1) singly or in combination with the following compound on the hole transporting layer.

For the hole transporting layer, an aromatic amine compound, a carbazole derivative, an anthracene derivative, or the like can be used. Specifically, an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB) can be used. The materials described herein are a material having a hole mobility of mainly $10^{-6}$ cm$^2$/Vs or more.

For the hole transporting layer, a carbazole derivative such as CSP, CzPA, and PCzPA, an anthracene derivative such as t-BuDNA, DNA, and DPAnth, and a polymeric compound such as poly(N-vinylcarbazole) (abbreviation: PVK) and poly(4-vinyltriphenylamine) (abbreviation: PVTPA) may be used.

In addition, other materials can also be used if their hole transporting property is higher than their electron transporting property.

Furthermore, a layer including a highly hole-transporting material may be a single layer or a laminate of two or more layers each including the material mentioned above.

In the organic EL device in one embodiment of the present invention, a layer including an electron-accepting compound (also referred to as an acceptor material) may be formed on the anode side of the hole transporting layer or the first hole transporting layer. Thus, it is expected that the driving voltage is lowered and the production cost is reduced.

As the electron accepting compound, a compound represented by the following formula (A) or (B) is preferred.

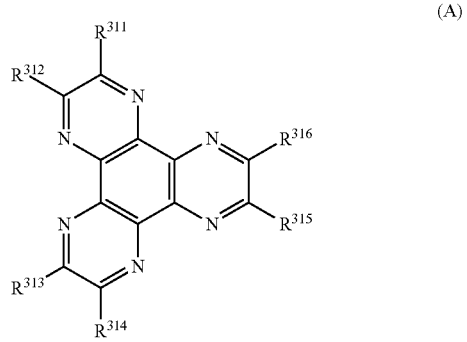

(A)

In the formula (A), $R^{311}$ to $R^{316}$ may be the same as or different from each other and each independently represent a cyano group, —CONH$_2$, a carboxyl group, or —COOR$^{317}$ ($R^{317}$ represents an alkyl group having 1 to 20 carbon atoms or a cycloalkyl group having 3 to 20 carbon atoms), provided that one or two or more pairs of $R^{311}$ and $R^{312}$, $R^{313}$ and $R^{314}$, and $R^{315}$ and $R^{316}$ may form a group represented by —CO—O—CO—.

Examples of $R^{317}$ include a methyl group, an ethyl group, an n-propyl group, an isopropyl group, an n-butyl group, an isobutyl group, a t-butyl group, a cyclopentyl group, and a cyclohexyl group.

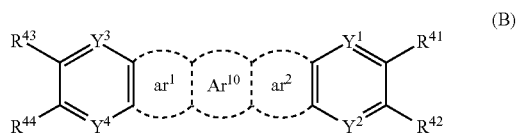

(B)

In the general formula (B), $R^{41}$ to $R^{44}$ may be the same as or different from each other, and are each a hydrogen atom, a substituted or unsubstituted alkyl group having 1 to 20 carbon atoms, a substituted or unsubstituted aryl group having 6 to 50 carbon atoms, a substituted or unsubstituted heterocyclic group having 5 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted aryloxy group having 6 to 50 carbon atoms, or a cyano group. Adjacent groups out of $R^{41}$ to $R^{44}$ are optionally bonded to each other to form a ring.

$Y^1$ to $Y^4$ are the same as or different from each other, and are each —N═, —CH═, or C($R^{45}$)═, and $R^{45}$ is a substituted or unsubstituted alkyl group having 1 to 20 carbon atoms, a substituted or unsubstituted aryl group having 6 to 50 carbon atoms, a substituted or unsubstituted heterocyclic group having 5 to 50 ring atoms, a halogen atom, a substituted or unsubstituted alkoxy group having 1 to 20 carbon atoms, a substituted or unsubstituted aryloxy group having 6 to 50 carbon atoms, or a cyano group.

$Ar^{10}$ is a fused ring having 6 to 24 ring carbon atoms or a heterocycle having 6 to 24 ring atoms. $ar^1$ and $ar^2$ each independently represent a ring of the following general formula (i) or (ii).

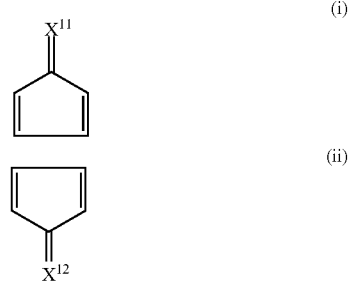

In the formulae, $X^{11}$ and $X^{12}$ are the same as or different from each other, and are each any one of divalent groups represented by the following (a) to (g).

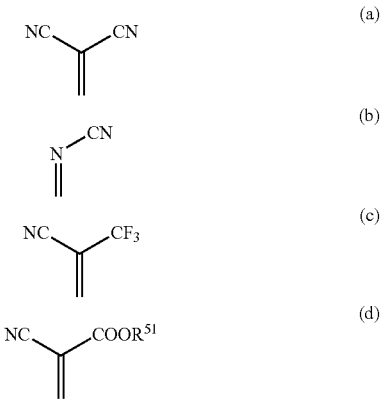

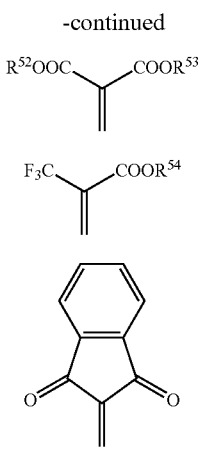

In the formulae, $R^{51}$ to $R^{54}$ are the same as or different from each other, and are each a hydrogen atom, a substituted or unsubstituted alkyl group having 1 to 20 carbon atoms, a substituted or unsubstituted aryl group having 6 to 50 carbon atoms, or a substituted or unsubstituted heterocyclic group having 5 to 50 ring atoms, and $R^{52}$ and $R^{53}$ are optionally bonded to each other to form a ring.

Examples of each group of $R^{41}$ to $R^{44}$ and $R^{51}$ to $R^{54}$ are as follows.

Examples of the alkyl group include a methyl group, an ethyl group, an n-propyl group, an isopropyl group, an n-butyl group, an isobutyl group, a tert-butyl group, a cyclopentyl group, and a cyclohexyl group.

Examples of the aryl group include a phenyl group, a biphenyl group, and a naphthyl group.

Examples of the heterocyclic group include residues of pyridine, pyrazine, furan, imidazole, benzimidazole, thiophene, and the like.

Examples of the halogen atom include a fluorine atom, a chlorine atom, a bromine atom, and an iodine atom.

Examples of the alkoxy group include a methoxy group and an ethoxy group.

Examples of the aryloxy group include a phenyloxy group.

(Guest Material for Light Emitting Layer)

The light emitting layer is a layer having a highly light emitting material and may be formed using various materials. For example, a fluorescent emitting compound and a phosphorescent emitting compound can be used as the highly light emitting material. The fluorescent emitting compound is a compound capable of emitting light from a singlet excited state, and the phosphorescent emitting compound is a compound capable of emitting light from a triplet excited state.

As the blue fluorescent emitting material which can be used in the light emitting layer, a pyrene derivative, a styrylamine derivative, a chrysene derivative, a fluoranthene derivative, a fluorene derivative, a diamine derivative, a triarylamine derivative, or the like can be used. Specific examples thereof include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA).

As the green fluorescent emitting material which can be used in the light emitting layer, an aromatic amine derivative or the like can be used. Specific examples thereof include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA).

As the red fluorescent emitting material which can be used in the light emitting layer, a tetracene derivative, a diamine derivative, or the like can be used. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

In one embodiment of the present invention, it is preferable that the fluorescent light emitting material contains at least one selected from an anthracene derivative, a fluoranthene derivative, a styrylamine derivative, and an arylamine derivative.

As the blue phosphorescent emitting material which can be used in the light emitting layer, a metal complex such as an iridium complex, an osmium complex, and a platinum complex is used. Specific examples thereof include bis[2-(4',6'-difluorophenyl)pyridinato-N,C2']iridium (III) tetrakis(1-pyrazolyl)borate (abbreviation: $FIr_6$), bis[2-(4',6'-difluoropheny)pyridinato-N,C2']iridium (III) picolinate (abbreviation: FIrpic), bis[2-(3',5'-bistrifluoromethylphenyl)pyridinato-N,C2']iridium picolinate (abbreviation: $Ir(CF_3ppy)_2(pic)$), and bis[2-(4',6'-difluorophenyl)pyridinato-N,C2']iridium (III) acetylacetonate (abbreviation: FIracac).

As the green phosphorescent emitting material which can be used in the light emitting layer, an iridium complex or the like is used. Examples thereof include tris(2-phenylpyridinato-N,C2')iridium (III) (abbreviation: $Ir(ppy)_3$), bis(2-phenylpyridinato-N,C2')iridium (III) acetylacetonate (abbreviation: $Ir(ppy)_2(acac)$), bis(1,2-diphenyl-1H-benzimidazolato)iridium (III) acetylacetonate (abbreviation: $Ir(pbi)_2(acac)$), and bis(benzo[h]quinolinato)iridium (III) acetylacetonate (abbreviation: $Ir(bzq)_2(acac)$).

As the red phosphorescent emitting material which can be used in the light emitting layer, a metal complex such as an iridium complex, a platinum complex, a terbium complex, and a europium complex is used. Specific examples thereof include an organometallic complex such as bis[2-(2'-benzo[4,5-α]thienyl)pyridinato-N,C3']iridium (III) acetylacetonate (abbreviation: $Ir(btp)_2(acac)$), bis(1-phenylisoquinolinato-N,C2')iridium (III) acetylacetonate (abbreviation: $Ir(piq)_2(acac)$), (acetylacetonato)bis[2,3-bis(4-fluorophenyl)quinoxalinato]iridium (III) (abbreviation: $Ir(Fdpq)_2(acac)$), and 2,3,7,8,12,13,17,18-octaethyl-21H,23H-porphyrin platinum (II) (abbreviation: PtOEP).

Furthermore, a rare earth metal complex such as tris(acetylacetonato)(monophenanthroline)terbium (III) (abbreviation: $Tb(acac)_3(Phen)$), tris(1,3-diphenyl-1,3-propanedionato)(monophenanthroline)europium (III) (abbreviation: $Eu(DBM)_3(Phen)$), and tris[1-(2-thenoyl)-3,3,3-trifluoroacetonato](monophenanthroline)europium (III) (abbreviation: $Eu(TTA)_3(Phen)$) emits light from the rare earth metal ion (electron transition between different multiple states), and can be therefore used as a phosphorescent emitting compound.

In one embodiment of the present invention, the phosphorescent light emitting material is preferably an ortho-metallated complex with a metal atom selected from iridium (Ir), osmium (Os), and platinum (Pt).

The phosphorescent light emitting material which is an ortho-metallated complex with a metal atom selected from iridium (Ir), osmium (Os), and platinum (Pt) is preferably a complex represented by the following formula (V), (X), (Y), or W.

Examples of the substituents represented by $R^{50}$ to $R^{54}$ include those as same ones as the substituents exemplified as $R^1$ in the formula (1).

The formula (V) is preferably represented by the following formula (V-1), and formula (X) is preferably represented by the following formula (X-1) or formula (X-2). In the following formulae (X-1), (X-1), and (X-1), $R^{50}$, k, and M are the same as $R^{50}$, k, and M above.

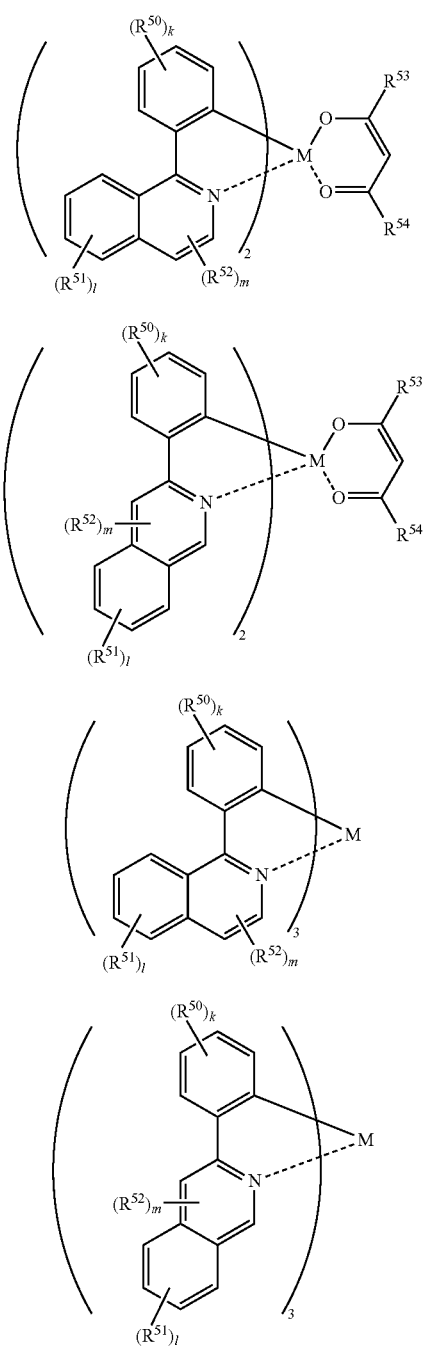

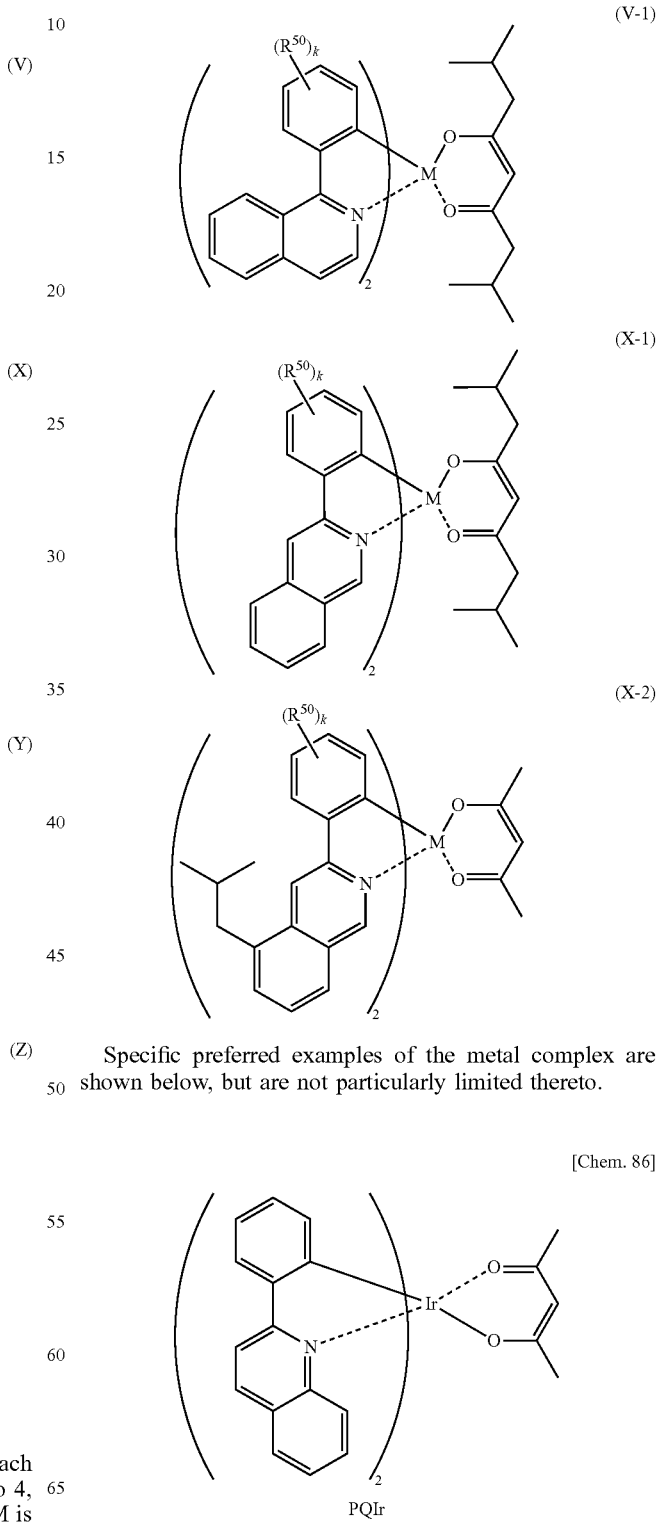

In the formula (V), (X), (Y), or (Z), $R^{50}$ to $R^{54}$ are each a hydrogen atom or a substituent, k is an integer of 1 to 4, l is an integer of 1 to 4, and m is an integer of 1 or 2. M is Ir, Os, or Pt.

Specific preferred examples of the metal complex are shown below, but are not particularly limited thereto.

[Chem. 86]

PQIr

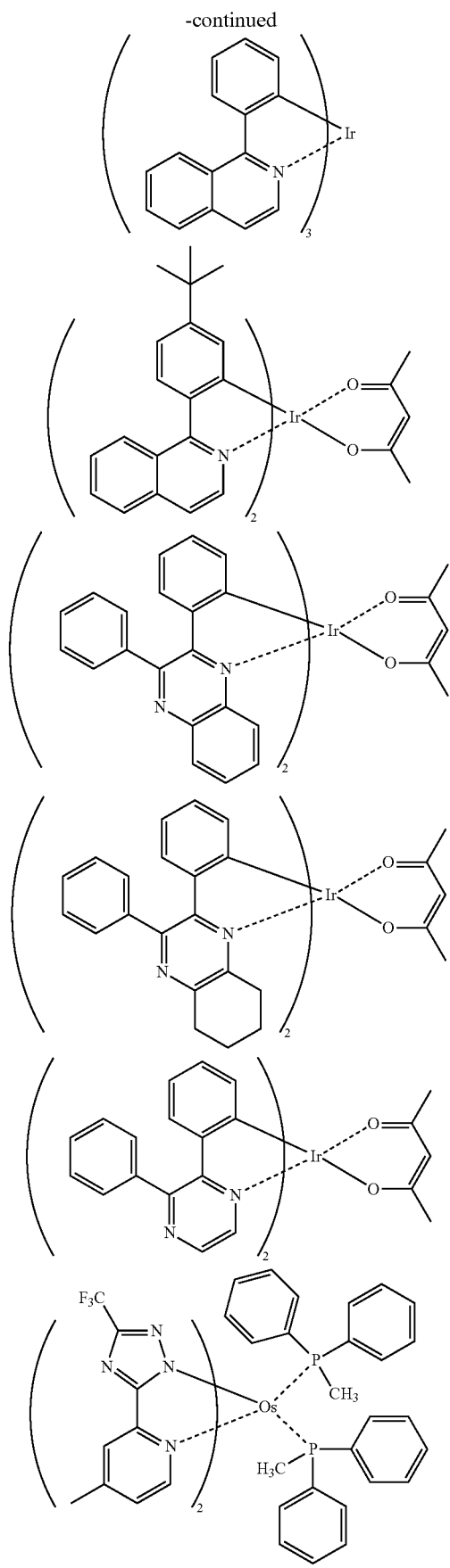
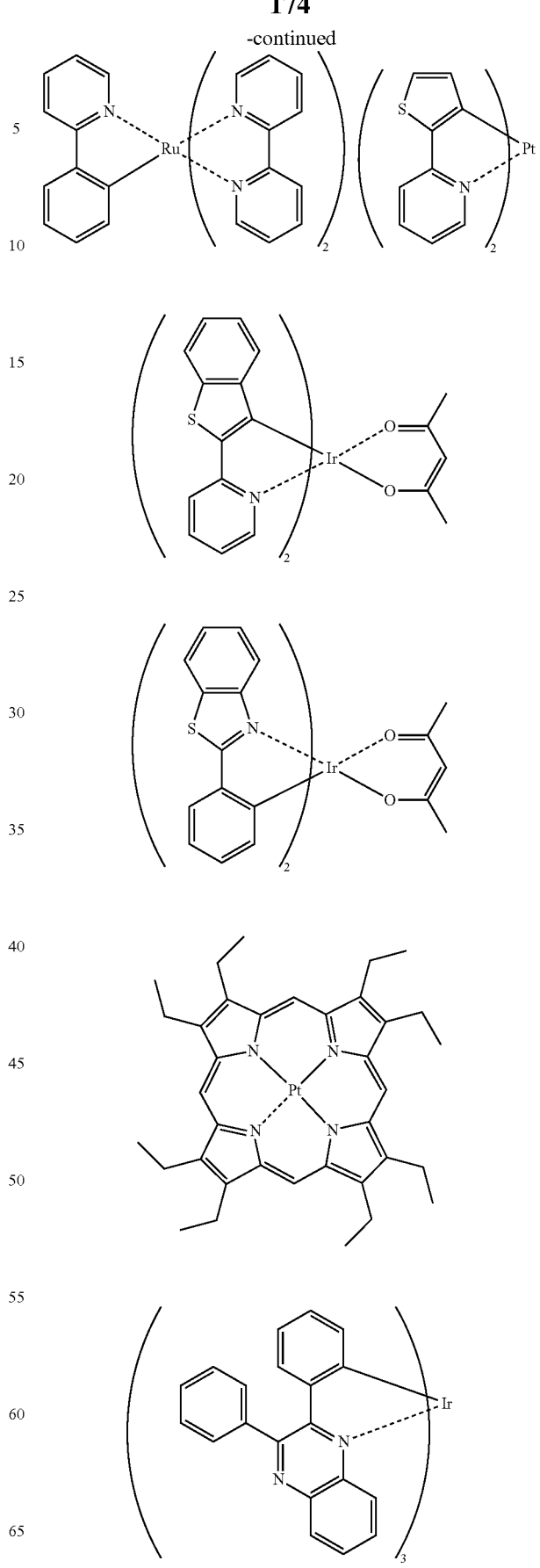

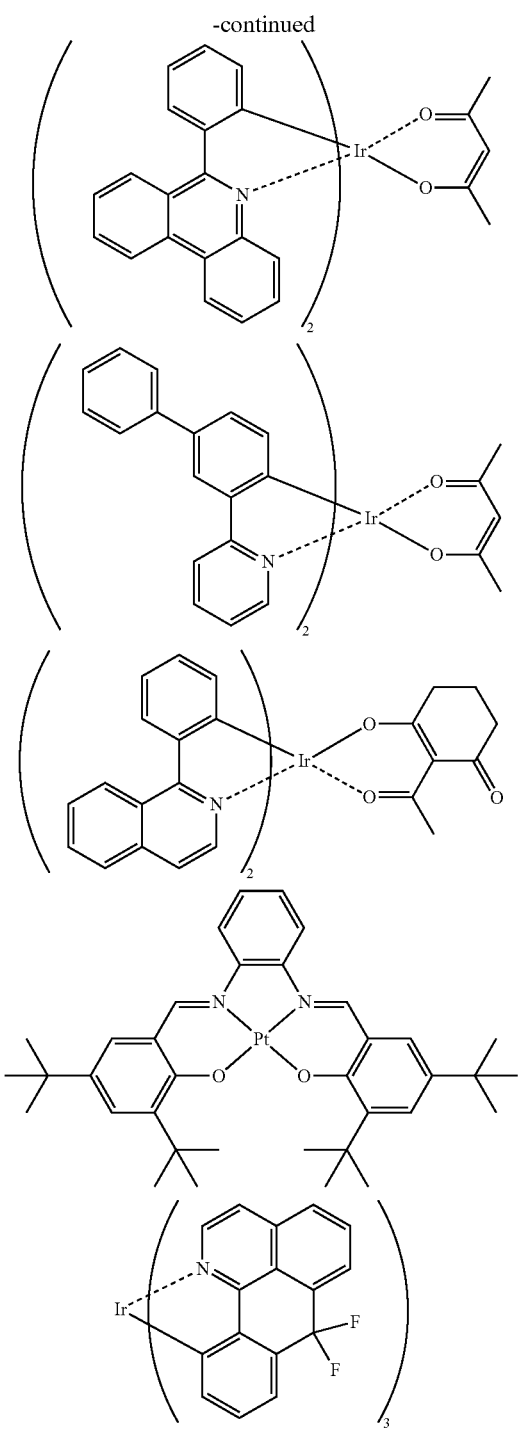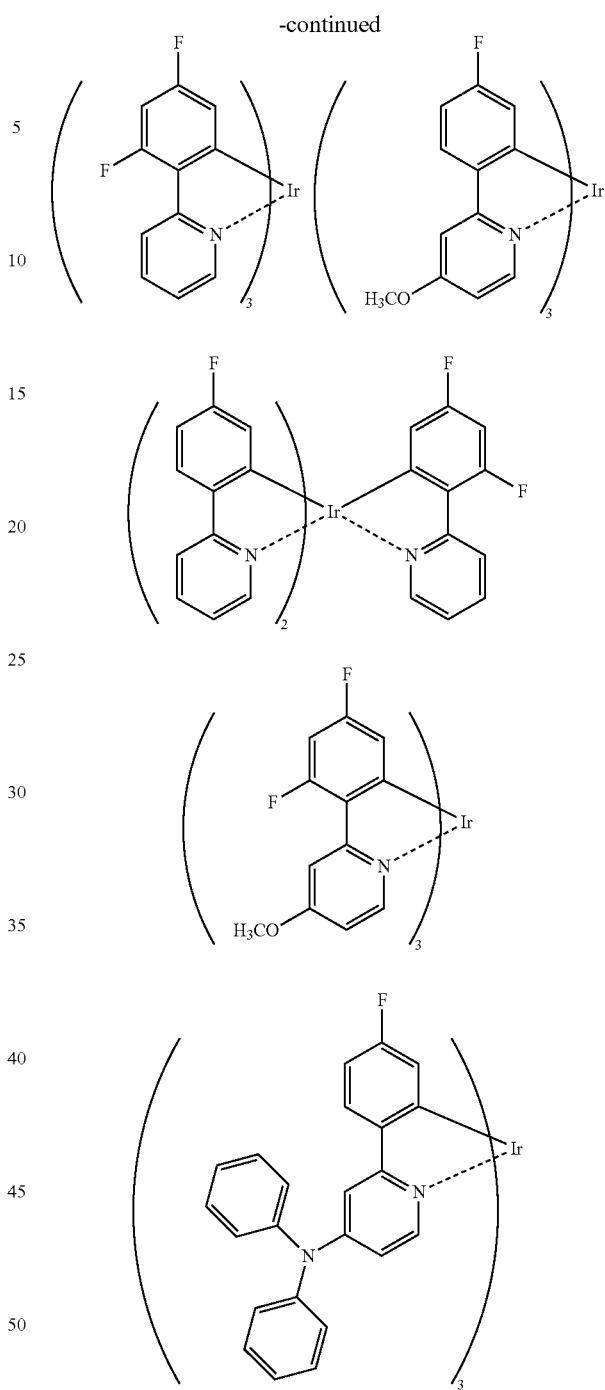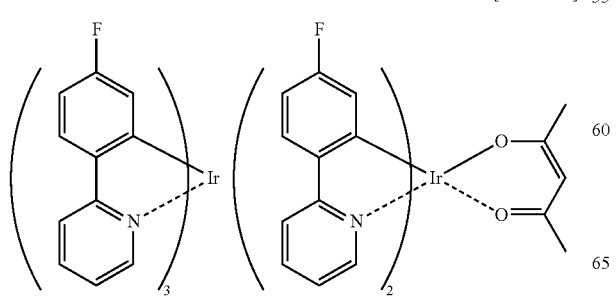

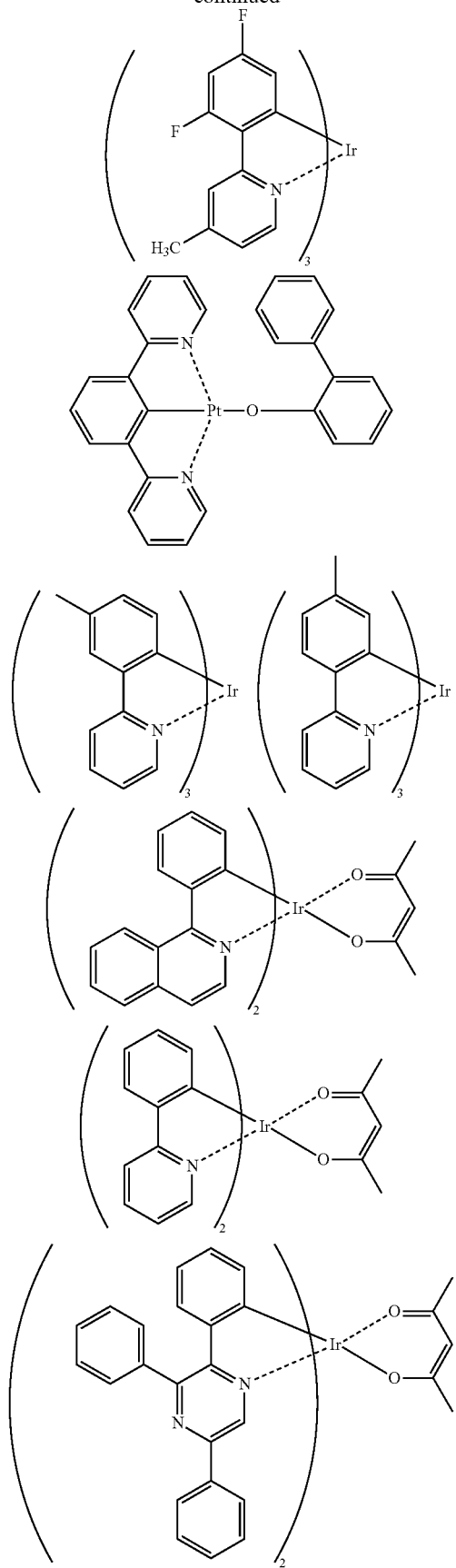

-continued
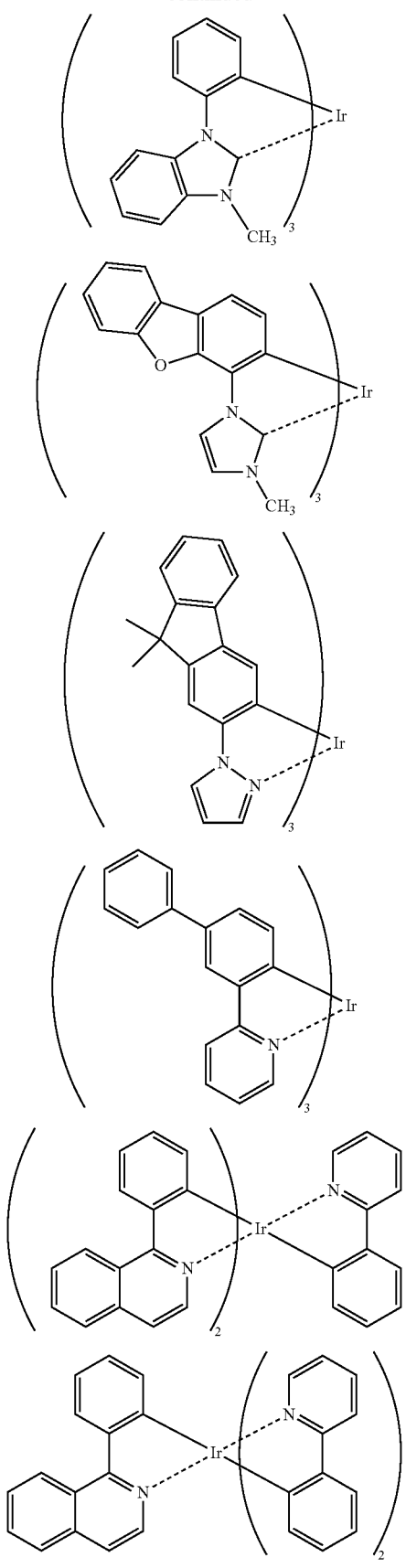
[Chem. 89]
-continued
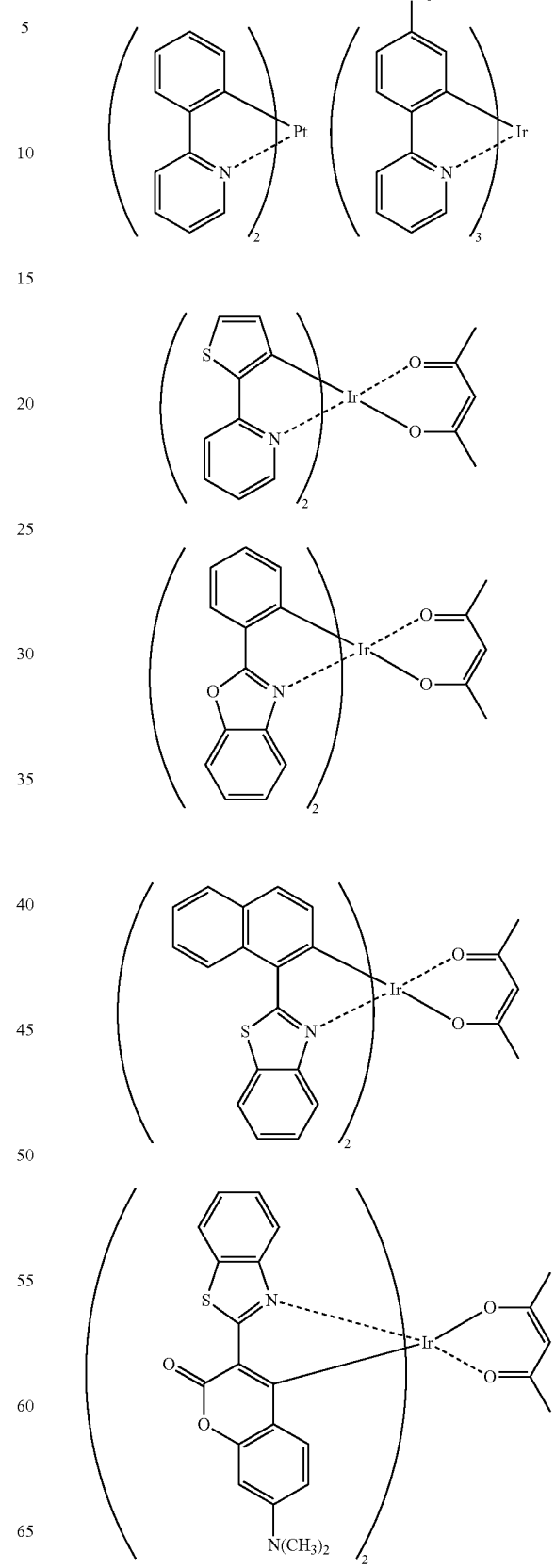

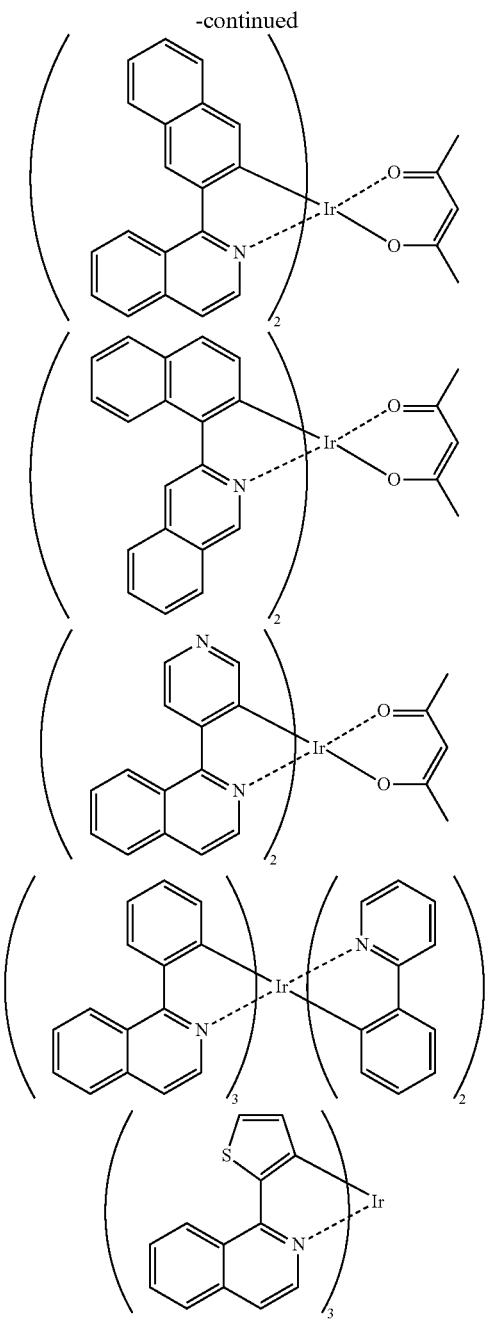

(Host Material for Light Emitting Layer)

The light emitting layer may be configured by dispersing the highly light emitting material (guest material) mentioned above in another material (host material). As the material in which the highly light emitting material is to be dispersed, various materials can be used, and a material having a lowest unoccupied molecular orbital level (LUMO level) higher than that of the highly light emitting material and a highest occupied molecular orbital level (HOMO level) lower than that of the highly light emitting material is preferably used.

In one embodiment of the organic EL device of the present invention, the compound (1) of the present invention can also be used as the host material for the light emitting layer.

As the material (host material) in which the highly light emitting material is to be dispersed, for example, (1) a metal complex such as an aluminum complex, a lithium complex, a beryllium complex, and a zinc complex, (2) a heterocyclic compound such as an oxadiazole derivative, a benzimidazole derivative, and a phenanthroline derivative, (3) a fused aromatic compound such as a carbazole derivative, an anthracene derivative, a phenanthrene derivative, a pyrene derivative, and a chrysene derivative, and (4) an aromatic amine compound such as a triarylamine derivative and a fused aromatic polycyclic amine derivative. is used.

Specifically, a metal complex such as tris(8-quinolinolato)aluminum (III) (abbreviation: Alq), tris(4-methyl-8-quinolinolato)aluminum (III) (abbreviation: Almq$_3$), 8-quinolinolatolithium (Liq) bis(10-hydroxybenzo[h]quinolinato)beryllium (II) (abbreviation: BeBq$_2$), bis(2-methyl-8-quinolinolato)(4-phenylphenolato)aluminum (III) (abbreviation: BAlq), bis(8-quinolinolato)zinc (II) (abbreviation: Znq), bis[2-(2-benzoxazolyl)phenolato]zinc (II) (abbreviation: ZnPBO), and bis[2-(2-benzothiazolyl)phenolato]zinc (II) (abbreviation: ZnBTZ); a heterocyclic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), and bathocuproin (abbreviation: BCP); a fused aromatic compound such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl) anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB$_3$), 9,10-diphenylanthracene (abbreviation: DPAnth), and 6,12-dimethoxy-5,11-diphenylchrysene; and an aromatic amine compound such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB can be used. Further, a plurality of materials (host materials) for dispersing the highly light emitting material (guest material) may be used.

(Electron Transporting Layer)

The electron transporting layer is a layer including a highly electron-transporting material. For the electron transporting layer, (1) a metal complex such as an aluminum complex, a beryllium complex, and a zinc complex, (2) an aromatic heterocyclic compound such as an imidazole derivative, a benzimidazole derivative, an azine derivative, a carbazole derivative, and a phenanthroline derivative, or (3) a polymeric compound.

Specifically, as the low molecular organic compound, a metal complex such as Alq, tris(4-methyl-8-quinolinolato)aluminum (abbreviation: Almq$_3$), bis(10-hydroxybenzo[h]quinolinato)beryllium (abbreviation: BeBq$_2$), BAlq, Znq, ZnPBO, and ZnBTZ can be used. Further, in addition to the metal complex, an aromatic heterocyclic compound such as 2-(4-biphenylyl)-5-(4-tert-butylphenyl)-1,3,4-oxadiazole (abbreviation: PBD), 1,3-bis[5-(4-tert-butylphenyl)-1,3,4- oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazol-2-yl) stilbene (abbreviation: BzOs) can also be used. The material described herein is a material having an electron mobility of mainly $10^{-6}$ cm$^2$/Vs or more. Further, other materials may also be used in the electron transporting layer if their electron transporting property is higher than their hole transporting property. Further, the electron transporting layer may be a single layer or a laminate of two or more layers each including the material.

Moreover, a polymeric compound can also be used in the electron transporting layer. For example, poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be used.

In one embodiment of the present invention, the electron transporting layer preferably contains the aromatic heterocyclic compound, and more preferably contains a carbazole derivative.

(Electron Injecting Layer)

The electron injecting layer is a layer including a highly electron-injecting material. For electron injecting layer, an alkali metal, an alkaline earth metal, and a compound thereof, such as lithium (Li), cesium (Cs), calcium (Ca), lithium fluoride (LiF), cesium fluoride (CsF), calcium fluoride (CaF$_2$), and lithium oxide (LiOx) can be used. In addition, an electron transporting material which is incorporated with an alkali metal, an alkaline earth metal, or a compound thereof, for example, Alq doped with magnesium (Mg), may also be used. Further, in this case, electrons can be more efficiently injected from the cathode.

Alternatively, a composite material obtained by mixing an organic compound and an electron donor may also be used in the electron injecting layer. Such a composite material is excellent in the electron injecting property and the electron transporting property since the electron donor donates electrons to the organic compound. In this case, the organic compound is preferably a material excellent in transporting the received electrons, and specifically, for example, the materials (a metal complex, an aromatic heterocyclic compound, or the like) constituting the electron transporting layer mentioned above such as the metal complex and the aromatic heterocyclic compound can be used. Any material capable of giving its electron to another organic compound can be used as the electron donor. Specifically, an alkali metal, an alkaline earth metal, and a rare earth metal are preferred, and examples thereof include lithium, cesium, magnesium, calcium, erbium, and ytterbium. Further, an alkali metal oxide and an alkaline earth metal oxide are preferred, and examples thereof include lithium oxide, calcium oxide, and barium oxide. In addition, a Lewis base such as magnesium oxide and an organic compound such as tetrathiafulvalene (abbreviation: TTF) can also be used.

(Cathode)

For the cathode, a metal, an alloy, an electrically conductive compound, and a mixture thereof, each having a small work function (specifically a work function of 3.8 eV or less) is preferably used. Specific examples of the material for such a cathode include a metal of the group 1 or 2 of the periodic table, that is, an alkali metal such as lithium (Li) and cesium (Cs), an alkaline earth metal such as magnesium (Mg), calcium (Ca), strontium (Sr), an alloy containing these metals (for example, MgAg and AlLi), a rare earth metal such as europium (Eu) and ytterbium (Yb), and an alloy containing a rare earth metal.

Furthermore, in the case of forming a cathode using the alkali metal, the alkaline earth metal, and the alloy thereof, a vacuum vapor deposition or a sputtering method can be employed. Further, in the case of using a silver paste or the like, a coating method, an inkjet method, or the like can be employed.

Moreover, by providing the electron injecting layer, various electrically conductive materials such as Al, Ag, ITO, graphene, and indium oxide-tin oxide doped with silicon or silicon oxide, selected independently from the work function, can be used to form the cathode. These electrically conductive materials are made into films using a sputtering method, an inkjet method, a spin coating method, or the like.

Each layer of the organic EL device can be formed using any of a dry film-forming method such as vacuum vapor deposition, sputtering, plasma, and ion plating, and a wet film-forming method such as spin coating, dip coating, and flow coating.

In the case of the wet film-forming method, the material for each layer is dissolved or dispersed in an appropriate solvent such as ethanol, chloroform, tetrahydrofuran, and dioxane, and then the obtained solution or dispersion is used to form a thin film. Further, in order to improve the film-forming properties and prevent pin holes on the film, the solution and the dispersion may include a resin or an additive. Examples of the resin include an insulating resin and a copolymer thereof such as polystyrene, polycarbonate, polyarylate, polyester, polyamide, polyurethane, polysulfone, polymethyl methacrylate, polymethyl acrylate, and cellulose; and a photoconductive resin such as poly-N-vinylcarbazole and polysilane; and an electrically conductive resin such as polythiophene and polypyrrole. In addition, examples of the additive include an antioxidant, an ultraviolet absorber, and a plasticizer.

The film thickness of each layer is not particularly limited and may be selected so as to obtain good device performance. If extremely thick, a large applied voltage is needed to obtain a desired emission output, thereby reducing the efficiency. If extremely thin, pinholes occur on the film to make it difficult to obtain a sufficient luminance even when applying an electric field. The thickness is generally 5 nm to 10 µm, and more preferably 10 nm to 0.2 µm. In particular, the film thickness of the light emitting layer is not particularly limited, but is preferably 5 nm to 100 nm, more preferably 7 nm to 70 nm, and still more preferably 10 nm to 50 nm. In addition, the film thickness of the hole transporting layer is preferably 10 nm to 300 nm.

[Electronic Equipment]

The electronic equipment in one embodiment of the present invention includes the above-described organic EL device in one embodiment of the present invention.

Examples of the electronic equipment include display parts such as an organic EL panel module; display devices of television sets, mobile phones, personal computer, or the like; and light emitting devices of a lighting device and a vehicle lighting device.

EXAMPLES

Next, the present invention will be described in more detail with reference to Examples and Comparative Examples, but it should be noted that the scope of the invention is not limited to the descriptions in Examples.

Furthermore, the compounds recited in the claims of this application can be synthesized by referring to the following synthetic reactions while using a known synthetic reaction and a starting material in accordance with the target compound.

Synthesis Example 1 (Synthesis of Compound 1)

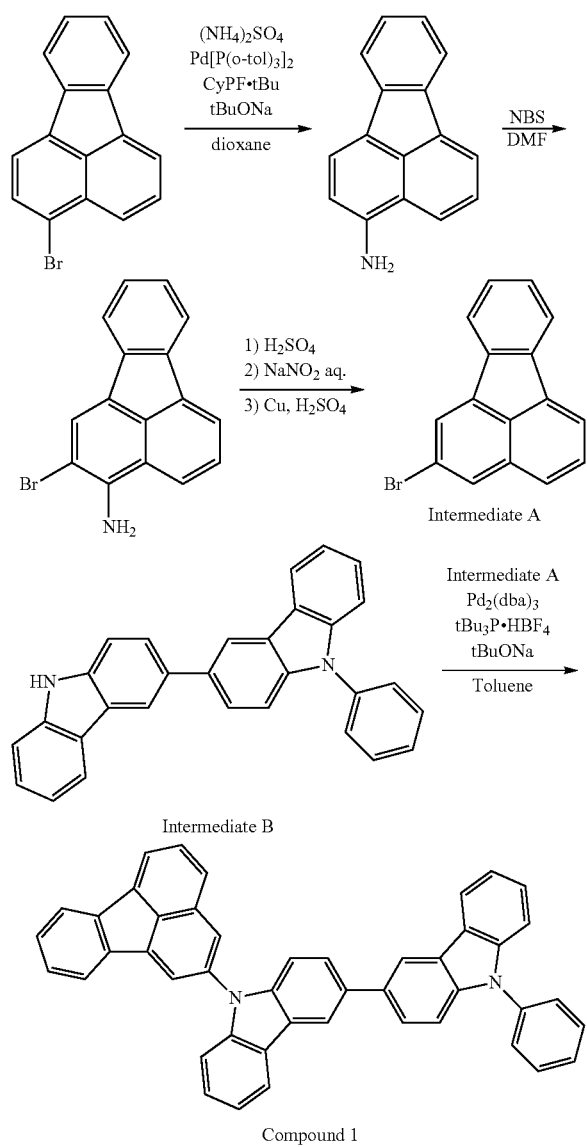

In an argon atmosphere, 3-bromofluoranthene (1.0 g), sulfuric acid ammonium (706 mg), bis[tris(2-methylphenyl) phosphine]palladium (5.0 mg), 1-dicyclohexylphosphino-2-di-t-butylphosphinoethylferrocene (4.0 mg), sodium-t-butoxide (1.54 g), and dioxane (35 mL) were stirred at 80° C. for 5 hours. The obtained mixture was filtered through Celite to obtain 3-aminofluoranthene as a brown red oily substance (754 mg, yield 99%).

3-Aminofluoranthene (6.06 g) was dissolved in DMF (140 mL), and NBS (4.73 g) which had been dissolved in DMF (50 mL) was added dropwise thereto under ice-cooling. Thereafter, the mixture was warmed to room temperature and stirred for 5 hours. An aqueous sodium hydrogen carbonate solution and water were added dropwise to the obtained mixed solution under ice-cooling, followed by extraction with dichloromethane. The organic layer was concentrated and then purified by column chromatography to obtain 2-bromo-3-aminofluoranthene as a brown product (5.45 g, yield 66%).

2-Bromo-3-aminofluoranthene (7.94 g) was dissolved in ethanol (270 mL), and sulfuric acid (7.2 mL) was added dropwise thereto for 30 minutes under ice-cooling. Thereafter, a 13 M aqueous sodium nitrite solution (44 mL) was added dropwise thereto for 30 minutes under ice-cooling, and the mixture was stirred at the same temperature for 30 minutes. Copper (1.71 g) was introduced to the mixed reaction solution under ice-cooling, sulfuric acid (15.7 mL) was then added dropwise thereto, and then the mixture was heated and refluxed for 1 hour. The mixture was extracted with dichloromethane, and the organic layer was concentrated, followed by purification by silica gel chromatography, to obtain an intermediate A as a red product (6.28 g, yield 83%). As a result of mass spectrum analysis, m/e was 383 for a molecular weight of 383 of the intermediate A.

Next, in an argon atmosphere, an intermediate B (3.4 g), the intermediate A (2.34 g), tris(dibenzylideneacetone)dipalladium (0) (150 mg), tetrafluoroboric acid tri-t-butylphosphine (190 mg), and toluene (60 mL) were added and the mixture was stirred under heating and refluxing for 7 hours. The precipitated crystal was separated by filtration, recrystallized, and purified to obtain a compound 1 as a yellow product (5.03 g, 99%). As a result of mass spectrum analysis, m/e was 608 for a molecular weight of 608 of the compound 1.

In addition, the dipole moment of the obtained compound 1 was calculated by a time-dependent density functional method, and was found to be 0.927 debyes.

Synthesis Example 2 (Synthesis of Compound 2)

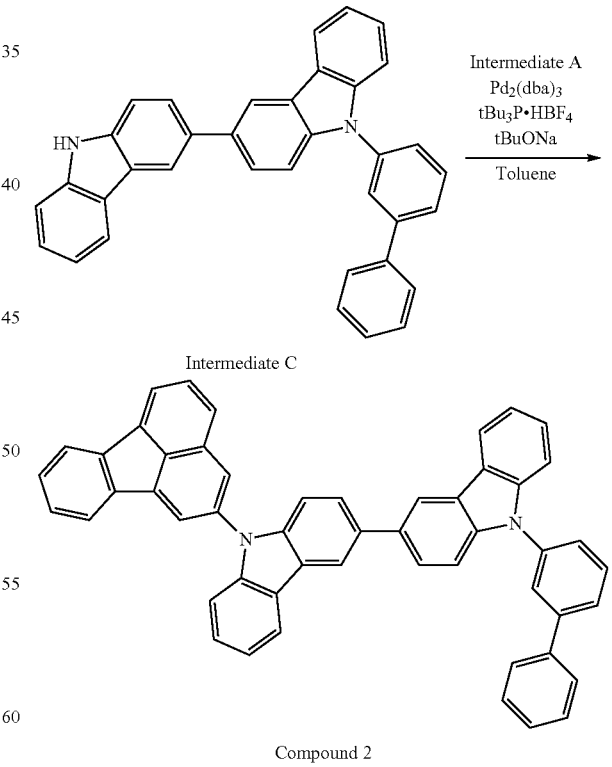

A compound 2 was synthesized by the same method as in Synthesis Example 1 except that an intermediate C was used instead of the intermediate B. As a result of mass spectrum analysis, m/e was 684 for a molecular weight of 684 of the compound 2.

Synthesis Example 3 (Synthesis of Compound 3)

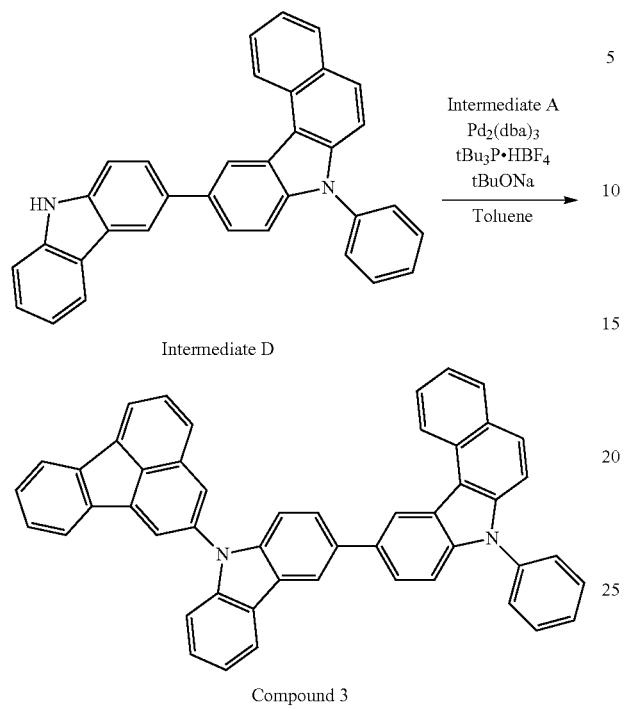

Intermediate D

Compound 3

A compound 3 was synthesized by the same method as in Synthesis Example 1 except that an intermediate D was used instead of the intermediate B. As a result of mass spectrum analysis, m/e was 658 for a molecular weight of 658 of the compound 3.

Synthesis Example 4 (Synthesis of Compound 4)

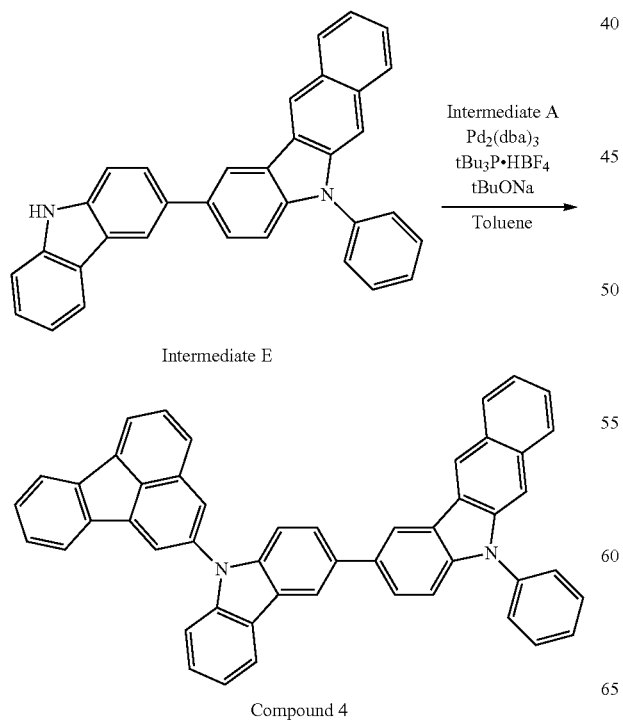

Intermediate E

Compound 4

A compound 4 was synthesized by the same method as in Synthesis Example 1 except that an intermediate E was used instead of the intermediate B. As a result of mass spectrum analysis, m/e was 658 for a molecular weight of 658 of the compound 4.

Synthesis Example 5 (Synthesis of Compound 5)

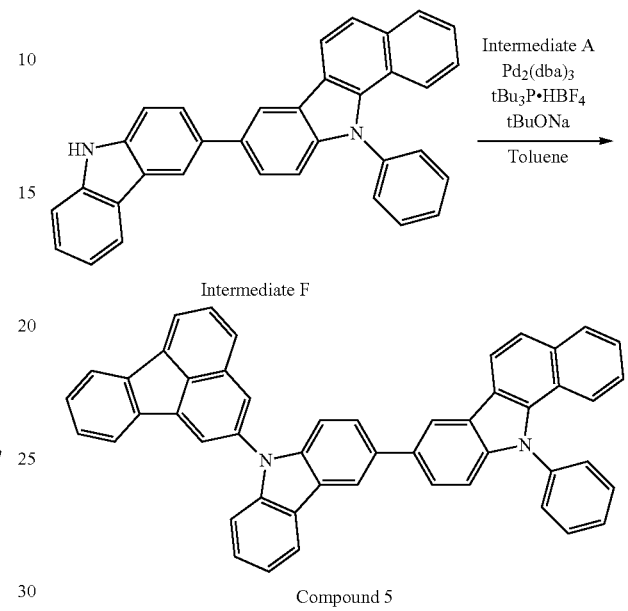

Intermediate F

Compound 5

A compound 5 was synthesized by the same method as in Synthesis Example 1 except that an intermediate F was used instead of the intermediate B. As a result of mass spectrum analysis, m/e was 658 for a molecular weight of 658 of the compound 5.

Synthesis Example 6 (Synthesis of Compound 6)

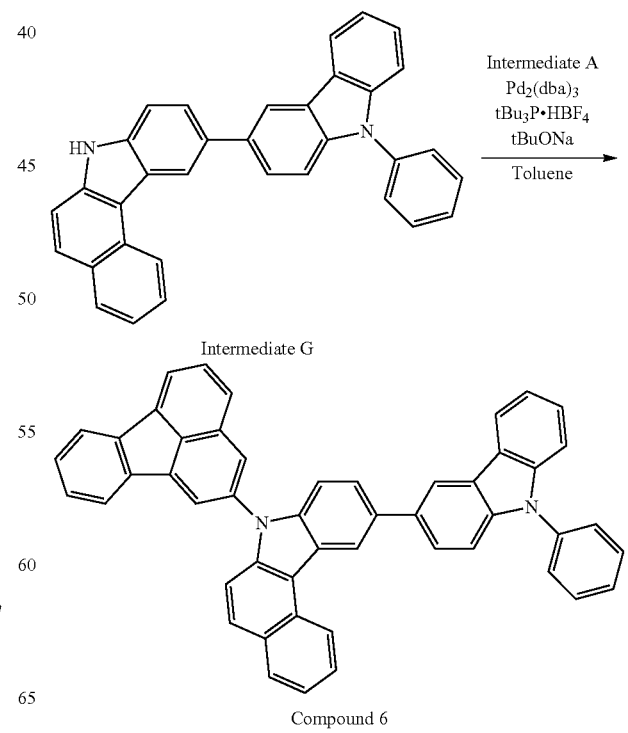

Intermediate G

Compound 6

A compound 6 was synthesized by the same method as in Synthesis Example 1 except that an intermediate G was used instead of the intermediate B. As a result of mass spectrum analysis, m/e was 658 for a molecular weight of 658 of the compound 6.

Synthesis Example 7 (Synthesis of Compound 7)

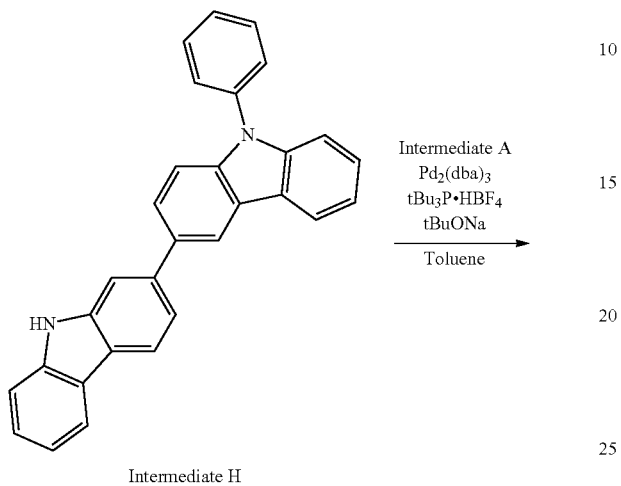

Intermediate H

Intermediate A
Pd₂(dba)₃
tBu₃P·HBF₄
tBuONa
Toluene

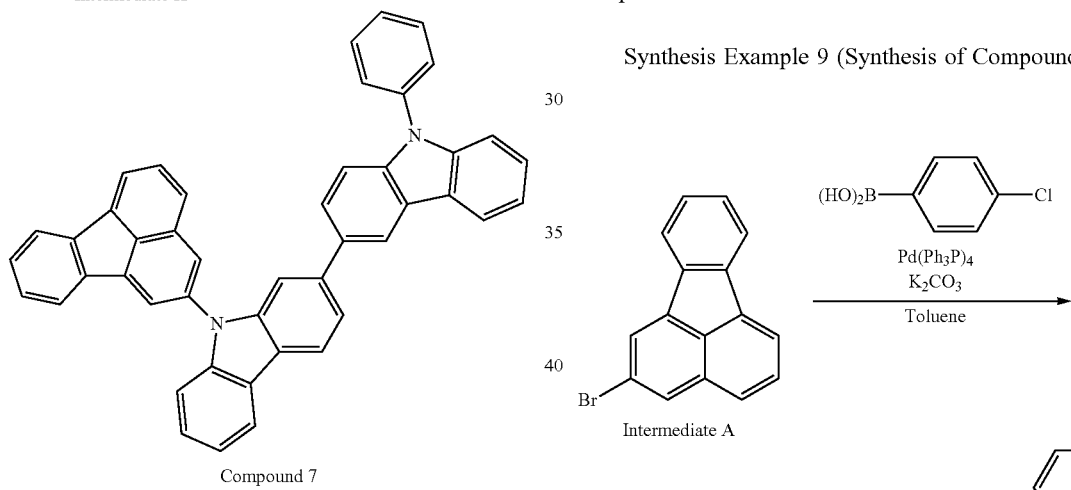

Compound 7

A compound 7 was synthesized by the same method as in Synthesis Example 1 except that an intermediate H was used instead of the intermediate B. As a result of mass spectrum analysis, m/e was 608 for a molecular weight of 608 of the compound 7.

Synthesis Example 8 (Synthesis of Compound 8)

Intermediate I

Intermediate A
Pd₂(dba)₃
tBu₃P·HBF₄
tBuONa
Toluene

-continued

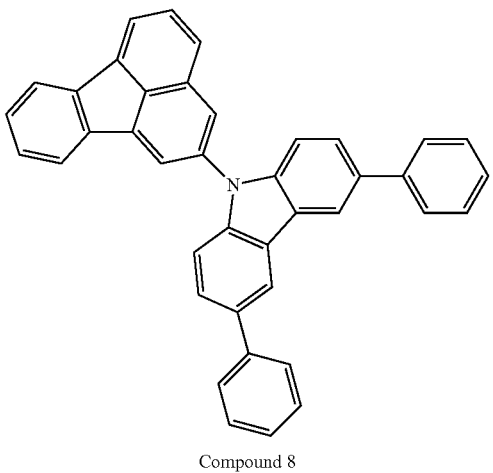

Compound 8

A compound 8 was synthesized by the same method as in Synthesis Example 1 except that an intermediate I was used instead of the intermediate B. As a result of mass spectrum analysis, m/e was 519 for a molecular weight of 519 of the compound 8.

Synthesis Example 9 (Synthesis of Compound 9)

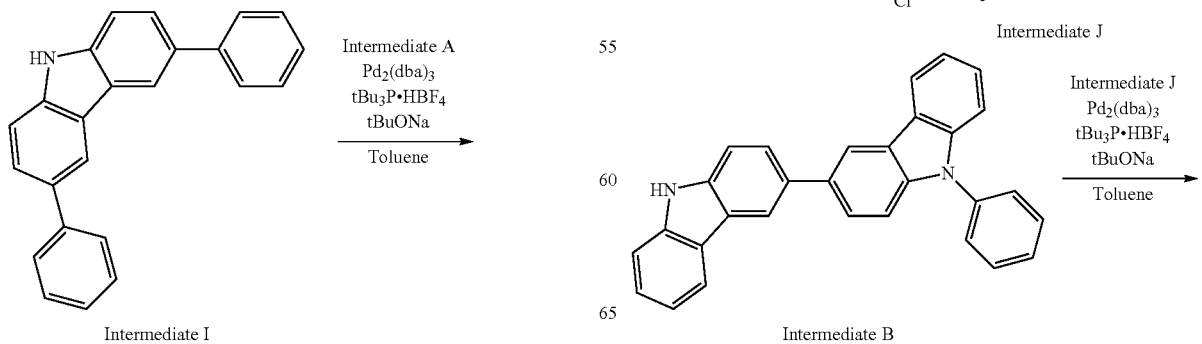

Intermediate A (HO)₂B—⟨ ⟩—Cl

Pd(Ph₃P)₄
K₂CO₃
Toluene

Intermediate J

Intermediate B

Intermediate J
Pd₂(dba)₃
tBu₃P·HBF₄
tBuONa
Toluene

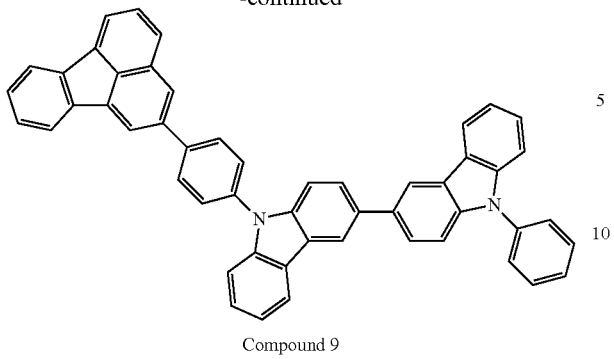

Compound 9

First, the intermediate A (3.0 g), 4-chlorophenylboronic acid (1.84 g), tetrakis(triphenylphosphine)palladium (0) (618 mg), potassium carbonate (2.96 g), and toluene (100 mL) were put into a reaction container, and the mixture was stirred under heating and refluxing for 8 hours. The mixture was filtered through Celite and the obtained mixture was purified by silica gel column chromatography to obtain an intermediate J (2.54 g, yield 76%). As a result of mass spectrum analysis, m/e was 312 for a molecular weight of 312 of the intermediate J.

Subsequently, a compound 9 was synthesized by the same method as in Synthesis Example 1 except that an intermediate J was used instead of the intermediate A. As a result of mass spectrum analysis, m/e was 684 for a molecular weight of 684 of the compound 9.

Example 1 (Preparation of Organic EL Device)

A glass substrate (manufactured by Geomatec Company) provided with an ITO transparent electrode with a size of 25 mm×75 mm×1.1 mm was subjected to ultrasonic cleaning in isopropyl alcohol for 5 minutes, and then to ultraviolet (UV) ozone cleaning for 30 minutes. The thickness of the ITO transparent electrode was 130 nm.

The cleaned glass substrate having a transparent electrode line was mounted on a substrate holder in a vacuum vapor deposition apparatus. First, the following acceptor material (HA) was deposited on the surface having the transparent electrode line formed thereon, so as to cover the transparent electrode to form an acceptor layer with a film thickness of 5 nm. The following aromatic amine compound (HT) was deposited on the acceptor layer to form a hole transporting layer with a film thickness of 210 nm.

Next, the following compound RD-1 (dopant material) was co-deposited together with the compound 1 (host material) obtained in Synthesis Example 1 to form a co-deposited film with a film thickness of 40 nm on the hole transporting layer. The concentration of the compound RD-1 was 2.0% by mass. The co-deposited film functions as a light emitting layer.

Furthermore, the following compound (ET) (50% by mass) and an electron donating dopant Liq (50% by mass) were dual-deposited on the light emitting layer to form an electron transporting layer with a film thickness of 30 nm.

Next, Liq was deposited on the electron transporting layer at a film-forming speed of 0.1 angstrom/min to form an Liq film with a film thickness of 1 nm, thereby forming an electron injecting electrode (cathode).

In addition, a metal Al was deposited on the Liq film to form a metal Al film with a film thickness of 80 nm, thereby forming a metal Al cathode, and thus manufacturing an organic EL device.

(Evaluation of Organic EL Device)

The organic EL device thus prepared above was driven to emit light by direct current application thereto, and the external quantum efficiency (%) and the chromaticity (x, y) at a current density of 10 mA/cm$^2$ were measured. The results are shown in Table 1.

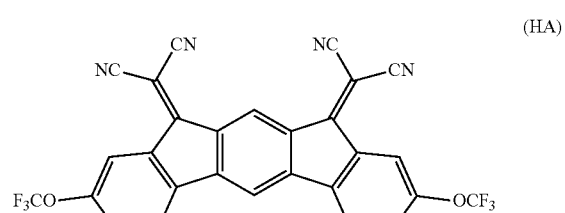
(HA)

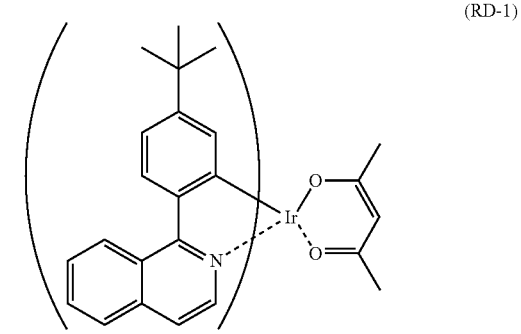
(RD-1)

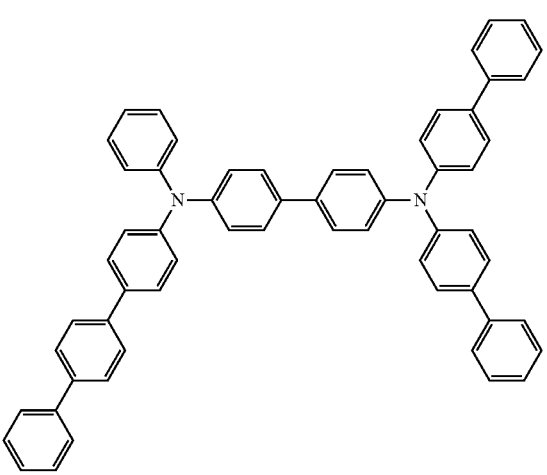
(HT)

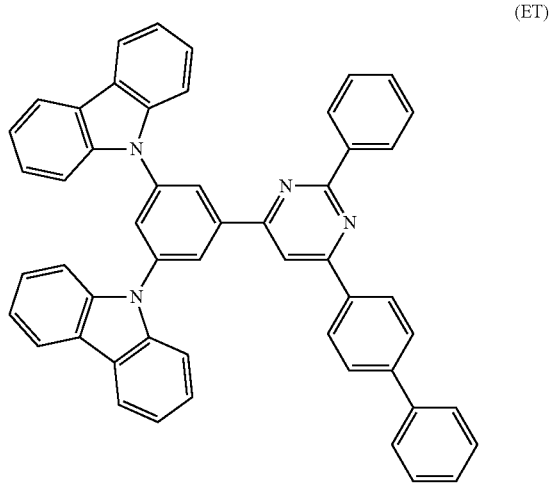
(ET)

-continued

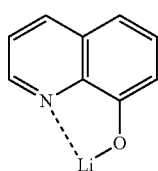

Comparative Examples 1 and 2 (Preparation of Organic EL Device)

Organic EL devices of Comparative Examples 1 and 2 each were prepared as a host material in the same manner as in Example 1 except that the comparative compound 1 or the comparative compound 2 listed in Table 1 was used, and the external quantum efficiency was measured. The results are shown in Table 1.

In addition, the dipole moment of the comparative compound 1 was calculated by a time-dependent density functional method, and was found to be 0.571 debyes.

Comparative Compound 1

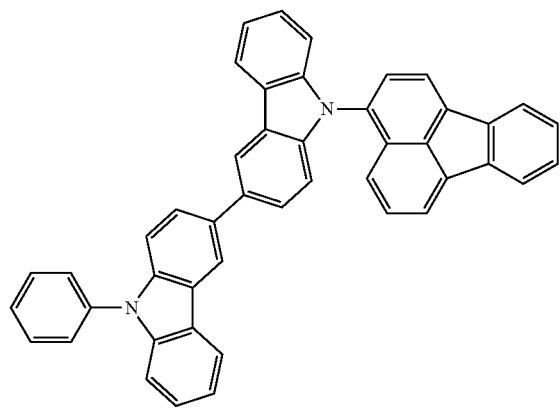

Comparative Compound 2

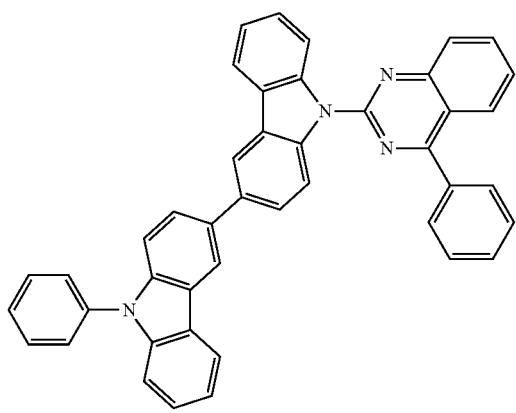

TABLE 1

|  |  | External Quantum Efficiency (%) | Chromaticity Coordinates (x, y) |
| --- | --- | --- | --- |
| Example 1 | Compound 1 | 19.4 | (0.662, 0.335) |
| Comparative Example 1 | Comparative compound 1 | 18.8 | (0.663, 0.335) |
| Comparative Example 2 | Comparative compound 2 | 17.1 | (0.655, 0.342) |

From the results in Table 1, it could be seen that by using the compound 1 as a host material, an organic EL device with high external quantum efficiency and high emission efficiency is obtained. On the other hand, in Comparative Example 1 using the comparative compound 1 substituted at the 3-position of the fluoranthene skeleton, the external quantum efficiency was lower than that in the case of the organic EL device in Example 1. Further, also in Comparative Example 2 using the comparative compound 2 having no fluoranthene skeleton, the external quantum efficiency was lower than that in the organic EL device of Example 1.

The reason why such results were obtained is not clear, but could be presumed as follows. That is, the compound of the present invention, which is bonded to the 2-position of the fluoranthene skeleton, has a high dipole moment, an improved injecting property of a carrier, and correspondingly, an optimized carrier balance, as compared with a compound bonded to the 3-position of the fluoranthene skeleton such as the comparative compound 1, and therefore, the external quantum efficiency (emission efficiency) is further improved.

In addition, from the results of chromaticity coordinates, it could be seen that the organic EL device obtained in Example 1 emits red light.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Light emitting unit

The invention claimed is:
1. A compound represented by the following formula (1):

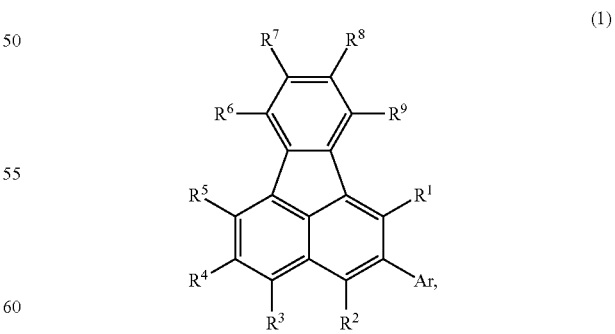

wherein
Ar represents a group formed by a combination of an unsubstituted aryl group having 6 to 50 ring carbon atoms and a substituted or unsubstituted heteroaryl group having 5 to 50 ring atoms;

the heteroaryl group having 5 to 50 ring atoms is selected from the group consisting of a pyrimidinyl group, a triazinyl group, an imidazolyl group and a benzimidazolyl group, $R^1$ to $R^9$ each independently represent a hydrogen atom or a substituent, provided that none from the group consisting of $R^2$ and $R^3$, $R^3$ and $R^4$, $R^4$ and $R^5$, $R^6$ and $R^7$, $R^7$ and $R^8$, and $R^8$ and $R^9$ is bonded to each other, thereby failing to form a benzene ring, and provided that $R^4$ does not include a phenanthrolinyl group.

2. The compound according to claim 1, wherein the heteroaryl group having 5 to 50 ring atoms is selected from the group consisting of a pyrimidinyl group and a triazinyl group.

3. The compound according to claim 1, wherein the heteroaryl group having 5 to 50 ring atoms is a triazinyl group.

4. The compound according to claim 1, wherein the heteroaryl group having 5 to 50 ring atoms is a pyrimidinyl group.

5. The compound according to claim 1, wherein Ar represents a group formed by a combination of the unsubstituted aryl group having 6 to 20 ring carbon atoms and the substituted or unsubstituted heteroaryl group having 5 to 50 ring atoms, and the heteroaryl group having 5 to 50 ring atoms is selected from the group consisting of a pyrimidinyl group, a triazinyl group, an imidazolyl group and a benzimidazolyl group.

6. The compound according to claim 1, wherein the unsubstituted aryl group having 6 to 50 ring atoms is selected from the group consisting of a phenyl group, a naphthyl group, a phenanthryl group, a biphenylyl group, and a fluorenyl group.

7. The compound according to claim 1, wherein a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms.

8. The compound according to claim 1, wherein $R^1$ to $R^9$ each are selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms.

9. The compound according to claim 1, wherein $R^1$ to $R^9$ each are selected from the group consisting of a phenyl group, a biphenylyl group, and a terphenylyl group.

10. The compound according to claim 1, wherein

Ar represents a group formed by a combination of the unsubstituted aryl group having 6 to 20 ring carbon atoms and a substituted or unsubstituted heteroaryl group having 5 to 50 ring atoms;

the heteroaryl group having 5 to 50 ring atoms is selected from the group consisting of a pyrimidinyl group, a triazinyl group, an imidazolyl group and a benzimidazolyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, a substituted or unsubstituted heteroaryl group having 5 to 50 ring atoms; and $R^1$ to $R^9$ each are selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms.

11. The compound according to claim 1, wherein

Ar represents a group formed by a combination of the unsubstituted aryl group having 6 to 20 ring carbon atoms and a substituted or unsubstituted heteroaryl group having 5 to 50 ring atoms;

the heteroaryl group having 5 to 50 ring atoms is selected from the group consisting of a pyrimidinyl group and a triazinyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms.

12. The compound according to claim 1, wherein

Ar represents a group formed by a combination of the unsubstituted aryl group having 6 to 50 ring atoms and a substituted or unsubstituted heteroaryl group having 5 to 50 ring atoms;

the unsubstituted aryl group having 6 to 50 ring atoms is selected from the group consisting of a phenyl group, a naphthyl group, a phenanthryl group, a biphenylyl group, and a fluorenyl group, and the heteroaryl group having 5 to 50 ring atoms is selected from the group consisting of a pyrimidinyl group, a triazinyl group, an imidazolyl group and a benzimidazolyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are selected from the group consisting of a phenyl group, a biphenylyl group, and a terphenylyl group.

13. The compound according to claim 1, wherein

Ar represents a group formed by a combination of the unsubstituted aryl group having 6 to 50 ring atoms and a substituted or unsubstituted heteroaryl group having 5 to 50 ring atoms;

the unsubstituted aryl group having 6 to 50 ring atoms is selected from the group consisting of a phenyl group, a naphthyl group, a phenanthryl group, a biphenylyl group, and a fluorenyl group, and the heteroaryl group having 5 to 50 ring atoms is selected from the group consisting of a pyrimidinyl group and a triazinyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are selected from the group consisting of a phenyl group, a biphenylyl group, and a terphenylyl group.

14. The compound according to claim 1, wherein $R^1$ to $R^9$ each are a hydrogen atom.

15. The compound according to claim 1, which has only one fluoranthene skeleton within one molecule.

16. The compound according to claim 1, wherein

Ar represents a group formed by a combination of the unsubstituted aryl group having 6 to 20 ring carbon atoms and a substituted or unsubstituted heteroaryl group having 5 to 50 ring atoms;

the heteroaryl group having 5 to 50 ring atoms is selected from the group consisting of a pyrimidinyl group, a triazinyl group, an imidazolyl group and a benzimidazolyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms.

17. The compound according to claim 1, wherein

Ar represents a group formed by a combination of the unsubstituted aryl group having 6 to 20 ring carbon atoms and a substituted or unsubstituted heteroaryl group having 5 to 50 ring atoms;

the heteroaryl group having 5 to 50 ring atoms is selected from the group consisting of a pyrimidinyl group and a triazinyl group, a substituent in the substituted or unsubstituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are a hydrogen atom.

18. The compound according to claim 1, wherein

Ar represents a group formed by a combination of the unsubstituted aryl group having 6 to 50 ring atoms and a substituted or unsubstituted heteroaryl group having 5 to 50 ring atoms;

the unsubstituted aryl group having 6 to 50 ring atoms is selected from the group consisting of a phenyl group, a naphthyl group, a phenanthryl group, a biphenylyl group, and a fluorenyl group, and the heteroaryl group having 5 to 50 ring atoms is selected from the group consisting of a pyrimidinyl group, a triazinyl group, an imidazolyl group and a benzimidazolyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are a hydrogen atom.

19. The compound according to claim 1, wherein

Ar represents a group formed by a combination of the unsubstituted aryl group having 6 to 50 ring atoms and a substituted or unsubstituted heteroaryl group having 5 to 50 ring atoms;

the unsubstituted aryl group having 6 to 50 ring atoms is selected from the group consisting of a phenyl group, a naphthyl group, a phenanthryl group, a biphenylyl group, and a fluorenyl group, and the heteroaryl group having 5 to 50 ring atoms is selected from the group consisting of a pyrimidinyl group and a triazinyl group, a substituent in the substituted heteroaryl group having 5 to 50 ring atoms is selected from the group consisting of a substituted or unsubstituted alkyl group having 1 to 50 carbon atoms, a substituted or unsubstituted aryl group having 6 to 50 ring carbon atoms, and a substituted or unsubstituted heteroaryl group having 5 to 50 ring atoms; and $R^1$ to $R^9$ each are a hydrogen atom.

20. The compound according to claim 1, which has a formula selected from the group consisting of:

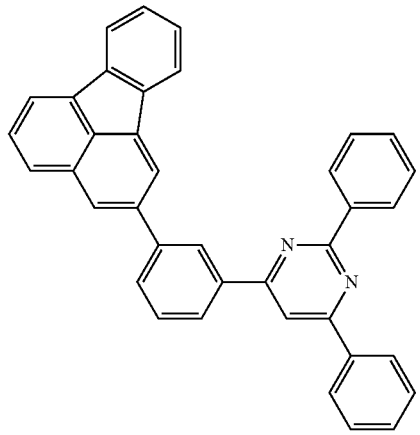

C1

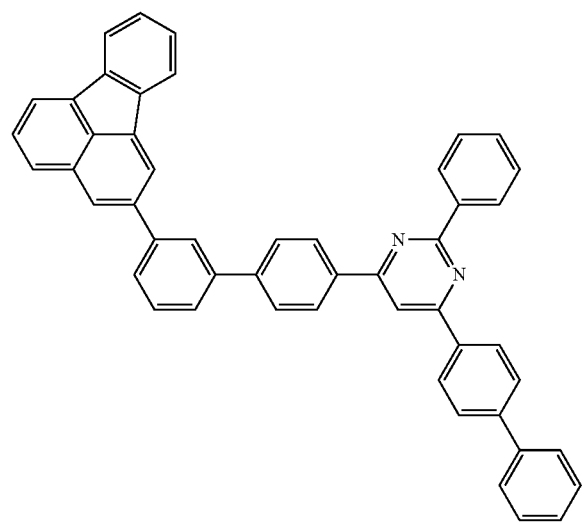

C2

C3
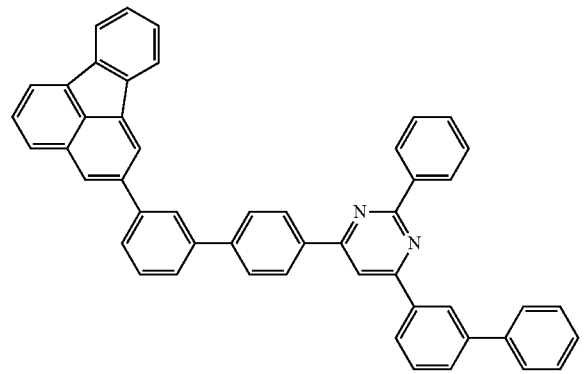
C4
C5
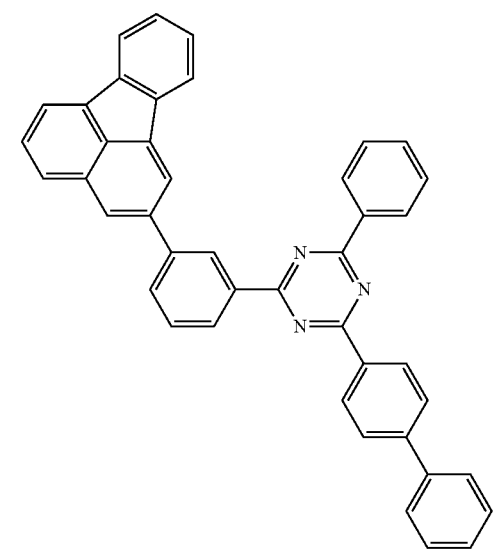
C6
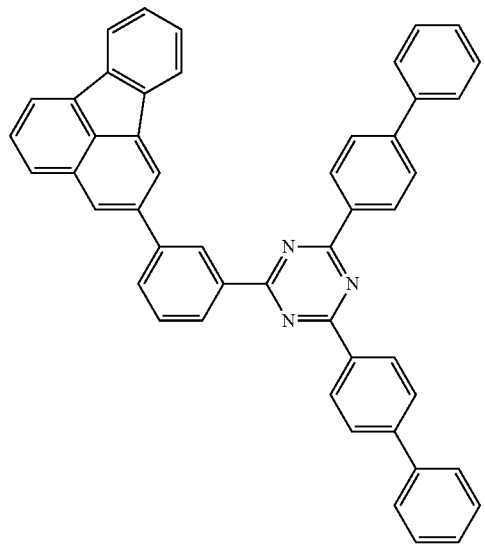
C7
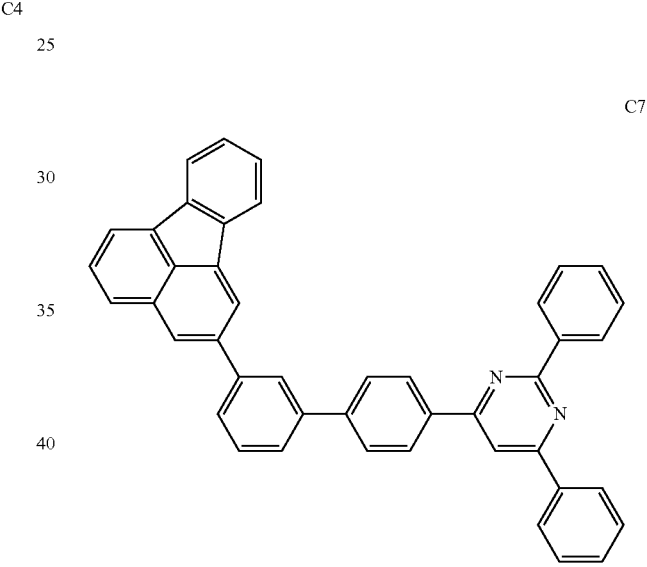
C8
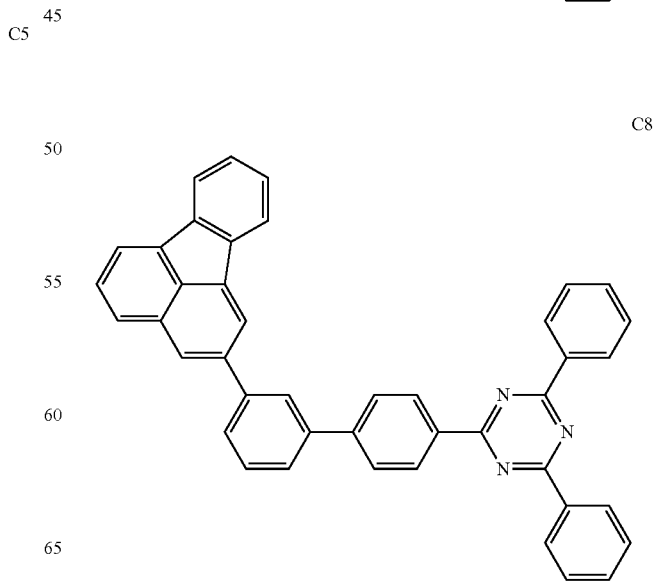

-continued
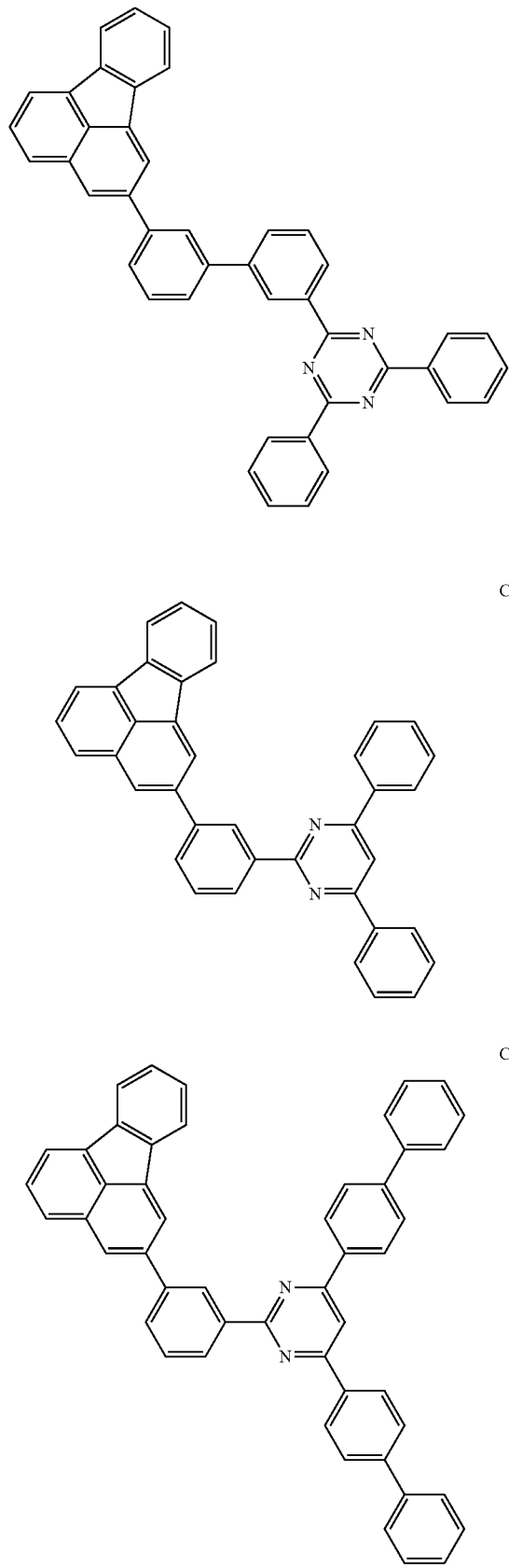
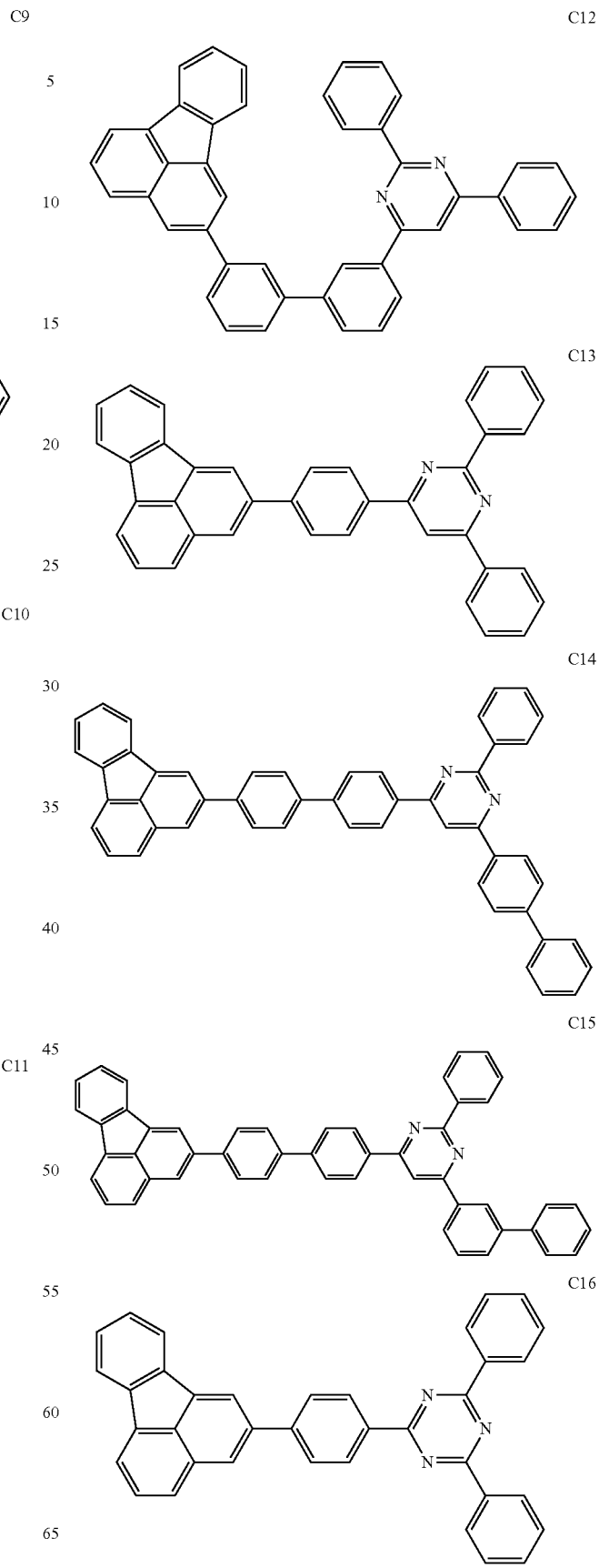

C17
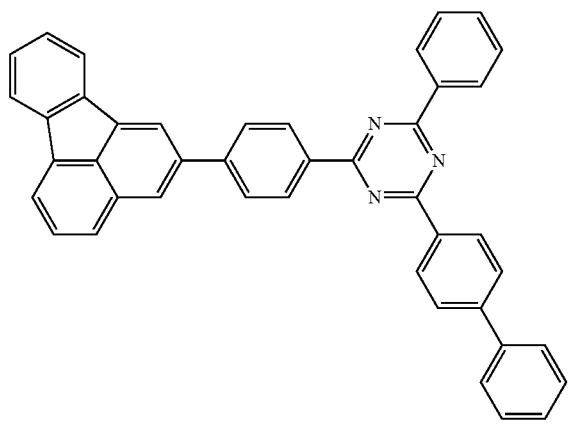
C21
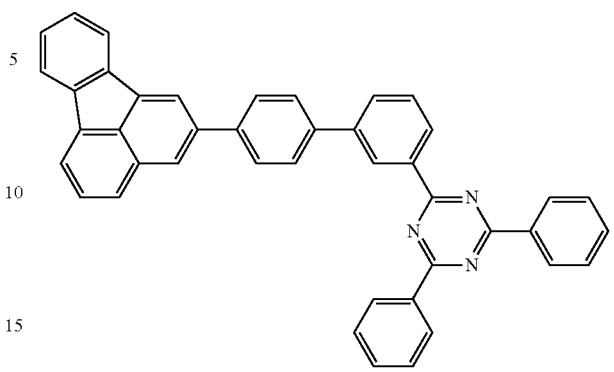
C18
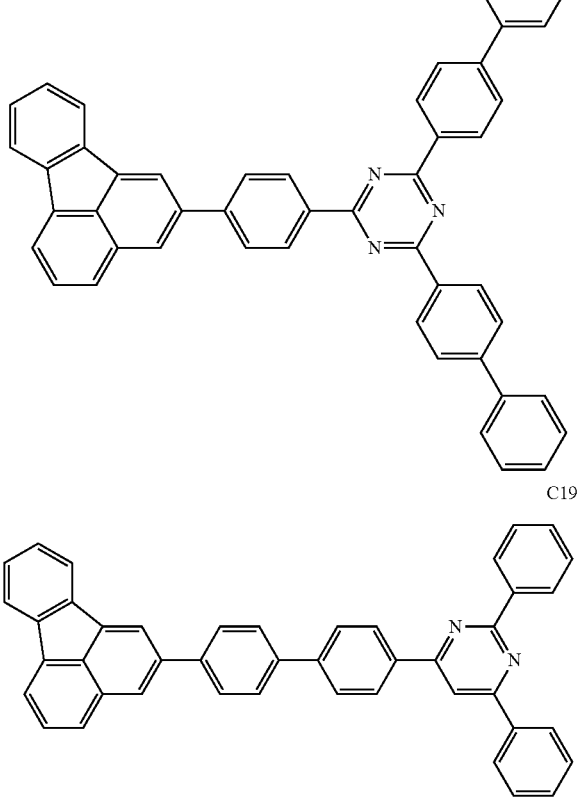
C22
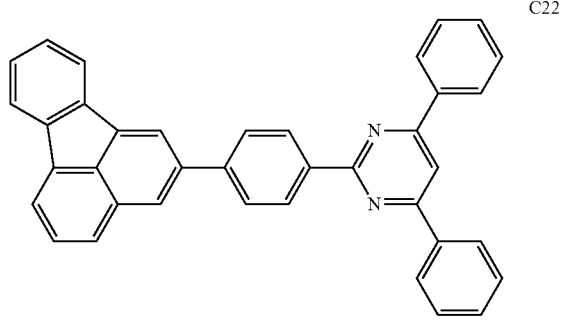
C19
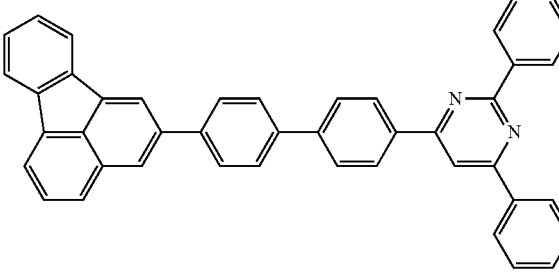
C23
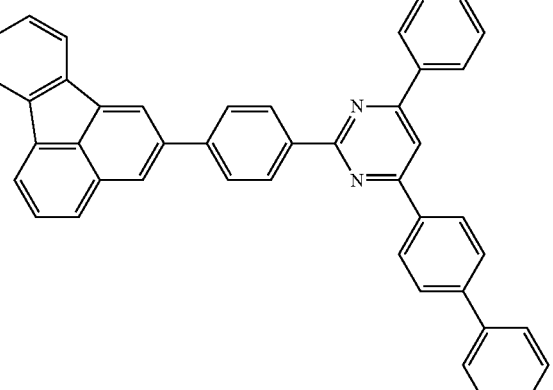
C20
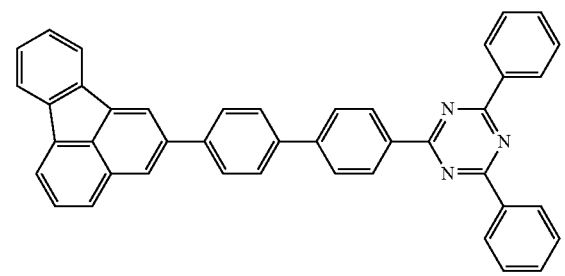
C24
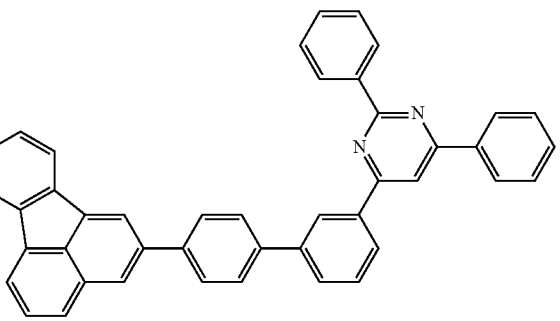

C25
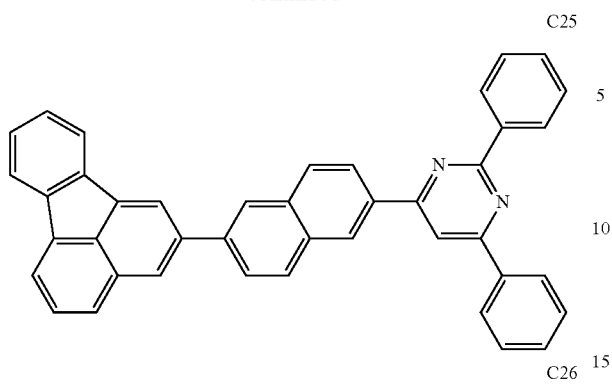
C26
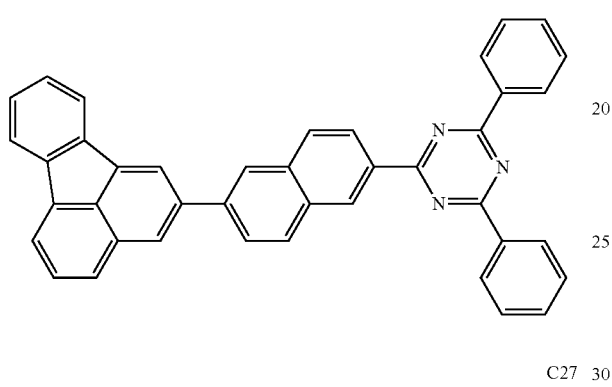
C27
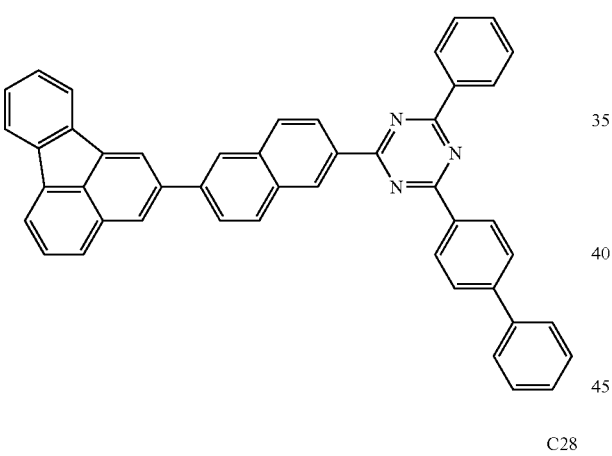
C28
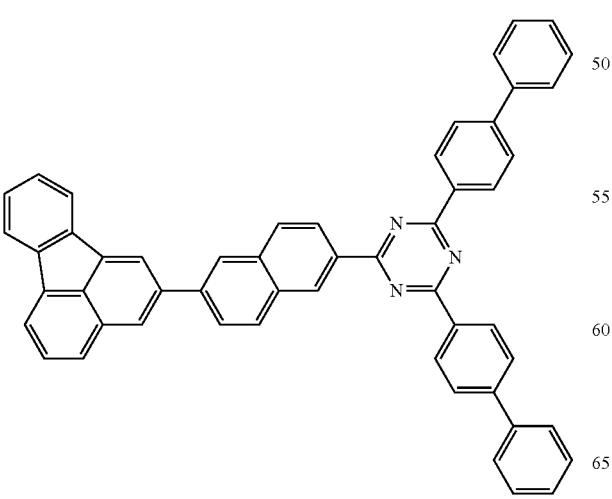
C29
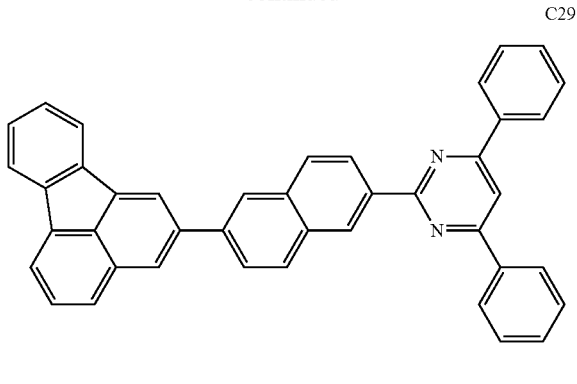
C30
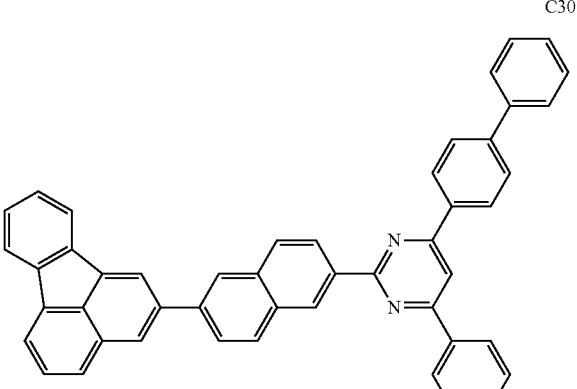
C31
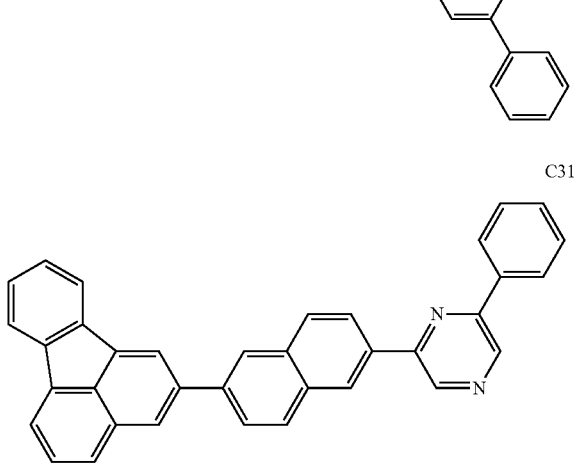
C32
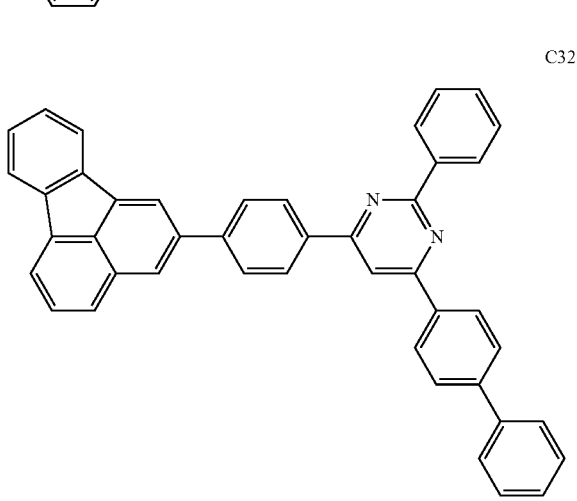

-continued
C33
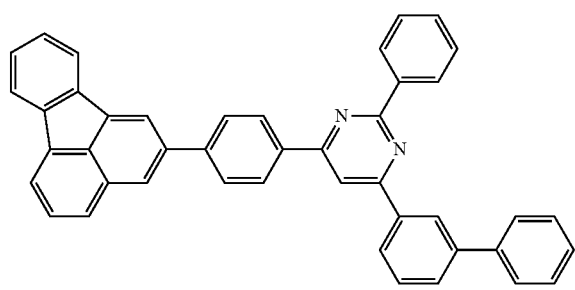
C34
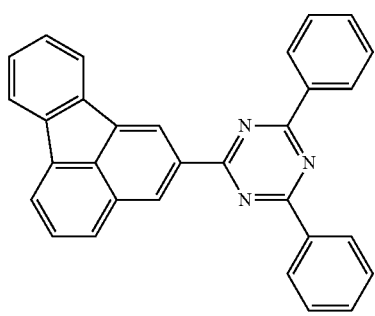
C35
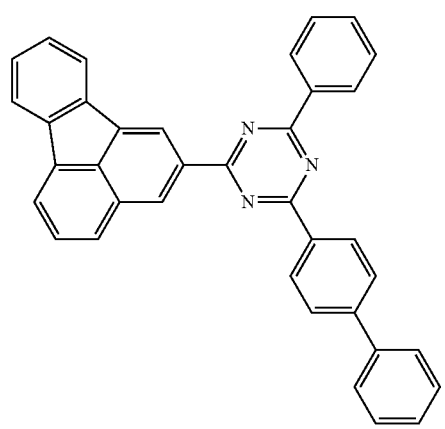
C36
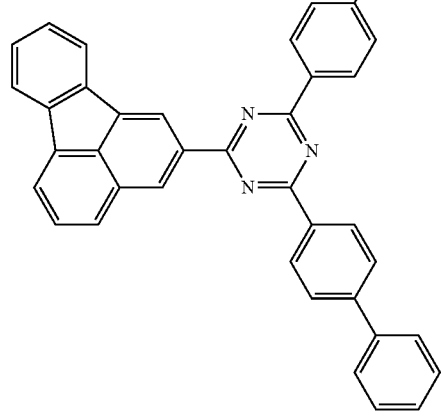
-continued
C37
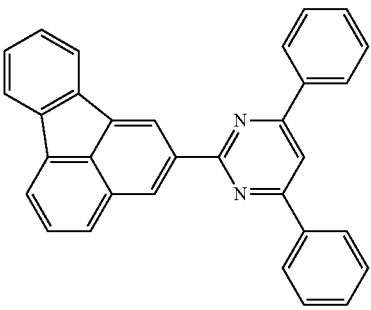
C38
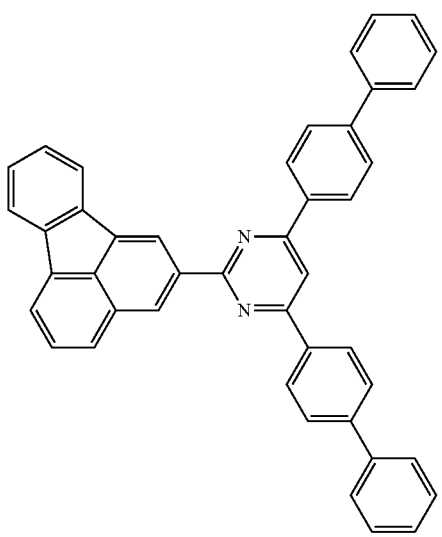
C39
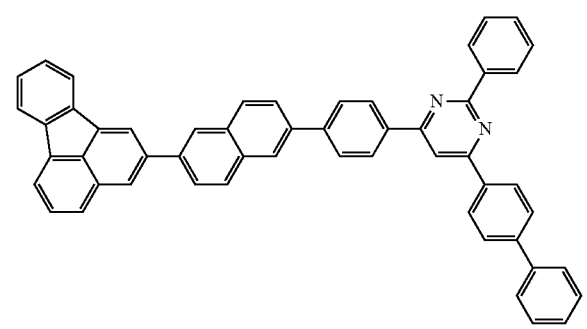
C40
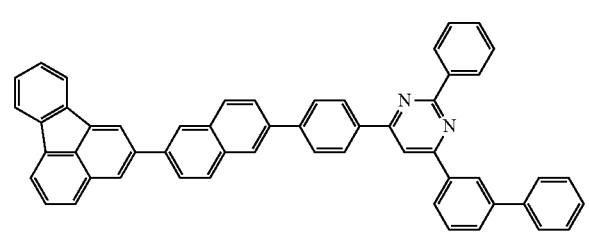

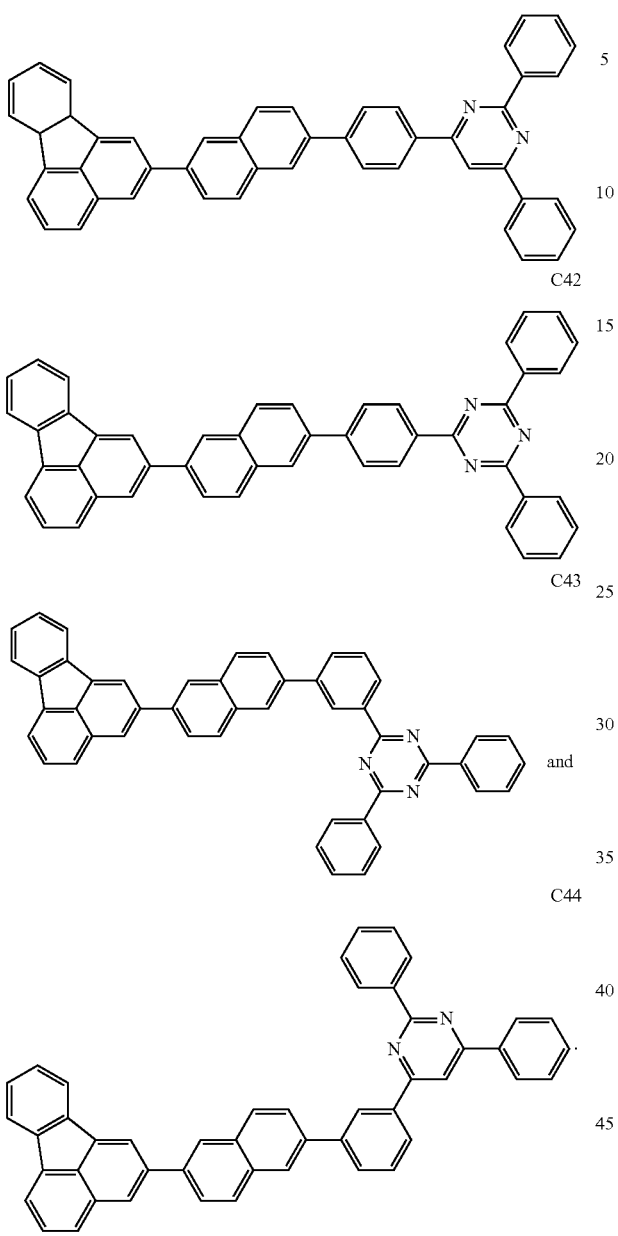

21. A material suitable for an organic electroluminescence device, comprising the compound according to claim 1.

22. An organic electroluminescence device comprising:
a cathode;

an anode; and an organic thin film layer formed of one layer or plural layers, which is sandwiched between the cathode and the anode, wherein the organic thin film layer comprises a light emitting layer, and at least one layer of the organic thin film layer comprises the compound according to claim 1.

23. The organic electroluminescence device according to claim 22, wherein the light emitting layer comprises the compound.

24. The organic electroluminescence device according to claim 22, wherein the light emitting layer comprises a phosphorescent light emitting material.

25. The organic electroluminescence device according to claim 24, wherein the phosphorescent light emitting material is an ortho-metallated complex with a metal atom selected from the group consisting of iridium (Ir), osmium (Os), and platinum (Pt).

26. The organic electroluminescence device according to claim 22, wherein the light emitting layer comprises a fluorescent light emitting material.

27. The organic electroluminescence device according to claim 22, wherein an electron transporting layer is provided between a cathode and a light emitting layer, and the electron transporting layer comprises the compound.

28. The organic electroluminescence device according to claim 22, wherein a hole transporting layer is provided between an anode and a light emitting layer, and the hole transporting layer comprises the compound.

29. An electronic equipment comprising the organic electroluminescence device according to claim 22.

* * * * *